(12) United States Patent
Schiffer et al.

(10) Patent No.: US 11,472,778 B2
(45) Date of Patent: Oct. 18, 2022

(54) HEPATITIS C VIRUS NS3/4A PROTEASE INHIBITORS

(71) Applicant: University of Massachusetts, Boston, MA (US)

(72) Inventors: Celia Schiffer, Shrewsbury, MA (US); Akbar Ali, Westborough, MA (US); Ashley Matthew, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 16/614,843

(22) PCT Filed: Jun. 19, 2018

(86) PCT No.: PCT/US2018/038362
§ 371 (c)(1),
(2) Date: Nov. 19, 2019

(87) PCT Pub. No.: WO2018/236928
PCT Pub. Date: Dec. 27, 2018

(65) Prior Publication Data
US 2020/0087265 A1    Mar. 19, 2020

Related U.S. Application Data

(60) Provisional application No. 62/522,633, filed on Jun. 20, 2017.

(51) Int. Cl.
| | |
|---|---|
| *C07D 241/20* | (2006.01) |
| *A61P 31/14* | (2006.01) |
| *A61K 31/498* | (2006.01) |
| *C07K 5/083* | (2006.01) |
| *C07K 5/103* | (2006.01) |
| *C07K 5/107* | (2006.01) |
| *A61K 45/06* | (2006.01) |

(52) U.S. Cl.
CPC .......... *C07D 241/20* (2013.01); *A61K 31/498* (2013.01); *A61P 31/14* (2018.01); *C07K 5/0808* (2013.01); *C07K 5/101* (2013.01); *C07K 5/1016* (2013.01); *A61K 45/06* (2013.01)

(58) Field of Classification Search
CPC ..... C07K 5/0808; C07K 5/101; C07K 5/1016
See application file for complete search history.

(56) References Cited

U.S. PATENT DOCUMENTS

| | | | | |
|---|---|---|---|---|
| 2004/0106559 A1* | 6/2004 | Wang | ................... | A61P 31/12 424/85.4 |
| 2008/0032936 A1* | 2/2008 | Gai | ................... | C07K 5/0808 424/85.4 |

OTHER PUBLICATIONS

Ali et al. (ACS Chemical Biology, 2013, 8(7), pp. 1469-1478 and supporting experimental section, pp. 1-27).*
Rusere et al. (ACS Med. Chem. Lett., 2018, 9, 691-696).*

* cited by examiner

*Primary Examiner* — Susanna Moore
(74) *Attorney, Agent, or Firm* — Milstein Zhang & Wu LLC

(57) ABSTRACT

The invention provides novel classes of HCV therapeutics that are orally available, safe and effective HCV NS3/4A protease inhibitors and are less susceptible to drug resistance than existing therapeutics. The invention also relates to pharmaceutical composition of these compounds and methods of preparation and use thereof.

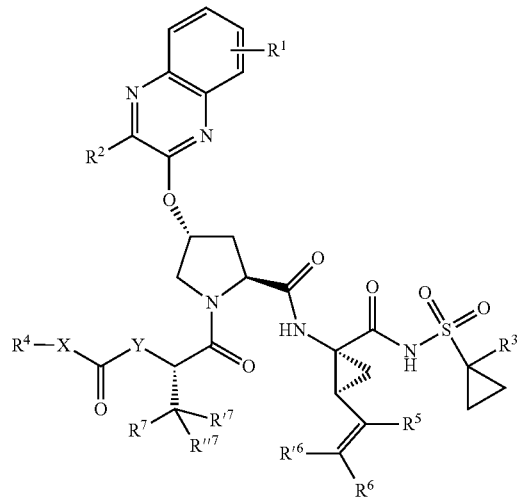

(I)

8 Claims, 13 Drawing Sheets

Simeprevir (TMC-435)

Paritaprevir (ABT-450)

Grazoprevir (MK-5172)

MK-6325

Voxilaprevir (GS-9857)

Glecaprevir (ABT-493)

HEPATITIS C VIRUS NS3/4A PROTEASE INHIBITORS

PRIORITY CLAIMS AND RELATED APPLICATIONS

This application is the U.S. national phase of and claims priority to PCT/US18/38362, filed Jun. 19, 2018, which claims the benefit of priority to U.S. Provisional Application No. 62/522,633, filed Jun. 20, 2017, the entire content of each of which is incorporated herein by reference for all purposes.

STATEMENT REGARDING FEDERALLY SPONSORED RESEARCH

This invention was made with government support under Grant nos. A1085051 and GM119345 awarded by the National Institutes of Health. The Government has certain rights in the invention.

TECHNICAL FIELDS OF THE INVENTION

The invention generally relates to novel compounds and methods for treating HCV infection. More particularly, the invention relates to novel classes of HCV therapeutics that are orally available, safe and effective HCV NS3/4A protease inhibitors, which are less susceptible to drug resistance than existing therapeutics. The invention also relates to pharmaceutical composition of these compounds and methods of preparation and use thereof.

BACKGROUND OF THE INVENTION

Hepatitis C virus (HCV) infects over 130 million people globally and is the leading cause of chronic liver disease, cirrhosis, and hepatocellular carcinoma. HCV is known as a "silent killer" as a majority of affected patients remain unaware of their infection, and over time the acute infection progresses to chronic liver disease. The rate of cirrhosis is estimated to increase from 16% to 32% by the year 2020 due to the high number of untreated patients. (World Health Organization (WHO). Hepatitis C Fact Sheet (2016); Hajarizadeh, et al. *Nat. Rev. Gastroenterol. Hepatol.* 2013, 10, 553-562; Razavi, et al. *J. Viral. Hepat.* 2014, 21 Suppl 1, 34-59.)

HCV infection is difficult to treat, as the virus is genetically diverse with six known genotypes (genotype 1-6), each of which is further sub-divided into numerous subtypes. Genotype 1 (GT1) and genotype 3 (GT3) are the most prevalent accounting for 46% and 30% of global infections, respectively. Therapeutic regimen and viral response are largely genotype dependent with most treatments being efficacious only against GT1. (Gower, et al. *J. Hepatol.* 2014, 61, S45-S57; Messina, et al. *Hepatology* 2015, 61, 77-87; WHO Guidelines for the screening, care and treatment of persons with chronic hepatitis C infection. April 2016.)

The recent advent of direct-acting antivirals (DAAs) targeting essential viral proteins NS3/4A, NS5A, and NS5B has remarkably improved therapeutic options and treatment outcomes for HCV infected patients. Four new all-oral treatments have been approved by the FDA: Harvoni® (sofosbuvir and ledipasvir), Viekira Pak® (ombitasvir, paritaprevir, ritonavir, and dasabuvir), Zepatier™ (elbasvir and grazoprevir), and more recently Epclusa® (sofosbuvir and velpatasvir). (Asselah, et al. *Liver Int.* 2016, 36, 47-57; Afdhal, et al. *N. Engl. J. Med.* 2014, 370, 1889-1898; Ferenci, et al. *N. Engl. J. Med.* 2014, 370, 1983-1992; Lawitz, et al. *Lancet* 2014, 385, 1075-; Everson, et al. *Ann. Intern. Med.* 2015, 163, 818-826.)

The DAA-based therapies are highly effective against GT1 with sustained virological response (SVR) rates greater than 90%. However, most of the FDA approved treatments and those in clinical development are not efficacious against other genotypes, especially GT3. Moreover, except for sofosbuvir, all current DAAs are susceptible to drug resistance. Therefore, more robust DAAs need to be developed with higher barriers to drug resistance and a broad spectrum of activity against different HCV genotypes. (Asselah, et al. *Liver Int.* 2016, 36, 47-57; Pawlotsky, et al. *Gastroenterology* 2016, 151, 70-86.)

The HCV NS3/4A protease is a major therapeutic target for the development of pan-genotypic HCV inhibitors. The NS3/4A protease inhibitors (PIs) telaprevir and boceprevir were the first DAAs approved for the treatment of HCV GT1 infection in combination therapy with pegylated-interferon and ribavirin. Three recently approved PIs, simeprevir (TMC-435), paritaprevir (ABT-450) and grazoprevir (MK-5172), (FIG. 1) are integral components of various combination therapies currently used as the standard of care for HCV infected patients. Two other NS3/4A PIs, asunaprevir and vaniprevir, have been approved in Japan. In addition, a number of next generation NS3/4A PIs are in clinical development including glecaprevir (ABT-493), MK-6325 and voxilaprevir (GS-9857) (FIG. 1). (Meanwell, et al. *J. Med. Chem.* 2016, 59, 7311-7351; McCauley, J. et al. *Curr. Opin. Pharmacol.* 2016, 30, 84-92; Kwong, et al. *Nat. Biotech.* 2011, 29, 993-1003; Venkatraman, et al. *J. Med. Chem.* 2006, 49, 6074-6086; Zeuzem, et al. *N. Engl. J. Med.* 2011, 364, 2417-2428; Poordad, et al. *N. Engl. J. Med.* 2011, 364, 1195-1206; Rosenquist, et al. *J. Med. Chem.* 2014, 57, 1673-1693; Pilot-Matias, et al. *Antimicrob. Agents Chemother.* 2015, 59, 988-997; Harper, et al. *ACS Med. Chem. Lett.* 2012, 3, 332-336; Scola, et al. *J. Med. Chem.* 2014, 57, 1730-1752; McCauley, et al. *J. Med. Chem.* 2010, 53, 2443-2463; Lawitz, et al. *Antimicrob. Agents Chemother.* 2015, 60, 1546-1555; Rudd, et al. *Chem Med Chem* 2015, 10, 727-735.)

All NS3/4A PIs share a common peptidomimetic scaffold and are either linear or macrocyclic; the macrocycle is located either between P1-P3 or P2-P4 moieties. In addition, these inhibitors contain a large heterocyclic moiety attached to the P2 proline, which significantly improves inhibitor potency against wild-type (WT) NS3/4A protease. (McCauley, J. et al. *Curr. Opin. Pharmacol.* 2016, 30, 84-92; Tsantrizos, et al. *Angew. Chem. Int. Ed. Engl.* 2003, 42, 1356-1360; LaPlante, et al. *J. Med. Chem.* 2013, 57, 1777-1789.)

All NS3/4A PIs are, however, susceptible to drug resistance, especially due to single site mutations at protease residues Arg155, Ala156 and Asp168. Notably, D168A/V mutations are present in nearly all patients who fail treatment with PIs. Moreover, natural polymorphisms at this position are responsible for significantly reduced inhibitor potency against GT3. (Pawlotsky, et al. *Gastroenterology* 2016, 151, 70-86; Lontok, et al. *Hepatology* 2015, 62, 1623-1632; Kieffer, et al. *Curr. Opin. Virol.* 2014, 8, 16-21; Chan, et al. In vitro efficacy and resistance profiling of protease inhibitors against a novel HCV genotype 3a replicon. In *International Workshop on HIV & Hepatitis Virus Drug Resistance and Curative Strategies*, Toronto, ON, Canada, 2013.)

Development of HCV NS3/4A protease inhibitors with pan-genotypic activity and low susceptibility to drug resistance remains challenging but necessary for improving the long-term effectiveness of this drug class. An urgent need exists for improved HCV therapeutics, especially safe and effective HCV NS3/4A protease inhibitors that are also less susceptible to drug resistance than existing therapeutics.

SUMMARY OF THE INVENTION

The invention provides novel, orally available, selective and potent HCV therapeutics that are safe and effective HCV NS3/4A protease inhibitors and are less susceptible to drug resistance than currently available drugs. The invention also provides pharmaceutical compositions of these compounds and methods of their preparation and use.

Compounds disclosed herein include a series of novel P1-P3 macrocyclic inhibitors that were specifically designed to improve their resistance profiles. In particular, structure-based studies on the compound-target interactions led to compound designs that exploit interfaces with the invariant catalytic triad and avoid contacts with the protease residues in the S2 subsite to improve the resistance profile of NS3/4A protease inhibitors.

Specifically, these macrocyclic inhibitors incorporate flexible quinoxalines at the P2 position. Investigation of structure-activity relationships showed that the P2 quinoxalines with small hydrophobic substituents at the 3-position were better for maintaining potency against drug resistant variants, likely due to reduced interactions with residues in the S2 subsite. In contrast, inhibitors with larger groups at this position were highly susceptible to mutations at Arg155, Ala156 and Asp168.

This new class of macrocyclic inhibitors exhibited exceptional potency profiles with $EC_{50}$ values less than 5 nM against major drug resistant HCV variants. These results further confirm that inhibitors designed to interact with evolutionarily constrained regions of the protease, while avoiding interactions with residues not essential for substrate recognition, are less likely to lead to drug resistance.

Also disclosed herein are HCV NS3/4A PIs that extend in the P4 direction leveraging unexploited areas in the substrate envelope to improve resistance profiles, particularly against multi-drug esistant mutations at Asp 168. As disclosed herein, optimally filling the P4 pocket of the substrate envelope improves inhibitor potency while avoiding resistance. Use of unexploited space in the pocket was critical for this improvement by enhanced hydrophobic packing, or fluorine-hydrogen bonding and avoiding forming an energetically frustrated pocket. These strategies achieved better resistance profiles and higher affinity over both FDA-approved NS3/4A PI grazoprevir and the parent compound.

Additional compounds disclosed herein include a series of novel linear HCV NS3/4A PIs. These compounds were designed by eliminating the P2-P4 macrocyclic linker in grazoprevir, which, in addition to conferring conformational flexibility, allowed structure-activity relationship (SAR) exploration of diverse quinoxalines at the P2 position.

In one aspect, the invention generally relates to a compound having the structural formula (I),

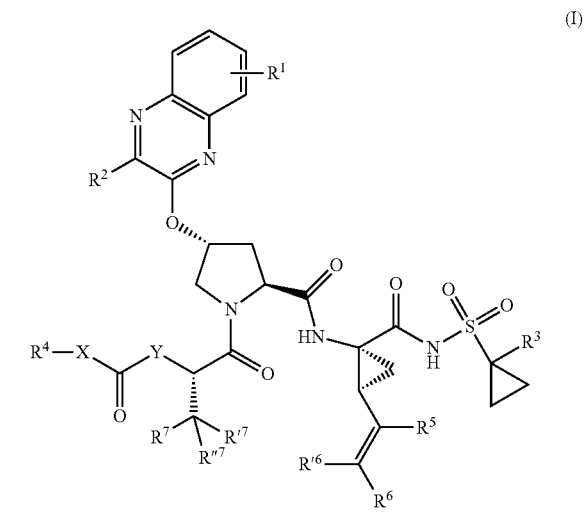

wherein each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group;

$R^2$ is selected from H, halogen, a $C_1$-$C_6$ alkyl, aryl, —CN, CF$_3$, CHF$_2$, CH$_2$F;

$R^3$ is selected from H, a $C_1$-$C_6$ alkyl, CH$_2$F, CHF$_2$;

$R^4$ is selected from an alkyl, hetero-alkyl, aryl, hetero-aryl group, —NH—C(=O)—R;

$R^5$ is H, halogen, or an alkyl group;

$R^6$, $R'^6$ each is independently H, halogen, or an alkyl group;

$R^7$, $R'^7$, $R''^7$ each is independently H, halogen, or an alkyl group;

$R^8$ is independently selected from H, halogen, or an alkyl group;

each R and R' is independently a H or an alkyl group; and provided that $R'^6$ and one of $R'^7$ and $R''^7$ optionally join together to form a 15-, 16- or 17-membered ring, or a pharmaceutically acceptable form thereof.

In another aspect, the invention generally relates to a compound having the structural formula (II),

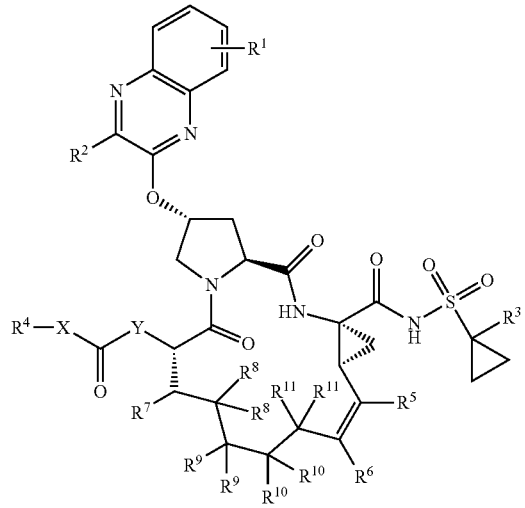

(II)

wherein each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group, —NH—C(=O)—R;

$R^5$ is H, halogen, or an alkyl group;

$R^6$ is H, halogen, or an alkyl group;

$R^7$ is H, halogen, or an alkyl group;

each $R^8$ is independently selected from H, halogen, or an alkyl group;

each $R^9$ is independently selected from H, halogen, or an alkyl group;

each $R^{10}$ is independently selected from H, halogen, or an alkyl group;

each $R^{11}$ is independently selected from H, halogen, or an alkyl group; and each R and R' is independently a H or an alkyl group, or a pharmaceutically acceptable form thereof.

In yet another aspect, the invention generally relates to a compound having the structural formula (IV):

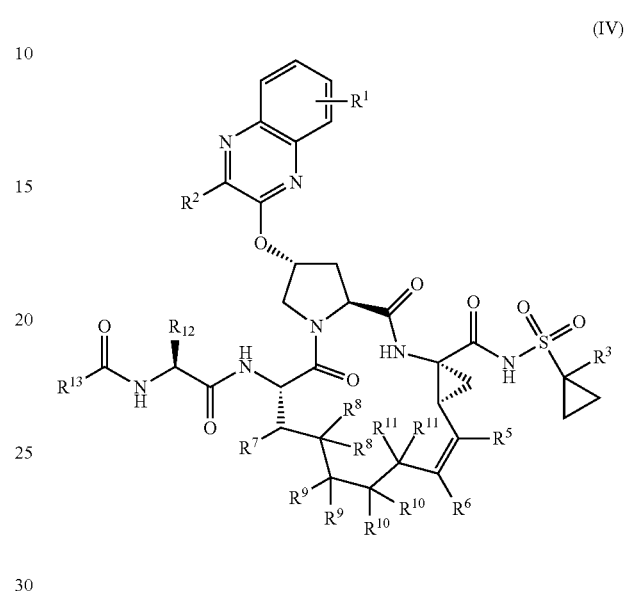

(IV)

wherein each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group, —NH—C(=O)—R;

$R^5$ is H, halogen, or an alkyl group;

$R^6$ is H, halogen, or an alkyl group;

$R^7$ is H, halogen, or an alkyl group;

each $R^8$ is independently selected from H, halogen, or an alkyl group;

each $R^9$ is independently selected from H, halogen, or an alkyl group;

each $R^{10}$ is independently selected from H, halogen, or an alkyl group;

each $R^{11}$ is independently selected from H, halogen, or an alkyl group;

$R^{12}$ is H, halogen, or an alkyl group;

$R^{13}$ is H, halogen, an alkyl group, hetero-alkyl, aryl, or hetero-aryl group; and each R and R' is independently a H or an alkyl group, or a pharmaceutically acceptable form thereof.

In yet another aspect, the invention generally relates to a pharmaceutical composition comprising a compound having the structural formula of (I):

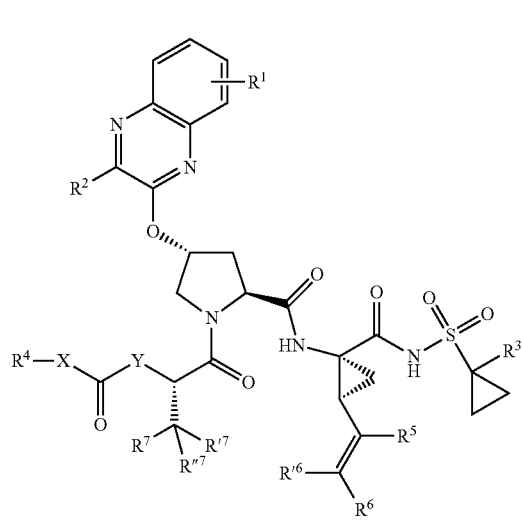

(I)

wherein each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group;

$R^2$ is selected from H, halogen, a $C_1$-$C_6$ alkyl, aryl, —CN, CF$_3$, CHF$_2$, CH$_2$F;

$R^3$ is selected from H, a $C_1$-$C_6$ alkyl, CH$_2$F, CHF$_2$;

$R^4$ is selected from an alkyl, hetero-alkyl, aryl, hetero-aryl group, —NH—C(=O)—R;

$R^5$ is H, halogen, or an alkyl group;

$R^6$, $R'^6$ each is independently H, halogen, or an alkyl group;

$R^7$, $R'^7$, $R''^7$ each is independently H, halogen, or an alkyl group;

$R^8$ is independently selected from H, halogen, or an alkyl group;

each R and R' is independently a H or an alkyl group; and provided that $R'^6$ and one of $R'^7$ and $R''^7$ optionally join together to form a 15-, 16- or 17-membered ring, or a pharmaceutically acceptable form thereof, effective to treat or reduce HCV infection or a related disease or disorder, in a mammal, including a human, and a pharmaceutically acceptable excipient, carrier, or diluent.

In yet another aspect, the invention generally relates to a pharmaceutical composition comprising a compound having the structural formula of (II):

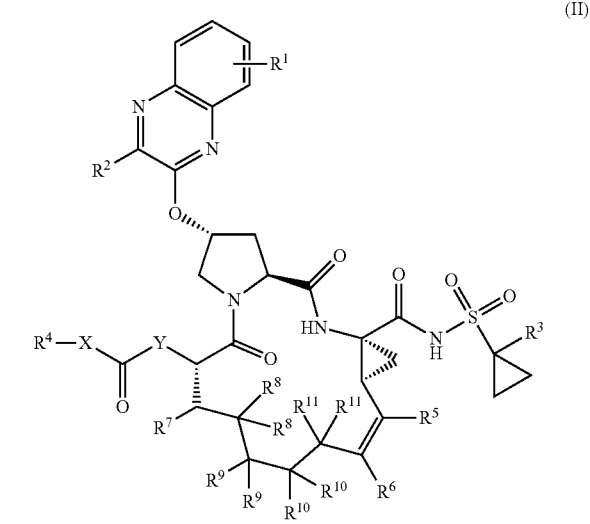

(II)

wherein each of X and Y is independently selected from O, NH and CH$_2$, provided that at least one of X and Y is NH;

$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group, wherein each R is independently a H or an alkyl group;

$R^2$ is selected from H, halogen, a $C_1$-$C_6$ alkyl, aryl, —CN, CF$_3$, CHF$_2$, CH$_2$F;

$R^3$ is selected from H, a $C_1$-$C_6$ alkyl, CH$_2$F, CHF$_2$;

$R^4$ is selected from an alkyl, hetero-alkyl, aryl, hetero-aryl group;

$R^5$ is H, halogen, or an alkyl group;

$R^6$ is H, halogen, or an alkyl group;

$R^7$ is H, halogen, or an alkyl group;

each $R^8$ is independently selected from H, halogen, or an alkyl group;

each $R^9$ is independently selected from H, halogen, or an alkyl group;

each $R^{10}$ is independently selected from H, halogen, or an alkyl group; and each $R^{11}$ is independently selected from H, halogen, or an alkyl group, or a pharmaceutically acceptable form thereof, effective to treat or reduce HCV infection or a related disease or disorder, in a mammal, including a human, and a pharmaceutically acceptable excipient, carrier, or diluent.

In yet another aspect, the invention generally relates to a pharmaceutical composition comprising a compound having the structural formula of (IV):

(IV)

wherein
each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=))N—R, —N(C=O)R, —(SO$_2$)NR$_2$ group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group, —NH—C(=O)—R;

$R^5$ is H, halogen, or an alkyl group;

$R^6$ is H, halogen, or an alkyl group;

$R^7$ is H, halogen, or an alkyl group;

each $R^8$ is independently selected from H, halogen, or an alkyl group;

each $R^9$ is independently selected from H, halogen, or an alkyl group;

each $R^{10}$ is independently selected from H, halogen, or an alkyl group;

each $R^{11}$ is independently selected from H, halogen, or an alkyl group;

$R^{12}$ is H, halogen, or an alkyl group;

$R^{13}$ is H, halogen, an alkyl group, hetero-alkyl, aryl, or hetero-aryl group; and each R and R' is independently a H or an alkyl group, or a pharmaceutically acceptable form thereof, effective to treat or reduce HCV infection or a related disease or disorder, in a mammal, including a human, and a pharmaceutically acceptable excipient, carrier, or diluent.

In yet another aspect, the invention generally relates to a pharmaceutical composition comprising a compound disclosed herein.

In yet another aspect, the invention generally relates to a unit dosage. The unit dosage form is comprised of a pharmaceutical herein disclosed.

In yet another aspect, the invention generally relates to a method for treating or reducing HCV infection, or a related disease or disorder. The method includes: administering to a subject in need thereof a pharmaceutical composition comprising a compound having the structural formula of (I):

(I)

wherein
each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group, —NH—C(=O)—R;

$R^5$ is H, halogen, or an alkyl group;

$R^6$, $R'^6$ each is independently H, halogen, or an alkyl group;

$R^7$, $R'^7$, $R''^7$ each is independently H, halogen, or an alkyl group;

$R^8$ is independently selected from H, halogen or an alkyl group;

each R and R' is independently a H or an alkyl group; and provided that $R'^6$ and one of $R'^7$ and $R''^7$ optionally join together to form a 15-, 16- or 17-membered ring, or a pharmaceutically acceptable form thereof, and a pharmaceutically acceptable excipient, carrier, or diluent.

In yet another aspect, the invention generally relates to a method for treating or reducing HCV infection, or a related disease or disorder. The method includes: administering to a subject in need thereof a pharmaceutical composition comprising a compound having the structural formula of (II):

(II)

wherein each of X and Y is independently selected from O, NH and $CH_2$, provided that at least one of X and Y is NH;

$R^1$ is selected from H, a $C_1$-$C_6$ alkoxy, aryloxy, $C_1$-$C_6$ alkyl, halogen, —(C=O)N—R, —N(C=O)R, —($SO_2$)$NR_2$ group, wherein each R is independently a H or an alkyl group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group;

$R^5$ is H, halogen, or an alkyl group;

$R^6$ is H, halogen, or an alkyl group;

$R^7$ is H, halogen, or an alkyl group;

each $R^8$ is independently selected from H, halogen, or an alkyl group;

each $R^9$ is independently selected from H, halogen, or an alkyl group;

each $R^{10}$ is independently selected from H, halogen, or an alkyl group; and each $R^{11}$ is independently selected from H, halogen, or an alkyl group, or a pharmaceutically acceptable form thereof, and a pharmaceutically acceptable excipient, carrier, or diluent.

In yet another aspect, the invention generally relates to a method for treating or reducing HCV infection, or a related disease or disorder. The method includes: administering to a subject in need thereof a pharmaceutical composition comprising a compound having the structural formula of (IV):

(IV)

wherein each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=O)N—R, —N(C=O)R, —($SO_2$)$NR_2$ group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group, —NH—C(=O)—R;

$R^5$ is H, halogen, or an alkyl group;

$R^6$ is H, halogen, or an alkyl group;

$R^7$ is H, halogen, or an alkyl group;

each $R^8$ is independently selected from H, halogen, or an alkyl group;

each $R^9$ is independently selected from H, halogen, or an alkyl group;

each $R^{10}$ is independently selected from H, halogen, or an alkyl group;

each $R^{11}$ is independently selected from H, halogen, or an alkyl group;

$R^{12}$ is H, halogen, or an alkyl group;

$R^{13}$ is H, halogen, an alkyl group, hetero-alkyl, aryl, or hetero-aryl group; and each R and R' is independently a H or an alkyl group, or a pharmaceutically acceptable form thereof, and a pharmaceutically acceptable excipient, carrier, or diluent.

In yet another aspect, the invention generally relates to a method for treating or reducing HCV infection, or a related disease or disorder, comprising administering to a subject in need thereof a pharmaceutical composition or a unit dosage form disclosed herein.

In yet another aspect, the invention generally relates to a method for inhibiting or inactivating HCV NS3/4A protease. The method includes: administering to a subject in need thereof a pharmaceutical composition comprising a compound having the structural formula of (I):

In yet another aspect, the invention generally relates to a method for inhibiting or inactivating HCV NS3/4A protease. The method includes: administering to a subject in need thereof a pharmaceutical composition comprising a compound having the structural formula of (II):

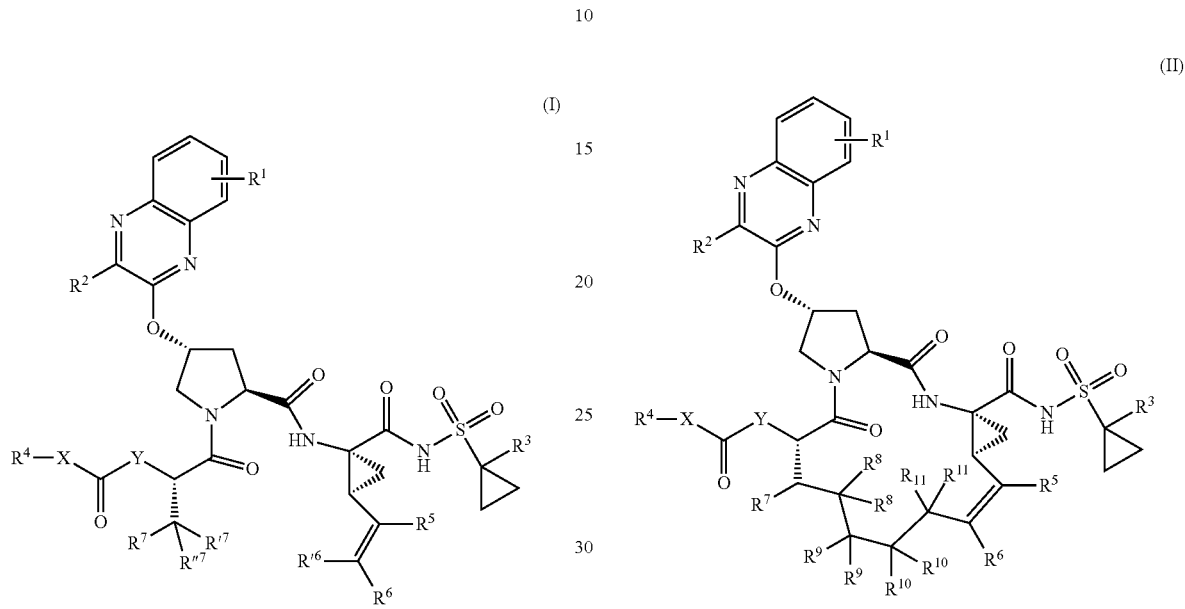

wherein each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group, —NH—C(=O)—R;

$R^5$ is H, halogen, or an alkyl group;

$R^6$, $R'^6$ each is independently H, halogen, or an alkyl group;

$R^7$, $R'^7$, $R''^7$ each is independently H, halogen, or an alkyl group;

$R^8$ is independently selected from H, halogen, or an alkyl group;

each R and R' is independently a H or an alkyl group; and provided that $R'^6$ and one of $R'^7$ and $R''^7$ optionally join together to form a 15-, 16- or 17-membered ring, or a pharmaceutically acceptable form thereof, and a pharmaceutically acceptable excipient, carrier, or diluent.

wherein each of X and Y is independently selected from O, NH and $CH_2$, provided that at least one of X and Y is NH;

$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group, wherein each R is independently a H or an alkyl group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group;

$R^5$ is H, halogen, or an alkyl group;

$R^6$ is H, halogen, or an alkyl group;

$R^7$ is H, halogen, or an alkyl group;

each $R^8$ is independently selected from H, halogen, or an alkyl group;

each $R^9$ is independently selected from H, halogen, or an alkyl group;

each $R^{10}$ is independently selected from H, halogen, or an alkyl group; and each $R^{11}$ is independently selected from H, halogen, or an alkyl group, or a pharmaceutically acceptable form thereof, and a pharmaceutically acceptable excipient, carrier, or diluent.

In yet another aspect, the invention generally relates to a method for inhibiting or inactivating HCV NS3/4A protease. The method includes: administering to a subject in need thereof a pharmaceutical composition comprising a compound having the structural formula of (IV):

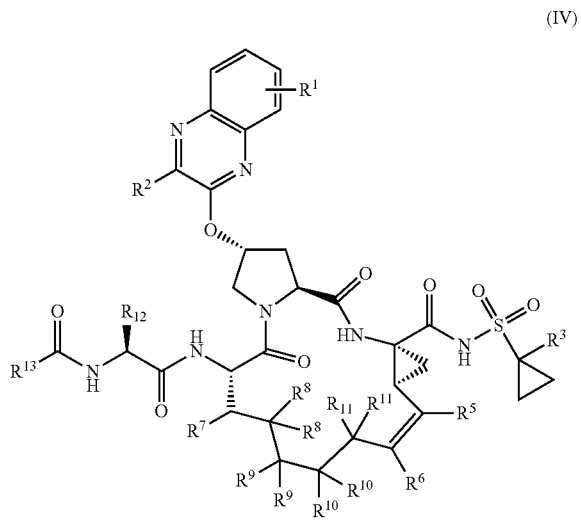

(IV)

wherein
each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group;

$R^2$ is selected from H, halogen, a $C_1$-$C_6$ alkyl, aryl, —CN, CF$_3$, CHF$_2$, CH$_2$F;

$R^3$ is selected from H, a $C_1$-$C_6$ alkyl, CH$_2$F, CHF$_2$;

$R^4$ is selected from an alkyl, hetero-alkyl, aryl, hetero-aryl group, —NH—C(=O)—R;

$R^5$ is H, halogen, or an alkyl group;

$R^6$ is H, halogen, or an alkyl group;

$R^7$ is H, halogen, or an alkyl group;

each $R^8$ is independently selected from H, halogen, or an alkyl group;

each $R^9$ is independently selected from H, halogen, or an alkyl group;

each $R^{10}$ is independently selected from H, halogen, or an alkyl group;

each $R^{11}$ is independently selected from H, halogen, or an alkyl group;

$R^{12}$ is H, halogen, or an alkyl group;

$R^{13}$ is H, halogen, an alkyl group, hetero-alkyl, aryl, or hetero-aryl group; and each R and R' is independently a H or an alkyl group, or a pharmaceutically acceptable form thereof, and a pharmaceutically acceptable excipient, carrier, or diluent.

In yet another aspect, the invention generally relates to a method for inhibiting or inactivating HCV NS3/4A protease. The method includes: administering to a subject in need thereof a pharmaceutical composition disclosed herein.

P4-P5-2 (purple) and (c) P4-P5-1 (orange) bound to the active site of wildtype protease. (d) P4-P5-2 bound to D168A protease. Substrate hydrogen bonds to Ser159 are shown in panel (a), which the P4-P5-cap inhibitors mimic. Catalytic triad residues are highlighted in yellow and drug resistance residues Arg155, Ala156, Asp168 and Ser159 are shown as purple, red, green and blue sticks, respectively.

Figure 11:
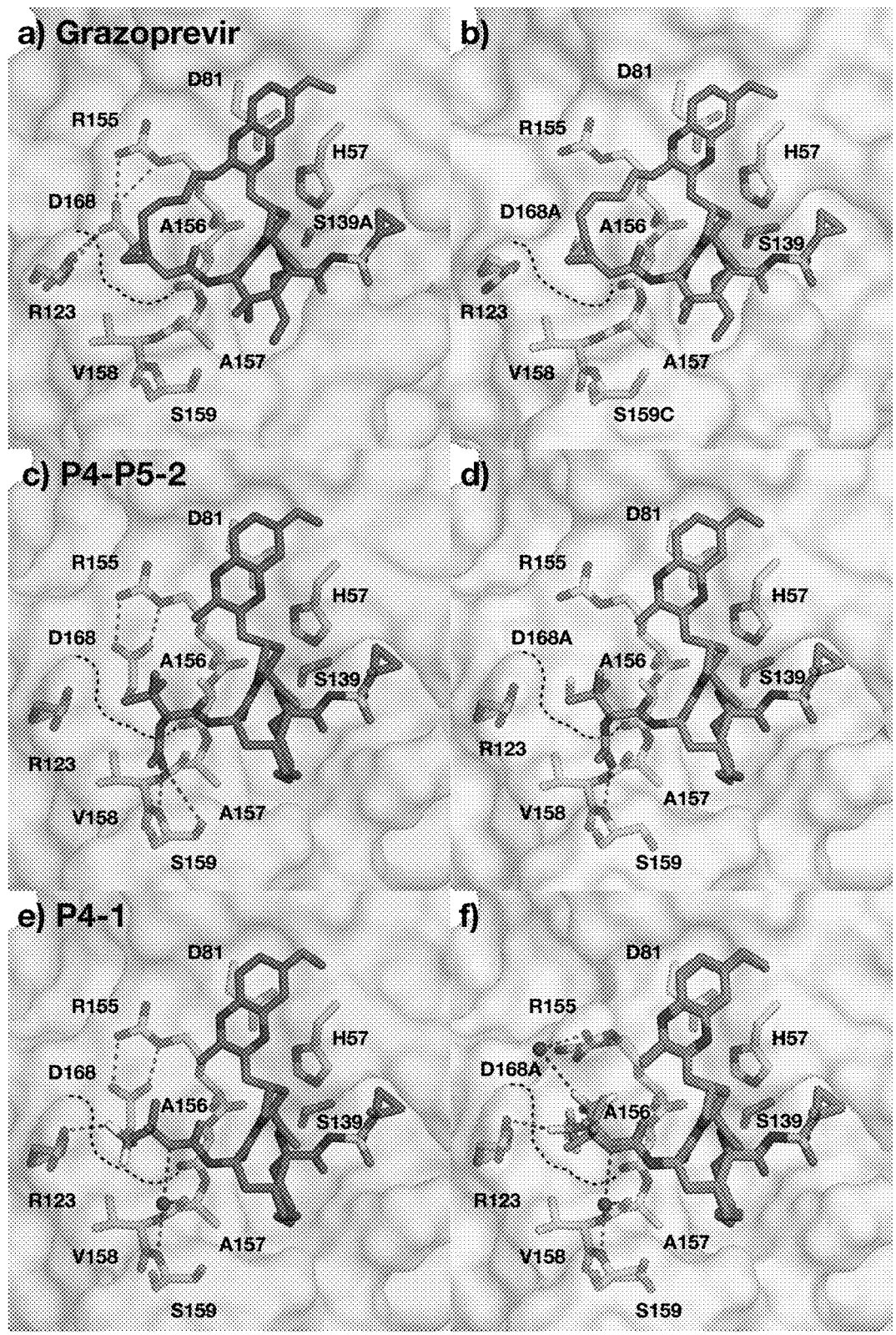

FIG. 11. Binding of grazoprevir and designed PIs to WT and D168A protease active site. Surface representation of (a, b) grazoprevir, (c, d) P4-P5-2 and (e, f) P4-1 bound to wildtype (blue) and D168A (orange) proteases, respectively. The catalytic triad and S4 subsite residues are shown as sticks. Water molecules are shown as non-bonded spheres (red) and hydrogen bonds (gray dashed lines) that stabilize S4 pocket side chains are displayed. Black dashed line outlines the surface of the S4 pocket where the D168A mutation is located.

Figure 12:
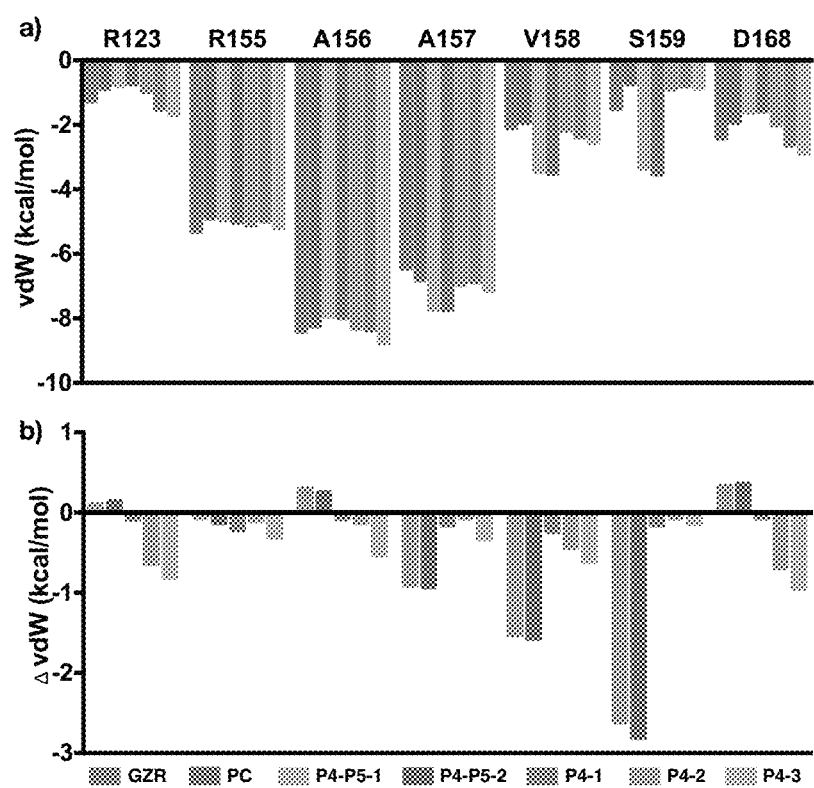

FIG. 12. Inhibitor interactions with S4 pocket residues of HCV NS3/4A protease. (a) Intermolecular van der Waals (vdW) contact energies for inhibitors with residues forming the S4 pocket in WT protease crystal structures. (b) Change in vdW contacts (AvdW) relative to parent compound (PC). GZR stands for grazoprevir. Negative values indicate enhanced contacts compared to the parent compound.

Figure 13:
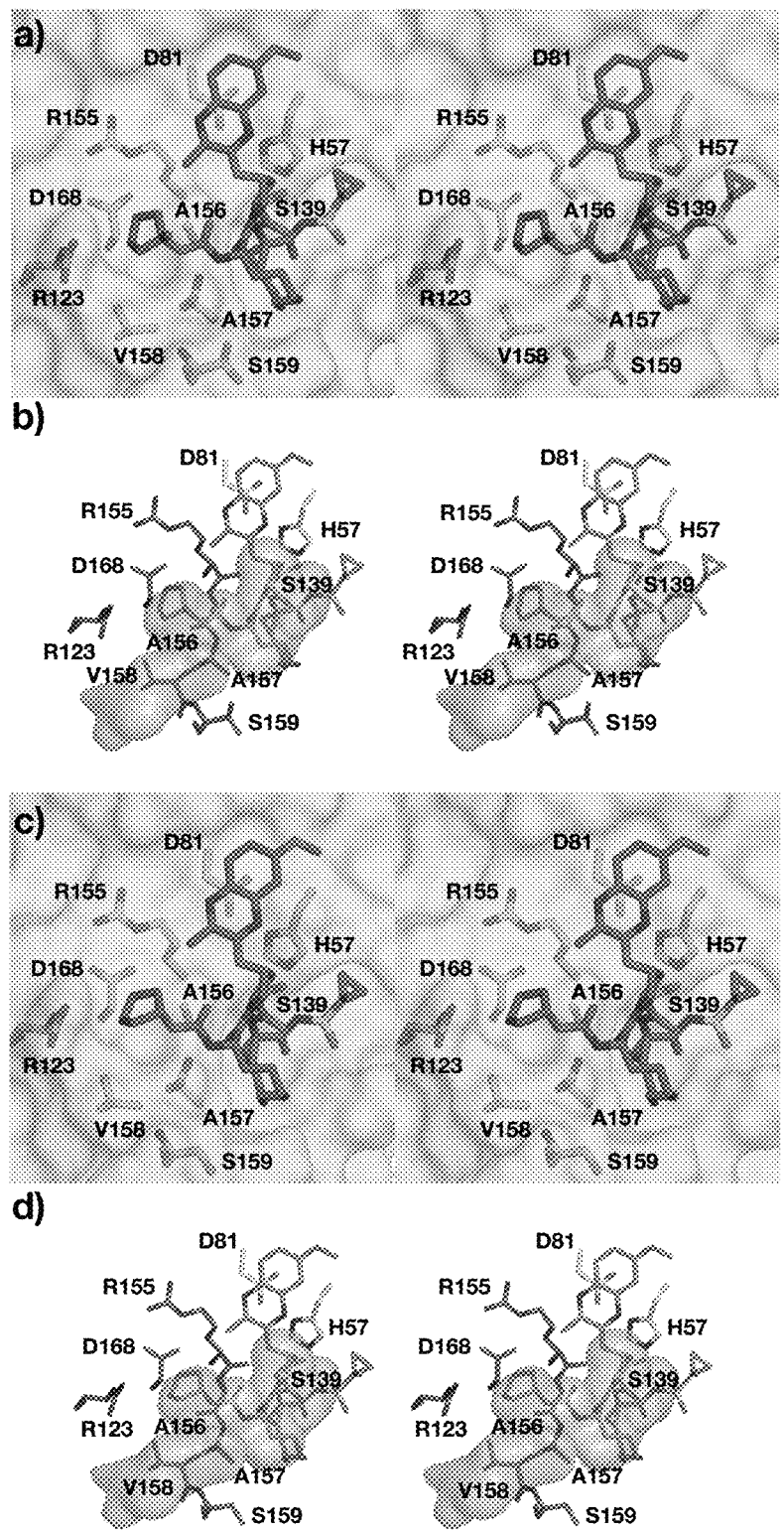

FIG. 13. Stereo view of P4-cap inhibitors filling the S4 pocket of the substrate envelope. (a) P4-3 bound to the wildtype protease active site in surface representation and (b) shown in the substrate envelope (blue). (c, d) same as above for P4-2. Inhibitors, S4 subsite residues, and catalytic triad residues are shown as sticks. In (b) and (d) catalytic triad residues are in yellow and S4 subsite residues are teal.

Figure 14:
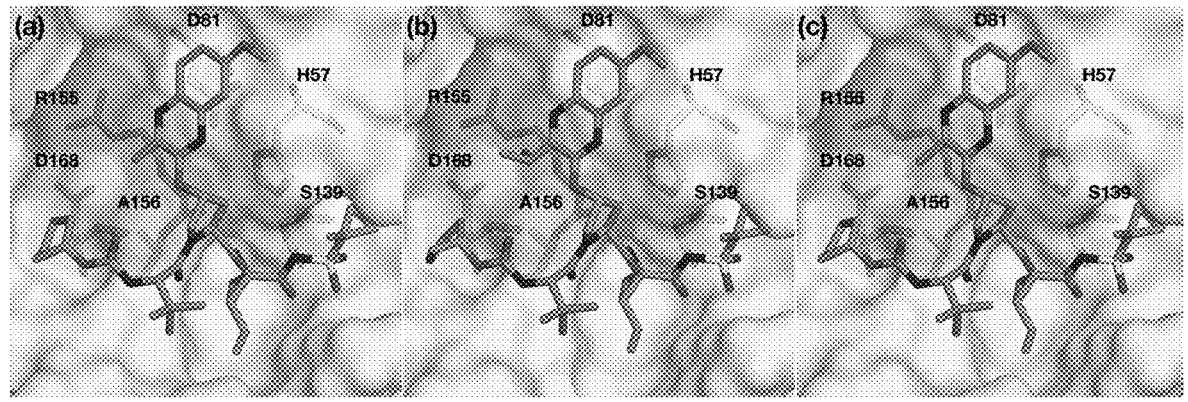

FIG. 14. Co-crystal structures of WT1a HCV NS3/4A protease in complex with linear inhibitors (a) 12b, (b) 12c, and (c) 12d. The protease active site is presented as a light grey surface with bound inhibitors depicted as orange sticks. The catalytic triad is highlighted in yellow, and drug resistance residues Arg155, Ala156, and Asp168 are shown as sticks.

Figure 15:
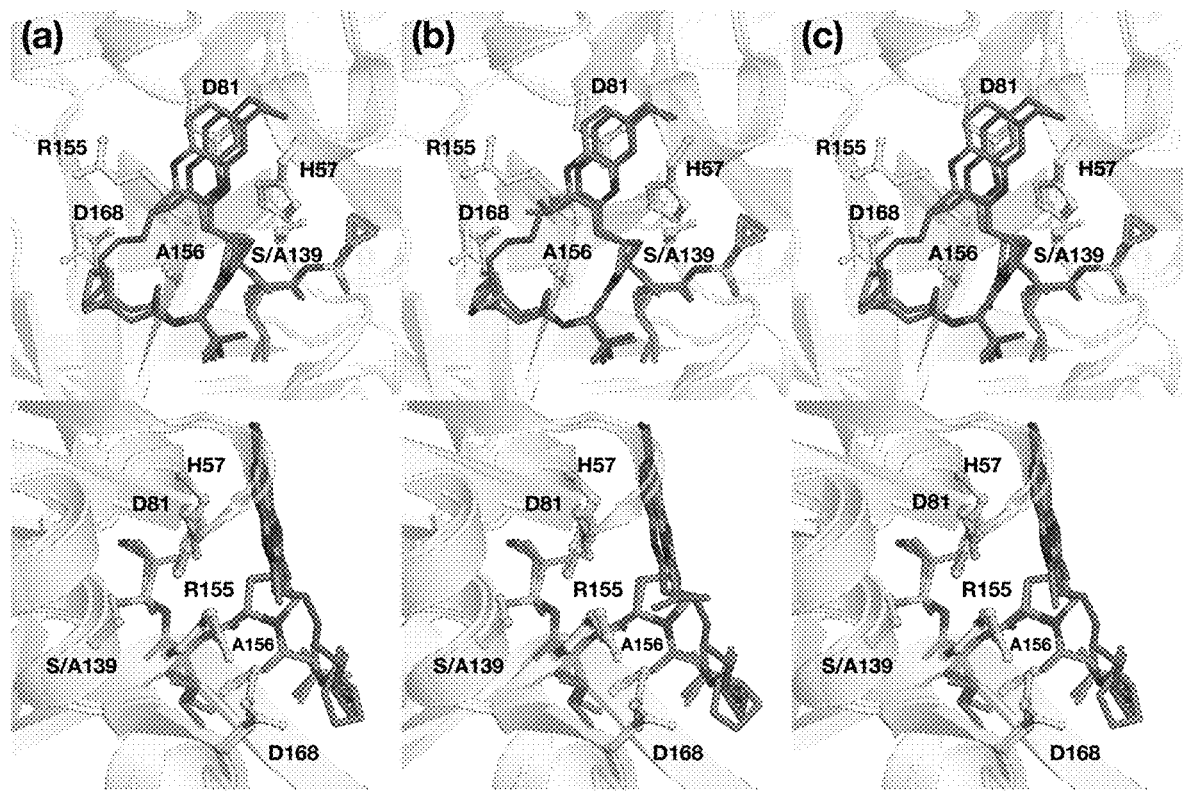

FIG. 15. Superposition of WT-1 and (a) WT-12b, (b) WT-12c, and (c) WT-12d complexes, focusing on the differences at the P2 quinoxaline. The protease is in ribbon representation (light grey), with bound inhibitors 1 (blue) and 12b-d (orange) depicted as sticks. The side chains of catalytic triad and drug resistance residues Arg155, Ala156, and Asp168 are shown as ball and sticks.

Figure 16:
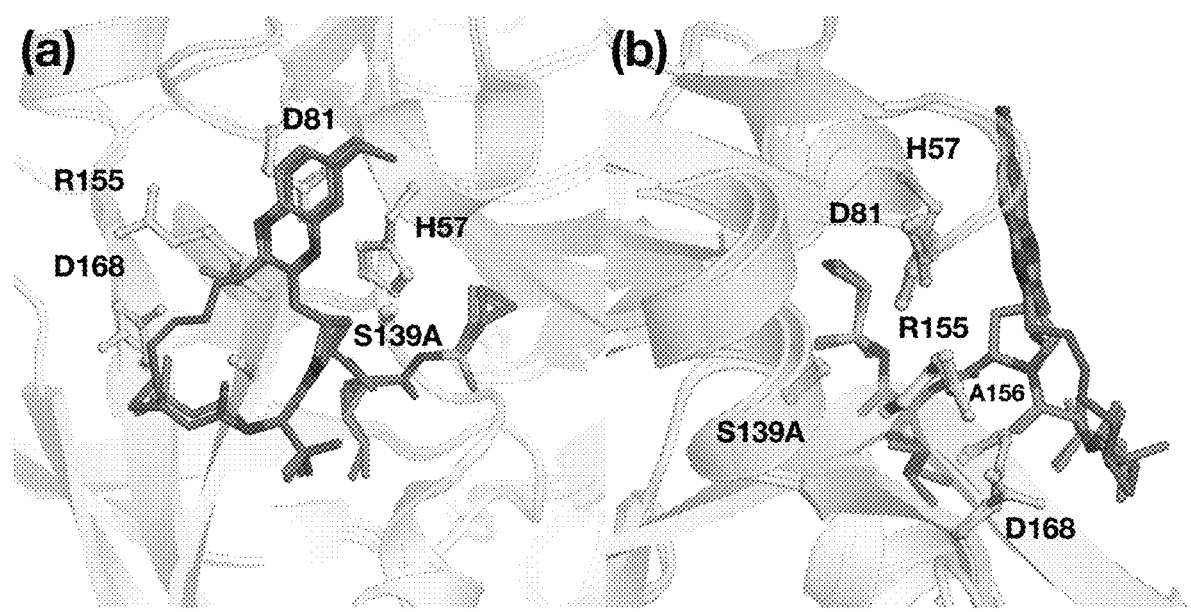

FIG. 16. Superposition of WT-1 and WT-3 complexes, focusing on the differences at the P2 quinoxaline. The protease is in ribbon representation (light grey), with bound inhibitors 1 (blue) and 3 (orange) depicted as sticks. The side chains of catalytic triad and drug resistance residues Arg155, Ala156, and Asp168 are shown as ball and sticks.

Figure 17:
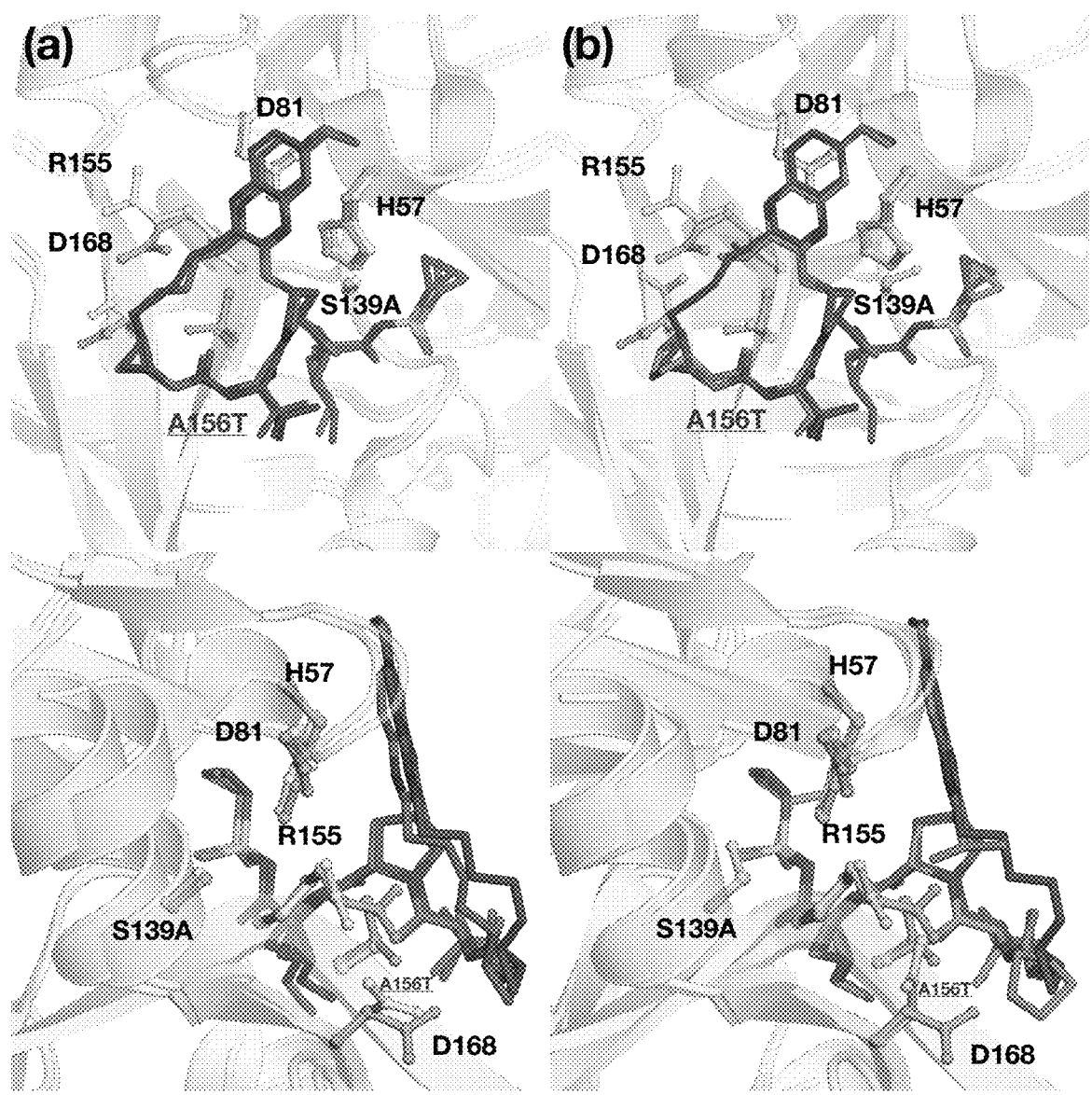

FIG. 17. (a) Superposition of WT-1 and A156T-1 and (b) A156T-1 and WT-12d complexes, focusing on the differences at the P2 quinoxaline. The protease is in ribbon representation (light grey) with bound inhibitor 1 depicted as sticks in blue (WT) and red (A156T), and inhibitor 12d (WT) in orange. The side chains of catalytic triad and drug resistance residues Arg155, Ala156, and Asp168 are shown as ball and sticks.

DEFINITIONS

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Solvates and polymorphs of the compounds of the invention are also contemplated herein. Solvates of the compounds of the present invention include, for example, hydrates.

Definitions of specific functional groups and chemical terms are described in more detail below. When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, the term "alkyl" refers to a straight or branched hydrocarbon chain radical consisting solely of carbon and hydrogen atoms, containing no unsaturation, having from one to ten carbon atoms (e.g., $C_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a $C_{1-6}$ alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R_a$, —C(O)P$R^a$, —O—OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, benzyl, and phenethyl.

As used herein, the term "alkoxy" refers to the group —O-alkyl, including from 1 to 10 carbon atoms ($C_{1-10}$) of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. "Lower alkoxy" refers to alkoxy groups containing one to six carbons. In some embodiments, $C_{1-3}$ alkoxy is an alkoxy group that encompasses both straight and branched chain alkyls of from 1 to 3 carbon atoms. Unless stated otherwise in the specification, an alkoxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "aromatic" or "aryl" refer to a radical with 6 to 14 ring atoms (e.g., $C_{6-14}$ aromatic or $C_{6-14}$ aryl) that has at least one ring having a conjugated pi electron system which is carbocyclic (e.g., phenyl, fluorenyl, and naphthyl). In some embodiments, the aryl is a $C_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "cycloalkyl" and "carbocyclyl" each refers to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_{3-13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. Polycyclic aryl groups include bicycles, tricycles, tetracycles, and the like. In some embodiments, "cycloalkyl" can be a $C_{3-8}$ cycloalkyl radical. In some embodiments, "cycloalkyl" can be a $C_{3-5}$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-13}$ carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein. For example, a cycloalkenyl group can have 3 to 13 ring atoms, such as 5 to 8 ring atoms. In some embodiments, a cycloalkynyl group can have 5 to 13 ring atoms.

As used herein, the term "halogen" refers to fluorine (F), chlorine (Cl), bromine (Br), or iodine (I). As used herein, the term "halide" or "halo", means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

As used herein, the term "heteroalkyl" refers to an alkyl radical, which have one or more skeletal chain atoms selected from an atom other than carbon, e.g., oxygen, nitrogen, sulfur, phosphorus or combinations thereof. A numerical range can be given, e.g., $C_{1-4}$ heteroalkyl, which refers to the chain length in total, which in this example is 4 atoms long. For example, a —CH$_2$OCH$_2$CH$_3$ radical is referred to as a "$C_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—CH$_2$CH$_2$OCH$_3$), ethoxymethanyl (—CH$_2$OCH$_2$CH$_3$), (methoxymethoxy)ethanyl (—CH$_2$CH$_2$OCH$_2$OCH$_3$), (methoxymethoxy) methanyl (—CH$_2$OCH$_2$OCH$_3$) and (methoxyethoxy)methanyl (—CH$_2$OCH$_2$CH$_2$OCH$_3$) and the like; amines such as (—CH$_2$CH$_2$NHCH$_3$, —CH$_2$CH$_2$N(CH$_3$)$_2$, —CH$_2$NHCH$_2$CH$_3$, —CH$_2$N(CH$_2$CH$_3$)(CH$_3$)) and the like.

As used herein, the term "heteroaryl" or, alternatively, "heteroaromatic" refers to a refers to a radical of a 5-18 membered monocyclic or polycyclic (e.g., bicyclic, tricyclic, tetracyclic and the like) aromatic ring system (e.g., having 6, 10 or 14 π electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms. In some embodiments, the heteroaryl has, for example, bivalent radicals derived from univalent heteroaryl radicals whose names end in "-yl" by removal of one hydrogen atom from the atom with the free valence are named by adding "-ene" to the name of the corresponding univalent radical, e.g., a pyridyl group with two points of attachment is a pyridylene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo [h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo [3,2-c]pyridinyl, 5,6,7,8,9,10-hexahydrocycloocta[d] pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5] thieno [2,3-d]pyrimdinyl, 6,7,8,9-tetrahydro-5H-cyclohepta[4,5]thieno [2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno [2,3-c]pridinyl, and thiophenyl (i.e., thienyl). Unless stated otherwise in the specification, a heteroaryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$_a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. The treatment can be any reduction and can be, but is not limited to, the complete ablation of the disease or the symptoms of the disease. As compared with an equivalent untreated control, such reduction or degree of prevention is at least 5%, 10%, 20%, 40%, 50%, 60%, 80%, 90%, 95%, or 100% as measured by any standard technique.

As used herein, the terms "prevent", "preventing", or "prevention" refer to a method for precluding, delaying, averting, or stopping the onset, incidence, severity, or recurrence of a disease or condition. For example, a method is considered to be a prevention if there is a reduction or delay in onset, incidence, severity, or recurrence of a disease or condition or one or more symptoms thereof in a subject susceptible to the disease or condition as compared to a subject not receiving the method. The disclosed method is also considered to be a prevention if there is a reduction or delay in onset, incidence, severity, or recurrence of osteoporosis or one or more symptoms of a disease or condition in a subject susceptible to the disease or condition after receiving the method as compared to the subject's progression prior to receiving treatment. Thus, the reduction or delay in onset, incidence, severity, or recurrence of osteoporosis can be about a 5, 10, 20, 30, 40, 50, 60, 70, 80, 90, 100%, or any amount of reduction in between.

As used herein, a "pharmaceutically acceptable form" of a disclosed compound includes, but is not limited to, pharmaceutically acceptable salts, esters, hydrates, solvates, isomers, prodrugs, and isotopically labeled derivatives thereof. In one embodiment, a "pharmaceutically acceptable form" includes, but is not limited to, pharmaceutically acceptable salts, esters, prodrugs and isotopically labeled derivatives thereof. In some embodiments, a "pharmaceutically acceptable form" includes, but is not limited to, pharmaceutically acceptable isomers and stereoisomers, prodrugs and isotopically labeled derivatives thereof.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchioric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" (or "pro-drug") refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the terms "isolated" or "purified" refer to a material that is substantially or essentially free from components that normally accompany it in its native state. Purity and homogeneity are typically determined using analytical chemistry techniques such as polyacrylamide gel electrophoresis or high performance liquid chromatography.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein, the term "low dosage" refers to at least 5% less (e.g., at least 10%, 20%, 50%, 80%, 90%, or even 95%) than the lowest standard recommended dosage of a particular compound formulated for a given route of administration for treatment of any human disease or condition. For example, a low dosage of an agent that is formulated for administration by inhalation will differ from a low dosage of the same agent formulated for oral administration.

As used herein, the term "high dosage" is meant at least 5% (e.g., at least 10%, 20%, 50%, 100%, 200%, or even 300%) more than the highest standard recommended dosage of a particular compound for treatment of any human disease or condition.

As used herein, the term "prodrug" (or "pro-drug") refers to a pharmacological derivative of a parent drug molecule that requires biotransformation, either spontaneous or enzymatic, within the organism to release the active drug. Such prodrugs are pharmaceutically active in vivo, when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form.

Prodrug forms often offer advantages of solubility, tissue compatibility, or delayed release in the mammalian organism. (See, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992). Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Of course, other prodrug derivatives may be combined with other features disclosed herein to enhance bioavailability. As such, those of skill in the art will appreciate that certain of the presently disclosed compounds having free amino, amido, hydroxy or carboxylic groups can be converted into prodrugs. Prodrugs include compounds having an amino acid residue, or a polypeptide chain of two or more (e.g., two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvaline, beta-alanine, gamma-aminobutyric acid, citrulline homocysteine, homoserine, ornithine and methionine sulfone. Prodrugs also include compounds having a carbonate, carbamate, amide or alkyl ester moiety covalently bonded to any of the above substituents disclosed herein.

DETAILED DESCRIPTION OF THE INVENTION

The invention is based on an unexpected discovery of a novel class of orally available, selective and potent HCV therapeutics that are less susceptible to drug resistance than existing therapeutics. The invention also provides pharmaceutical compositions of these compounds and methods of preparation and use thereof. The macrocyclic HCV NS3/4A protease inhibitors disclosed herein exhibited exceptional potency profiles with $EC_{50}$ values less than 5 nM against major drug resistant HCV variants.

Without wishing to be bound by the theory, the HCV NS3/4A PIs disclosed herein are less susceptible to drug resistance at least in part due to their interaction with evolutionarily constrained regions of the protease while avoiding interactions with residues not essential for substrate recognition.

Specifically, these macrocyclic inhibitors incorporate flexible quinoxalines at the P2 position. Investigation of structure-activity relationships showed that the P2 quinoxalines with small hydrophobic substituents at the 3-position were better for maintaining potency against drug resistant variants, likely due to reduced interactions with residues in the S2 subsite. In contrast, inhibitors with larger groups at this position were highly susceptible to mutations at Arg155, Ala156 and Asp168.

Drug resistance is a major problem across all DAA classes targeting HCV. As new therapies are developed the potential for drug resistance must be minimized at the outset of inhibitor design. The substrate envelope model provides a rational approach to design robust NS3/4A PIs with improved resistance profiles.

The present inventors previously determined the molecular mechanisms of drug resistance due to single site mutations by solving high-resolution crystal structures of PIs bound to WT and mutant proteases. These crystal structures revealed that the large heterocyclic P2 moieties of PIs bind outside the substrate-binding region, defined as the substrate envelope, and make extensive interactions with residues Arg155, Ala156 and Asp168. The inhibitor P2 moiety induces an extended S2 subsite by forcing the Arg155 side chain to rotate nearly 180° relative to its conformation in substrate complexes. This altered Arg155 conformation is stabilized by electrostatic interactions with Asp168, providing additional hydrophobic surface that is critical for efficient inhibitor binding. Disruption of electrostatic interactions between Arg155 and Asp168 due to mutations underlies drug resistance against NS3/4A PIs. Moreover, it has been shown that structural differences at the P2 moiety largely determine the resistance profile of these inhibitors. (Romano, et al. *Proc. Natl. Acad. Sci. U.S.A.* 2010, 107, 20986-20991; Romano, et al. *PLOS Pathog.* 2012, 8, e1002832; Soumana, et al. *ACS Chem. Biol.* 2014, 9, 2485-2490; Soumana, et al. *J. Am. Chem. Soc.* 2016, 138, 11850-11859; O'Meara, et al. *J. Biol. Chem.* 2013, 288, 5673-5681; Ali, et al. *ACS Chem. Biol.* 2013, 8, 1469-1478.)

Figure 1:
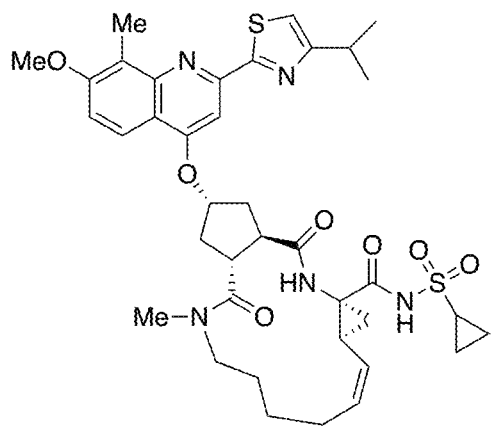
FIG. 1. Chemical structures of HCV NS3/4A protease inhibitors. Simeprevir, paritaprevir and grazoprevir are approved by the FDA; MK-6325, voxilaprevir and glecaprevir are in clinical development. The canonical nomenclature for drug moiety positioning is indicated using MK-5172.
Figure 1:
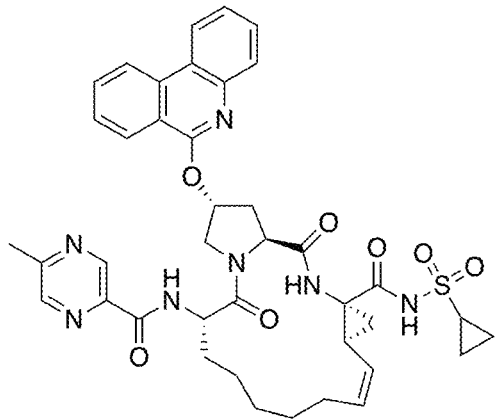
Figure 1:
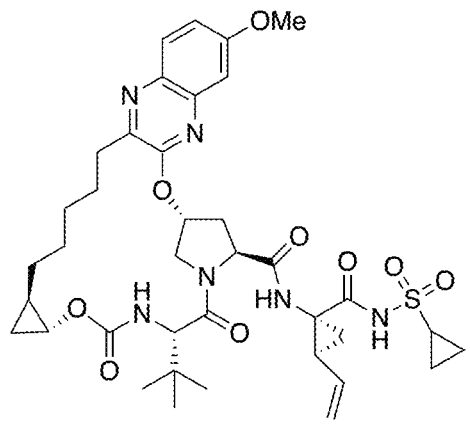
Figure 1:
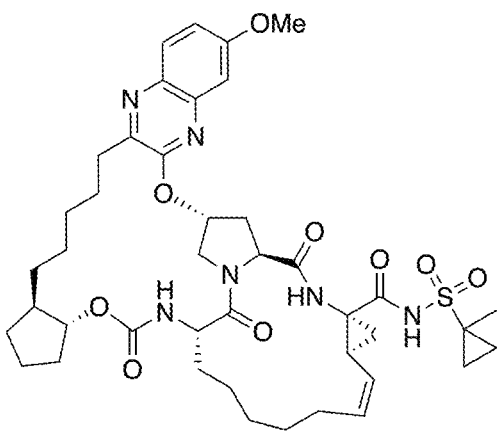
Figure 1:
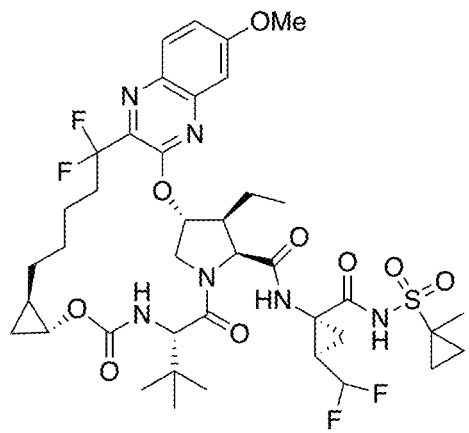
Figure 1:
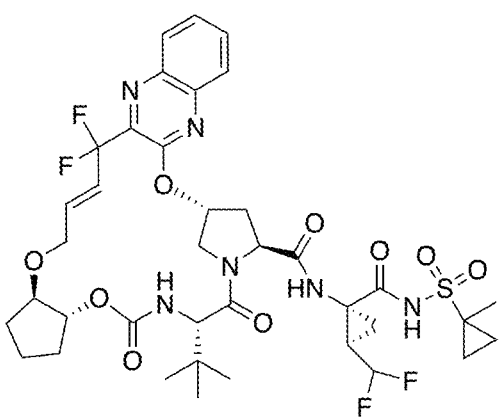
Figure 2:
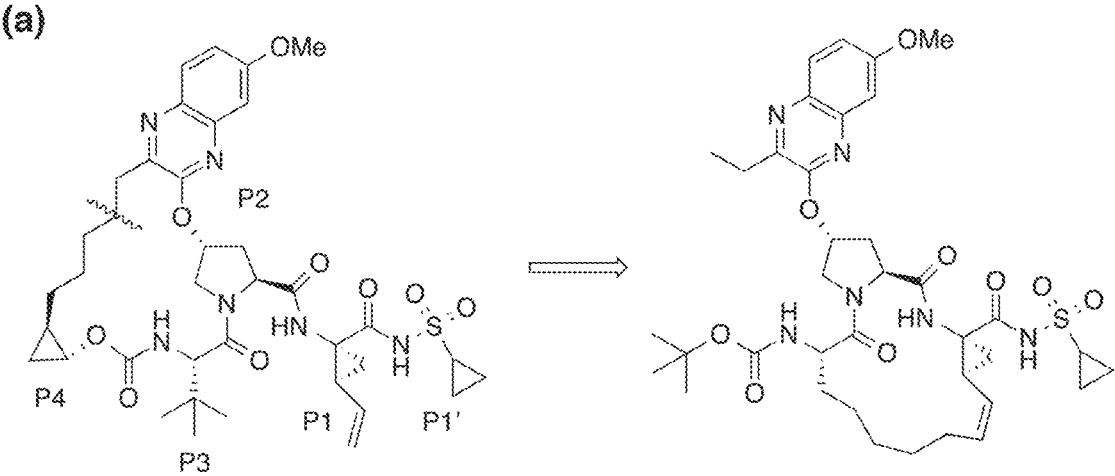
FIG. 2. Chemical structures and binding modes of MK-5172 (1) and 5172mcP1P3 (2). (a) Compound 2 was designed by replacing the P2-P4 macrocycle in 1 with a P1-P3 macrocycle. (b) The binding conformation of 1 (PDB ID: 3SUD) and 2 (PDB ID: 5EPN) in the active site of wild-type NS3/4A protease. Compound 2 maintains the unique binding mode of 1 whereby the P2 quinoxaline makes strong interactions with the catalytic residues avoiding contacts with known drug resistance residues. The catalytic triad is highlighted in yellow and drug resistance residues Arg155, Ala156, and Asp168 are shown in blue, red and green, respectively.
Figure 2:
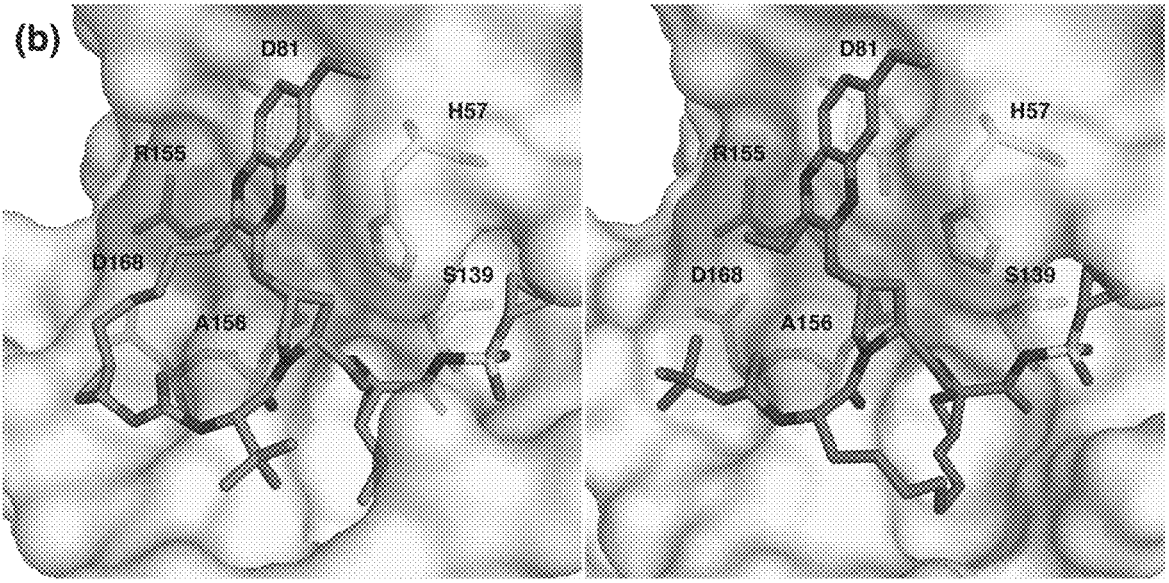

MK-5172 (1), a potent HCV NS3/4A PI, has a unique binding mode where the P2 quinoxaline moiety interacts with residues of the catalytic triad, avoiding direct interactions with Arg155 and Asp168 (FIG. 2). As a result, 1 has an excellent potency profile across different genotypes and relatively low susceptibility to drug resistance due to mutations at Arg155 and Asp168. (Romano, et al. PLOSPathog. 2012, 8, e1002832; Summa, et al. *Antimicrob. Agents Chemother.* 2012, 56, 4161-4167.)

However, 1 is highly susceptible to mutations at Ala156, mainly due to steric clashes of larger side chains with the P2-P4 macrocycle. It has been shown that the P1-P3 macrocyclic analogue 5172-mcP1P3 (2) avoids this steric clash while still maintaining the unique binding mode of 1 (FIG. 2). Compound 2, though slightly less potent than 1 against WT HCV, has an excellent potency profile with $EC_{50}$ values in the single digit nanomolar range against drug resistant variants including A156T. Similar to 1, the P2 quinoxaline moiety in 2 stacks against the catalytic residues His57 and Asp81 and largely avoids direct interactions with residues around the S2 subsite. Unlike 1, the flexible P2 quinoxaline moiety in 2 better accommodates mutations at Ala156, resulting in an overall improved resistance profile. (Ali, et al. *ACS Chem. Biol.* 2013, 8, 1469-1478; Soumana, et al. *ACS Chem. Biol.* 2016, 11, 900-909.)

SAR studies led the present inventors to believe that reducing PI interactions with residues in the S2 subsite is important to achieve inhibitors with exceptional potency and resistance profiles. Specifically, the P1-P3 macrocyclic inhibitors incorporating flexible P2 quinoxaline moieties bearing small hydrophobic groups at the 3-position maintain excellent potency in both enzymatic and antiviral assays against drug resistant variants.

Without wishing to be bound by the theory, these inhibitors leverage interactions with the essential catalytic triad residues and avoid direct contacts with residues that can mutate to confer resistance. Moreover, conformational flexibility at the P2 moiety is important to efficiently accommodate structural changes due to mutations in the S2 pocket in order to avoid resistance. These insights provide strategies for iterative rounds of inhibitor design with the paradigm that designing inhibitors with flexible P2 quinoxalines, leveraging evolutionarily constrained areas in the protease active site and expanding into the substrate envelope may provide inhibitors that are robust against drug resistant variants.

Modifications were also made at the P4-P5 positions to utilize unexploited space in the SE. Hydrophobic moieties at the P4 position were used to mimic substrate interactions, as HCV substrates across genotypes have hydrophobic residues at this position.

In one aspect, the invention generally relates to a compound having the structural formula (I),

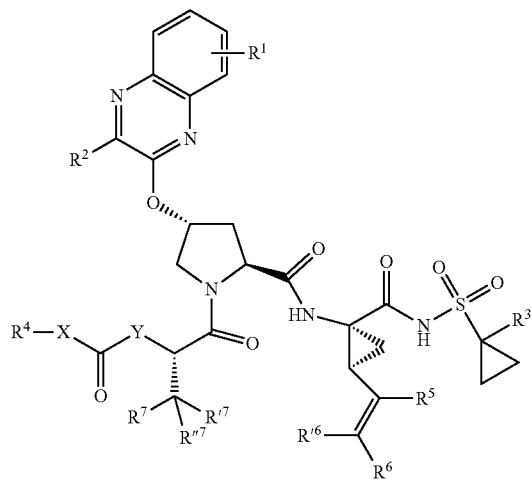

(I)

wherein
each of X and Y is independently selected from O, NR and CRR', provided that at least one of X and Y is NR;
$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group;
$R^2$ is selected from H, halogen, a $C_1$-$C_6$ alkyl, aryl, —CN, CF$_3$, CHF$_2$, CH$_2$F;
$R^3$ is selected from H, a $C_1$-$C_6$ alkyl, CH$_2$F, CHF$_2$;
$R^4$ is selected from an alkyl, hetero-alkyl, aryl, hetero-aryl group, —NH—C(=O)—R;
$R^5$ is H, halogen, or an alkyl group;
$R^6$, $R'^6$ each is independently H, halogen, or an alkyl group;
$R^7$, $R'^7$, each is independently H, halogen, or an alkyl group;
$R^8$ is independently selected from H, halogen, or an alkyl group;
each R and R' is independently a H or an alkyl group; and
provided that $R'^6$ and one of $R'^7$ and $R''^7$ optionally join together to form a 15-, 16- or 17-membered ring,
or a pharmaceutically acceptable form thereof.

In certain embodiments, each of $R^7$, $R'^7$, $R''^7$ is independently a $C_1$-$C_6$ alkyl group (e.g., methyl, ethyl, propyl, i-propyl). In certain embodiments, each of $R^7$, $R'^7$, $R''^7$ is a methyl group.

In certain embodiments, at least one of $R^6$ and $R'^6$ is H. In certain embodiments, both of $R^6$ and $R'^6$ is H.

In certain embodiments, X is O and Y is N, the compound has the structural formula:

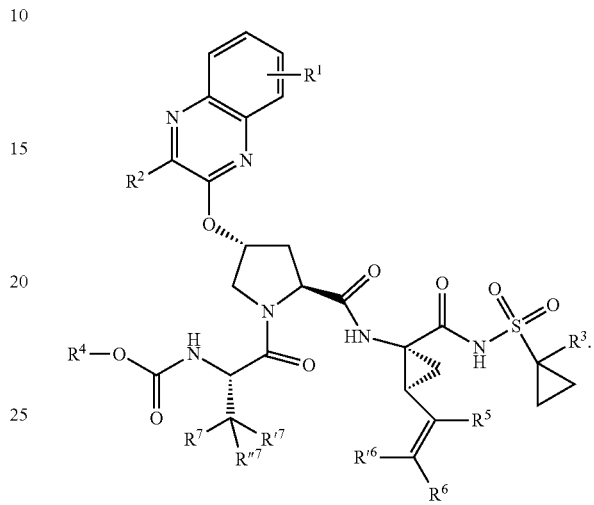

In certain embodiments, $R^1$ is at the 7-position and the compound has the structural formula:

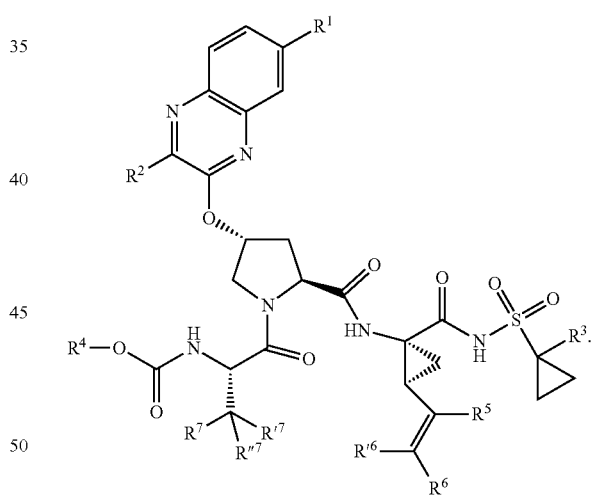

In certain embodiments, $R^1$ is H. In certain embodiments, $R^1$ is a $C_1$-$C_6$ alkoxy group. In certain embodiments, $R^1$ is a $C_1$-$C_2$ alkoxy (e.g., methoxy, ethoxy).

In certain embodiments, $R^2$ is a $C_1$-$C_6$ alkyl group (e.g., methyl, ethyl, propyl, i-propyl). In certain embodiments, $R^2$ is a halogen (e.g., F, In certain embodiments, $R^2$ is an aryl group. In certain embodiments, $R^2$ is 2-thiophene.

In certain embodiments, $R^3$ is H. In certain embodiments, $R^3$ is a $C_1$-$C_6$ alkyl group (e.g., methyl, ethyl, propyl, i-propyl). In certain embodiments, $R^3$ is a $C_1$-$C_2$ alkyl group.

In certain embodiments, $R^4$ is a $C_1$-$C_6$ alkyl group (e.g., methyl, ethyl, propyl, i-propyl). In certain embodiments, $R^4$ is a branched $C_3$-$C_6$ alkyl group. In certain embodiments, $R^4$ is a $C_3$-$C_6$ cycloalkyl group.

In certain embodiments, the compound is selected from:
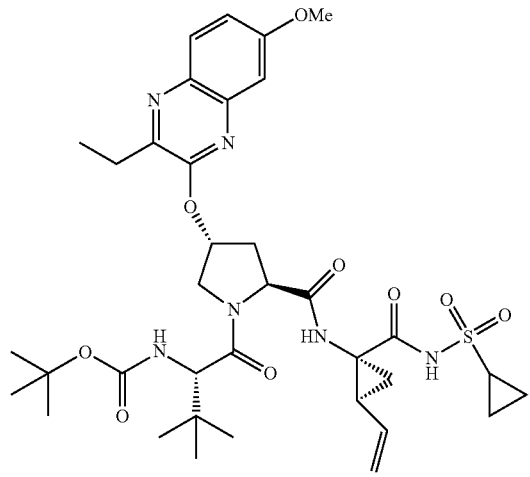
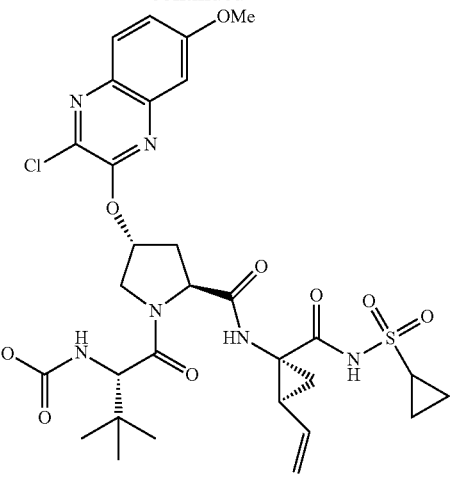
-continued
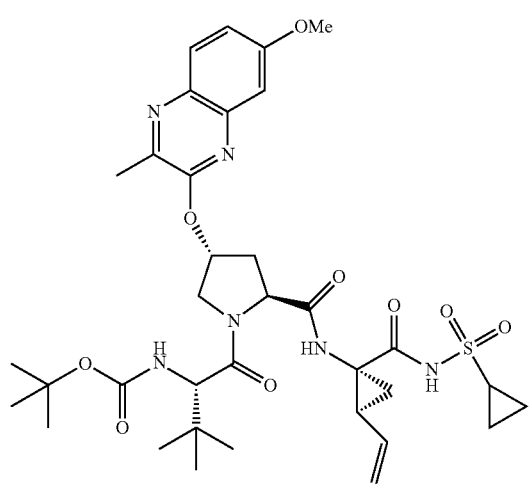
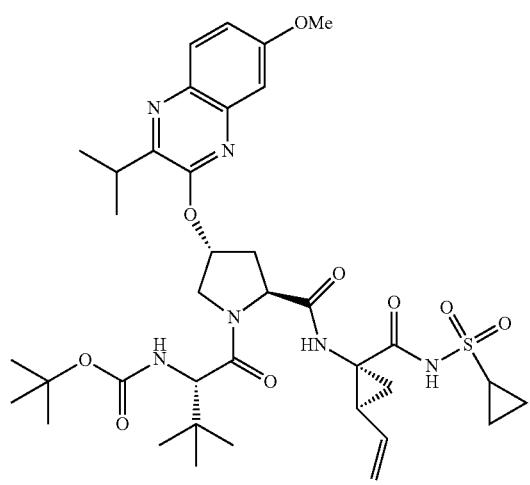
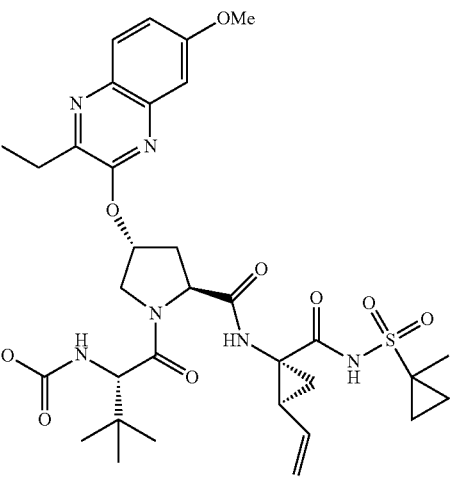

33
-continued
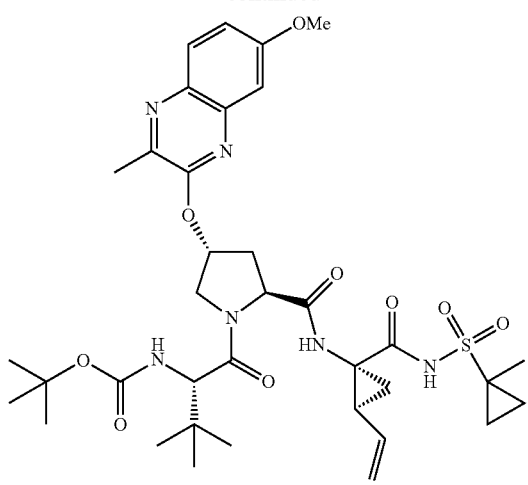
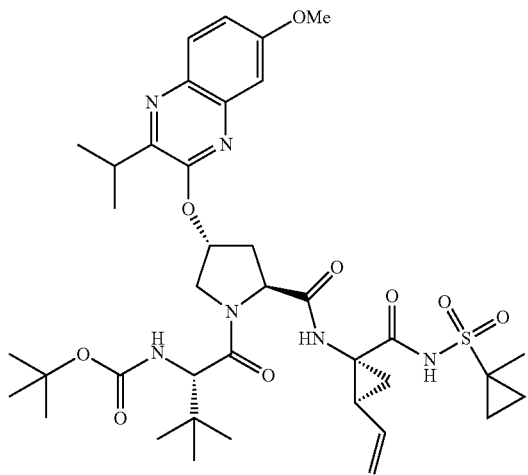
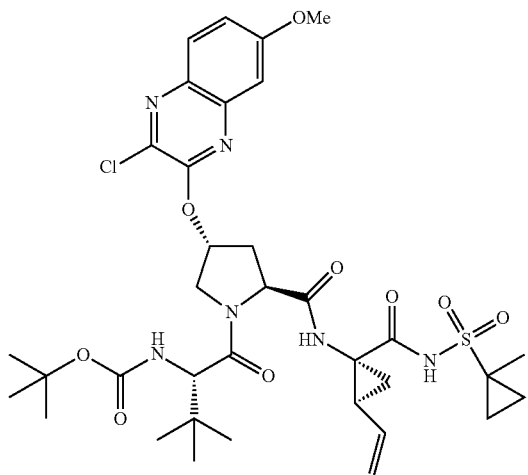
34
-continued
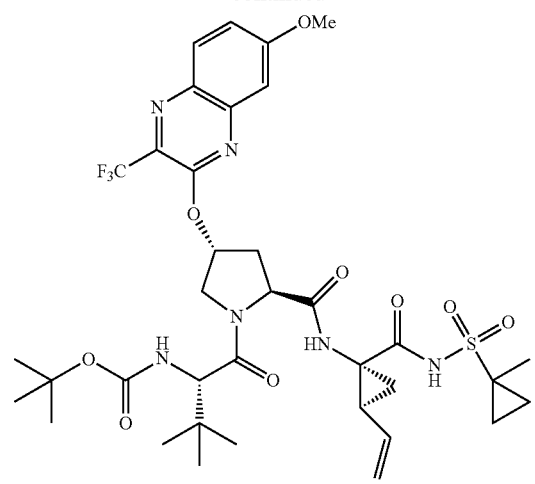
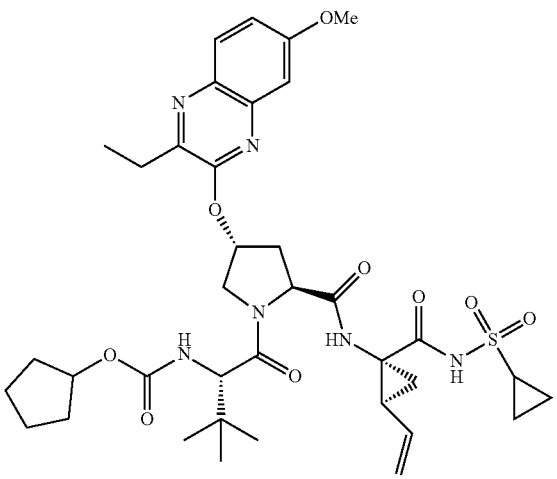
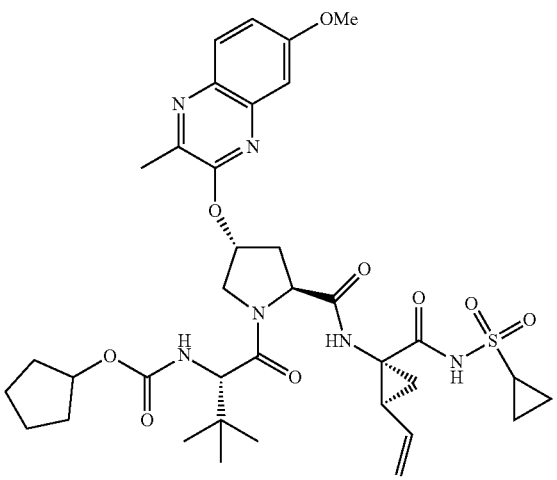

35
-continued
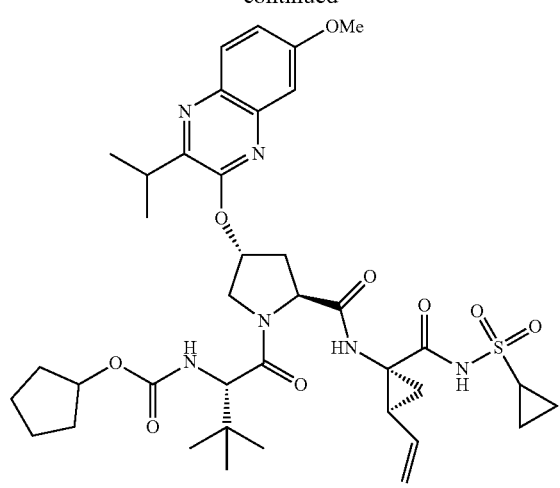
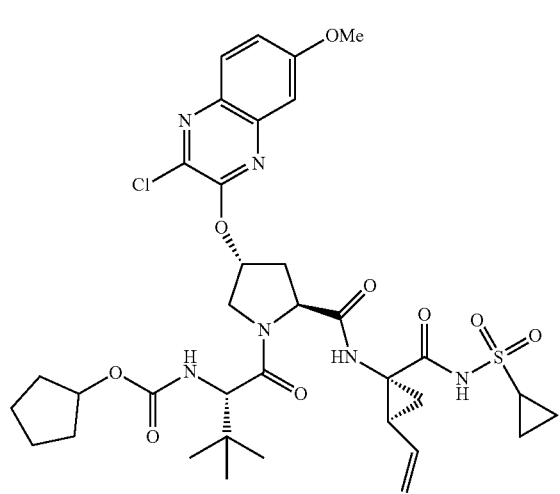
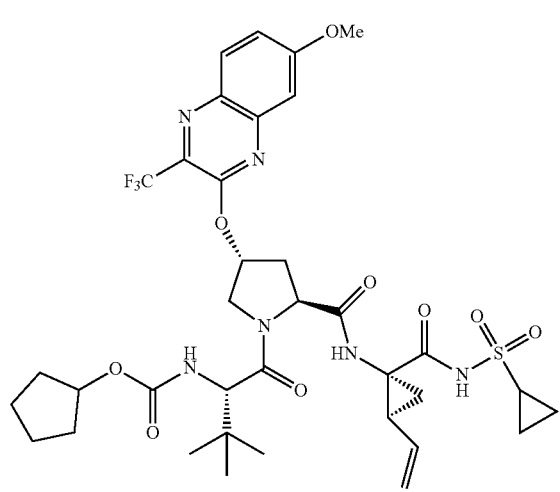
36
-continued
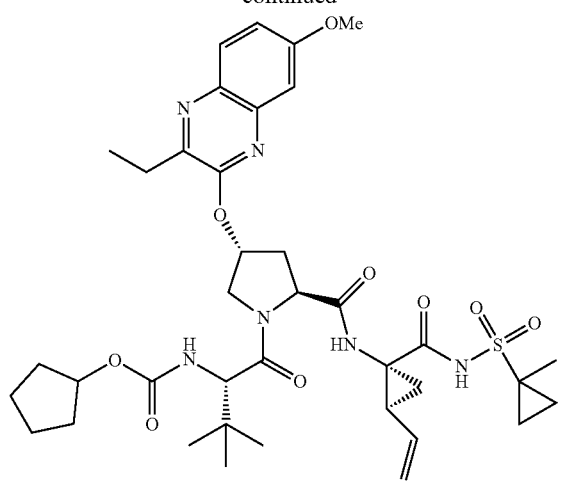
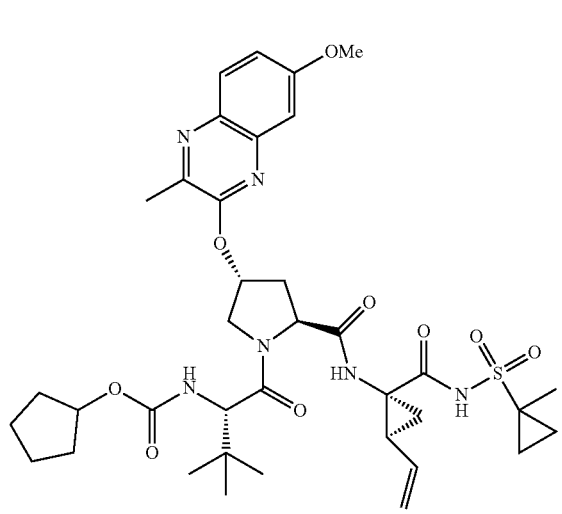
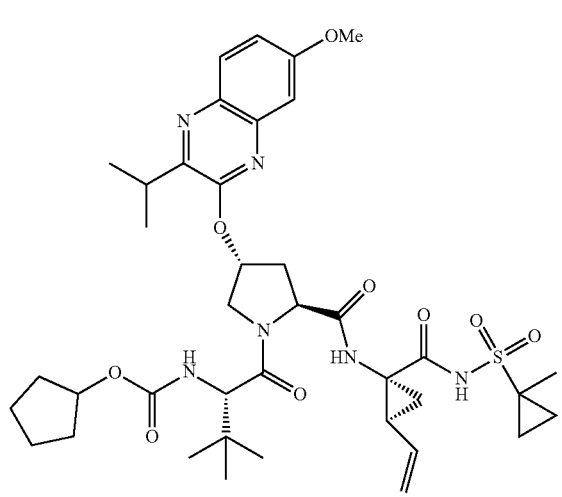

-continued

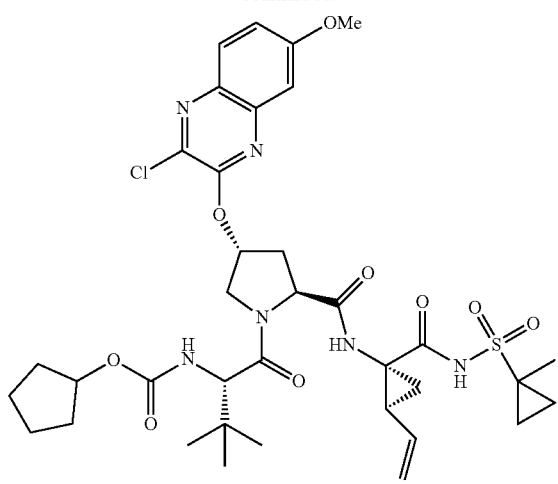

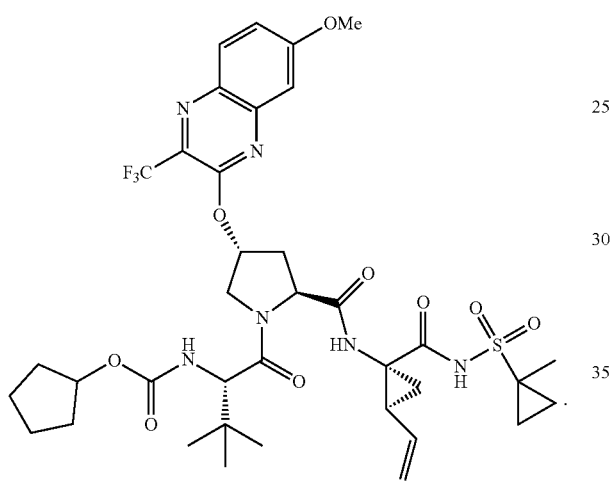

In another aspect, the invention generally relates to a compound having the structural formula (II), (II)

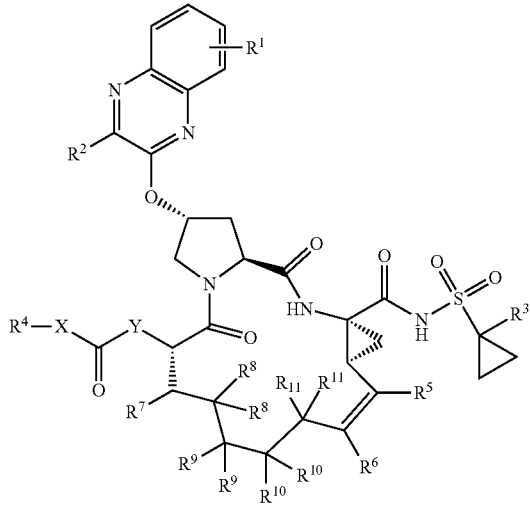

wherein each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group, —NH—C(=O)—R;

$R^5$ is H, halogen, or an alkyl group;

$R^6$ is H, halogen, or an alkyl group;

$R^7$ is H, halogen, or an alkyl group;

each $R^8$ is independently selected from H, halogen, or an alkyl group;

each $R^9$ is independently selected from H, halogen, or an alkyl group;

each $R^{10}$ is independently selected from H, halogen, or an alkyl group;

each $R^{11}$ is independently selected from H, halogen, or an alkyl group; and each R and R' is independently a H or an alkyl group, or a pharmaceutically acceptable form thereof.

In certain embodiments, the compound has the structural formula (IIa), (IIa)

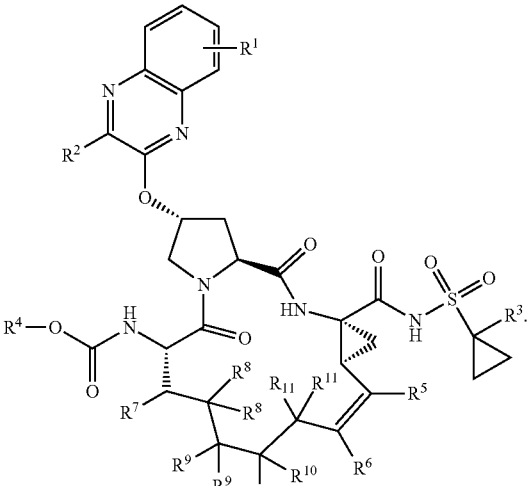

In certain embodiments, each of $R^5$, $R^6$, $R^7$, $R^8$, $R^9$, $R^{10}$, $R^{11}$ is H and the compound has the structural formula (IIb), (IIb)

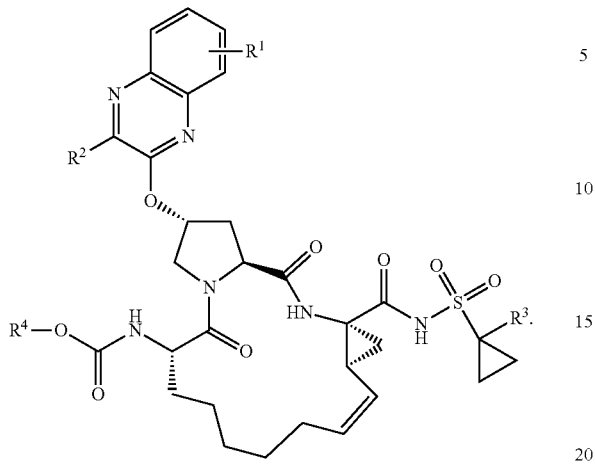

In certain embodiments of the compound of formula (II), $R^1$ is at the 7-position, having the structural formula (III), (III)

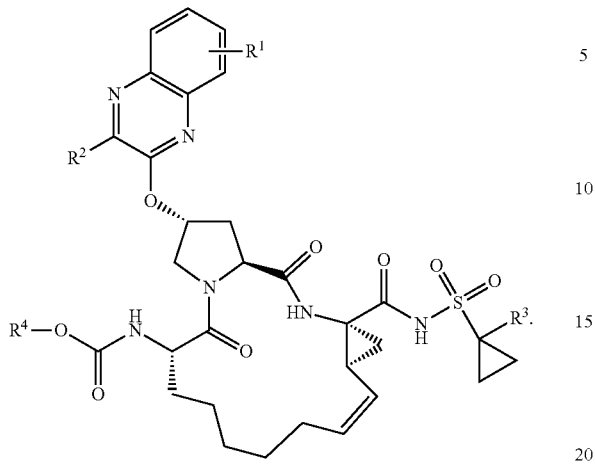

In certain embodiments, $R^3$ is H.

In certain embodiments, $R^3$ is a $C_1$-$C_6$ alkyl group. In certain embodiments, $R^3$ is a $C_1$-$C_2$ alkyl group (e.g., methyl, ethyl).

In certain embodiments, $R^1$ is H.

In certain embodiments, $R^1$ is a $C_1$-$C_6$ alkoxy group. In certain embodiments, $R^1$ is a $C_1$-$C_2$ alkoxy (e.g., methoxy, ethoxy).

In certain embodiments, $R^2$ is a $C_1$-$C_6$ alkyl group (e.g., methyl, ethyl, propyl, i-propyl).

In certain embodiments, $R^2$ is a halogen (e.g., F, Cl).

In certain embodiments, $R^2$ is an aryl group (e.g., thiophene).

In certain embodiments, $R^4$ is a $C_1$-$C_6$ alkyl group. In certain embodiments, $R^4$ is a $C_1$-$C_4$ alkyl group (e.g., methyl, ethyl, propyl, i-propyl). In certain embodiments, $R^4$ is a branched $C_3$ or $C_4$ alkyl group. In certain embodiments, $R^4$ is a linear $C_3$ or $C_4$ alkyl group. In certain embodiments, $R^4$ is a $C_3$, $C_4$, $C_5$ or $C_6$ cycloalkyl group having a 3-, 4-, 5-, or 6-membered ring.

Exemplary compounds include:

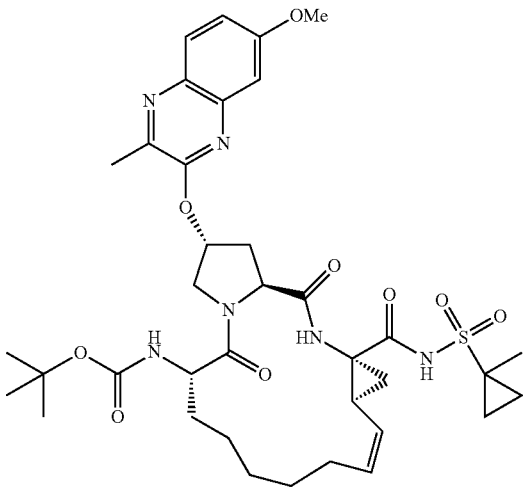

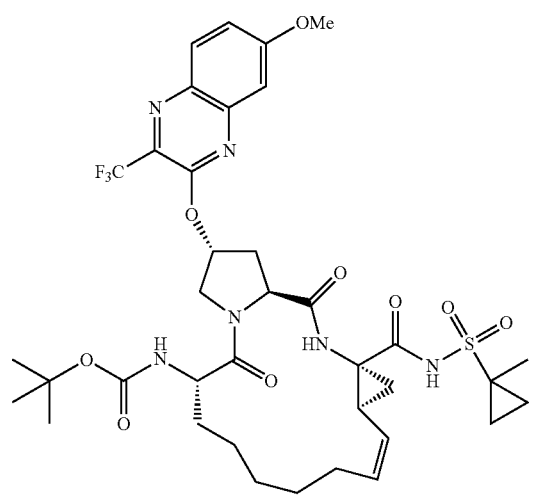

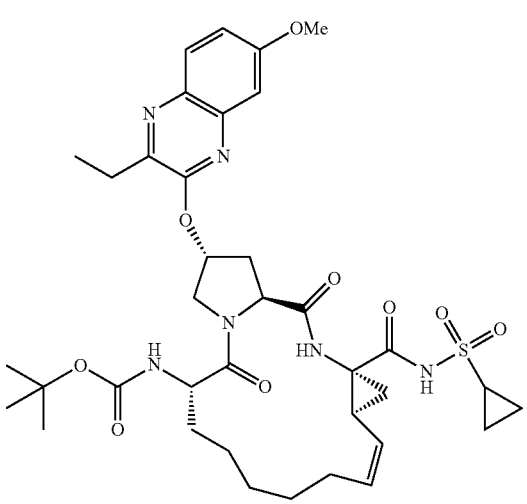

-continued
41
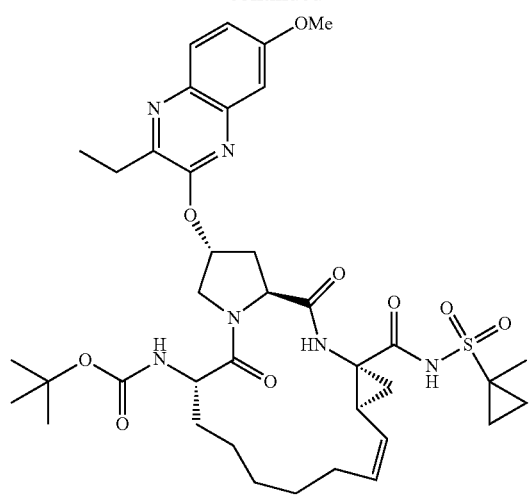
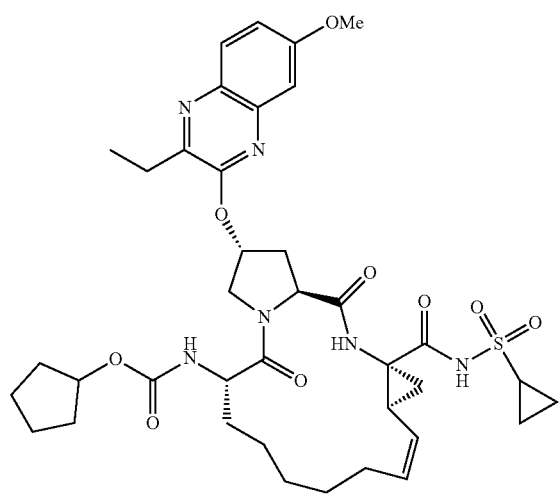
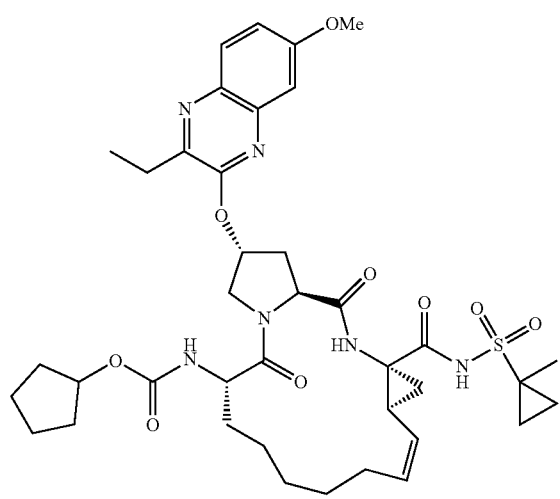
-continued
42
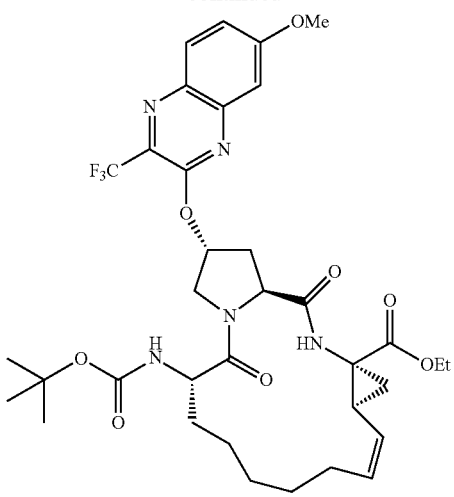
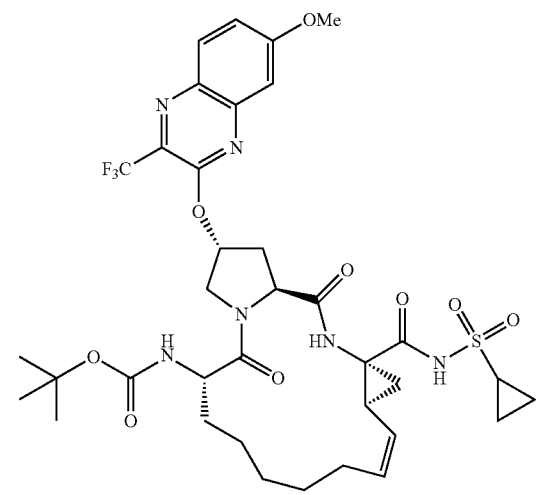
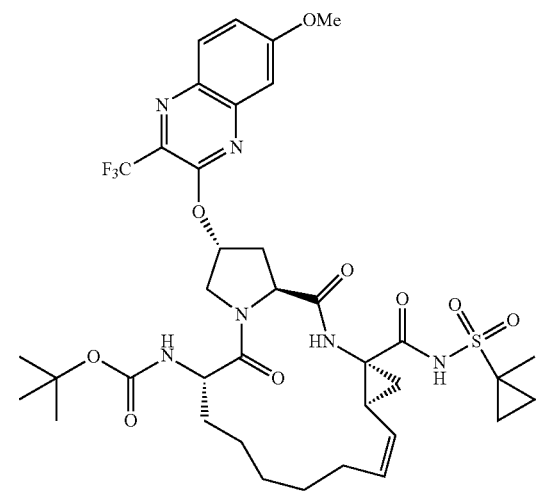

43
-continued
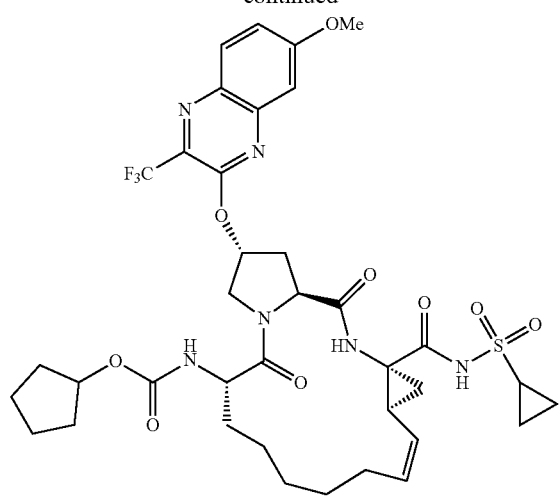
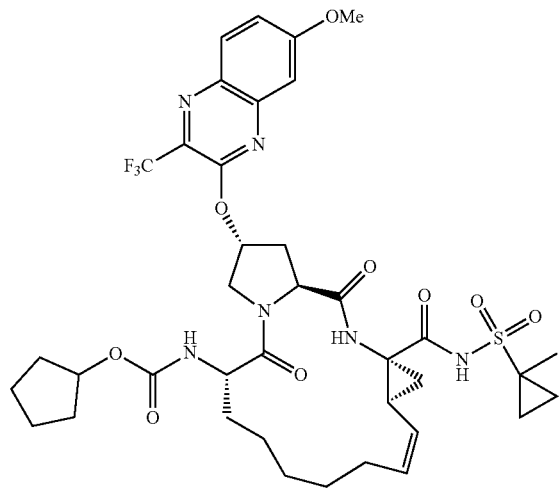
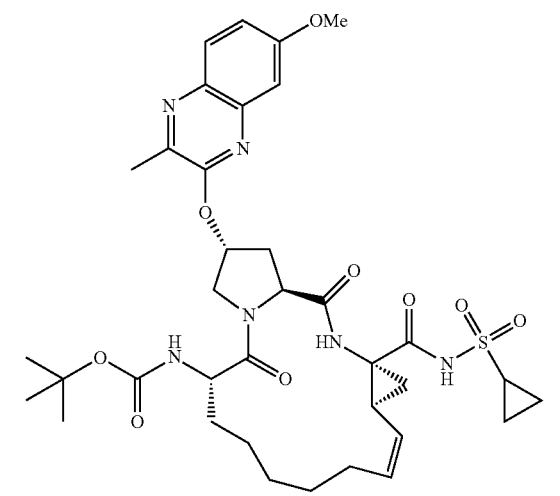
44
-continued
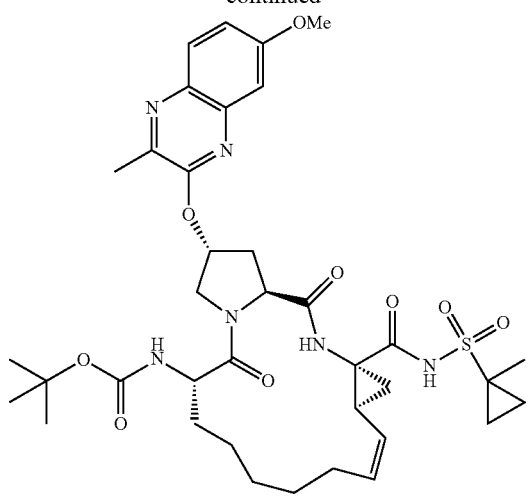
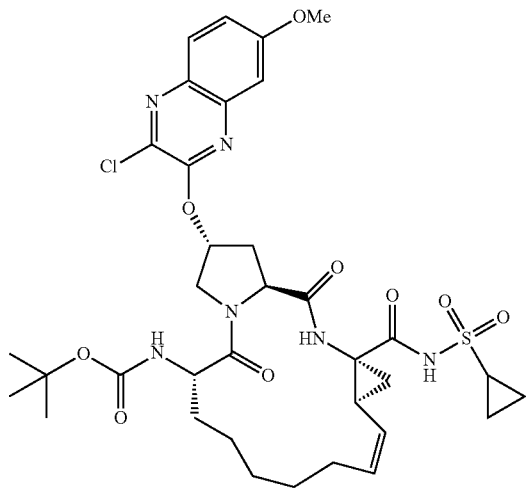
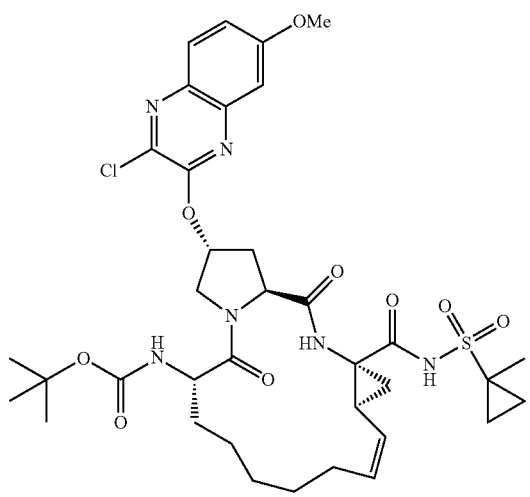

45
-continued
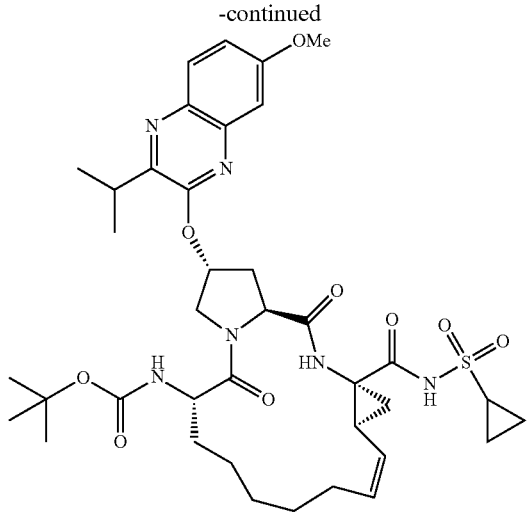
46
-continued
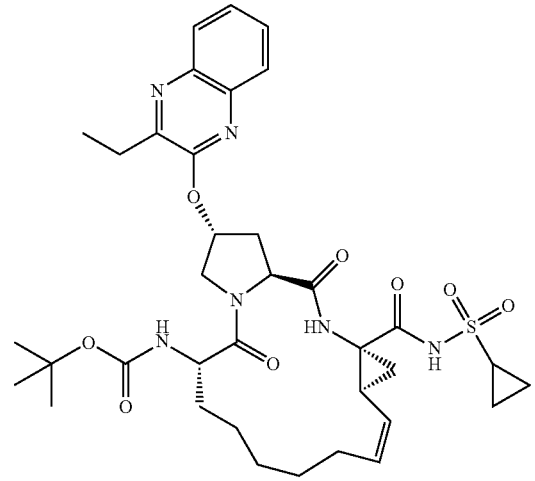
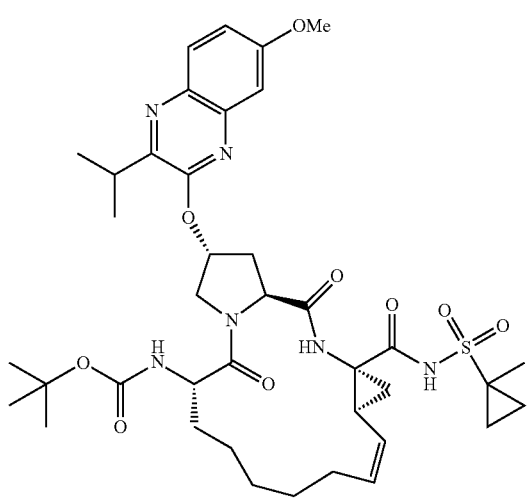
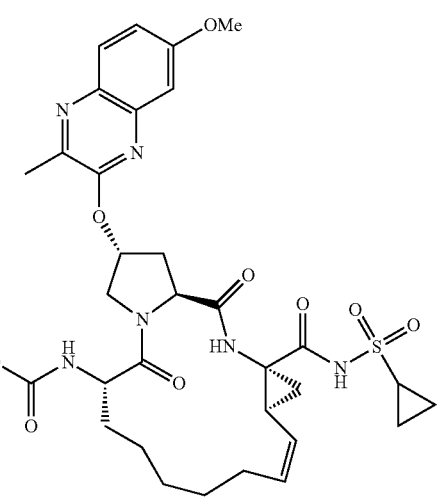
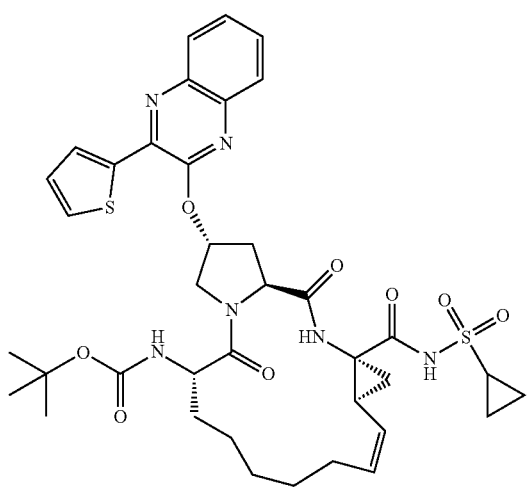
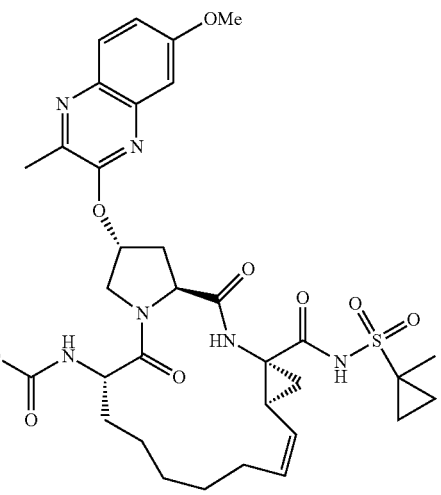

47
-continued
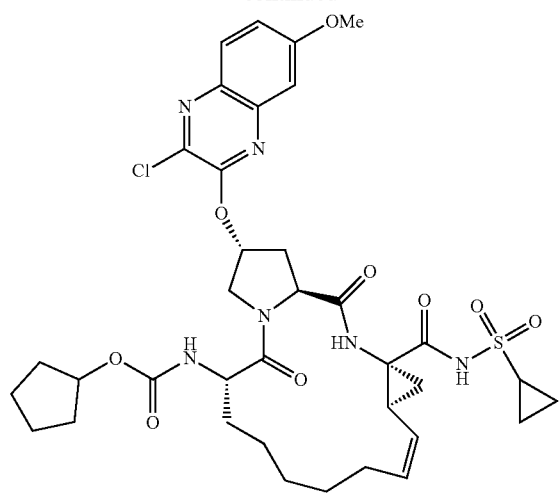
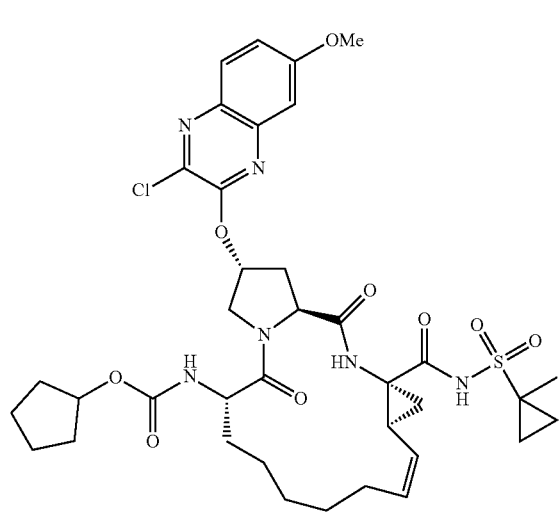
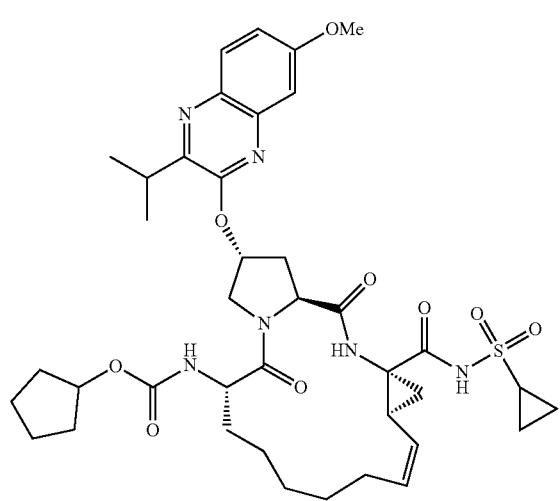
48
-continued
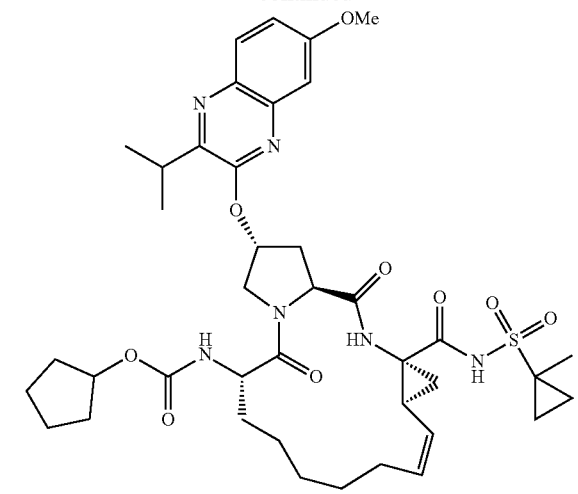
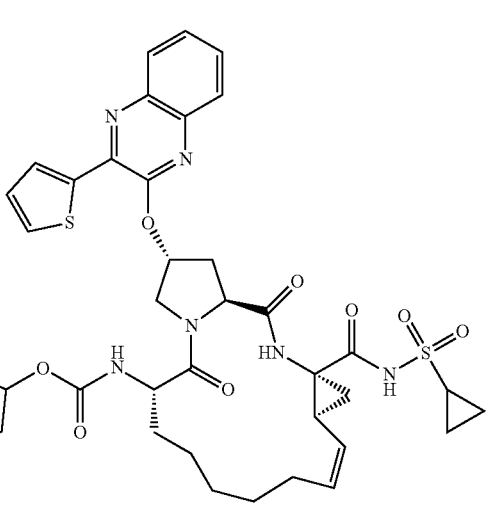
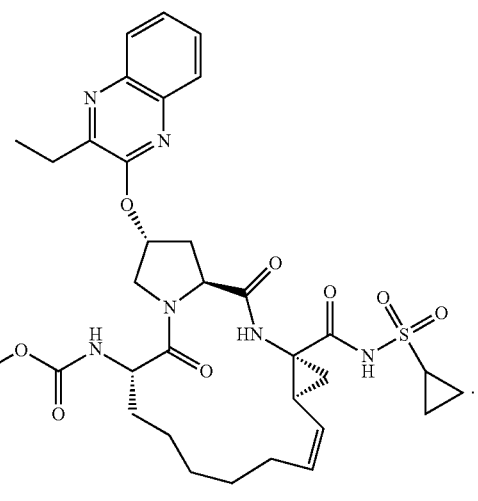

In yet another aspect, the invention generally relates to a compound having the structural formula (IV):

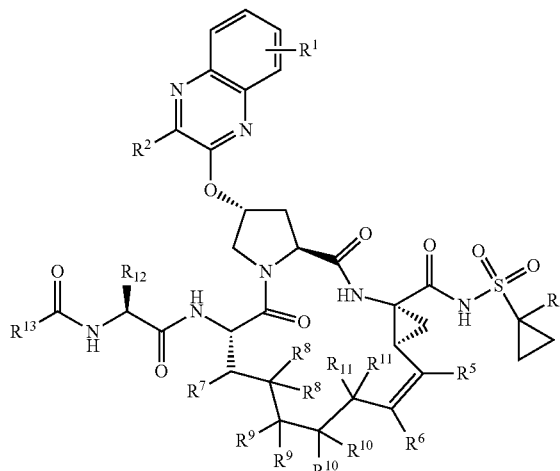

(IV)

wherein
each of X and Y is independently selected from O, NR and CRR', provided that at least one of X and Y is NR;
$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group;
$R^2$ is selected from H, halogen, a $C_1$-$C_6$ alkyl, aryl, —CN, CF$_3$, CHF$_2$, CH$_2$F; $R^3$ is selected from H, a $C_1$-$C_6$ alkyl, CH$_2$F, CHF$_2$;
$R^4$ is selected from an alkyl, hetero-alkyl, aryl, hetero-aryl group, —NH—C(=O)—R;
$R^5$ is H, halogen, or an alkyl group;
$R^6$ is H, halogen, or an alkyl group;
$R^7$ is H, halogen, or an alkyl group;
each $R^8$ is independently selected from H, halogen, or an alkyl group;
each $R^9$ is independently selected from H, halogen, or an alkyl group;
each $R^{10}$ is independently selected from H, halogen, or an alkyl group;
each $R^{11}$ is independently selected from H, halogen, or an alkyl group;
$R^{12}$ is H, halogen, or an alkyl group;
$R^{13}$ is H, halogen, an alkyl group, hetero-alkyl, aryl, or hetero-aryl group; and
each R and R' is independently a H or an alkyl group,
or a pharmaceutically acceptable form thereof.

In certain embodiments, $R^{12}$ is a $C_1$-$C_6$ alkyl (e.g., methyl, ethyl, propyl, i-propyl). In certain embodiments, $R^{12}$ is a $C_2$-$C_4$ alkyl. In certain embodiments, $R^{12}$ is a linear or branched $C_3$ alkyl.

In certain embodiments, $R^{13}$ is a $C_1$-$C_6$ alkyl (e.g., methyl, ethyl, propyl, i-propyl).

In certain embodiments, each of $R_5$, $R_6$, $R_7$, $R_8$, $R_9$, $R_{10}$, $R_{11}$ is H.

In certain embodiments, $R^1$ is at the 7-position. In certain embodiments, $R^1$ is H. In certain embodiments, $R^1$ is a $C_1$-$C_6$ alkoxy group (e.g., methoxy, ethoxy). In certain embodiments, $R^1$ is a $C_1$-$C_2$ alkoxy.

In certain embodiments, $R^2$ is a $C_1$-$C_6$ alkyl group (e.g., methyl, ethyl, propyl, i-propyl). In certain embodiments, $R^2$ is a halogen (e.g., F, Cl). In certain embodiments, $R^2$ is an aryl group. In certain embodiments, $R^2$ is 2-thiophene.

In certain embodiments, $R^3$ is H. In certain embodiments, $R^3$ is a $C_1$-$C_6$ alkyl group (e.g., methyl, ethyl, propyl, i-propyl). In certain embodiments, $R^3$ is a $C_1$-$C_2$ alkyl group.

In certain embodiments, the compound is selected from:

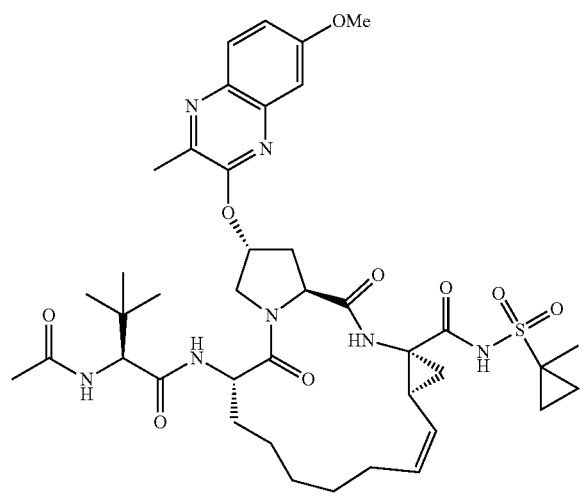

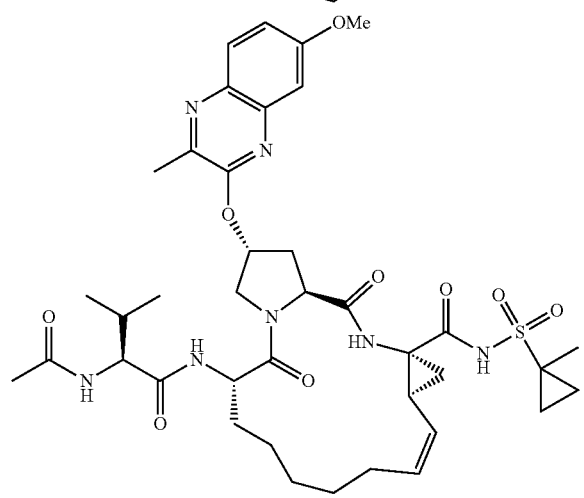

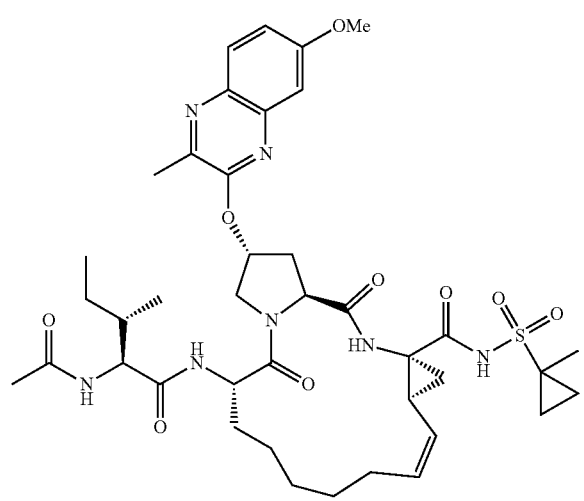

51
-continued
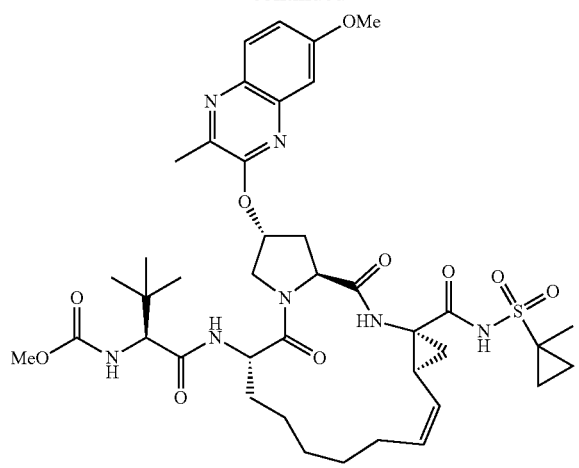
52
-continued
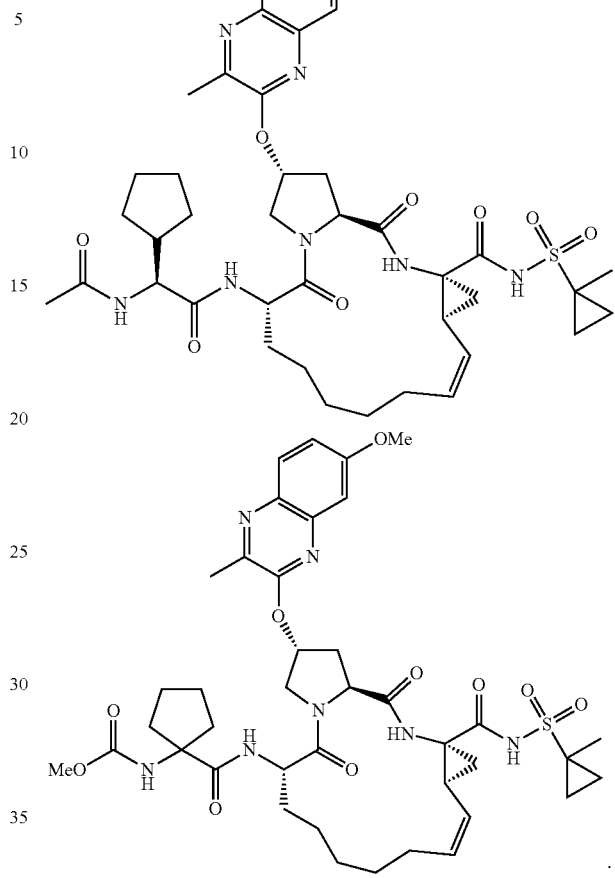
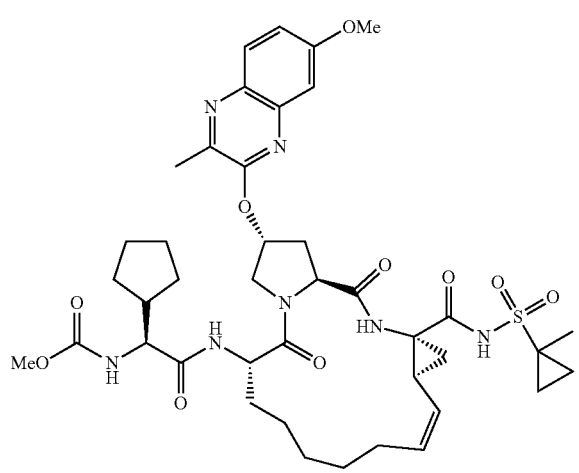
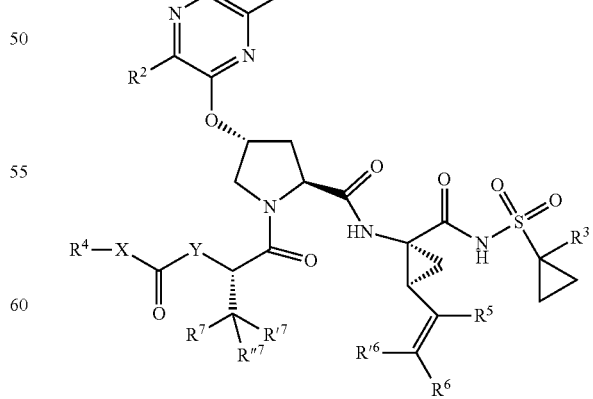
In yet another aspect, the invention generally relates to a pharmaceutical composition comprising a compound having the structural formula of (I):
(I)
wherein each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=O)N—R, —N(C=O)R, —(SP$_2$)NR$_2$ group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group, —NH—C(=O)—R;

$R^5$ is H, halogen, or an alkyl group;

$R^6$, $R'^6$ each is independently H, halogen, or an alkyl group;

$R^7$, $R'^7$, each is independently H, halogen, or an alkyl group;

$R^8$ is independently selected from H, halogen, or an alkyl group;

each R and R' is independently a H or an alkyl group; and provided that $R'^6$ and one of $R'^7$ and $R''^7$ optionally join together to form a 15-, 16- or 17-membered ring, or a pharmaceutically acceptable form thereof, effective to treat or reduce HCV infection or a related disease or disorder, in a mammal, including a human, and a pharmaceutically acceptable excipient, carrier, or diluent.

In yet another aspect, the invention generally relates to a pharmaceutical composition comprising a compound having the structural formula of (II):

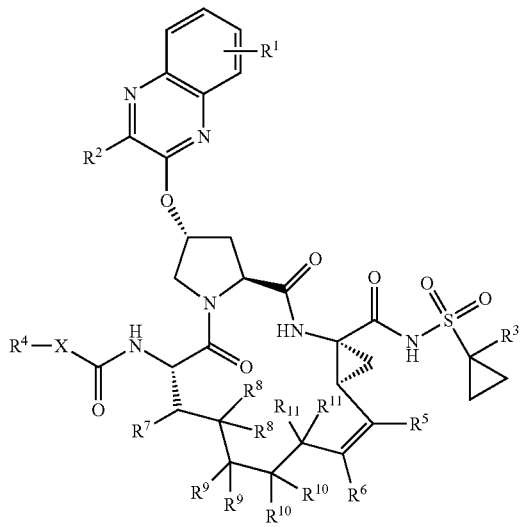

(II)

wherein
each of X and Y is independently selected from O, NH and $CH_2$, provided that at least one of X and Y is NH;

$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group, wherein each R is independently a H or an alkyl group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group;

$R^5$ is H, halogen, or an alkyl group;

$R^6$ is H, halogen, or an alkyl group;

$R^7$ is H, halogen, or an alkyl group;

each $R^8$ is independently selected from H, halogen, or an alkyl group;

each $R^9$ is independently selected from H, halogen, or an alkyl group;

each $R^{10}$ is independently selected from H, halogen, or an alkyl group; and each $R^{11}$ is independently selected from H, halogen, or an alkyl group, or a pharmaceutically acceptable form thereof, effective to treat or reduce HCV infection or a related disease or disorder, in a mammal, including a human, and a pharmaceutically acceptable excipient, carrier, or diluent.

In yet another aspect, the invention generally relates to a pharmaceutical composition comprising a compound having the structural formula of (IV):

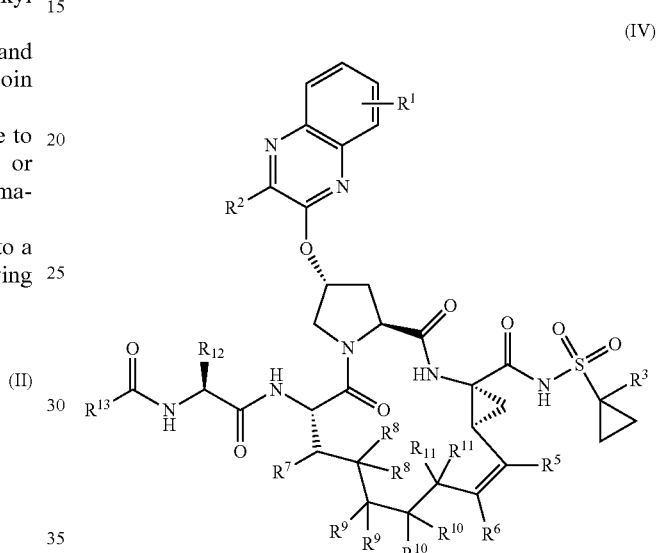

(IV)

wherein
each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group, —NH—C(=O)—R;

$R^5$ is H, halogen, or an alkyl group;

$R^6$ is H, halogen, or an alkyl group;

$R^7$ is H, halogen, or an alkyl group;

each $R^8$ is independently selected from H, halogen, or an alkyl group;

each $R^9$ is independently selected from H, halogen, or an alkyl group;

each $R^{10}$ is independently selected from H, halogen, or an alkyl group;

each $R^{11}$ is independently selected from H, halogen, or an alkyl group;

$R^{12}$ is H, halogen, or an alkyl group;

$R^{13}$ is H, halogen, an alkyl group, hetero-alkyl, aryl, or hetero-aryl group; and each R and R' is independently a H or an alkyl group, or a pharmaceutically acceptable form thereof, effective to treat or reduce HCV infection or a related disease or disorder, in a mammal, including a human, and a pharmaceutically acceptable excipient, carrier, or diluent.

In yet another aspect, the invention generally relates to a pharmaceutical composition comprising a compound disclosed herein.

In certain embodiments, the pharmaceutical composition is effective to treat or reduce an HCV infection of a Genotype 1 (GT1) or genotype 3 (GT3). In certain embodiments, the HCV infection is a genotype 1 (GT1) infection. In certain embodiments, the HCV infection is a genotype 3 (GT3) infection.

In certain embodiments, the pharmaceutical composition is effective to treat or reduce HCV infection comprising D168A/V mutations.

The pharmaceutical composition of the invention may be comprised of any of the protease inhibitor or inactivator herein disclosed.

In yet another aspect, the invention generally relates to a unit dosage. The unit dosage form is comprised of a pharmaceutical herein disclosed.

In certain embodiments, the unit dosage is in the form of a tablet or capsule suitable for oral administration.

In yet another aspect, the invention generally relates to a method for treating or reducing HCV infection, or a related disease or disorder. The method includes: administering to a subject in need thereof a pharmaceutical composition comprising a compound having the structural formula of (I):

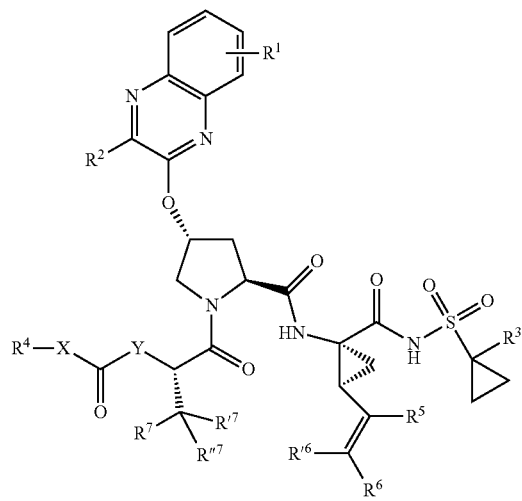

wherein
each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group, —NH—C(=O)—R;

$R^5$ is H, halogen, or an alkyl group;

$R^6$, $R'^6$ each is independently H, halogen, or an alkyl group;

$R^7$, $R'^7$, $R''^7$ each is independently H, halogen, or an alkyl group;

$R^8$ is independently selected from H, halogen, or an alkyl group;

each R and R' is independently a H or an alkyl group; and
provided that $R'^6$ and one of $R'^7$ and $R''^7$ optionally join together to form a 15-, 16- or 17-membered ring, or a pharmaceutically acceptable form thereof, and a pharmaceutically acceptable excipient, carrier, or diluent.

In yet another aspect, the invention generally relates to a method for treating or reducing HCV infection, or a related disease or disorder. The method includes: administering to a subject in need thereof a pharmaceutical composition comprising a compound having the structural formula of (II):

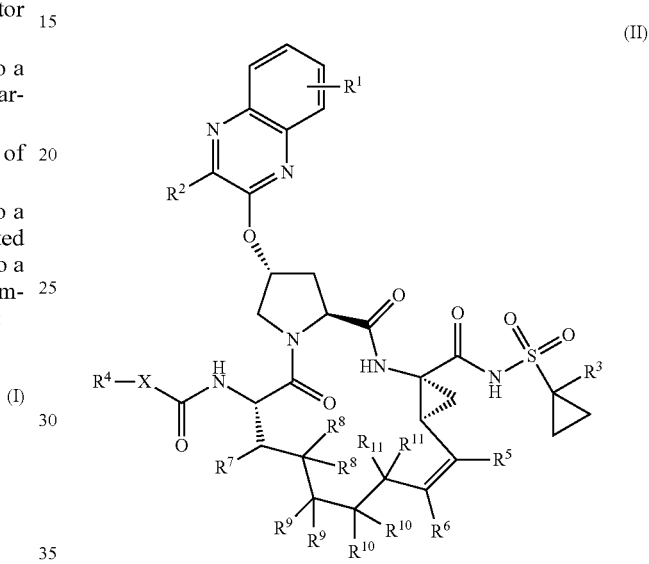

wherein
each of X and Y is independently selected from O, NH and CH$_2$, provided that at least one of X and Y is NH;

$R^1$ is selected from H, a $C_1$-$C_6$ alkoxy, aryloxy, $C_1$-$C_6$ alkyl, halogen, —(C=O)N—R, —N(C=O)R, —(SO$_2$)NR$_2$ group, wherein each R is independently a H or an alkyl group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group;

$R^5$ is H, halogen, or an alkyl group;
$R^6$ is H, halogen, or an alkyl group;
$R^7$ is H, halogen, or an alkyl group;
each $R^8$ is independently selected from H, halogen, or an alkyl group;
each $R^9$ is independently selected from H, halogen, or an alkyl group;
each $R^{10}$ is independently selected from H, halogen, or an alkyl group; and
each $R^{11}$ is independently selected from H, halogen, or an alkyl group, or a pharmaceutically acceptable form thereof, and a pharmaceutically acceptable excipient, carrier, or diluent.

In yet another aspect, the invention generally relates to a method for treating or reducing HCV infection, or a related disease or disorder. The method includes: administering to a subject in need thereof a pharmaceutical composition comprising a compound having the structural formula of (IV):

(IV)

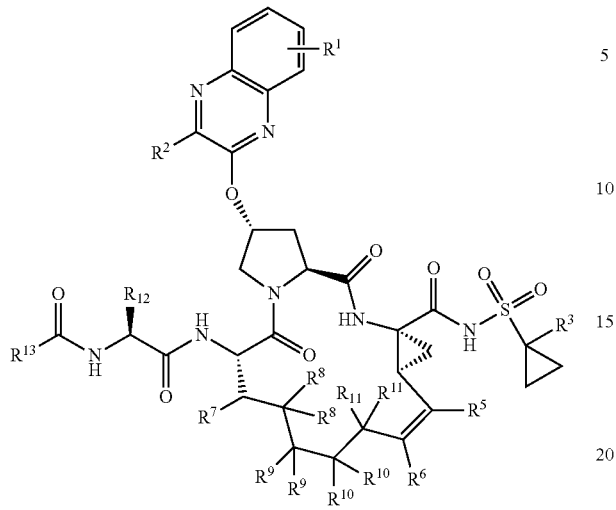

wherein each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=O)N—R, —N(C=O)R, —($SO_2$)$NR_2$ group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group, —NH—C(=O)—R;

$R^5$ is H, halogen, or an alkyl group;

$R^6$ is H, halogen, or an alkyl group;

$R^7$ is H, halogen, or an alkyl group;

each $R^8$ is independently selected from H, halogen, or an alkyl group;

each $R^9$ is independently selected from H, halogen, or an alkyl group;

each $R^{10}$ is independently selected from H, halogen, or an alkyl group;

each $R^{11}$ is independently selected from H, halogen, or an alkyl group;

$R^{12}$ is H, halogen, or an alkyl group;

$R^{13}$ is H, halogen, an alkyl group, hetero-alkyl, aryl, or hetero-aryl group; and each R and R' is independently a H or an alkyl group, or a pharmaceutically acceptable form thereof, and a pharmaceutically acceptable excipient, carrier, or diluent.

In yet another aspect, the invention generally relates to a method for treating or reducing HCV infection, or a related disease or disorder, comprising administering to a subject in need thereof a pharmaceutical composition or a unit dosage form disclosed herein.

In certain embodiments, the method is effective to treat or reduce an HCV infection of a Genotype 1 (GT1) or genotype 3 (GT3). In certain embodiments, the HCV infection is a genotype 1 (GT1) infection. In certain embodiments, the HCV infection is a genotype 3 (GT3) infection.

In certain embodiments, the method is effective to treat or reduce HCV infection comprising D168A/V mutations.

In certain embodiments, the method further includes administering to the subject one or more other anti-viral agents.

The one or more other anti-viral agents are selected any suitable anti-viral agents, for example, polymerase inhibitors.

In yet another aspect, the invention generally relates to a method for inhibiting or inactivating HCV NS3/4A protease. The method includes: administering to a subject in need thereof a pharmaceutical composition comprising a compound having the structural formula of (I):

(I)

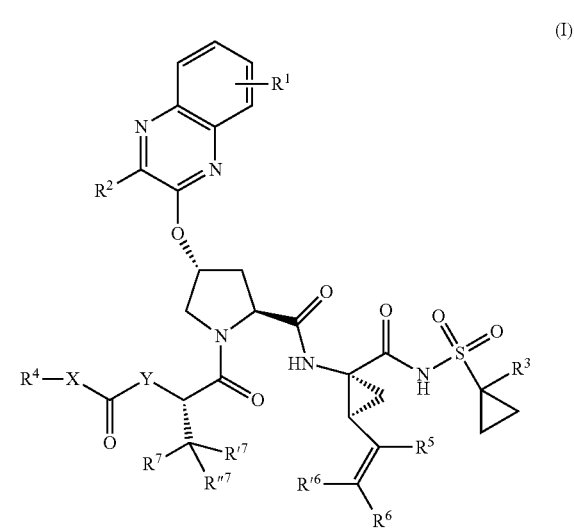

wherein each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=O)N—R, —N(C=O)R, —($SO_2$)$NR_2$ group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group, —NH—C(=O)—R;

$R^5$ is H, halogen, or an alkyl group;

$R^6$, $R'^6$ each is independently H, halogen, or an alkyl group;

$R^7$, $R'^7$, $R''^7$ each is independently H, halogen, or an alkyl group;

$R^8$ is independently selected from H, halogen, or an alkyl group;

each R and R' is independently a H or an alkyl group; and provided that $R'^6$ and one of $R'^7$ and $R''^7$ optionally join together to form a 15-, 16- or 17-membered ring, or a pharmaceutically acceptable form thereof, and a pharmaceutically acceptable excipient, carrier, or diluent.

In yet another aspect, the invention generally relates to a method for inhibiting or inactivating HCV NS3/4A protease. The method includes: administering to a subject in need thereof a pharmaceutical composition comprising a compound having the structural formula of (II):

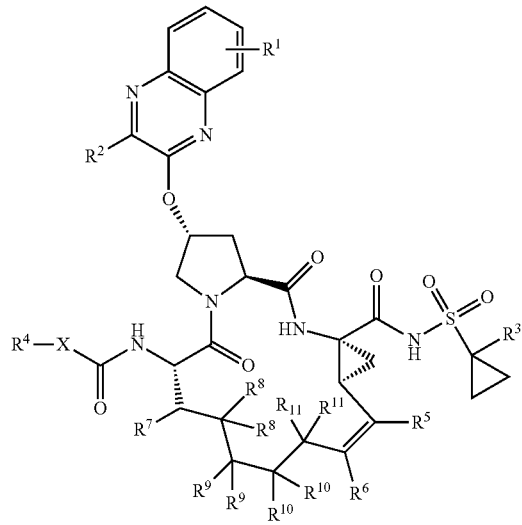

(II)

wherein
each of X and Y is independently selected from O, NH and $CH_2$, provided that at least one of X and Y is NH;

$R^1$ is selected from H, a $C_1$-$C_6$ alkoxy, aryloxy, $C_1$-$C_6$ alkyl, halogen, —(C=O)N—R, —N(C=O)R, —($SO_2$)$NR_2$ group, wherein each R is independently a H or an alkyl group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group;

$R^5$ is H, halogen, or an alkyl group;

$R^6$ is H, halogen, or an alkyl group;

$R^7$ is H, halogen, or an alkyl group;

each $R^8$ is independently selected from H, halogen, or an alkyl group;

each $R^9$ is independently selected from H, halogen, or an alkyl group;

each $R^{10}$ is independently selected from H, halogen, or an alkyl group; and each $R^{11}$ is independently selected from H, halogen, or an alkyl group, or a pharmaceutically acceptable form thereof, and a pharmaceutically acceptable excipient, carrier, or diluent.

In yet another aspect, the invention generally relates to a method for inhibiting or inactivating HCV NS3/4A protease. The method includes: administering to a subject in need thereof a pharmaceutical composition comprising a compound having the structural formula of (IV):

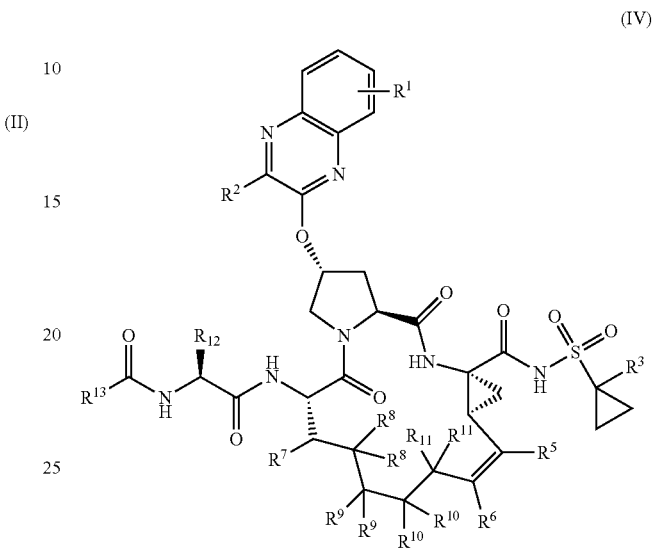

(IV)

wherein
each of X and Y is independently selected from O, NR and CRR', provided that at least one of X and Y is NR;

$R^1$ is selected from H, a $C_1$-$C_6$ alkoxy, aryloxy, $C_1$-$C_6$ alkyl, halogen, —(C=O)N—R, —N(C=O)R, —($SO_2$)$NR_2$ group;

$R^2$ is selected from H, halogen, a $C_1$-$C_6$ alkyl, aryl, —CN, $CF_3$, $CHF_2$, $CH_2F$;

$R^3$ is selected from H, a $C_1$-$C_6$ alkyl, $CH_2F$, $CHF_2$;

$R^4$ is selected from an alkyl, hetero-alkyl, aryl, hetero-aryl group, —NH—C(=O)—R;

$R^5$ is H, halogen, or an alkyl group;

$R^6$ is H, halogen, or an alkyl group;

$R^7$ is H, halogen, or an alkyl group;

each $R^8$ is independently selected from H, halogen, or an alkyl group;

each $R^9$ is independently selected from H, halogen, or an alkyl group;

each $R^{10}$ is independently selected from H, halogen, or an alkyl group;

each $R^{11}$ is independently selected from H, halogen, or an alkyl group;

$R^{12}$ is H, halogen, or an alkyl group;

$R^{13}$ is H, halogen, an alkyl group, hetero-alkyl, aryl, or hetero-aryl group; and each R and R' is independently a H or an alkyl group, or a pharmaceutically acceptable form thereof, and a pharmaceutically acceptable excipient, carrier, or diluent.

In yet another aspect, the invention generally relates to a method for inhibiting or inactivating HCV NS3/4A protease. The method includes: administering to a subject in need thereof a pharmaceutical composition disclosed herein.

In certain embodiments, the HCV NS3/4A protease is a wild-type protease.

In certain embodiments, the HCV NS3/4A protease is a mutant variant of the wild-type protease.

In certain embodiments, the subject does not develop resistance to a compound of the invention after extended time of administration of the compound.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^3H$) and carbon-14 ($^{14}C$) labeled compounds are particularly preferred for their ease of preparation and detectability. Further, substitution with heavier isotopes such as deuterium ($^2H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts, esters, and prodrugs thereof, can be prepared by any means known in the art.

Further, substitution of normally abundant hydrogen ($^1H$) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}C$ with $^{13}C$. (See, WO 2007/005643, WO 2007/005644, WO 2007/016361, and WO 2007/016431.)

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure. Solvates and polymorphs of the compounds of the invention are also contemplated herein. Solvates of the compounds of the present invention include, for example, hydrates.

Any appropriate route of administration can be employed, for example, parenteral, intravenous, subcutaneous, intramuscular, intraventricular, intracorporeal, intraperitoneal, rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds described herein or derivatives thereof are admixed with at least one inert customary excipient (or carrier) such as sodium citrate or dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

EXAMPLES

Herein described is a substrate envelope-guided strategy that led to the design of NS3/4A PIs with exceptional potency profiles against major drug resistant HCV variants.

PART 1. P1-P3 Macrocyclic Inhibitors

A series of analogues were designed and synthesized with diverse substituents at the 3-position of P2 quinoxaline moiety. Investigation of structure-activity relationships (SARs) identified P2 quinoxaline derivatives that predominantly interact with the invariant catalytic triad and avoid contacts with the S2 subsite residues. Inhibitors with small hydrophobic substituents at the 3-position of P2 quinoxaline maintained better potency against drug resistant variants, likely due to reduced interactions with residues in the S2 subsite. A novel class of HCV therapeutics was achieved that are safe and effective HCV NS3/4A protease inhibitors and are less susceptible to drug resistance than existing therapeutics.

Structure-Guided SAR Investigation and Compound Design

From structure-guided SAR investigations, compound 2 was identified as a starting point for modification due to its unique structural features: (1) the P2 quinoxaline moiety that predominantly interacts with the highly conserved catalytic residues Asp81 and His57 and (2) the conformational flexibility that allows the inhibitor to efficiently accommodate structural changes in the S2 subsite due to resistance mutations.

Identifying and optimizing substituents at the P2 quinoxaline and the N-terminal capping remains challenging in discerning analogues with improved potency and resistance profiles. To address the challenge, efforts were focused on exploration of SARs at the P2 quinoxaline moiety in 2, for example, substituting the ethyl group at the 3-position that directly interacts with protease S2 subsite residues Arg155 and Ala156. The SAR strategy was based on insights from detailed structural analysis of 1 and 2 bound to wild-type NS3/4A protease and drug resistant variants.

A series of inhibitors with diverse substituents at the 3-position of P2 quinoxaline were designed and synthesized. In particular, SAR information based on these compounds was used to investigate whether small hydrophobic groups at the 3-position of the quinoxaline would be preferred for retaining inhibitor potency against drug resistant variants as larger groups that make extensive interactions with Arg155, Ala156 and Asp168 would result in inhibitors highly susceptible to mutations at these positions.

The potency and resistance profiles of NS3/4A PIs were assessed using biochemical and replicon assays. The enzyme inhibition constants (Ki) were determined against wild-type GT1a NS3/4A protease, drug-resistant variant D168A, and GT3a NS3/4A protease (Table 1). The cellular antiviral potencies ($EC_{50}$) were determined using HCV replicon-based antiviral assays against wild-type and drug-resistant variants R155K, A156T, D168A, and D168V (Table 2). Compound 1 was used as a control in all assays.

TABLE 1

Inhibitory activity against wild-type NS3/4A protease and drug resistant variants

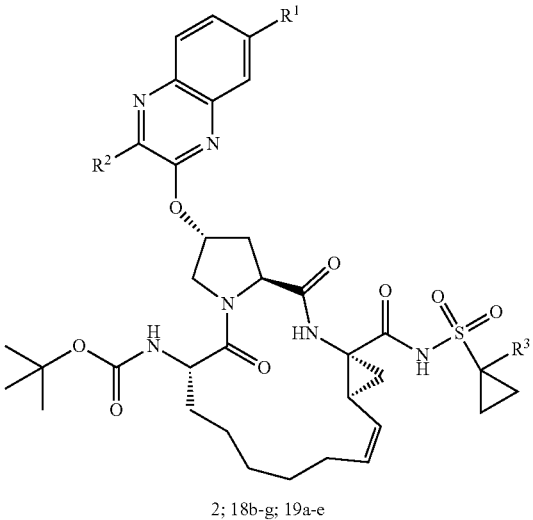

2; 18b-g; 19a-e

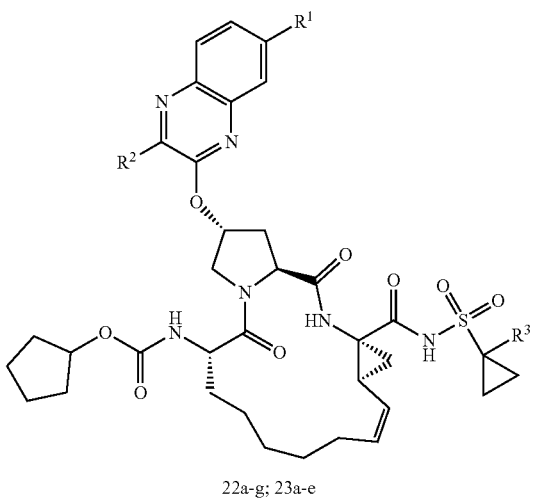

22a-g; 23a-e

TABLE 1-continued

| Inhibitor | R¹ | R² | R³ | Ki (nM) GT1a WT NS3/4A Protease | Ki (nM) GT1a D168A NS3/4A Protease | Ki (nM) GT3a NS3/4A Protease |
|---|---|---|---|---|---|---|
| 2 | OMe | Et | H | 3.29 ± 0.52 | 82.4 ± 4.4 | 204 ± 19 |
| 19a | OMe | Et | Me | 1.82 ± 0.38 | 55.2 ± 5.3 | 171 ± 23 |
| 22a | OMe | Et | H | 1.24 ± 0.14 | 52.3 ± 3.2 | 211 ± 18 |
| 23a | OMe | Et | Me | 1.37 ± 0.34 | 55.2 ± 5.3 | 186 ± 30 |
| 18b | OMe | Me | H | 3.40 ± 0.47 | 50.9 ± 3.7 | 152 ± 18 |
| 19b | OMe | Me | Me | 3.60 ± 0.44 | 52.0 ± 2.4 | 119 ± 18 |
| 22b | OMe | Me | H | 0.93 ± 0.15 | 31.9 ± 2.5 | 147 ± 20 |
| 23b | OMe | Me | Me | 1.13 ± 0.22 | 36.3 ± 1.8 | 121 ± 16 |
| 18c | OMe | Cl | H | 1.07 ± 0.17 | 39.8 ± 3.4 | 67.5 ± 8.0 |
| 19c | OMe | Cl | Me | 1.11 ± 0.38 | 77.7 ± 6.1 | 53.6 ± 5.9 |
| 22c | OMe | Cl | H | 0.49 ± 0.15 | 30.6 ± 2.6 | 85.6 ± 11 |
| 23c | OMe | Cl | Me | 0.44 ± 0.15 | 25.7 ± 1.8 | 61.0 ± 12 |
| 18d | OMe | CF₃ | H | 13.3 ± 3.9 | 157 ± 12 | 344 ± 141 |
| 19d | OMe | CF₃ | Me | 5.77 ± 1.78 | 118 ± 13 | 231 ± 74 |
| 22d | OMe | CF₃ | H | 7.55 ± 2.39 | 115 ± 12 | 757 ± 334 |
| 23d | OMe | CF₃ | Me | 8.14 ± 2.37 | 110 ± 14 | 433 ± 206 |
| 18e | OMe | i-Pr | H | 4.27 ± 1.34 | 239 ± 20 | NT |
| 19e | OMe | i-Pr | Me | 0.58 ± 0.08 | 211 ± 19 | NT |
| 22e | OMe | i-Pr | H | 1.44 ± 0.46 | 161 ± 11 | NT |
| 23e | OMe | i-Pr | Me | 1.34 ± 0.48 | 156 ± 17 | NT |
| 18f | H | 2-thiophene | H | 1.03 ± 0.13 | 1823 ± 347 | NT |
| 22f | H | 2-thiophene | H | 1.59 ± 0.56 | 900 ± 81 | NT |
| 18g | H | Et | H | 7.18 ± 1.02 | 190 ± 13 | NT |
| 22g | H | Et | H | 1.99 ± 0.48 | 107 ± 7.0 | NT |
| MK-5172 (1) | | | | 0.21 ± 0.03 | 49.1 ± 1.6 | 30.3 ± 1.9 |

TABLE 2

Antiviral activity against wild-type HCV and drug resistant variants

2; 18b-g; 19a-e 22a-g; 23a-e

| Inhibitor | R¹ | R² | R³ | Replicon EC₅₀ (nM) WT | R155K | A156T | D168A | D168V |
|---|---|---|---|---|---|---|---|---|
| 2 | OMe | Et | H | 0.33 | 1.75 | 9.65 | 6.31 | 9.10 |
| 19a | OMe | Et | Me | 0.43 | 1.80 | 4.52 | 4.97 | 6.42 |
| 22a | OMe | Et | H | 0.14 | 2.08 | 11.8 | 3.60 | 11.9 |
| 23a | OMe | Et | Me | 0.16 | 2.07 | 10.6 | 3.45 | 7.08 |
| 18b | OMe | Me | H | 0.39 | 1.17 | 5.95 | 4.24 | 3.17 |
| 19b | OMe | Me | Me | 0.30 | 0.80 | 1.57 | 2.37 | 1.60 |
| 22b | OMe | Me | H | 0.11 | 0.89 | 2.88 | 2.63 | 4.32 |
| 23b | OMe | Me | Me | 0.13 | 1.09 | 3.99 | 2.16 | 2.85 |
| 18c | OMe | Cl | H | 0.16 | 0.44 | 16.2 | 1.42 | 0.73 |
| 19c | OMe | Cl | Me | 0.18 | 0.40 | 8.86 | 1.07 | 0.49 |
| 22c | OMe | Cl | H | 0.15 | 0.59 | 3.55 | 1.32 | 1.55 |
| 23c | OMe | Cl | Me | 0.15 | 0.56 | 4.32 | 0.97 | 1.09 |
| 18d | OMe | CF₃ | H | 1.98 | 3.45 | 36.2 | 16.8 | 17.1 |
| 19d | OMe | CF₃ | Me | 1.52 | 2.30 | 20.5 | 8.64 | 8.31 |
| 22d | OMe | CF₃ | H | 4.86 | 7.97 | 117 | 15.1 | 24.0 |
| 23d | OMe | CF₃ | Me | 4.04 | 6.90 | 75.9 | 8.46 | 11.4 |
| 18e | OMe | i-Pr | H | 1.43 | 5.02 | 25.7 | 15.3 | 23.7 |
| 19e | OMe | i-Pr | Me | 1.86 | 4.14 | 21.2 | 11.9 | 18.1 |

TABLE 2-continued

| | | | | | | | | |
|---|---|---|---|---|---|---|---|---|
| 22e | OMe | i-Pr | H | 0.48 | 7.63 | 32.1 | 7.96 | 30.1 |
| 23e | OMe | i-Pr | Me | 0.59 | 6.83 | 27.6 | 7.91 | 18.2 |
| 18f | H | 2-thiophene | H | 0.98 | 21.7 | 256 | 111 | 193 |
| 22f | H | 2-thiophene | H | 0.40 | 19.2 | 183 | 42.2 | 70.0 |
| 18g | H | Et | H | 0.46 | 1.81 | 10.6 | 8.55 | 14.0 |
| 22g | H | Et | H | 0.24 | 4.28 | 24.6 | 7.50 | 19.3 |
| MK-5172 (1) | | | | 0.14 | 1.89 | 238 | 9.69 | 5.41 |

Compound 1 showed sub-nanomolar inhibitory potency against WT NS3/4A protease and maintained nanomolar activity against drug resistant variant D168A and GT3a protease. Similarly, in replicon assays 1 exhibited an excellent potency profile with sub-nanomolar activity against WT HCV ($EC_{50}$=0.14 nM) and low nanomolar activity against drug resistant variants R155K, D168A, and D168V. However, in line with previous reports, 1 was highly susceptible to the A156T mutation ($EC_{50}$=238 nM), losing over 1000-fold potency against this variant. (Ali, et al. *ACS Chem. Biol.* 2013, 8, 1469-1478.)

Compared to 1, the P1-P3 macrocyclic analogue 2 exhibited lower inhibitory potency against WT protease and the D168A variant. Also, the inhibitory activity of 2 against the GT3a protease was considerably lower than that of 1. Compound 2 displayed a superior potency profile in replicon assays with sub-nanomolar activity against WT HCV ($EC_{50}$=0.33 nM) and maintained single digit nanomolar potency against all drug-resistant variants tested. Notably, unlike 1, compound 2 maintained low nanomolar potency against the A156T variant ($EC_{50}$=9.65 nM). Thus, with an improved resistance profile compared to 1, the P1-P3 macrocyclic analogue 2 is an attractive lead compound for further optimization. (Ali, et al. *ACS Chem. Biol.* 2013, 8, 1469-1478.)

Modifications of P1' and P4 Capping Groups

Early SAR efforts to modify compound 2 focused on exploring changes at the P1' position and N-terminal capping group. Recent SAR studies of diverse NS3/4A PIs indicate that replacement of the cyclopropylsulfonamide moiety at the P1' position with a slightly more hydrophobic 1-methylcyclopropylsulfonamide improves inhibitor potency in replicon assays. Moreover, changes at the P4 position have been shown to affect inhibitor potency against drug resistant variants, as these groups bind in close proximity to the pivotal drug resistance site Asp168. For carbamate-linked P4 capping groups, generally bulky hydrophobic moieties are preferred but the size of the group appears to be dependent on the heterocyclic moiety present at the P2 position. (Rudd, et al. *Chem Med Chem* 2015, 10, 727-735; Vendeville, et al. *Bioorg. Med. Chem. Lett.* 2008, 18, 6189-6193; Moreau, et al. *J. Med. Chem.* 2014, 57, 1770-1776; O'Meara, et al. *J. Biol. Chem.* 2013, 288, 5673-5681.)

First, replacing the cyclopropylsulfonamide at the P1' position in 2 with 1-methylcyclopropylsulfonamide provided the analogue 19a. Compared to the parent compound 2, 19a showed slightly better Ki values against WT, D168A and GT3a proteases and exhibited similar or slightly better antiviral potency against WT and drug resistant variants.

Next, the tert-butyl P4 capping group in both 2 and 19a was replaced with a larger cyclopentyl moiety, resulting in analogues 22a and 23a. Unlike the change at the P1' position, the P4 cyclopentyl modification provided mixed results. Compound 22a afforded a 2-fold increase in potency than 2 in biochemical assays against WT protease and a slight improvement against the D168A variant, but was equipotent to 2 against GT3a protease. Similarly, in replicon assays 22a exhibited 2-fold enhanced potency against WT HCV and D168A variant, but showed similar potency as 2 against the R155K and D168V variants.

Compound 23a, with a 1-methylcyclopropylsulfonamide moiety at the P1' position and a cyclopentyl group at the P4 position, exhibited potency profile largely similar to 22a. Surprisingly, a slight loss in potency was observed against the A156T variant for compounds with a cyclopentyl versus tert-butyl capping group. Overall, these minor modifications at the P1' and N-terminal capping regions of inhibitor 2 were tolerated and provided analogues with improved potency profiles.

SAR Exploration of P2 Quinoxaline

Next, SARs at the P2 quinoxaline in compound 2 were explored. Efforts mainly focused on replacing the 3-position ethyl group with diverse functional groups with respect to size and electronic properties. Replacement of the ethyl group in 2 with a smaller methyl group provided analogue 18b. As expected, reducing the size of the hydrophobic group at this position resulted in improved potency profile. Compound 18b showed slightly enhanced potency against drug resistant variants in biochemical and antiviral assays, with a notable ~2-fold improvement against the D168V variant ($EC_{50}$=3.17 nM). The introduction of 1-methylcyclopropylsulfonamide moiety at the P1' position afforded inhibitor 19b with protease inhibitory activity comparable to the parent compound 18b.

However, similar to the 3-ethylquinoxaline analogue (19a), compound 19b demonstrated significant gain in potency in replicon assays. In fact, compared to 2, 19b exhibited 2- to 6-fold enhancement in potency against drug resistant variants R155K ($EC_{50}$=0.80 nM), A156T ($EC_{50}$=1.57 nM), D168A ($EC_{50}$=2.37 nM), and D168V ($EC_{50}$=1.6 nM). Replacement of the tert-butyl P4 capping in 18b and 19b with a cyclopentyl group, providing 22b and 23b, resulted in an increase in WT and D168A inhibitory activity as well as 2- to 3-fold increase in WT replicon potency. Unlike the corresponding 3-ethylquinoxaline analogues (22a and 23a), the 3-methyquinoxaline compounds 22b and 23b maintained the excellent potency profile observed for the corresponding tert-butyl analogues. Remarkably, with the exception of 18b (A156T $EC_{50}$=5.95 nM), all compounds in the 3-methylquinoxaline series display exceptional potency profiles with $EC_{50}$ values below 5 nM against WT and clinically relevant drug resistant variants.

Figure 3:
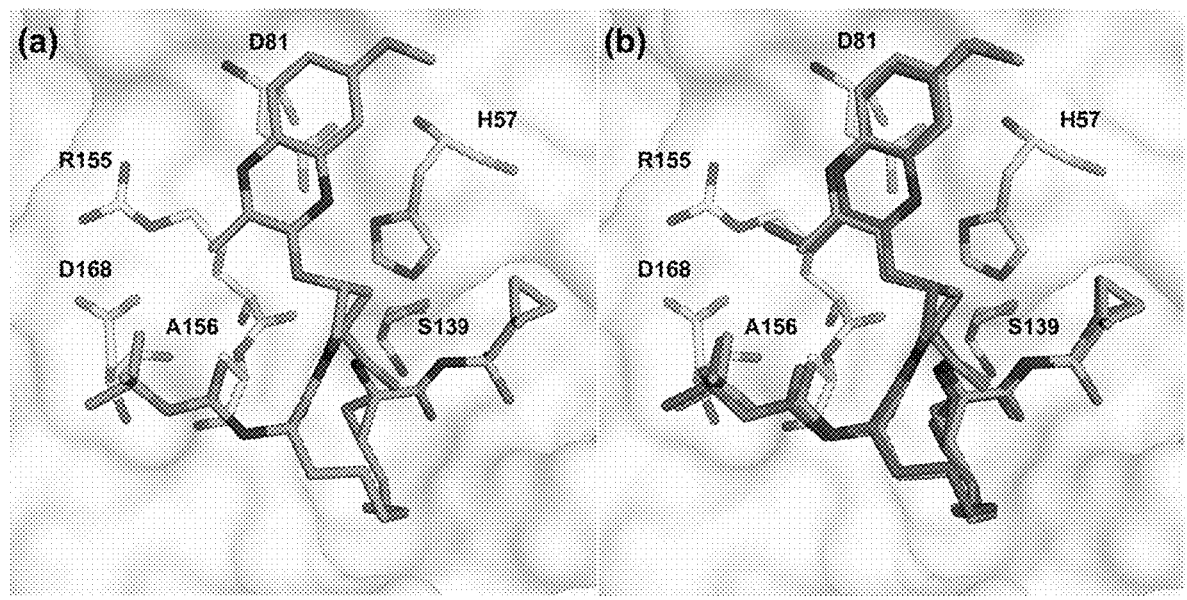
FIG. 3. (a) X-ray crystal structure of WT1a HCV NS3/4A protease in complex with inhibitor 19b and (b) superposition of WT-2 and WT-19a complexes. The protease active site is shown as a surface with inhibitor 19b shown in orange and 2 shown in blue. The catalytic triad is highlighted in yellow, and drug resistance residues Arg155, Ala156, and Asp168 are shown as sticks.

To gain insights into the excellent potency profile observed for the 3-methyquinoxaline series, the X-ray crystal structure of inhibitor 19b in complex with the WT NS3/4A protease was determined at a resolution of 1.8 Å (FIG. 3, Table 5, PDB code: 5VOJ). The WT-19b complex structure was compared with the previously reported structures of compound 2 in complex with WT protease and the A156T variant (PDB codes: 5EPN and 5EPY). (Soumana, et al. *ACS Chem. Biol.* 2016, 11, 900-909.)

The two WT structures overlap very well, with only minor differences in the S1 and S2 subsites because of modifications in the inhibitor structure. In the WT-2 crystal structure, the 3-ethyl group at the P2 quinoxaline makes hydrophobic interactions with the hydrocarbon portion of the Arg155 side-chain, while the methylene portion of this group interacts with the side-chain of Ala156. The smaller methyl group at this position in the WT-19b structure maintains hydrophobic interactions with Ala156, while minimizing chances of steric clash with a larger side-chain, such as in A156T.

Unlike inhibitor 1, the P1-P3 macrocyclic analogues retain potency against the A156T variant. Comparison of the WT-2 and A156T-2 (PDB code: 5EPY) structures shows subtle changes in inhibitor interactions with the mutant protease. (Soumana, et al. *ACS Chem. Biol.* 2016, 11, 900-909.)

In the A156T-2 structure the P2 quinoxaline largely maintains interactions with the catalytic residues, but the ethyl group is shifted away from Arg155 side chain toward A156T. Moreover, to accommodate a larger Thr side-chain, the Asp168 side chain adopts another conformation, moving away from Arg155. These changes underlie reduced inhibitor potency against the A156T variant, but unlike 1, inhibitor 2 is able to better accommodate these changes due to a flexible P2 moiety. The 3-methylquinoxaline analogues are more potent against the A156T variant than the corresponding 3-ethylquinoxaline compounds likely due the reduced interactions of the smaller methyl group with the Thr side-chain. Replacing the methyl group with hydrogen at the 3-position of quinoxaline would further reduce interactions with the S2 subsite residues, but was predicted to result in a highly flexible P2 moiety, likely destabilizing interactions with the catalytic residues. Thus, a small hydrophobic group at the 3-position of P2 quinoxaline is preferred to maintain favorable interactions with Ala156 and avoid steric clashes with the Thr side-chain in the A156T variant.

The improved potency profile of 3-methyquinoxaline compounds led to exploration of bioisosteric replacements of the 3-methyl group with varied size and electronic properties. To that end, analogues 18c and 19c bearing the 3-chloro-7-methoxyquinoxaline at the P2 position were prepared. The protease inhibitory potency profiles of these compounds were excellent and showed improvement against WT, D168A and GT3a over 2. These potency gains were not only maintained in replicon assays but were more significant, with the only exception of A156T variant. Both compounds 18c and 19c were more active than the corresponding 3-methylquinoxaline analogues (18b and 19b) with $EC_{50}$ values less than 1 nM against WT, R155K and D168V and less than 2 nM against the D168A variant, but experienced about 3- to 6-fold reduction in potency against the A156T variant. However, potency losses against the A156T variant were largely reversed when the P4 tert-butyl group in 18c and 19c was replaced with a larger cyclopentyl moiety to afford 22c and 23c. Similar to the 3-methylquinoxaline compounds, the 3-chloroquinoxaline analogues displayed exceptional potency profiles with $EC_{50}$ values of less than 5 nM against all drug resistant variants including A156T. These results clearly demonstrate that small hydrophobic groups with weak electron-donating properties at the 3-position of P2 quinoxaline can be replaced with weak electron-withdrawing groups without affecting the overall potency profile.

Next, a larger and strongly electron-withdrawing trifluoromethyl moiety was explored at the 3-position of P2 quinoxaline, leading to inhibitors 18d and 19d. This modification, however, resulted in significant potency losses in both biochemical and replicon assays. Compound 18d was about 2- to 4-fold less active than 2 against WT protease and variants. Analogue 19d with the 1-methylcyclopropylsulfonamide moiety at the P1' position showed similar trends when compared to the corresponding 19a. In line with biochemical data, both 18d and 19d suffered 2- to 6-fold decrease in replicon potency against WT and drug resistant variants, though 19d maintained relatively good potency profile.

In contrast to the results in previous series, the introduction of the larger cyclopentyl P4 capping group, as in 22d and 23d, was detrimental to replicon potency, particularly against the A156T variant. Moreover, compounds in the 3-(trifluoromethyl)quinoxaline series were among the least active against the GT3a protease in biochemical assays. These results indicate that strong electron-withdrawing groups at the 3-position of the P2 quinoxaline may be detrimental to potency. It is noted that a recent SAR study indicates that PIs incorporating the 3-(trifluoromethyl)quinoxaline can be optimized with modifications at the 7-position of quinoxaline in combination with changes at the P1-P3 macrocycle and P4 capping group. (Gillis, et al. *In Abstract of Papers, 2nd Generation HCV protease inhibitors: Part 2, optimization of P2*, 250th ACS National Meeting & Exposition, Boston, Mass., United States, Aug. 16-20, 2015, pp MEDI-240.)

To isolate the effects of larger size versus electronic properties on potency, inhibitors 18e and 19e with the larger isopropyl group at the 3-position of the P2 quinoxaline were designed, synthesized and evaluated. These compounds showed WT protease inhibitory activity similar to the corresponding 3-ethylquinoxaline analogues (2 and 19a), but experienced 2- to 4-fold reduced activity against the D168A variant. A broader reduction in potency was observed for both 18e and 19e in replicon assays against WT and drug resistant variants.

The cyclopentyl P4 group in analogues 22e and 23e slightly improved biochemical and replicon potency against WT and D168A variants, but was largely unfavorable to replicon potency against R155K and A156T variants. This trend is broadly similar to the results observed with the 3-(trifluoromethyl)quinoxaline series.

Figure 4:
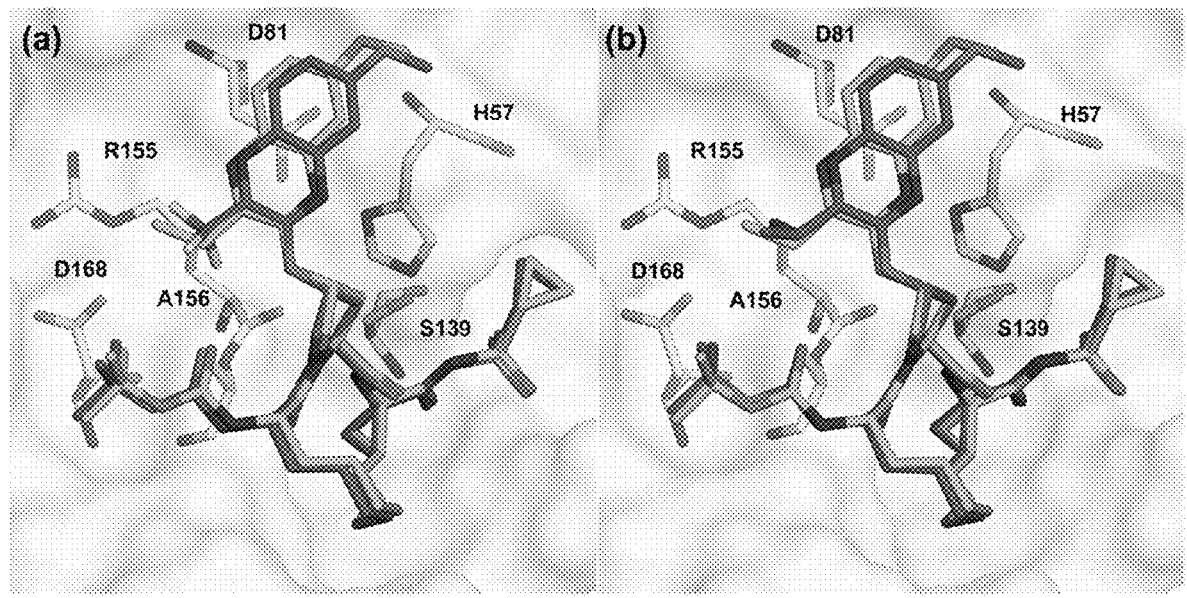
FIG. 4. Comparison of lead compound 2 with analogues (a) 18d and (b) 18e modeled in the active site of WT HCV NS3/4A protease. Compound 2 is shown in salmon, and modified inhibitors are in green. The catalytic triad is highlighted in yellow, and drug resistance residues Arg155, Ala156, and Asp168 are in sticks.

Without wishing to be bound by the theory, the results indicated that both electronic properties and size of the group at the 3-position of P2 quinoxaline are important for maintaining potency against drug resistant variants. Modeling indicated that compared to 2 the P2 quinoxaline moiety in 18e has to shift away from the catalytic triad in order to accommodate the larger isopropyl group thereby weakening critical stacking interactions with His57 (FIG. 4).

Overall, SAR data from the 3-isopropyl- and 3-(trifluoromethyl)-quinoxaline series supports that large substituents at the 3-position of P2 quinoxaline have detrimental effect on inhibitor potency against drug resistant variants.

Figure 6:
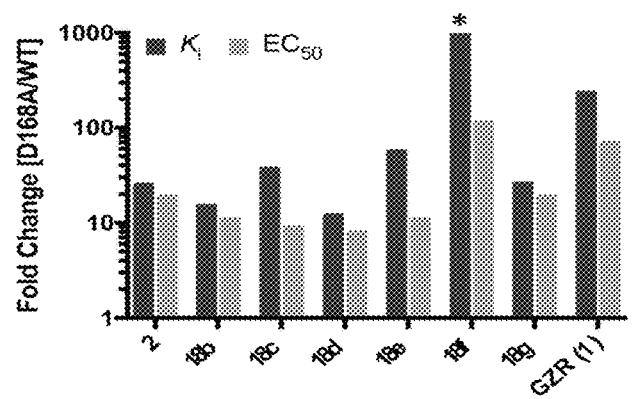
FIG. 6. Resistance profiles of protease inhibitors in enzyme inhibition and antiviral assays for PIs with (a) tert-butyl and (b) cyclopentyl P4 capping groups. Enzyme inhibitory (blue bars) and antiviral (orange bars) activities against the D168A variant were normalized with respect to the wild-type NS3/4A protease domain or wild-type HCV GT1b replicon. *Indicates value higher than 1000.
Figure 6:
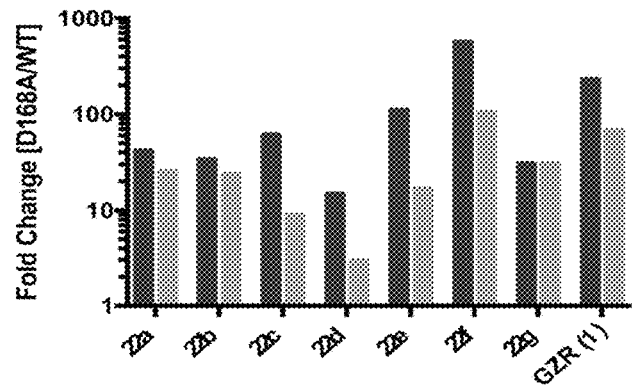

These findings were further reinforced by the results obtained for the 3-(thiophen-2-yl)quinoxaline analogues 18f and 22f. Based on molecular modeling, the large thiophene moiety in these compounds was expected to make extensive interactions with the residues Arg155 and Ala156 (FIG. 4), resulting in improved potency against WT protease. However, mutations at these positions as well as at Asp168 would cause significant potency losses, as these residues are crucial for efficient inhibitor binding. Compound 18f (a previously reported NS3/4A protease inhibitor incorrectly labeled as ABT-450, Rosenquist, et al. *J. Med. Chem.* 2014, 57, 1673-1693; WO 2008/002924) showed a 3-fold enhancement in WT biochemical potency but was dramatically less active against the D168A variant, losing over 1800-fold potency (FIG. 6). Similarly, in replicon assays analogue 18f showed considerably reduced potency against all drug resistant variants with losses ranging from 20- to 250-fold compared to WT (Table 3 and Table 4). The cyclopentyl P4 analogue 22f also experienced large potency losses against the variants, albeit to a lesser extent than 18f. Thus inhibitors with large groups at the 3-position of P2 quinoxaline are highly susceptible to mutations at residues Arg155, Ala156 and Asp168, leading to poor resistance profiles.

Figure 5:
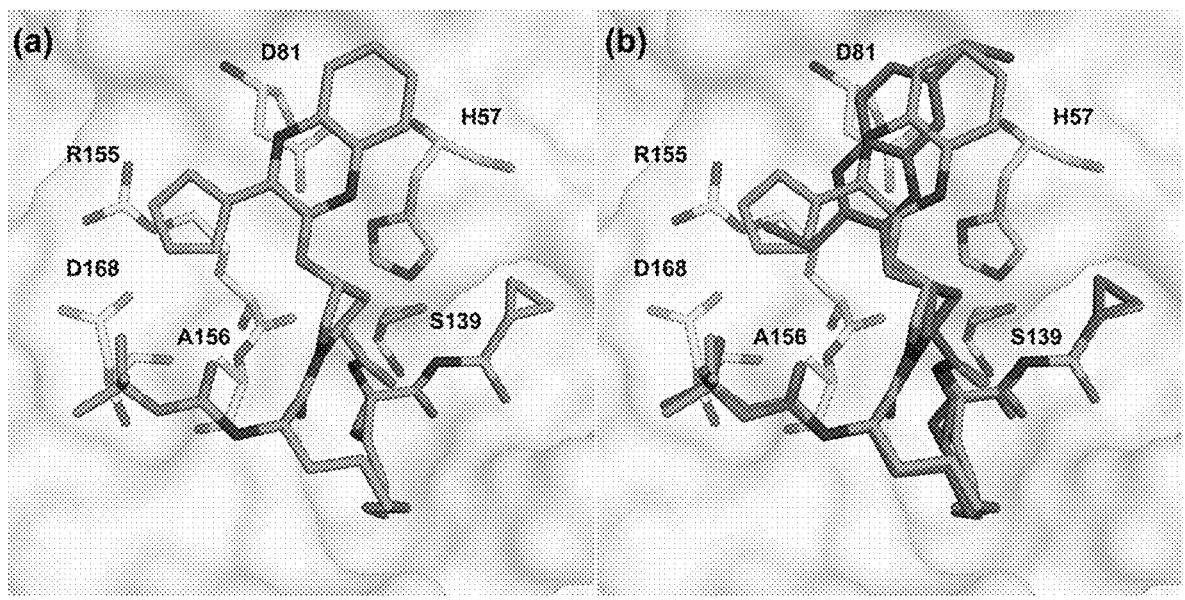
FIG. 5. (a) X-ray crystal structure of WT1a HCV NS3/4A protease in complex with inhibitor 18f and (b) superposition of WT-2 and WT-18f complexes. The protease active site is shown as a surface with inhibitor 18f shown in orange and 2 shown in blue. The catalytic triad is highlighted in yellow, and drug resistance residues Arg155, Ala156, and Asp168 are shown as sticks.

The X-ray crystal structure of inhibitor 18f in complex with WT NS3/4A protease was determined at a resolution of 1.8 Å, providing insights into the binding modes of P2 quinoxaline with a larger thiophene substituent at the 3-position (FIG. 5, Table 5, PDB code: 5VP9). Comparison of the WT-18f and WT-2 crystal structures showed significant differences in the interactions of quinoxaline moieties with the catalytic triad and S2 subsite residues. As predicted by modeling, the quinoxaline moiety in WT-18f structure is shifted toward the active site to accommodate the larger thiophene substituent. The thiophene ring makes extensive interactions with residues in the S2 subsite, including cation-π interactions with Arg155, resulting in improved inhibitory potency against the WT protease. As this Arg155 conformation is stabilized by electrostatic interactions with Asp168, mutations at either residue would disrupt inhibitor binding by loss of direct interactions as well as indirect structural effects. In addition, the A156T mutation would result in steric clash with the thiophene ring, as reflected in the antiviral data for this variant. These biochemical and structural findings are in line with previous studies that show inhibitors that are dependent on extensive interactions with the S2 subsite residues for potency are highly susceptible to mutations at residues Arg155, Ala156 and Asp168.

TABLE 3

Inhibitory activity against wild-type NS3/4A protease and drug resistant variants

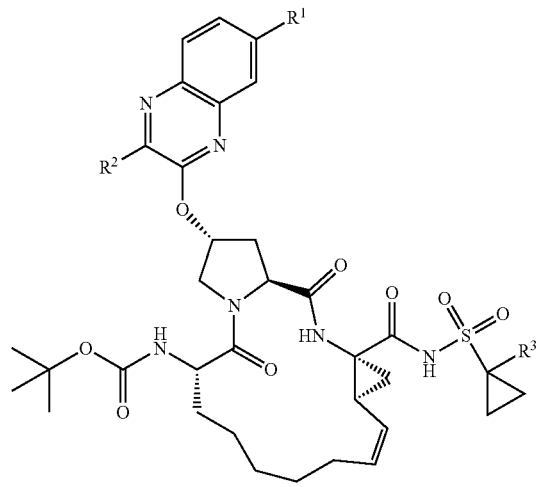

2; 18b-g; 19a-e

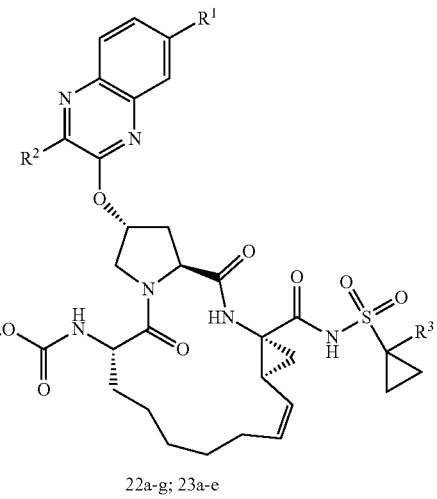

22a-g; 23a-e

| Inhibitor | R¹ | R² | R³ | GT1a WT NS3/4A Protease | GT1a D168A NS3/4A Protease | GT3a NS3/4A Protease |
|---|---|---|---|---|---|---|
| 2 | OMe | Et | H | 3.29 ± 0.52 | 82.4 ± 4.4 (25) | 204 ± 19 (62) |
| 19a | OMe | Et | Me | 1.82 ± 0.38 | 55.2 ± 5.3 (30) | 171 ± 23 (94) |
| 22a | OMe | Et | H | 1.24 ± 0.14 | 52.3 ± 3.2 (42) | 211 ± 18 (170) |
| 23a | OMe | Et | Me | 1.37 ± 0.34 | 55.2 ± 5.3 (40) | 186 ± 30 (136) |
| 18b | OMe | Me | H | 3.40 ± 0.47 | 50.9 ± 3.7 (15) | 152 ± 18 (45) |
| 19b | OMe | Me | Me | 3.60 ± 0.44 | 52.0 ± 2.4 (14) | 119 ± 18 (33) |
| 22b | OMe | Me | H | 0.93 ± 0.15 | 31.9 ± 2.5 (34) | 147 ± 20 (158) |
| 23b | OMe | Me | Me | 1.13 ± 0.22 | 36.3 ± 1.8 (32) | 121 ± 16 (107) |
| 18c | OMe | Cl | H | 1.07 ± 0.17 | 39.8 ± 3.4 (37) | 67.5 ± 8.0 (63) |
| 19c | OMe | Cl | Me | 1.11 ± 0.38 | 77.7 ± 6.1 (70) | 53.6 ± 5.9 (48) |
| 22c | OMe | Cl | H | 0.49 ± 0.15 | 30.6 ± 2.6 (62) | 85.6 ± 11 (175) |
| 23c | OMe | Cl | Me | 0.44 ± 0.15 | 25.7 ± 1.8 (58) | 61.0 ± 12 (139) |
| 18d | OMe | CF₃ | H | 13.3 ± 3.9 | 157 ± 12 (12) | 344 ± 141 (26) |
| 19d | OMe | CF₃ | Me | 5.77 ± 1.78 | 118 ± 13 (20) | 231 ± 74 (40) |
| 22d | OMe | CF₃ | H | 7.55 ± 2.39 | 115 ± 12 (15) | 757 ± 334 (100) |
| 23d | OMe | CF₃ | Me | 8.14 ± 2.37 | 110 ± 14 (14) | 433 ± 206 (53) |
| 18e | OMe | i-Pr | H | 4.27 ± 1.34 | 239 ± 20 (56) | NT |
| 19e | OMe | i-Pr | Me | 0.58 ± 0.08 | 211 ± 19 (364) | NT |
| 22e | OMe | i-Pr | H | 1.44 ± 0.46 | 161 ± 11 (112) | NT |
| 23e | OMe | i-Pr | Me | 1.34 ± 0.48 | 156 ± 17 (116) | NT |
| 18f | H | 2-thiophene | H | 1.03 ± 0.13 | 1823 ± 347 (1770) | NT |
| 22f | H | 2-thiophene | H | 1.59 ± 0.56 | 900 ± 81 (566) | NT |
| 18g | H | Et | H | 7.18 ± 1.02 | 190 ± 13 (26) | NT |

TABLE 3-continued

| | | | | | |
|---|---|---|---|---|---|
| 22g | H | Et | H | 1.99 ± 0.48 | 107 ± 7.0 (54) | NT |
| GZR (1) | | | | 0.21 ± 0.03 | 49.1 ± 1.6 (234) | 30.3 ± 1.9 (144) |

TABLE 4

Antiviral activity against wild-type HCV and drug resistant variants

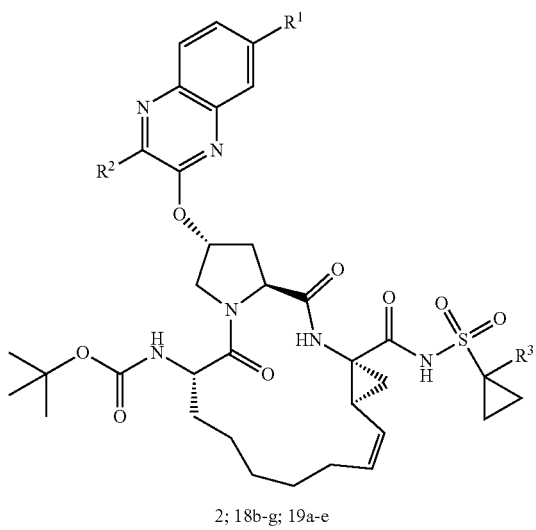

2; 18b-g; 19a-e

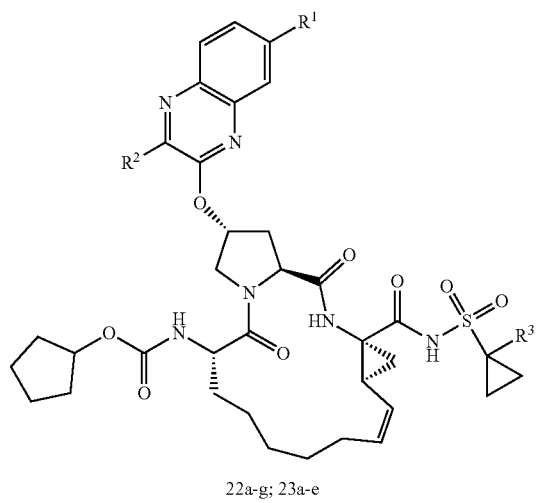

22a-g; 23a-e

| Inhibitor | R$^1$ | R$^2$ | R$^3$ | Replicon EC$_{50}$ (nM) (Fold change) | | | | |
|---|---|---|---|---|---|---|---|---|
| | | | | WT | R155K | A156T | D168A | D168V |
| 2 | OMe | Et | H | 0.33 | 1.75 (5) | 9.65 (29) | 6.31 (19) | 9.10 (28) |
| 19a | OMe | Et | Me | 0.43 | 1.80 (4) | 4.52 (11) | 4.97 (12) | 6.42 (15) |
| 22a | OMe | Et | H | 0.14 | 2.08 (15) | 11.8 (84) | 3.60 (26) | 11.9 (85) |
| 23a | OMe | Et | Me | 0.16 | 2.07 (13) | 10.6 (66) | 3.45 (22) | 7.08 (44) |
| 18b | OMe | Me | H | 0.39 | 1.17 (3) | 5.95 (15) | 4.24 (11) | 3.17 (8) |
| 19b | OMe | Me | Me | 0.30 | 0.80 (3) | 1.57 (5) | 2.37 (8) | 1.60 (5) |
| 22b | OMe | Me | H | 0.11 | 0.89 (8) | 2.88 (26) | 2.63 (24) | 4.32 (39) |
| 23b | OMe | Me | Me | 0.13 | 1.09 (8) | 3.99 (31) | 2.16 (17) | 2.85 (22) |
| 18c | OMe | Cl | H | 0.16 | 0.44 (3) | 16.2 (101) | 1.42 (9) | 0.73 (5) |
| 19c | OMe | Cl | Me | 0.18 | 0.40 (2) | 8.86 (49) | 1.07 (6) | 0.49 (3) |
| 22c | OMe | Cl | H | 0.15 | 0.59 (4) | 3.55 (24) | 1.32 (9) | 1.55 (10) |
| 23c | OMe | Cl | Me | 0.15 | 0.56 (4) | 4.32 (29) | 0.97 (6) | 1.09 (7) |
| 18d | OMe | CF$_3$ | H | 1.98 | 3.45 (2) | 36.2 (18) | 16.8 (8) | 17.1 (9) |
| 19d | OMe | CF$_3$ | Me | 1.52 | 2.30 (2) | 20.5 (13) | 8.64 (6) | 8.31 (5) |
| 22d | OMe | CF$_3$ | H | 4.86 | 7.97 (2) | 117 (24) | 15.1 (3) | 24.0 (5) |
| 23d | OMe | CF$_3$ | Me | 4.04 | 6.90 (2) | 75.9 (19) | 8.46 (2) | 11.4 (3) |
| 18e | OMe | i-Pr | H | 1.43 | 5.02 (4) | 25.7 (18) | 15.3 (11) | 23.7 (17) |
| 19e | OMe | i-Pr | Me | 1.86 | 4.14 (2) | 21.2 (11) | 11.9 (6) | 18.1 (10) |
| 22e | OMe | i-Pr | H | 0.48 | 7.63 (16) | 32.1 (67) | 7.96 (17) | 30.1 (63) |
| 23e | OMe | i-Pr | Me | 0.59 | 6.83 (12) | 27.6 (47) | 7.91 (13) | 18.2 (31) |
| 18f | H | 2-thiophene | H | 0.98 | 21.7 (22) | 256 (261) | 111 (113) | 193 (197) |
| 22f | H | 2-thiophene | H | 0.40 | 19.2 (48) | 183 (458) | 42.2 (106) | 70.0 (175) |
| 18g | H | Et | H | 0.46 | 1.81 (4) | 10.6 (23) | 8.55 (19) | 14.0 (30) |
| 22g | H | Et | H | 0.24 | 4.28 (18) | 24.6 (103) | 7.50 (31) | 19.3 (80) |
| GZR (1) | | | | 0.14 | 1.89 (14) | 238 (1700) | 9.69 (69) | 5.41 (39) |

TABLE 5

X-ray data collection and crystallographic refinement statistics

| | WT1a-19b | WT1a-18f |
|---|---|---|
| PDB code: | 5VOJ | 5VP9 |
| Resolution | 1.80 Å | 1.86 Å |
| Space group | P2$_1$2$_1$2$_1$ | P2$_1$2$_1$2$_1$ |
| Molecules in AU$^a$ | 1 | 1 |
| Cell dimensions | | |
| a (Å) | 55.4 | 54.8 |
| b (Å) | 58.6 | 58.4 |
| c (Å) | 59.9 | 60.4 |
| β (°) | 90 | 90 |
| Completeness (%) | 94.1 | 99.9 |
| Total reflections | 120670 | 111301 |
| Unique reflections | 17608 | 16852 |
| Average I/σ | 7.8 | 15.7 |
| Redundancy | 6.9 | 6.6 |
| R$_{sym}$ (%)$^b$ | 5.0 (15.9) | 6.0 (31.7) |

TABLE 5-continued

X-ray data collection and crystallographic refinement statistics

|  | WT1a-19b | WT1a-18f |
|---|---|---|
| RMSD[c] in | | |
| Bond lengths (Å) | 0.005 | 0.005 |
| Bond angles (°) | 1.1 | 0.9 |
| $R_{factor}$ (%)[d] | 16.0 | 16.8 |
| $R_{free}$ (%)[e] | 19.3 | 20.8 |

[a]AU, asymmetric unit.
[b]$R_{sym} = \Sigma|I - <I>|/\Sigma I$, where I = observed intensity, <I> = average intensity over symmetry equivalent; values in parentheses are for the highest resolution shell.
[c]RMSD, root mean square deviation.
[d]$R_{factor} = \Sigma||F_o| - |F_c||/\Sigma|F_o|$.
[e]$R_{free}$ was calculated from 5% of reflections, chosen randomly, which were omitted from the refinement process.

As compounds 18f and 22f lacked the C-7 substituent at the P2 quinoxaline, analogues 18g and 22g were prepared to investigate the effect of this group on inhibitor potency. Compared to 2, analogue 18g experienced about 2-fold decrease in biochemical potency and only minor loss in replicon potency against WT and drug resistant variants. The P4 cyclopentyl analogue 22g resulted in about 2-fold reduced potency compared to the corresponding compound 22a. Thus removal of the C-7 methoxy group has minimal effect on inhibitor potency. Without wishing to be bound by the theory, the slightly reduced potency of 18g and 22g is likely due to the reduced hydrophobic interactions with the aromatic ring of Tyr56 and the methylene portion of His57 of the catalytic triad. In contrast, the observed potency losses against resistant variants for the 3-(thiophen-2-yl)quinoxaline compounds most likely result from loss of interactions of the 2-thiophene moiety with the S2 subsite residues of the protease.

Effects of P2 Substituent Size and Flexibility

Taken together, the SAR results indicate that resistance profiles of compound 2 and analogues are strongly influenced by the substituent at the 3-position of P2 quinoxaline and N-terminal capping group. While all PIs showed reduced potency against drug resistance variants in both enzyme inhibition and replicon assays, fold potency losses varied significantly depending on the substituents at the 3-position of P2 quinoxaline. To evaluate susceptibility to the clinically important D168A variant, to which all current NS3/4A PIs are susceptible, potencies were normalized to WT for PIs with the same P4 capping groups (FIG. 6). Fold changes in Ki against the D168A protease variant for PIs with the same P1' and P4 capping groups largely trended with the size of the substituent at the 3-position of P2 quinoxaline, with the exception of trifluoromethyl compounds. Losses in potency were significantly higher for compounds with the larger 2-thiophene substituent at the P2 quinoxaline. These results strongly support using the substrate envelope model to reduce direct inhibitor interactions in the S2 subsite, thereby reducing inhibitor susceptibility to drug resistance.

The reduced potencies of NS3/4A PIs against drug resistant variants R155K, A156T, and D168A/V mainly result from disruption of the electrostatic interactions between Arg155 and Asp168. Compared to 1, compound 2 and most analogues incorporating flexible P2 quinoxaline showed lower fold-changes in potency against these variants (Table 3 and Table 4).

In these P1-P3 macrocyclic PIs the conformational flexibility of the P2 allows this moiety to adapt to the structural changes caused by mutations at Arg155, Ala156 and Asp168, resulting in better resistance profiles. Potency losses were higher for compound 1 because constraint imposed by the macrocycle does not allow the P2 moiety to adapt to the structural changes resulting from these mutations. Compound 1 and similar P2-P4 macrocyclic PIs, such as voxilaprevir and glecaprevir, are likely to be more susceptible to mutations that cause significant structural changes in the protease active site. However, the P1-P3 macrocyclic compounds disclosed herein are likely to be more effective against clinically relevant drug resistant variants. More broadly, combining the substrate envelope model with optimal conformational flexibility provides a rational approach to design NS3/4A PIs with improved resistance profiles.

Compound Syntheses

The NS3/4A PIs with diverse P2 quinoxaline moieties were synthesized using the reaction sequence outlined in Scheme 1.

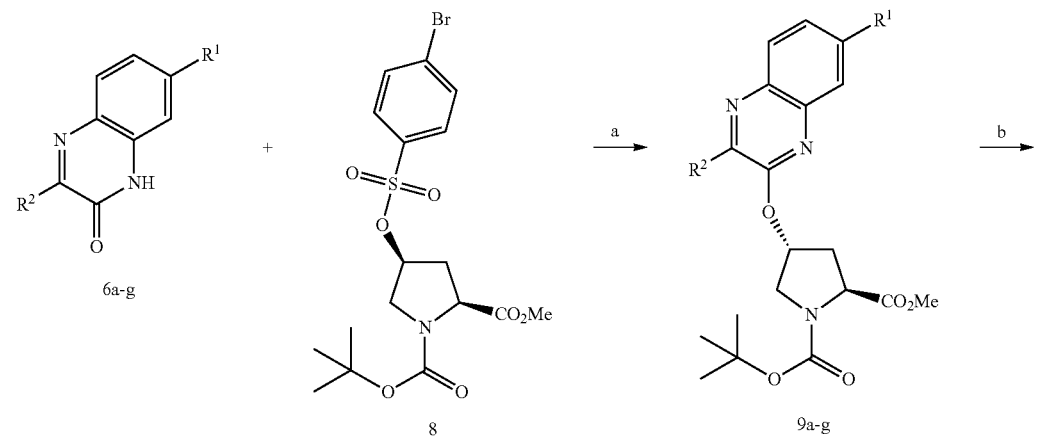

Scheme 1. Synthesis of HCV NS3/4A protease inhibitors

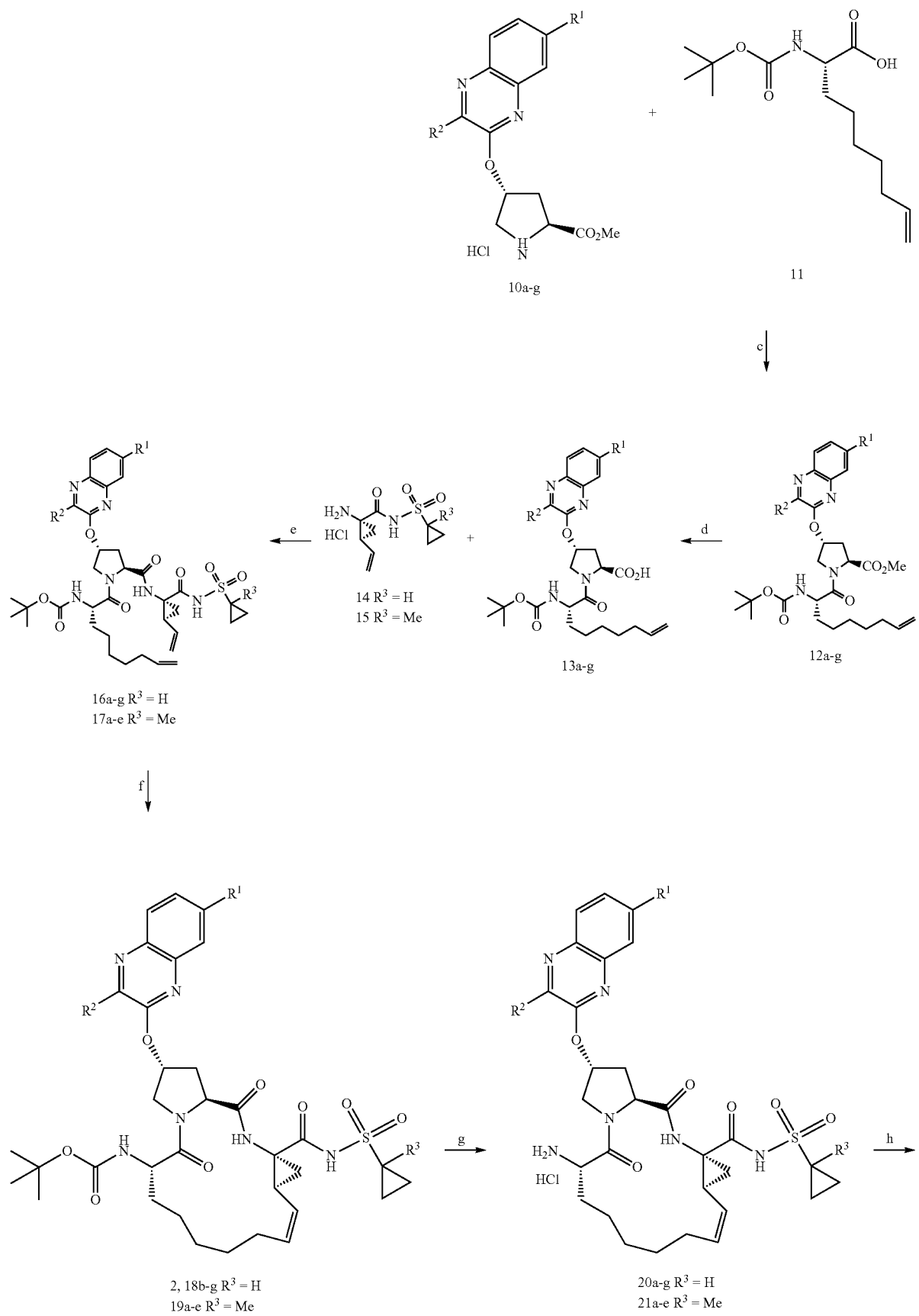
-continued

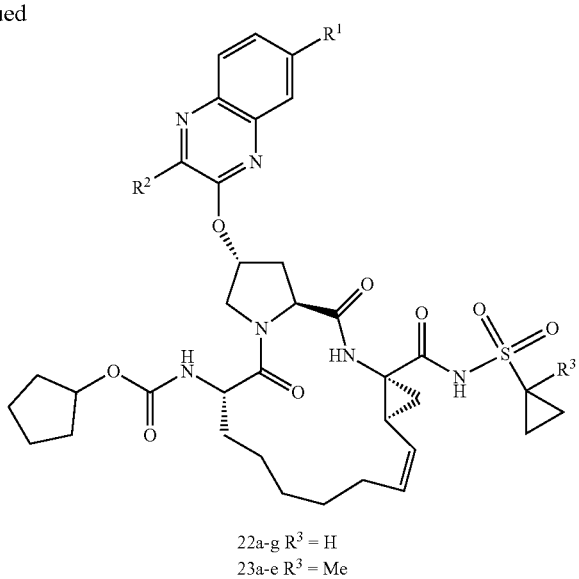

22a-g R³ = H
23a-e R³ = Me

Reagents and conditions: (a) Cs₂CO₃, NMP, 55° C., 6 h; (b) 4N HCl in dioxane, CH₂Cl₂, RT, 3 h; (c) HATU, DIEA, DMF, RT, 4 h; (d) LiOH·H₂O, THF, H₂O, RT, 24 h; (e) HATU, DIEA, DMF, RT, 2 h; (f) Zhan 1B catalyst, 1,2-DCE, 70° C., 6 h; (g) 4N HCl, dioxane, RT, 3 h; (h) N-(cyclopentyloxycarbonyloxy)-succinimide, DIEA, CH₃CN, RT, 36 h.

A $Cs_2CO_3$-mediated $S_N2$ reaction of 3-substituted quinoxalin-2-ones 6a-g with the activated proline derivative 8 provided the key P2 intermediates 9a-g in 75-90% yield. The alternate $S_NAr$ reaction between activated quinoxaline derivatives and Boc-protected hydroxy-proline resulted in lower yields, and purification of the resulting P2 acid products was significantly more challenging. The 3-substituted 7-methoxy-quinoxalin-2-ones 6a-b and 6d-e were prepared by condensation reactions of 4-methoxybenzene-1,2-diamine with the corresponding ethyl glyoxylates. The 3-chloro-7-methoxyquinoxalin-2-one 6c was prepared according to a reported method. (Harper, et al. *ACS Med. Chem. Lett.* 2012, 3, 332-336.)

The P1-P3 macrocyclic PIs were assembled from the P2 intermediates 9a-g using a sequence of deprotection and peptide coupling steps followed by the ring-closing metathesis (RCM) reaction (Method A). Removal of the Boc group in 9a-g using 4 N HCl provided the amine salts 10a-g, which were coupled with the amino acid 11 in the presence of HATU and DIEA to yield the P2-P3 ester intermediate 12a-g.

Hydrolysis of these esters with LiOH and reaction of the resulting carboxylic acids 13a-g with the P1-P1' fragments 14 and 15 under HATU/DIEA coupling conditions provided the bis-olefin intermediates 16a-g and 17a-e. Cyclization of the bis-olefin intermediates was accomplished using a highly efficient RCM catalyst Zhan 1B, and provided the inhibitors 18b-g and 19a-e in 45-80% yield.

Interestingly, RCM reactions of bis-olefins 17a-e bearing the 1-methylcyclopropylsulfonamide provided higher yield than the corresponding cyclopropylsulfonamide analogues 16a-g. Removal of the Boc group and reaction of the resulting amine salts 20a-g and 21a-e with the N-(cyclopentyloxycarbonyloxy)-succinimide in the presence of DIEA afforded the inhibitors 22a-g and 23a-e with the N-terminal cyclopentyl P4 moiety.

Scheme 2. Alternative synthesis of HCV NS3/4A protease inhibitors.

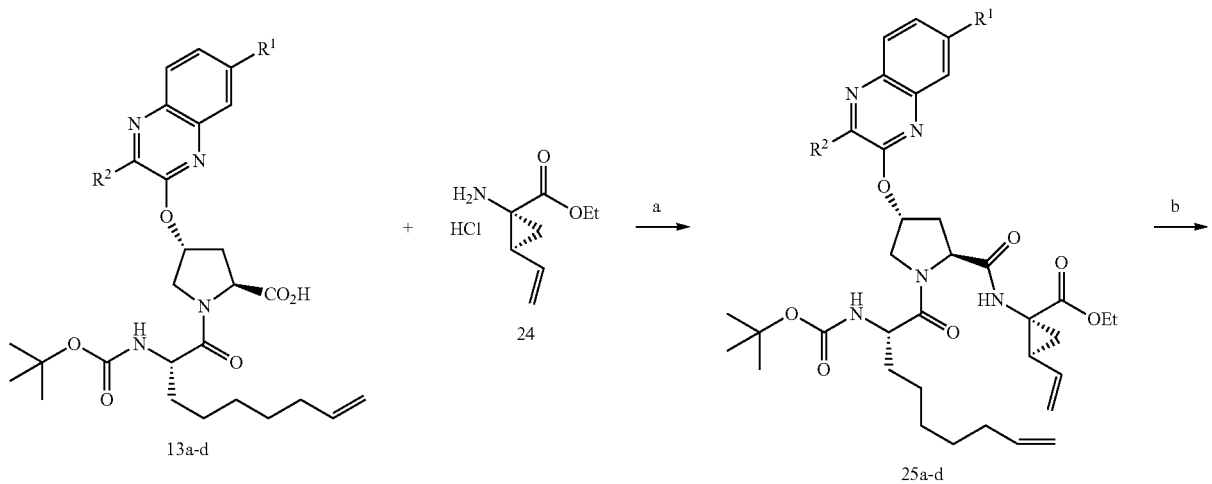

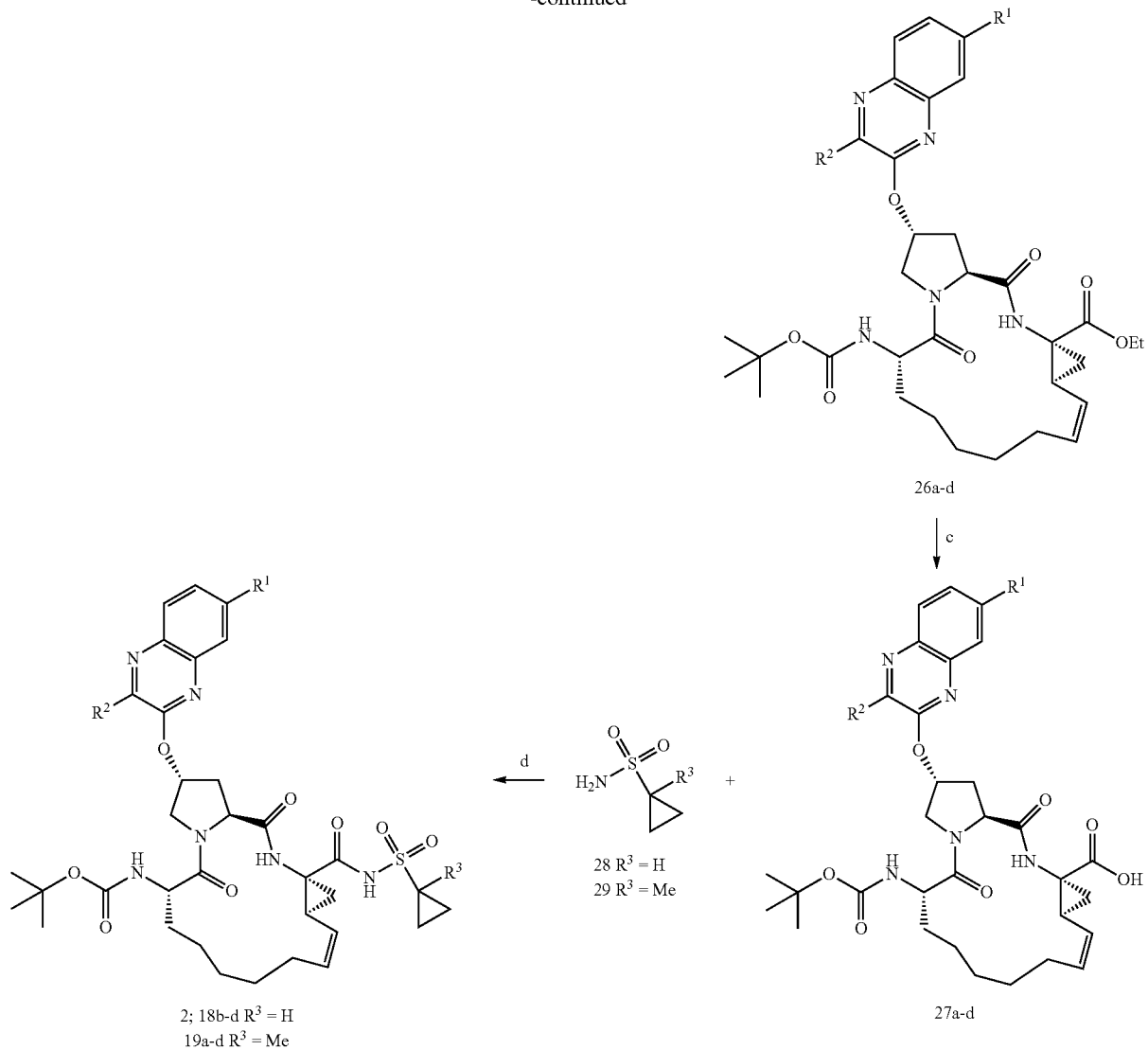

Reagents and conditions: (a) HATU, DIEA, DMF, RT, 2 h; (b) Zhan 1B catalyst, 1,2-DCE, 70° C., 5 h; (c) LiOH·H₂O, THF, MeOH, H₂O, RT, 24 h; (d) CDI, THF, DBU, reflux, 1.5 h, RT, 36 h.

A subset of inhibitors was synthesized using an alternate reaction sequence that allowed late-stage modification at both the P1' and P4 positions as illustrated in Scheme 2 (Method B). The P2-P3 acid intermediates 13a-d were reacted with the commercially available amine 24 under HATU/DIEA coupling conditions to afford the bis-olefin intermediates 25a-d. RCM reaction in the presence of Zhan 1B catalyst provided the macrocyclic intermediates 26a-d in 75-90% yield, which was better than that obtained in the presence of the P1' acylsulfonamide.

The P1-P3 macrocyclic core intermediates 26a-d can be modified in either direction after removing the C- or N-terminal protecting groups. Thus, hydrolysis of the C-terminal ethyl ester with LiOH provided the acids 27a-d, which were then reacted with either cyclopropylsulfonamide 28 or 1-methylcyclopropylsulfonamide 29 in the presence of CDI and DBU to afford the final inhibitors 18b-d and 19a-d. The N-terminal tert-butyl capping group was replaced with the cyclopentyl moiety as described earlier to provide the target inhibitors 22a-d and 23a-d.

Experimental

All reactions were performed in oven-dried round bottomed or modified Schlenk flasks fitted with rubber septa under argon atmosphere, unless otherwise noted. All reagents and solvents, including anhydrous solvents, were purchased from commercial sources and used as received. Flash column chromatography was performed using silica gel (230-400 mesh, EMD Millipore). Thin-layer chromatography (TLC) was performed using silica gel (60 F-254) coated aluminum plates (EMD Millipore), and spots were visualized by exposure to ultraviolet light (UV), exposure to iodine adsorbed on silica gel, and/or exposure to an acidic solution of p-anisaldehyde (anisaldehyde) followed by brief heating. ¹H NMR and ¹³C NMR spectra were acquired on Varian Mercury 400 MHz and Bruker Avance III HD 500 MHz NMR instruments. Chemical shifts are reported in ppm (δ scale) with the residual solvent signal used as reference and coupling constant (J) values are reported in hertz (Hz). Data are presented as follows: chemical shift, multiplicity (s=singlet, d=doublet, dd=doublet of doublet, t=triplet, q=quartet, m=multiplet, br s=broad singlet), coupling constant in Hz, and integration. High-resolution mass spectra (HRMS) were recorded on a Thermo Scientific Orbitrap Velos Pro mass spectrometer coupled with a Thermo Scientific Accela 1250 UPLC and an autosampler using electrospray ionization (ESI) in the positive mode. The purity of final compounds was determined by analytical HPLC and was found to be ≥95% pure. HPLC was performed on a Waters Alliance 2690 system equipped with a Waters 2996 photodiode array detector and an autosampler under the following conditions: column, Phenomenex Luna-2 RP-C18 (5 μm, 4.6×250 mm, 120 Å, Torrance, Calif.); solvent A, $H_2O$ containing 0.1% formic acid (FA), solvent B, $CH_3CN$ containing 0.1% FA; gradient, 50% B to 100% B over 15 min followed by 100% B over 5 min; injection volume, 10 μL; flow rate, 1 mL/min. Retention times and purity data for each target compound are provided in the experimental section.

Typical Procedures for Synthesis of Protease IOnhibitors using Method A 1-(tert-Butyl) 2-methyl (2S,4R)-4-((3-ethyl-7-methoxyquinoxalin-2-yl)oxy)pyrrolidine-1,2-dicarboxylate (9a)

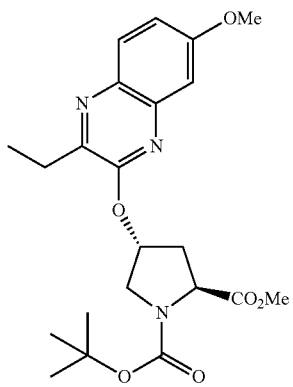 [SMILES: CCc1nc2ccc(OC)cc2nc1O[C@@H]1C[C@@H](C(=O)OC)N(C(=O)OC(C)(C)C)C1]

A solution of 3-ethyl-7-methoxyquinoxalin-2-one 6a (3.0 g, 14.7 mmol) in anhydrous NMP (45 mL) was treated with $Cs_2CO_3$ (7.40 g, 22.7 mmol). After stirring the reaction mixture at room temperature for 15 min, proline derivative 8 (6.20 g, 13.3 mmol) was added in one portion. The reaction mixture was heated to 55° C., stirred for 4 h, and then another portion of proline derivative 8 (0.48 g, 1.0 mmol) was added. The resulting reaction mixture was stirred at 55° C. for additional 2 h, cooled to room temperature, quenched with aqueous 1 N HCl solution (150 mL), and extracted with EtOAc (300 mL). The organic fraction was washed successively with saturated aqueous $NaHCO_3$ and NaCl (150 mL each), dried ($Na_2SO_4$), filtered, and evaporated under reduced pressure. The residue was purified by flash column chromatography using 15-30% EtOAc/hexanes as the eluent to provide 9a (5.50 g, 87%) as a white foamy solid. $^1H$ NMR (400 MHz, $CDCl_3$) (mixture of rotamers, major rotamer) δ 7.85 (d, J=9.0 Hz, 1H), 7.18 (m, 1H), 7.11 (d, J=2.8 Hz, 1H), 5.73 (br s, 1H), 4.47 (t, J=8.0 Hz, 1H), 3.98-3.86 (m, 5H), 3.78 (s, 3H), 2.92 (q, J=7.2 Hz, 2H), 2.68-2.60 (m, 1H), 2.43-2.36 (m, 1H), 1.43 (s, 9H), 1.31 (t, J=7.2 Hz, 3H) ppm; $^{13}C$ NMR (100 MHz, $CDCl_3$) δ 173.56, 160.59, 155.38, 154.02, 148.95, 141.26, 134.12, 129.07, 119.02, 106.11, 80.76, 73.81, 58.43, 55.93, 52.73, 52.40, 36.88, 28.47, 26.68, 11.97 ppm; HRMS (ESI) m/z: $[M+H]^+$ calcd for $C_{22}H_{30}N_3O_6$, 432.2129; found 432.2135.

1-(tert-Butyl) 2-methyl (2S,4R)-4-((7-methoxy-3-(trifluoromethyl)quinoxalin-2-yl)oxy)pyrrolidine-1,2-dicarboxylate (9d)

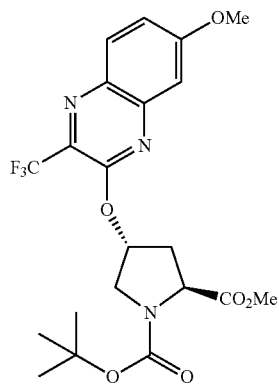 [SMILES: COC(=O)[C@@H]1C[C@@H](Oc2nc3cc(OC)ccc3nc2C(F)(F)F)CN1C(=O)OC(C)(C)C]

The same procedure was used as described above for compound 9a. 7-methoxy-3-(trifluoromethyl)quinoxalin-2(1H)-one 8d (4.76 g, 19.5 mmol) in NMP (65 mL) was treated with $Cs_2CO_3$ (9.80 g, 30.0 mmol) and proline derivative 3 (9.0 g, 19.3 mmol) to provide 9d (6.50 g, 71%) as a pale yellow foamy solid. $^1H$ NMR (500 MHz, $CDCl_3$) (mixture of rotamers, major rotamer) δ 7.77 (d, J=9.0 Hz, 1H), 7.48-7.43 (m, 2H), 5.76 (br s, 1H), 4.50 (t, J=8.0 Hz, 1H), 3.97-3.91 (m, 5H), 3.78 (s, 3H), 2.69-2.64 (m, 1H), 2.41-2.34 (m, 1H), 1.42 (s, 9H) ppm; $^{13}C$ NMR (125 MHz, $CDCl_3$) δ 173.43, 159.58, 153.98, 152.11, 138.39, 137.22, 127.99, 125.73, 120.70 (q, J=273.4 Hz), 107.64, 80.69, 74.62, 58.27, 56.02, 52.32, 52.11, 36.70, 28.34 ppm; $^{19}F$ NMR (470 MHz, $CDCl_3$); −67.73 ppm; HRMS (ESI) m/z: $[M+H]^+$ calcd for $C_{21}H_{25}F_3N_3O_6$, 472.1690; found 472.1689.

Methyl (2S,4R)-1-((S)-2-((tert-butoxycarbonyl)amino)non-8-enoyl)-4-((3-ethyl-7-methoxyquinoxalin-2-yl)oxy)pyrrolidine-2-carboxylate (12a)

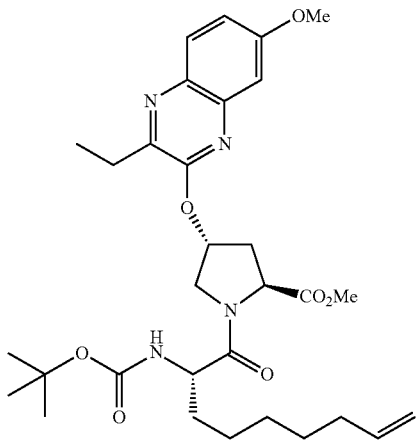 [SMILES: C=CCCCCC[C@H](NC(=O)OC(C)(C)C)C(=O)N1C[C@H](Oc2nc3cc(OC)ccc3nc2CC)C[C@H]1C(=O)OC]

A solution of ester 9a (4.80 g, 11.1 mmol) in anhydrous CH$_2$Cl$_2$ (30 mL) was treated with a solution of 4 N HCl in 1,4-dioxane (30 mL). After stirring the reaction mixture at room temperature for 3 h, solvents were evaporated under reduced pressure, and the residue was dried under high vacuum. The pale yellow solid was triturated with diethyl ether (3×30 mL) and dried under high vacuum to yield the amine salt 10a (4.0 g, 98%) as an off-white powder.

A mixture of amine salt 10a (4.0 g, 10.9 mmol) and (S)-2-((tert-butoxycarbonyl)amino)non-8-enoic acid 11 (3.0 g, 11.1 mmol) in anhydrous DMF (60 mL) was treated with DIEA (7.30 mL, 44.2 mmol) and HATU (6.35 g, 16.7 mmol). The resulting reaction mixture was stirred at room temperature for 4 h, then diluted with EtOAc (400 mL), and washed successively with aqueous 0.5 N HCl, saturated aqueous NaHCO$_3$, and saturated aqueous NaCl (250 mL each). The organic portion was dried (Na$_2$SO$_4$), filtered, and evaporated under reduced pressure. The residue was purified by flash chromatography using 20-30% EtOAc/hexanes as the eluent to provide 12a (5.50 g, 86%) as a white foamy solid. $^1$H NMR (400 MHz, CDCl$_3$) (mixture of rotamers, major rotamer) δ 7.86 (d, J=8.8 Hz, 1H), 7.20 (dd, J=9.2, 2.8 Hz, 1H), 7.12 (d, J=2.8 Hz, 1H), 5.87-5.75 (m, 2H), 5.20 (d, J=8.4 Hz, 1H), 5.02-4.92 (m, 2H), 4.73 (t, J=8.4 Hz, 1H), 4.38 (q, J=7.2 Hz, 1H), 4.17 (d, J=12.0 Hz, 1H), 4.06 (dd, J=11.6, 4.4 Hz, 1H), 3.94 (s, 3H), 3.78 (s, 3H), 2.90 (q, J=7.6 Hz, 2H), 2.69-2.64 (m, 1H), 2.41-2.34 (m, 1H), 2.05 (app q, J=6.8 Hz, 2H), 1.82-1.74 (m, 1H), 1.63-1.56 (m, 1H), 1.45-1.25 (m, 18H) ppm; $^{13}$C NMR (100 MHz, CDCl$_3$) δ 172.34, 171.96, 160.61, 155.61, 155.13, 148.95, 141.08, 139.18, 129.22, 119.08, 114.58, 106.14, 79.84, 74.48, 58.19, 55.91, 52.88, 52.67, 52.05, 35.16, 33.88, 32.88, 29.14, 28.96, 28.46, 26.52, 24.92, 11.86 ppm; HRMS (ESI) m/z: [M+H]$^+$ calcd for C$_{31}$H$_{45}$N$_4$O$_7$ 585.3283; found 585.3286.

Methyl (2S,4R)-1-((S)-2-((tert-butoxycarbonyl)amino)non-8-enoyl)-4-((7-methoxy-3-(trifluoromethyl)quinoxalin-2-yl)oxy)pyrrolidine-2-carboxylate (12d)

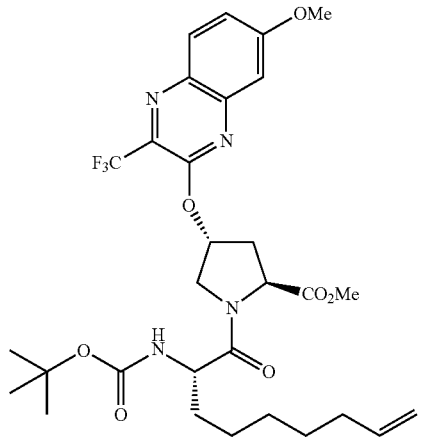 [SMILES: C=CCCCCC[C@H](NC(=O)OC(C)(C)C)C(=O)N1C[C@H](Oc2nc3cc(OC)ccc3nc2C(F)(F)F)C[C@H]1C(=O)OC]

The same procedure was used as described above for compound 12a. Compound 9d (6.0 g, 12.7 mmol) was treated with 4 N HCl (40 mL) to afford amine salt 10d (5.10 g, 12.5 mmol), which was coupled with acid 11 (3.80 g, 14.0 mmol) using DIEA (9.25 mL, 56.0 mmol) and HATU (7.60 g, 20.0 mmol) to provide 12d (6.40 g, 81%) as a pale yellow foamy solid. $^1$H NMR (500 MHz, CDCl$_3$) (mixture of rotamers, major rotamer) δ 7.78 (d, J=9.0 Hz, 1H), 7.48 (dd, J=9.0, 2.5 Hz, 1H), 7.44 (d, J=2.5 Hz, 1H), 5.86 (br s, 1H), 5.84-5.78 (m, 1H), 5.18 (d, J=9.0 Hz, 1H), 5.01-4.92 (m, 2H), 4.75 (t, J=8.0 Hz, 1H), 4.35 (q, J=7.5 Hz, 1H), 4.19 (d, J=12.0 Hz, 1H), 4.08 (dd, J=11.5, 4.5 Hz, 1H), 3.95 (s, 3H), 3.78 (s, 3H), 2.70-2.65 (m, 1H), 2.41-2.35 (m, 1H), 2.04 (app q, J=7.0 Hz, 2H), 1.80-1.75 (m, 1H), 1.60-1.54 (m, 1H), 1.45-1.28 (m, 15H) ppm; $^{13}$C NMR (125 MHz, CDCl$_3$) δ 172.10, 171.60, 159.99, 155.37, 151.78, 138.98, 138.41, 136.93, 134.40 (q, J=36.3 Hz), 127.85, 125.66, 120.53 (q, J=273.4 Hz), 114.33, 107.54, 79.58, 75.05, 57.83, 55.91, 52.44, 52.33, 51.75, 34.77, 33.65, 32.70, 28.91, 28.73, 28.18, 24.70 ppm; $^{19}$F NMR (470 MHz, CDCl$_3$); −67.73 ppm; HRMS (ESI) m/z: [M+H]$^+$ calcd for C$_{30}$H$_{40}$F$_3$N$_4$O$_7$, 625.2844; found 625.2844.

tert-Butyl ((S)-1-((2S,4R)-2-(((1R,2S)-1-((cyclopropylsulfonyl)carbamoyl)-2-vinylcyclopropyl)carbamoyl)-4-((3-ethyl-7-methoxyquinoxalin-2-yl)oxy)pyrrolidin-1-yl)-1-oxonon-8-en-2-yl)carbamate (16a)

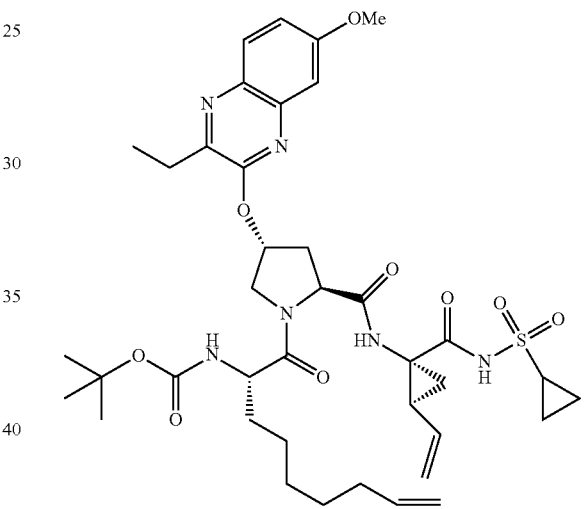

A solution of ester 12a (5.86 g, 10.0 mmol) in THF-H$_2$O mixture (1:1, 140 mL) was treated with LiOH.H$_2$O (1.40 g, 33.4 mmol). The resulting reaction mixture was stirred at room temperature for 24 h. The reaction mixture was cooled to ~5° C., acidified to a pH of 2.0 by slow addition of aqueous 0.25 N HCl (~200 mL), and extracted with EtOAc (2×400 mL). The organic portions were washed separately with saturated aqueous NaCl (200 ml), dried (Na$_2$SO$_4$), filtered, and evaporated under reduced pressure. The gummy residue was dissolved in CHCl$_3$ (50 mL), concentrated under reduced pressure, and the residue was dried under high vacuum overnight to yield the acid 13a (5.70 g, 100%) as a white foamy solid.

A mixture of acid 13a (2.10 g, 3.7 mmol) and amine salt 14 (1.20 g, 4.5 mmol) in anhydrous DMF (35 mL) was treated with DIEA (2.43 mL, 14.7 mmol) and HATU (2.1 g, 5.5 mmol). The resulting reaction mixture was stirred at room temperature for 2.5 h, then diluted with EtOAc (300 mL) and washed successively with aqueous 0.5 N HCl, saturated aqueous NaHCO3, and saturated aqueous NaCl (200 mL each). The organic portion was dried (Na$_2$SO$_4$), filtered, and evaporated under reduced pressure. The residue was purified by flash chromatography using 50-70% EtOAc/ hexanes as the eluent to provide the bis-olefin compound 16a (2.50 g, 86%) as a white solid.

$^1$H NMR (400 MHz, CDCl$_3$) δ 10.24 (s, 1H), 7.84 (d, J=8.8 Hz, 1H), 7.18 (dd, J=8.8, 2.4 Hz, 1H), 7.13 (d, J=2.8 Hz, 1H), 7.04 (s, 1H), 5.91 (br s, 1H), 5.85-5.73 (m, 2H), 5.32 (d, J=8.4 Hz, 1H), 5.27 (d, J=17.2 Hz, 1H), 5.14 (d, J=11.2 Hz, 1H), 5.01-4.90 (m, 2H), 4.47 (t, J=7.6 Hz, 1H), 4.38-4.33 (m, 1H), 4.20 (d, J=11.6 Hz, 1H), 4.02 (dd, J=11.2, 4.0 Hz, 1H), 3.94 (s, 3H), 2.96-2.84 (m, 3H), 2.56-2.51 (m, 2H), 2.11 (q, J=8.8 Hz, 1H), 2.05-1.99 (m, 3H), 1.74-1.54 (m, 2H), 1.47-1.10 (m, 21H), 1.08-1.03 (m, 2H) ppm; $^{13}$C NMR (100 MHz, CDCl$_3$) δ 174.09, 172.58, 168.69, 160.54, 155.89, 154.99, 148.88, 140.95, 139.07, 134.69, 132.71, 129.45, 119.02, 118.77, 114.67, 106.13, 80.0, 74.66, 60.61, 55.91, 53.42, 52.62, 41.83, 35.46, 34.47, 33.89, 32.40, 31.39, 28.98, 28.89, 28.47, 26.68, 25.47, 23.83, 11.85, 6.68, 6.26 ppm; HRMS (ESI) m/z: [M+H]$^+$ calcd for C$_{39}$H$_{55}$N$_6$O$_9$S, 783.3746; found 783.3734.

tert-Butyl ((S)-1-((2S,4R)-4-((3-ethyl-7-methoxyquinoxalin-2-yl)oxy)-2-(((1R,2S)-1-(((1-methylcyclopropyl)sulfonyl)carbamoyl)-2-vinylcyclopropyl)carbamoyl)pyrrolidin-1-yl)-1-oxonon-8-en-2-yl)carbamate (17a)

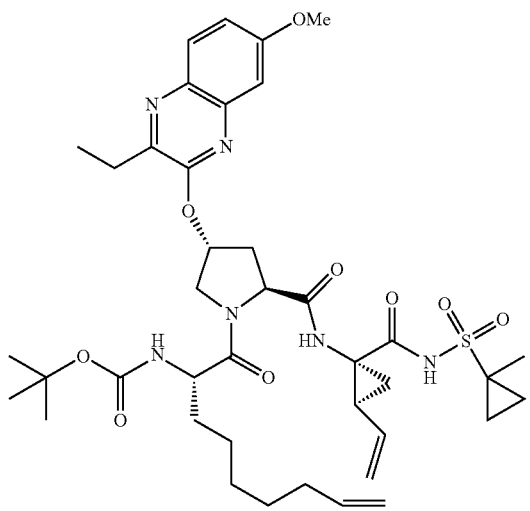 [SMILES: C=CCCCCC[C@H](NC(=O)OC(C)(C)C)C(=O)N1C[C@H](Oc2nc3cc(OC)ccc3nc2CC)C[C@H]1C(=O)N[C@]1(C(=O)NS(=O)(=O)C2(C)CC2)C[C@H]1C=C]

The same procedure was used as described above for compound 16a. Acid 13a (1.50 g, 2.6 mmol) was coupled with amine salt 15 (0.90 g, 3.2 mmol) using DIEA (1.75 mL, 10.6 mmol) and HATU (1.50 g, 3.9 mmol) to provide the bis-olefin compound 17a (1.75 g, 84%) as a white solid. $^1$H NMR (400 MHz, CDCl$_3$) δ 10.02 (s, 1H), 7.84 (d, J=9.2 Hz, 1H), 7.19 (dd, J=8.8, 2.8 Hz, 1H), 7.13 (d, J=2.8 Hz, 1H), 7.06 (s, 1H), 5.90 (br s, 1H), 5.83-5.73 (m, 2H), 5.37 (d, J=9.2 Hz, 1H), 5.27 (d, J=17.2 Hz, 1H), 5.14 (d, J=10.8 Hz, 1H), 5.98 (dd, J=17.2, 1.6 Hz, 1H), 4.92 (dd, J=10.4, 1.2 Hz, 1H), 4.48 (t, J=8.0 Hz, 1H), 4.39-4.33 (m, 1H), 4.16 (d, J=12.0 Hz, 1H), 4.02 (dd, J=11.6, 4.0 Hz, 1H), 3.94 (s, 3H), 2.89 (q, J=7.6 Hz, 2H), 2.57-2.50 (m, 2H), 2.12 (q, J=8.8 Hz, 1H), 2.05-1.99 (m, 3H), 1.75-1.58 (m, 4H), 1.49 (s, 3H), 1.45-1.18 (m, 19H), 0.93-0.79 (m, 2H) ppm; $^{13}$C NMR (100 MHz, CDCl$_3$) δ 173.79, 172.41, 167.51, 160.31, 155.71, 154.76, 148.63, 140.73, 138.85, 134.41, 132.60, 129.18, 118.80, 118.54, 114.41, 105.89, 79.74, 74.42, 60.36, 55.68, 53.17, 52.43, 41.71, 36.56, 35.23, 34.22, 33.64, 32.19, 28.70, 28.67, 28.25, 26.43, 25.35, 23.49, 18.37, 14.27, 13.29, 11.64 ppm; HRMS (ESI) m/z: [M+H]$^+$ calcd for C$_{40}$H$_{57}$N$_6$O$_9$S, 797.3902; found 797.3887.

tert-Butyl ((2R,6S,13aS,14aR,16aS,Z)-14a-((cyclopropylsulfonyl)carbamoyl)-2-((3-ethyl-7-methoxyquinoxalin-2-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (2)

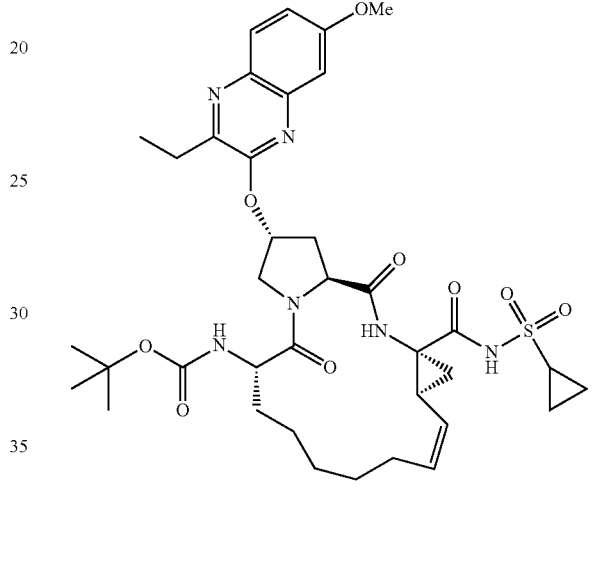

A degassed solution of bis-olefin 16a (1.40 g, 1.8 mmol) in 1,2-DCE (300 mL) was heated to 50° C. under argon, then Zhan 1b catalyst (0.150 g, 0.20 mmol) was added in two portions over 10 min. The resulting reaction mixture was heated to 70° C. and stirred for 6 h. The reaction mixture was cooled to room temperature and concentrated under reduced pressure. The residue was purified by flash chromatography using 50-80% EtOAc/hexanes as the eluent to yield the P1-P3 macrocyclic product 2 (0.72 g, 53%) as an off-white solid. $^1$H NMR (400 MHz, CDCl$_3$) δ 10.28 (s, 1H), 7.84 (d, J=9.6 Hz, 1H), 7.20-7.15 (m, 2H), 6.91 (s, 1H), 5.90 (br s, 1H), 5.69 (q, J=8.8 Hz, 1H), 5.14 (d, J=7.6 Hz, 1H), 4.96 (t, J=9.2 Hz, 1H), 4.59 (t, J=7.6 Hz, 1H), 4.49 (d, J=11.6 Hz, 1H), 4.30-4.24 (m, 1H), 4.02 (dd, J=10.8, 4.0 Hz, 1H), 3.94 (s, 3H), 2.94-2.85 (m, 3H), 2.70-2.51 (m, 3H), 2.31 (q, J=8.8 Hz, 1H), 1.93-1.64 (m, 2H), 1.60-1.05 (m, 24H), 0.95-0.89 (m, 1H) ppm; $^{13}$C NMR (100 MHz, CDCl$_3$) δ 177.15, 173.28, 168.02, 160.29, 155.00, 154.90, 148.66, 140.88, 136.31, 134.28, 128.90, 124.47, 118.82, 105.91, 79.84, 74.68, 59.45, 55.72, 53.08, 51.92, 44.57, 34.65, 32.81, 31.01, 29.70, 28.14, 27.11, 27.16, 26.31, 26.06, 22.16, 20.92, 11.56, 6.67, 6.12 ppm; HRMS (ESI) m/z: [M+H]$^+$ calcd for C$_{37}$H$_{51}$N$_6$O$_9$S, 755.3433; found 755.3410. Anal. HPLC: t$_R$ 14.23 min, purity 97%.

89 tert-Butyl ((2R,6S,13aS,14aR,16aS,Z)-2-((3-ethyl-7-methoxyquinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (19a)

90

Cyclopentyl ((2R,6S,13aS,14aR,16aS,Z)-14a-((cyclopropylsulfonyl)carbamoyl)-2-((3-ethyl-7-methoxyquinoxalin-2-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (22a)

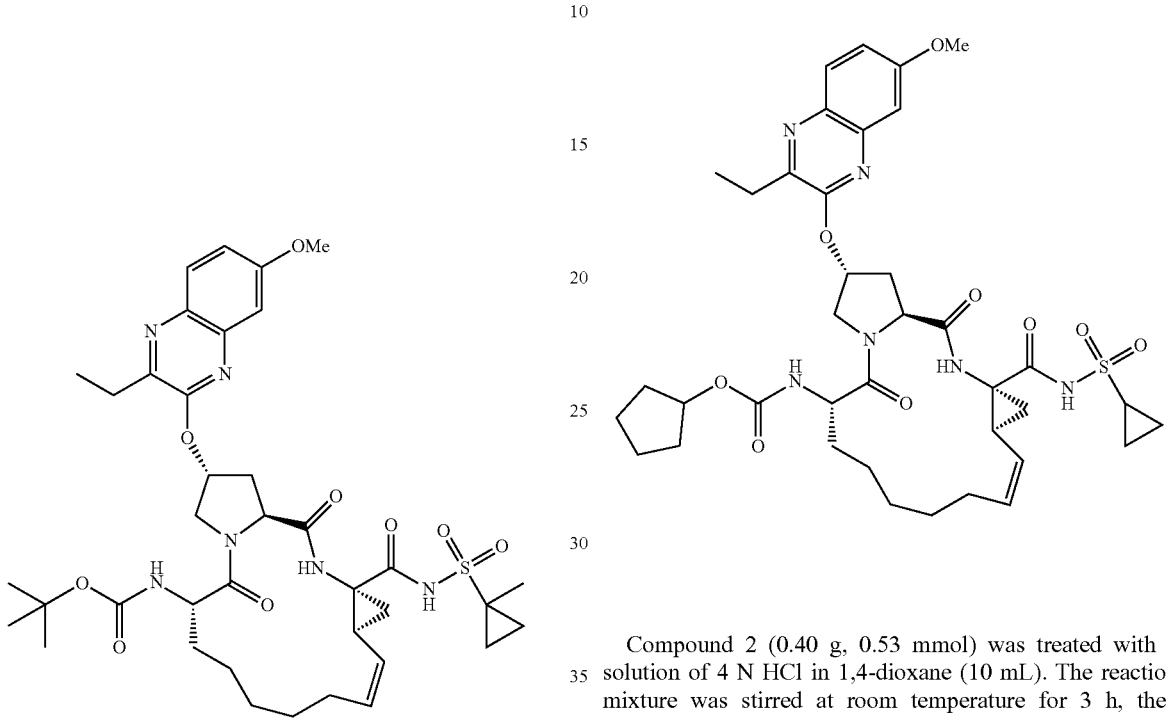

The same procedure was used as described above for compound 2. Bis-olefin 17a (1.45 g, 1.8 mmol) was treated with Zhan 1b catalyst (0.150 g, 0.20 mmol) in 1,2-DCE (300 mL) to afford the P1-P3 macrocyclic product 19a (1.0 g, 71%) as an off-white solid. $^1$H NMR (400 MHz, CDCl$_3$) δ 10.16 (s, 1H), 7.82 (d, J=10.0 Hz, 1H), 7.18-7.15 (m, 2H), 6.94 (s, 1H), 5.90 (br s, 1H), 5.69 (q, J=9.2 Hz, 1H), 5.16 (d, J=8.0 Hz, 1H), 4.99 (t, J=9.2 Hz, 1H), 4.59 (t, J=8.0 Hz, 1H), 4.49 (d, J=11.6 Hz, 1H), 4.30-4.25 (m, 1H), 4.04 (dd, J=11.6, 4.0 Hz, 1H), 3.94 (s, 3H), 2.87 (q, J=7.6 Hz, 2H), 2.70-2.51 (m, 3H), 2.33 (q, J=8.0 Hz, 1H), 1.92-1.68 (m, 4H), 1.60-1.15 (m, 24H), 0.85-0.78 (m, 2H) ppm; $^{13}$C NMR (100 MHz, CDCl$_3$) δ 177.19, 173.24, 167.0, 160.23, 154.99, 154.88, 148.73, 140.84, 136.26, 134.25, 129.03, 124.89, 118.72, 105.92, 79.84, 74.67, 59.48, 55.72, 53.11, 51.92, 44.71, 36.43, 34.68, 32.80, 29.62, 28.14, 27.09, 26.38, 26.12, 22.19, 20.93, 18.17, 14.51, 12.50, 11.54 ppm; HRMS (ESI) m/z: [M+H]$^+$ calcd for C$_{38}$H$_{53}$N$_6$O$_9$S, 769.3589; found 769.3561. Anal. HPLC: t$_R$ 15.01 min, purity 99%.

Compound 2 (0.40 g, 0.53 mmol) was treated with a solution of 4 N HCl in 1,4-dioxane (10 mL). The reaction mixture was stirred at room temperature for 3 h, then concentrated under reduced pressure, and the residue was dried under high vacuum. The off-white solid was triturated with diethyl ether (3×10 mL) and dried under high vacuum to yield the amine salt 20a (0.37 g, 100%) as a white powder.

A solution of the above amine salt 20a (0.37 g, 0.53 mmol) in anhydrous CH$_3$CN (15 mL) was treated with DIEA (0.35 mL, 2.1 mmol) and N-(cyclopentyloxycarbonyloxy)-succinimide (0.15 g, 0.66 mmol). The reaction mixture was stirred at room temperature for 36 h, then concentrated under reduced pressure and dried under high vacuum. The residue was purified by flash chromatography using 50-90% EtOAc/hexanes as the eluent to provide the target compound 22a (0.32 g, 79%) as a white solid. $^1$H NMR (400 MHz, CDCl$_3$) δ 10.29 (s, 1H), 7.83 (d, J=9.6 Hz, 1H), 7.21-7.16 (m, 2H), 6.94 (s, 1H), 5.93 (br s, 1H), 5.70 (q, J=8.8 Hz, 1H), 5.26 (d, J=8.0 Hz, 1H), 4.96 (t, J=8.4 Hz, 1H), 4.86-4.82 (m, 1H), 4.60 (t, J=7.6 Hz, 1H), 4.45 (d, J=11.2 Hz, 1H), 4.34-4.28 (m, 1H), 4.03 (dd, J=11.2, 4.0 Hz, 1H), 3.94 (s, 3H), 2.93-2.85 (m, 3H), 2.70-2.48 (m, 3H), 2.30 (q, J=8.8 Hz, 1H), 1.93-1.23 (m, 23H), 1.15-1.06 (m, 2H), 0.96-0.88 (m, 1H) ppm;

$^{13}$C NMR (100 MHz, CDCl$_3$) δ 177.18, 173.03, 168.04, 160.28, 155.65, 154.93, 148.78, 140.90, 136.27, 134.20, 128.92, 124.46, 118.80, 105.92, 77.87, 74.55, 59.47, 55.72, 53.01, 52.17, 44.54, 34.58, 32.72, 32.63, 32.59, 31.01, 29.70, 27.14, 27.05, 26.40, 26.05, 23.56, 22.16, 20.90, 11.61, 6.67, 6.12 ppm; HRMS (ESI) m/z: [M+H]$^+$ calcd for C$_{38}$H$_{51}$N$_6$O$_9$S, 767.3433; found 767.3408. Anal. HPLC: t$_R$ 14.50 min, purity 98%.

Cyclopentyl ((2R,6S,13aS,14aR,16aS,Z)-2-((3-ethyl-7-methoxyquinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (23a)

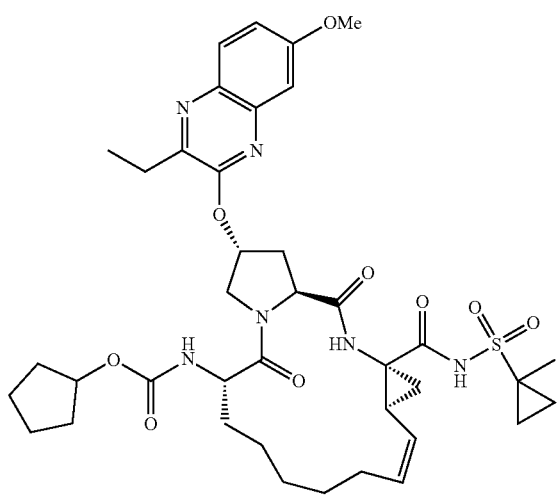 [SMILES: CCc1nc2ccc(OC)cc2nc1O[C@@H]1C[C@H]2C(=O)N[C@]3(C(=O)NS(=O)(=O)C4(C)CC4)C[C@H]3/C=C\CCCCC[C@H](NC(=O)OC3CCCC3)C(=O)N2C1]

The same procedure was used as described above for compound 22a. Compound 19a (0.40 g, 0.52 mmol) was treated 4 N HCl in 1,4-dioxane (10 mL) to yield the amine salt 21a, which was treated with DIEA (0.35 mL, 2.1 mmol) and N-(cyclopentyloxycarbonyloxy)-succinimide (0.15 g, 0.66 mmol) to provide the target compound 23a (0.30 g, 74%) as a white solid. $^1$H NMR (400 MHz, CDCl$_3$) δ 10.17 (s, 1H), 7.81 (d, J=9.6 Hz, 1H), 7.21-7.16 (m, 2H), 6.93 (s, 1H), 5.92 (br s, 1H), 5.70 (q, J=9.2 Hz, 1H), 5.26 (d, J=7.6 Hz, 1H), 4.99 (t, J=9.6 Hz, 1H), 4.86-4.81 (m, 1H), 4.59 (t, J=7.6 Hz, 1H), 4.45 (d, J=11.2 Hz, 1H), 4.34-4.28 (m, 1H), 4.04 (dd, J=11.6, 4.0 Hz, 1H), 3.94 (s, 3H), 2.87 (q, J=7.2 Hz, 2H), 2.70-2.48 (m, 3H), 2.32 (q, J=8.8 Hz, 1H), 1.92-1.23 (m, 27H), 0.85-0.78 (m, 2H) ppm; $^{13}$C NMR (100 MHz, CDCl$_3$) δ 177.21, 172.99, 166.98, 160.22, 155.63, 154.90, 148.84, 140.85, 136.22, 134.36, 129.05, 124.88, 118.70, 105.93, 77.86, 74.54, 59.51, 55.71, 53.05, 52.16, 44.70, 36.43, 34.61, 32.72, 32.64, 32.58, 29.63, 27.13, 27.06, 26.47, 26.12, 23.56, 22.18, 20.94, 18.17, 14.49, 12.50, 11.59 ppm; HRMS (ESI) m/z: [M+H]$^+$ calcd for C$_{39}$H$_{53}$N$_6$O$_9$S, 781.3589; found 781.3561. Anal. HPLC: tR 15.25 min, purity 99%.

Typical Procedures for Synthesis of Protease Inhibitors Using Method B 1-(tert-Butyl) 2-methyl (2S,4R)-4-((7-methoxy-3-(trifluoromethyl)quinoxalin-2-yl)oxy)pyrrolidine-1,2-dicarboxylate (9d)

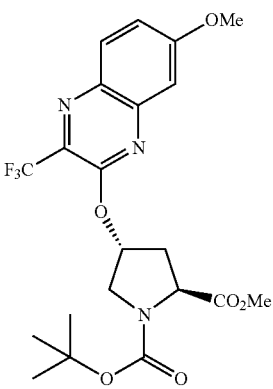 [SMILES: COC(=O)[C@@H]1C[C@@H](Oc2nc3cc(OC)ccc3nc2C(F)(F)F)CN1C(=O)OC(C)(C)C]

A solution of 7-methoxy-3-(trifluoromethyl)quinoxalin-2(1H)-one 6d (4.76 g, 19.5 mmol) in anhydrous NMP (65 mL) was treated with Cs$_2$CO$_3$ (9.80 g, 30.0 mmol). After stirring the reaction mixture at room temperature for 15 min, proline derivative 8 (8.50 g, 18.3 mmol) was added in one portion. The reaction mixture was heated to 55° C., stirred for 4 h, and then another portion of proline derivative 8 (0.48 g, 1.0 mmol) was added. The resulting reaction mixture was stirred at 55° C. for additional 2 h, cooled to room temperature, quenched with aqueous 1 N HCl solution (200 mL), and extracted with EtOAc (400 mL). The organic fraction was washed successively with saturated aqueous NaHCO$_3$ and NaCl (200 mL each), dried (Na$_2$SO$_4$), filtered, and evaporated under reduced pressure. The residue was purified by flash column chromatography using 15-30% EtOAc/hexanes as the eluent to provide 9d (6.50 g, 71%) as a pale yellow foamy solid. $^1$H NMR (500 MHz, CDCl$_3$) (mixture of rotamers, major rotamer) δ 7.77 (d, J=9.0 Hz, 1H), 7.48-7.43 (m, 2H), 5.76 (br s, 1H), 4.50 (t, J=8.0 Hz, 1H), 3.97-3.91 (m, 5H), 3.78 (s, 3H), 2.69-2.64 (m, 1H), 2.41-2.34 (m, 1H), 1.42 (s, 9H) ppm; $^{13}$C NMR (125 MHz, CDCl$_3$) δ 173.43, 159.58, 153.98, 152.11, 138.39, 137.22, 127.99, 125.73, 120.70 (q, J=273.4 Hz), 107.64, 80.69, 74.62, 58.27, 56.02, 52.32, 52.11, 36.70, 28.34 ppm; $^{19}$F NMR (470 MHz, CDCl$_3$); −67.73 ppm; HRMS (ESI) m/z: [M+H]$^+$ calcd for C$_{21}$H$_{25}$F$_3$N$_3$O$_6$, 472.1690; found 472.1689.

Methyl (2S,4R)-1-((S)-2-((tert-butoxycarbonyl)amino)non-8-enoyl)-4-((7-methoxy-3-(trifluoromethyl)quinoxalin-2-yl)oxy)pyrrolidine-2-carboxylate (12d)

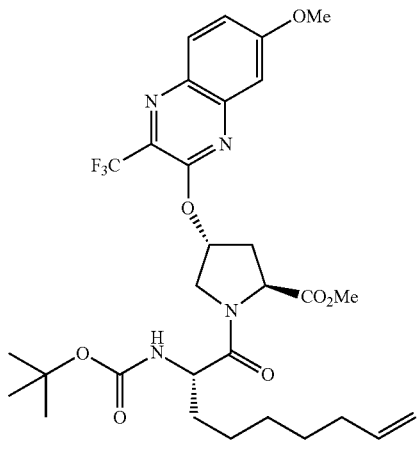

Ethyl (1R,2S)-1-((2S,4R)-1-((S)-2-((tert-butoxycarbonyl)amino)non-8-enoyl)-4-((7-methoxy-3-(trifluoromethyl)quinoxalin-2-yl)oxy)pyrrolidine-2-carboxamido)-2-vinylcyclopropane-1-carboxylate (25d)

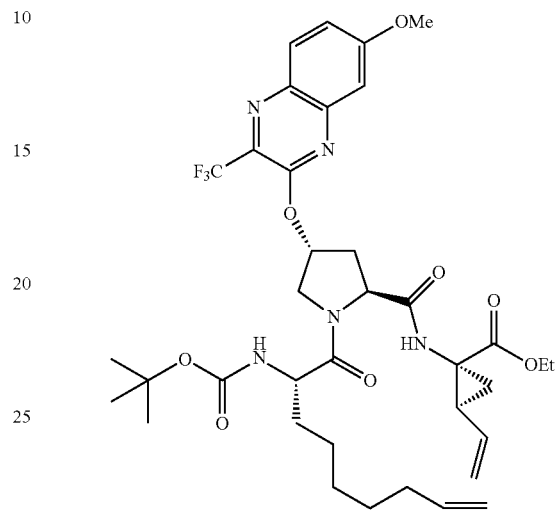

A solution of ester 9d (6.0 g, 12.7 mmol) in anhydrous $CH_2Cl_2$ (40 mL) was treated with a solution of 4 N HCl in 1,4-dioxane (40 mL). After stirring the reaction mixture at room temperature for 3 h, solvents were evaporated under reduced pressure, and the residue was dried under high vacuum. The pale yellow solid was triturated with diethyl ether (3×30 mL) and dried under high vacuum to yield the amine salt 10d (5.10 g, 98%) as a pale yellow powder.

A mixture of amine salt 10d (5.10 g, 12.5 mmol) and (S)-2-((tert-butoxycarbonyl)amino)non-8-enoic acid 11 (3.80 g, 14.0 mmol) in anhydrous DMF (65 mL) was treated with DIEA (9.25 mL, 56.0 mmol) and HATU (7.60 g, 20.0 mmol). The resulting reaction mixture was stirred at room temperature for 4 h, then diluted with EtOAc (500 mL), and washed successively with aqueous 0.5 N HCl, saturated aqueous $NaHCO_3$, and saturated aqueous NaCl (300 mL each). The organic portion was dried ($Na_2SO_4$), filtered, and evaporated under reduced pressure. The residue was purified by flash chromatography using 20-30% EtOAc/hexanes as the eluent to provide 12d (6.40 g, 81%) as a pale yellow foamy solid. $^1$H NMR (500 MHz, $CDCl_3$) (mixture of rotamers, major rotamer) δ 7.78 (d, J=9.0 Hz, 1H), 7.48 (dd, J=9.0, 2.5 Hz, 1H), 7.44 (d, J=2.5 Hz, 1H), 5.86 (br s, 1H), 5.84-5.78 (m, 1H), 5.18 (d, J=9.0 Hz, 1H), 5.01-4.92 (m, 2H), 4.75 (t, J=8.0 Hz, 1H), 4.35 (q, J=7.5 Hz, 1H), 4.19 (d, J=12.0 Hz, 1H), 4.08 (dd, J=11.5, 4.5 Hz, 1H), 3.95 (s, 3H), 3.78 (s, 3H), 2.70-2.65 (m, 1H), 2.41-2.35 (m, 1H), 2.04 (app q, J=7.0 Hz, 2H), 1.80-1.75 (m, 1H), 1.60-1.54 (m, 1H), 1.45-1.28 (m, 15H) ppm; $^{13}$C NMR (125 MHz, $CDCl_3$) δ 172.10, 171.60, 159.99, 155.37, 151.78, 138.98, 138.41, 136.93, 134.40 (q, J=36.3 Hz), 127.85, 125.66, 120.53 (q, J=273.4 Hz), 114.33, 107.54, 79.58, 75.05, 57.83, 55.91, 52.44, 52.33, 51.75, 34.77, 33.65, 32.70, 28.91, 28.73, 28.18, 24.70 ppm; $^{19}$F NMR (470 MHz, $CDCl_3$); —67.73 ppm; HRMS (ESI) m/z: $[M+H]^+$ calcd for $C_{30}H_{40}F_3N_4O_7$, 625.2844; found 625.2844.

A solution of ester 12d (6.40 g, 10.25 mmol) in $THF-H_2O$ (1:1 mixture, 140 mL) was treated with $LiOH.H_2O$ (1.38 g, 32.0 mmol). The resulting reaction mixture was stirred at room temperature for 24 h, then cooled to ~5° C., acidified to a pH of 2.0 by slow addition of aqueous 0.25 N HCl (~200 mL), and extracted with EtOAc (2×500 mL). The organic portions were washed separately with saturated aqueous NaCl (250 ml), dried ($Na_2SO_4$), filtered, and evaporated under reduced pressure. The gummy residue was dissolved in $CHCl_3$ (50 mL), concentrated under reduced pressure, and the residue was dried under high vacuum to yield the acid 13d (6.12 g, 98%) as a pale yellow foamy solid.

A solution of acid 13d (6.12 g, 10.0 mmol) and amine salt 24 (2.50 g, 13.0 mmol) in anhydrous $CH_2Cl_2$ (100 mL) was treated with DIEA (9.10 mL, 55.0 mmol), HATU (5.30 g, 14.0 mmol) and DMAP (0.60 g, 4.9 mmol). The resulting reaction mixture was stirred at room temperature for 14 h, then diluted with EtOAc (500 mL), and washed successively with aqueous 1.0 N HCl, saturated aqueous $NaHCO_3$, and saturated aqueous NaCl (250 mL each). The organic portion was dried ($Na_2SO_4$), filtered, and evaporated under reduced pressure. The residue was purified by flash chromatography using 25-35% EtOAc/hexanes as the eluent to provide the bis-olefin compound 25d (6.54 g, 87%) as a pale yellow foamy solid. $^1$H NMR (500 MHz, $CDCl_3$) (mixture of rotamers, major rotamer) δ 7.78 (d, J=9.2 Hz, 1H), 7.53 (br s, 1H), 7.47 (dd, J=9.2, 2.8 Hz, 1H), 7.43 (d, J=2.4 Hz, 1H), 5.88 (br s, 1H), 5.81-5.70 (m, 2H), 5.30 (dd, J=16.8, 0.8 Hz, 1H), 5.14-5.10 (m, 2H), 5.01-4.89 (m, 2H), 4.79 (dd, J=14.0, 5.6 Hz, 1H), 4.35-4.29 (m, 1H), 4.21-4.08 (m, 3H), 3.94 (s, 3H), 2.90-2.82 (m, 1H), 2.48-2.38 (m, 1H), 2.16 (q, J=9.0 Hz, 1H), 2.04-1.98 (m, 2H), 1.86 (dd, J=8.0, 5.2 Hz, 1H), 1.66-1.52 (m, 2H), 1.46 (dd, J=9.6, 5.6 Hz, 1H), 1.43-1.21 (m, 19H) ppm; $^{13}$C NMR (125 MHz, $CDCl_3$) δ 173.02, 171.00, 169.87, 159.62, 155.52, 152.03, 138.92, 138.48, 137.16, 133.66, 128.02, 125.73, 120.72 (q, J=273.6 Hz), 118.08, 114.52, 107.66, 79.98, 75.26, 61.40, 58.41, 56.02, 52.58, 52.43, 40.14, 33.89, 33.77, 32.76, 32.62, 28.97, 28.78, 28.31, 25.18, 23.11, 14.48 ppm; $^{19}$F NMR (470 MHz, CDCl$_3$); −67.77 ppm; HRMS (ESI) m/z: [M+H]$^+$ calcd for C$_{37}$H$_{49}$F$_3$N$_5$O$_8$, 748.3528; found 748.3514.

Ethyl (2R,6S,13aS,14aR,16aS,Z)-6-((tert-butoxycarbonyl)amino)-2-((7-methoxy-3-(trifluoromethyl)quinoxalin-2-yl)oxy)-5,16-dioxo-1,2,3,6,7,8,9,10,11,13a,14,15,16,16a-tetradecahydrocyclopropa[e]pyrrolo[1,2-a][1,4]diazacyclopentadecine-14a(5H)-carboxylate (26d)

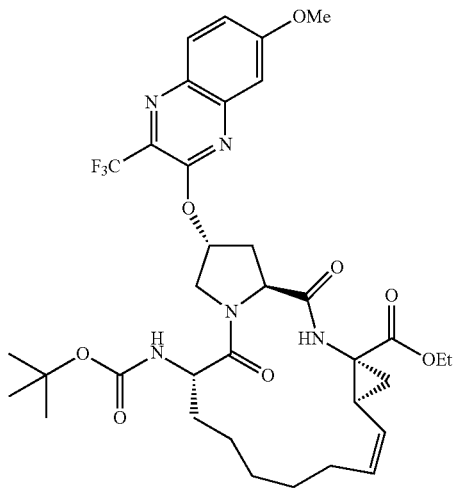 [SMILES: CCOC(=O)[C@@]12C[C@H]1/C=C\CCCCC[C@H](NC(=O)OC(C)(C)C)C(=O)N1C[C@H](Oc3nc4cc(OC)ccc4nc3C(F)(F)F)C[C@H]1C(=O)N2]

A degassed solution of bis-olefin 25d (1.50 g, 2.0 mmol) in 1,2-DCE (300 mL) was heated to 50° C. under argon, then Zhan 1b catalyst (0.150 g, 0.20 mmol) was added in two portions over 10 min. The resulting mixture was heated to 70° C. and stirred for 5 h. The reaction mixture was cooled to room temperature and concentrated under reduced pressure. The residue was purified by flash chromatography using 25-35% EtOAc/hexanes as the eluent to yield the P1-P3 macrocyclic product 26d (1.0 g, 70%) as an off-white foamy solid. $^1$H NMR (400 MHz, CDCl$_3$) δ 7.77 (d, J=8.8 Hz, 1H), 7.47 (dd, J=8.8, 2.8 Hz, 1H), 7.44 (d, J=2.4 Hz, 1H), 7.03 (br s, 1H), 5.84-5.80 (m, 1H), 5.56-5.49 (m, 1H), 5.32-5.22 (m, 2H), 4.92 (q, J=4.4 Hz, 1H), 4.49 (t, J=7.6 Hz, 1H), 4.24-4.05 (m, 4H), 3.95 (s, 3H), 3.05-2.99 (m, 1H), 2.41-2.35 (m, 1H), 2.24-2.14 (m, 3H), 1.93-1.86 (m, 2H), 1.66-1.60 (m, 1H), 1.55 (dd, J=96, 5.2 Hz, 1H), 1.46-1.20 (m, 18H) ppm; $^{13}$C NMR (100 MHz, CDCl$_3$) δ 172.81, 171.95, 169.74, 159.69, 155.21, 152.20, 138.56, 137.25, 134.50, 128.08, 125.91, 125.84, 120.80 (q, J=276 Hz), 107.73, 80.04, 75.42, 61.50, 58.08, 56.13, 52.21, 51.39, 41.36, 32.16, 31.77, 28.45, 28.10, 28.02, 26.37, 25.74, 23.70, 22.57, 14.72 ppm; HRMS (ESI) m/z: [M+H]$^+$ calcd for C$_{35}$H$_{45}$F$_3$N$_5$O$_8$, 720.3215; found 720.3203.

tert-Butyl 42R,6S,13aS,14aR,16aS,Z)-14a-((cyclopropylsulfonyl)carbamoyl)-2-((7-methoxy-3-(trifluoromethyl)quinoxalin-2-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (18d)

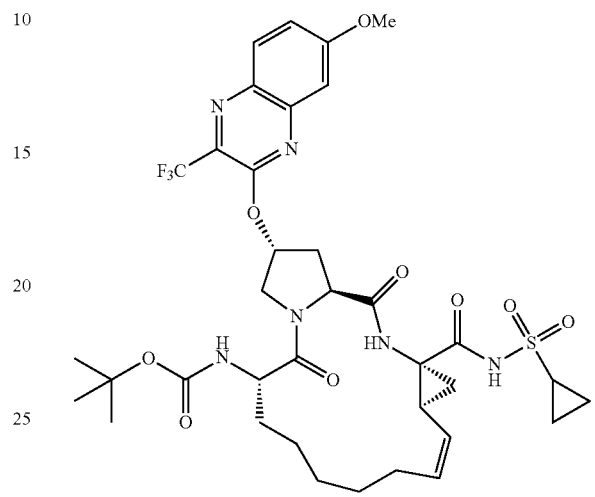

A solution of ester 12d (1.0 g, 1.4 mmol) in THF-MeOH—H$_2$O (1:1:1 mixture, 20 mL) was treated with LiOH.H$_2$O (0.18 g, 4.2 mmol). The resulting reaction mixture was stirred at room temperature for 24 h, then cooled to −5° C., acidified to a pH of 2.0 by slow addition of aqueous 0.25 N HCl, and extracted with EtOAc (2×150 mL). The organic portions were washed separately with saturated aqueous NaCl (100 ml), dried (Na$_2$SO$_4$), filtered, and evaporated under reduced pressure. The gummy residue was dissolved in CHCl$_3$ (10 mL), concentrated under reduced pressure, and the residue was dried under high vacuum to yield the acid 27d (0.95 g, 98%) as a pale yellow foamy solid.

A mixture of acid 27d (0.40 g, 0.58 mmol) and CDI (0.131 g, 0.81 mmol) in anhydrous THF (8 mL) was heated at reflux for 1.5 h. The solution was cooled to room temperature and slowly added to a solution of cyclopropanesulfonamide 28 (0.10 g, 0.82 mmol) in anhydrous THF (4 mL) followed by DBU (0.12 mL, 0.81 mmol). The resulting reaction mixture was stirred at room temperature for 24 h, then quenched with aqueous 0.5 N HCl to pH ~2. Solvents were partially evaporated under reduced pressure, and the residue was extracted with EtOAc (2×100 mL). The combined organic portions were washed with saturated aqueous NaCl (100 mL), dried (Na$_2$SO$_4$), filtered, and evaporated under reduced pressure. The residue was purified by flash chromatography using 40-70% EtOAc/hexanes as the eluent to afford the title compound 18d (0.28 g, 60%) as a white solid. $^1$H NMR (400 MHz, CDCl$_3$) δ 10.28 (s, 1H), 7.83 (d, J=9.2 Hz, 1H), 7.49 (dd, J=8.8, 2.8 Hz, 1H), 7.42 (d, J=2.8 Hz, 1H), 6.87 (s, 1H), 5.92 (br s, 1H), 5.70 (q, J=8.8 Hz, 1H), 5.13 (d, J=7.6 Hz, 1H), 4.97 (t, J=8.4 Hz, 1H), 4.62-4.56 (m, 2H), 4.23-4.17 (m, 1H), 4.01 (dd, J=11.6, 3.2 Hz, 1H), 3.94 (s, 3H), 2.93-2.87 (m, 1H), 2.68-2.50 (m, 3H), 2.31 (q, J=8.8 Hz, 1H), 1.95-1.54 (m, 2H), 1.53-1.02 (m, 21H), 0.96-0.88 (m, 1H) ppm; $^{13}$C NMR (100 MHz, CDCl$_3$) δ 176.99, 173.31, 167.91, 159.45, 154.93, 151.76, 138.27, 136.99, 136.32, 134.56 (q, J=36.2 Hz), 127.99, 125.57, 124.53, 120.8 (q, J=274.0 Hz), 107.40, 79.76, 75.54, 59.44, 55.89, 52.72, 51.86, 44.65, 34.61, 32.82, 31.02, 29.61, 28.02, 27.04, 25.99, 22.21, 20.93, 6.67, 6.12 ppm; HRMS (ESI) m/z: [M+H]$^+$ calcd for $C_{36}H_{46}F_3N_6O_9S$, 795.2994; found 795.2974. Anal. HPLC: $t_R$ 14.59 min, purity 100%.

tert-Butyl ((2R,6S,13aS,14aR,16aS,Z)-2-((7-methoxy-3-(trifluoromethyl)quinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (19d)

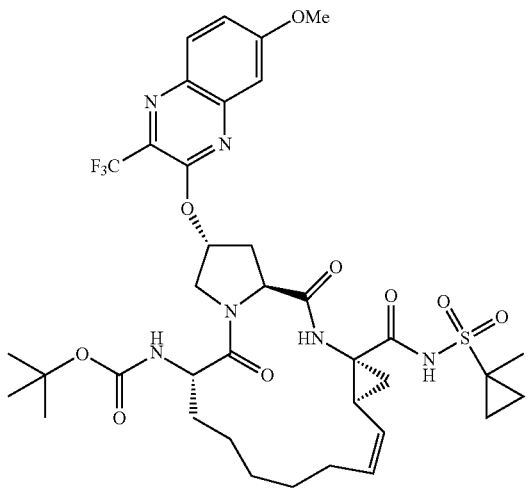 [SMILES: COc1ccc2nc(C(F)(F)F)c(O[C@@H]3C[C@H]4C(=O)N[C@]5(C(=O)NS(=O)(=O)C6(C)CC6)C[C@H]5/C=C\CCCCC[C@H](NC(=O)OC(C)(C)C)C(=O)N4C3)nc2c1]

The same procedure was used as described above for compound 18d. Acid 27d (0.43 g, 0.62 mmol) was treated with CDI (0.141 g, 0.87 mmol), 1-methylcyclopropanesulfonamide 29 (0.118 g, 0.87 mmol) and DBU (0.13 mL, 0.87 mmol) to afford the title compound 19d (0.34 g, 68%) as a white solid. $^1$H NMR (400 MHz, CDCl$_3$) δ 10.15 (s, 1H), 7.83 (d, J=9.2 Hz, 1H), 7.48 (dd, J=9.2, 2.8 Hz, 1H), 7.42 (d, J=2.8 Hz, 1H), 6.90 (s, 1H), 5.91 (s, 1H), 5.70 (q, J=9.2 Hz, 1H), 5.14 (d, J=7.6 Hz, 1H), 5.00 (t, J=9.2 Hz, 1H), 4.62-4.55 (m, 2H), 4.24-4.18 (m, 1H), 4.02 (dd, J=11.6, 3.6 Hz, 1H), 3.94 (s, 3H), 2.71-2.51 (m, 3H), 2.33 (q, J=8.4 Hz, 1H), 1.93-1.75 (m, 4H), 1.56-1.18 (m, 21H), 0.85-0.78 (m, 2H) ppm; $^{13}$C NMR (100 MHz, CDCl$_3$) δ 177.30, 173.46, 167.15, 159.68, 155.16, 152.01, 138.50, 137.23, 136.50, 134.60 (q, J=36.0 Hz), 128.23, 125.79, 125.19, 120.83 (d, J=274.0 Hz), 107.65, 80.01, 75.79, 59.70, 56.12, 52.97, 52.08, 45.03, 36.65, 34.86, 33.06, 29.81, 28.26, 27.31, 27.24, 26.32, 22.47, 21.21, 18.42, 14.73, 12.77 ppm; HRMS (ESI) m/z: [M+H]$^+$ calcd for $C_{37}H_{48}F_3N_6O_9S$, 809.3150; found 809.3129. Anal. HPLC: $t_R$ 15.23 min, purity 99%.

Cyclopentyl ((2R,6S,13aS,14aR,16aS,Z)-14a-((cyclopropylsulfonyl)carbamoyl)-2-((7-methoxy-3-(trifluoromethyl)quinoxalin-2-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (22d)

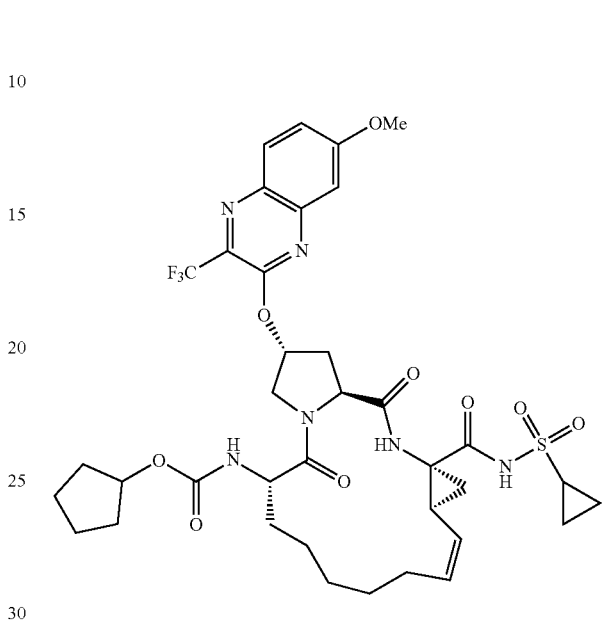

Compound 18d (0.40 g, 0.52 mmol) was treated with a solution of 4 N HCl in 1,4-dioxane (10 mL). The reaction mixture was stirred at room temperature for 3 h, concentrated under reduced pressure, and the residue was dried under high vacuum. The pale yellow solid was triturated with diethyl ether (3×10 mL) and dried under high vacuum to yield the amine salt 20d (0.37 g, 100%) as a white powder.

A solution of the above amine salt 20d (0.37 g, 0.52 mmol) in anhydrous CH$_3$CN (15 mL) was treated with DIEA (0.35 mL, 2.1 mmol) and N-(cyclopentyloxycarbonyloxy)-succinimide (0.15 g, 0.66 mmol). The reaction mixture was stirred at room temperature for 24 h, then concentrated under reduced pressure and dried under high vacuum. The residue was purified by flash chromatography using 50-90% EtOAc/hexanes as the eluent to provide the target compound 22d (0.30 g, 74%) as a white solid. $^1$H NMR (400 MHz, CDCl$_3$) δ 10.27 (s, 1H), 7.82 (d, J=9.2 Hz, 1H), 7.48 (dd, J=9.2, 2.8 Hz, 1H), 7.42 (d, J=2.8 Hz, 1H), 6.78 (s, 1H), 5.95 (s, 1H), 5.70 (q, J=9.6 Hz, 1H), 5.23 (d, J=8.0 Hz, 1H), 4.98 (t, J=8.8 Hz, 1H), 4.74-4.69 (m, 1H), 4.60 (t, J=7.6 Hz, 1H), 4.54 (d, J=11.6 Hz, 1H), 4.25-4.19 (m, 1H), 3.99 (dd, J=11.6, 4.0 Hz, 1H), 3.94 (s, 3H), 2.94-2.88 (m, 1H), 2.68-2.50 (m, 3H), 2.31 (q, J=8.8 Hz, 1H), 1.94-1.24 (m, 21H), 1.20-1.07 (m, 2H), 0.96-0.89 (m, 1H) ppm; $^{13}$C NMR (100 MHz, CDCl$_3$) δ 177.33, 173.29, 168.27, 159.68, 155.87, 152.08, 138.56, 137.24, 136.47, 134.74 (q, J=36.0 Hz), 128.24, 125.75, 124.79, 120.87 (d, J=273.2 Hz), 107.62, 78.02, 75.70, 59.68, 56.11, 52.90, 52.35, 44.83, 34.71, 32.92, 32.81, 32.64, 31.26, 29.87, 27.27, 26.24, 23.81, 23.75, 22.49, 21.11, 6.89, 6.34 ppm; HRMS (ESI) m/z: [M+H]+ calcd for $C_{37}H_{46}F_3N_6O_9S$, 807.2994; found 807.2976. Anal. HPLC: $t_R$ 14.98 min, purity 99%.

Cyclopentyl ((2R,6S,13aS,14aR,16aS,Z)-2-((7-methoxy-3-(trifluoromethyl)quinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (23d)

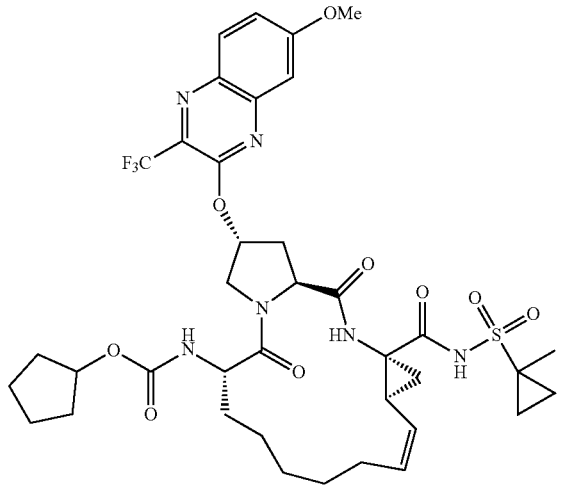 [SMILES: COc1ccc2nc(C(F)(F)F)c(O[C@@H]3C[C@H]4C(=O)N[C@]5(C(=O)NS(=O)(=O)C6(C)CC6)C[C@H]5/C=C\CCCCC[C@H](NC(=O)OC5CCCC5)C(=O)N4C3)nc2c1]

The same procedure was used as described above for compound 22d. Compound 19d (0.40 g, 0.52 mmol) was treated with 4 N HCl in 1,4-dioxane (10 mL) to yield the amine salt 21d, which was treated with DIEA (0.35 mL, 2.1 mmol) and N-(cyclopentyloxycarbonyloxy)-succinimide (0.15 g, 0.66 mmol) to provide the target compound 23d (0.30 g, 74%) as a white solid. $^1$H NMR (400 MHz, CDCl$_3$) δ 10.18 (s, 1H), 7.83 (d, J=9.6 Hz, 1H), 7.48 (dd, J=8.8, 2.8 Hz, 1H), 7.41 (d, J=2.8 Hz, 1H), 6.94 (s, 1H), 5.94 (s, 1H), 5.70 (q, J=8.8 Hz, 1H), 5.28 (d, J=7.6 Hz, 1H), 5.00 (t, J=8.8 Hz, 1H), 4.74-4.69 (m, 1H), 4.60 (t, J=7.6 Hz, 1H), 4.54 (d, J=12.0, 1H), 4.25-4.19 (m, 1H), 4.00 (dd, J=11.6, 3.6 Hz, 1H), 3.94 (s, 3H), 2.68-2.50 (m, 3H), 2.31 (q, J=8.4 Hz, 1H), 1.92-1.20 (m, 24H), 0.85-0.78 (m, 2H) ppm; $^{13}$C NMR (100 MHz, CDCl$_3$) δ 177.33, 173.25, 167.13, 159.68, 155.84, 152.08, 138.56, 137.24, 136.44, 134.75 (q, J=35.2 Hz), 128.25, 125.74, 125.21, 120.86 (d, J=274.0 Hz), 107.62, 78.02, 75.71, 59.73, 56.12, 52.89, 52.34, 45.03, 36.65, 34.73, 32.93, 32.82, 32.64, 29.83, 27.26, 27.21, 26.29, 23.81, 23.75, 22.52, 21.23, 18.42, 14.73, 12.76 ppm. HRMS (ESI) m/z: [M+H]$^+$ calcd for C$_{38}$H$_{48}$F$_3$N$_6$O$_9$S, 821.3150; found 821.3133. Anal. HPLC: t$_R$ 15.65 min, purity 97%.

Synthesis of Quinoxalines

Scheme 3: Synthesis of quinoxalines

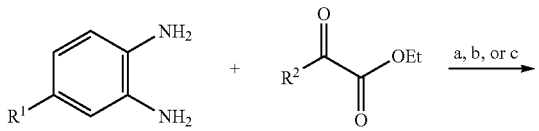

4 R$^1$ = OMe
5 R$^1$ = H

6a R$^2$ = Et
6b R$^2$ = Me
6d R$^2$ = CF$_3$
6e R$^2$ = i-Pr
6f R$^2$ = 2-thiophene

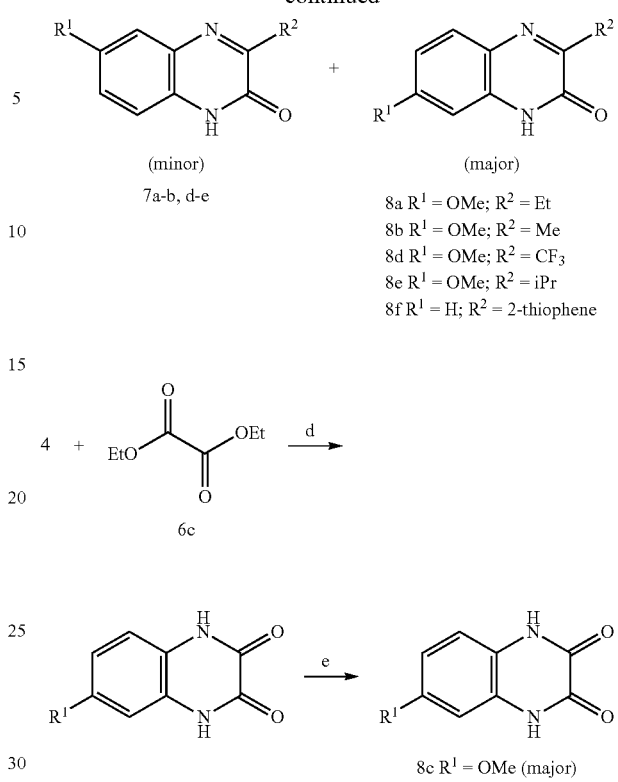

7a-b, d-e

8a R$^1$ = OMe; R$^2$ = Et
8b R$^1$ = OMe; R$^2$ = Me
8d R$^1$ = OMe; R$^2$ = CF$_3$
8e R$^1$ = OMe; R$^2$ = iPr
8f R$^1$ = H; R$^2$ = 2-thiophene 8c R$^1$ = OMe (major)

Reagents and conditions: (a) AcOH, rt, overnight, 50° C., 2 h; (b) aq. H$_2$SO$_4$ (1.8M), rt, 24 h; (c) MeOH, rt, 24 h; (d) Et$_3$N, 150° C., 2 h; (e) SOCl$_2$, DMF, 110° C., 1.5 h.

3-Ethyl-7-methoxyquinoxalin-2(1H)-one (8a)

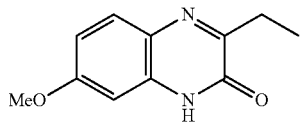

A mixture of 4-methoxy-1,2-diaminobenzene 4 (5.0 g, 36.2 mmol) and ethyl 2-oxobutanoate 6a (5.70 g, 43.8 mmol) in AcOH (25 mL) was stirred at room temperature overnight and then heated at 50° C. for 2 h. AcOH was removed under reduced pressure, and the reside was extracted with CH$_2$Cl$_2$ (2×150 mL). The combined organic portions were washed with H$_2$O and 10% aqueous Na$_2$CO$_3$ solution, dried (Na$_2$SO$_4$), and evaporated under reduced pressure. The residue was triturated with hexanes and filtered. The solid was mixed with EtOAc (25 mL), stirred at room temperature for 30 min, filtered, and dried under high vacuum to provide the 3-ethyl-7-methoxyquinoxaline 8a (6.0 g, 81%) as a light purple solid. $^1$HNMR (500 MHz, DMSO-d$_6$) δ 12.17 (s, 1H), 7.61 (d, J=8.5 Hz, 1H), 6.85 (dd, J=9.0, 2.5 Hz, 1H), 6.73 (d, J=2.5 Hz, 1H), 3.80 (s, 3H), 2.74 (q, J=7.5 Hz, 3H), 1.19 (t, J=7.5 Hz, 3H) ppm; $^{13}$C NMR (125 MHz, DMSO-d$_6$) δ 160.30, 159.35, 155.26, 133.63, 129.78, 127.01, 111.78, 98.26, 55.97, 26.17, 10.08 ppm; MS (ESI) m/z: [M+H]$^+$ calcd for C$_{11}$H$_{13}$N$_2$O$_2$, 205.24; found 205.90.

7-Methoxy-3-methylquinoxalin-2(1H)-one (8b)

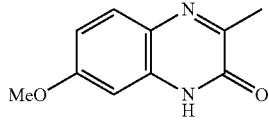

4-Methoxy-1,2-diaminobenzene 4 (130 g, 0.94 mol) was added to an aqueous solution of sulfuric acid (1.8 M, 1300 mL) and the mixture was treated with ethyl pyruvate 6b (132 g, 1.14 mol). The resulting reaction mixture was stirred at room temperature for 24 h, then treated with an aqueous solution of 3 N NaOH till pH 7. After stirring the mixture for 30 min, the solid precipitate was filtered, washed with water and dried. The solid product was mixed with EtOAc (1000 mL), heated to 60° C., and vigorously stirred for 1 h. The solid was filtered, washed with EtOAc and dried under high vacuum to provide the 3-methyl-7-methoxyquinoxaline 8b (135 g, 75%) as a light purple solid. $^1$H NMR (500 MHz, DMSO-$d_6$) δ 12.18 (s, 1H), 7.59 (d, J=9.0 Hz, 1H), 6.86 (dd, J=9.0, 3.0 Hz, 1H), 6.73 (d, J=2.5 Hz, 1H), 3.81 (s, 3H), 2.34 (s, 3H) ppm; $^{13}$C NMR (125 MHz, DMSO-$d_6$) δ 160.30, 155.85, 155.62, 133.82, 129.58, 127.02, 111.82, 98.29, 55.97, 20.63 ppm; MS (ESI)m/z: [M+H]$^+$ calcd for $C_{10}H_{11}N_2O_2$, 191.21; found 191.30.

3-Chloro-7-methoxyquinoxalin-2(1H)-one (8c)

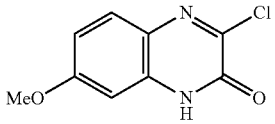

The title compound was prepared according to the method described by Harper et al.[1] $^1$H NMR (500 MHz, DMSO-$d_6$) δ 7.35 (d, J=8.5 Hz, 1H), 6.65 (d, J=2.5 Hz, 1H), 6.62 (dd, J=8.5, 2.5 Hz, 1H), 3.77 (s, 3H), 3.71 (br s, 1H) ppm; $^{13}$C NMR (125 MHz, DMSO-$d_6$) δ 159.79, 159.30, 145.76, 145.62, 128.88, 128.02, 110.57, 103.48, 55.56 ppm; MS (ESI) m/z: [M+H]$^+$ calcd for $C_9H_8ClN_2O_2$, 211.62; found 211.60.

7-Methoxy-3-(trifluoromethyl)quinoxalin-2(1H)-one (8d)

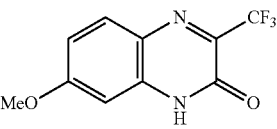 [SMILES: COc1ccc2nc(C(F)(F)F)c(=O)[nH]c2c1]

A solution of ethyl trifluoropyruvate 6d (20.4 g, 120 mmol) in MeOH (50 mL) was slowly added to 4-methoxy-1,2-diaminobenzene 4 (15.0 g, 108 mmol). The resulting reaction mixture was stirred at room temperature for 24 h. The solid precipitate was filtered, washed with cold MeOH and dried. The solid residue was mixed with MeOH (60 mL), stirred at 50° C. for 30 min, cooled to 5° C., filtered, and dried under high vacuum to provide the 7-methoxy-3-(trifluoromethyl)quinoxalin-2(1H)-one 8d (12 g, 47%) as a mustard solid. $^1$H NMR (500 MHz, DMSO-$d_6$) δ 13.01 (s, 1H), 7.41 (d, J=2.5 Hz, 1H), 7.37 (dd, J=9.0, 2.5 Hz, 1H), 7.32 (d, J=9.0 Hz, 1H), 3.84 (s, 3H) ppm; $^{13}$C NMR (125 MHz, DMSO-$d_6$) δ 156.33, 151.77, 144.50 (q, J=36.4 Hz), 131.04, 128.59, 124.08, 120.66 (d, J=274.4 Hz), 117.23, 110.88, 56.26 ppm; $^{19}$F NMR (470 MHz, DMSO-$d_6$); −68.45 ppm; MS (ESI) m/z: [M+Na]$^+$ calcd for $C_{10}H_7F_3N_2O_2Na$, 267.16; found 267.40.

3-Isopropyl-7-methoxyquinoxalin-2(1H)-one (8e)

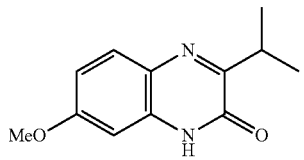 [SMILES: COc1ccc2nc(C(C)C)c(=O)[nH]c2c1]

A mixture of 4-methoxy-1,2-diaminobenzene 4 (130 g, 0.94 mol) and ethyl 3-methyl-2-oxobutanoate 6e (162 g, 1.12 mol) in AcOH (650 mL) was stirred at room temperature overnight, and then heated at 50° C. for 2 h. AcOH was removed under reduced pressure. The residue was diluted with H$_2$O (650 mL) and CH$_2$Cl$_2$ (800 mL) and the pH of the mixture was adjusted to pH ~10 by slow addition of 10% aqueous NaOH solution. The resulting precipitate was filtered, washed with CH$_2$Cl$_2$ (100 mL) and dried under vacuum to provide the 3-isopropyl-7-methoxyquinoxaline 8e (91 g, 45%) as a light brown solid. $^1$HNMR (500 MHz, DMSO-$d_6$) δ 12.22 (s, 1H), 7.62 (d, J=9.0 Hz, 1H), 6.86 (dd, J=9.0, 3.0 Hz, 1H), 6.75 (d, J=2.5 Hz, 1H), 3.81 (s, 3H), 3.43-3.37 (m, 1H), 1.19 (d, J=7.0 Hz, 6H) ppm; $^{13}$C NMR (125 MHz, DMSO-$d_6$) δ 162.35, 160.36, 154.91, 133.64, 129.90, 126.91, 111.80, 98.24, 55.97, 30.08, 20.57 ppm; MS (ESI) m/z: [M+H]$^+$ calcd for $C_{12}H_{15}N_2O_2$, 219.26; found 219.50.

3-(Thiophen-2-yl)quinoxalin-2(1H)-one (8f)

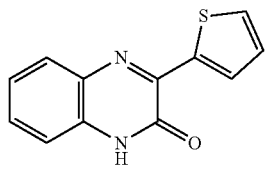 [SMILES: O=c1[nH]c2ccccc2nc1-c1cccs1]

A mixture of 1,2-diaminobenzene 5 (5.41 g, 50 mmol) and ethyl 2-oxo-2-(thiophen-2-yl)acetate 6f (9.2 g, 50 mmol) was stirred in ethanol (100 ml) at reflux for 18 h. The reaction mixture was cooled to 10° C. and stirred for 1 h. The solid precipitate was filtered, washed with ethanol (20 mL) and dried under high vacuum to give the title compound 8f (6.0 g, 53%) as a yellow solid. $^1$H NMR (500 MHz, DMSO-$d_6$) δ 12.69 (s, 1H), 8.41 (dd, J=4.0, 1.5 Hz, 1H), 7.83 (dd, J=5.0, 1.0 Hz, 1H), 7.77 (d, J=8.0 Hz, 1H), 7.51 (dt, J=8.0, 1.5 Hz, 1H), 7.35-7.30 (m, 2H), 7.23 (dd, J=5.0, 3.5 Hz, 1H) ppm; $^{13}$C NMR (125 MHz, DMSO-$d_6$) δ 153.42, 148.88, 138.92, 132.07, 131.89, 131.41, 131.36, 129.78, 128.11, 128.0, 123.65, 115.28 ppm; MS (ESI) m/z: [M+H]$^+$ calcd for $C_{12}H_9N_2OS$, 229.28; found 229.50.

1-(tert-Butyl) 2-methyl (2S,4R)-4-((7-methoxy-3-methylquinoxalin-2-yl)oxy)pyrrolidine-1,2-dicarboxylate (9b)

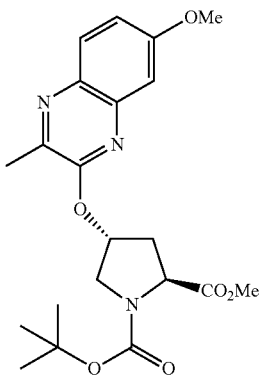 [SMILES: COC(=O)[C@@H]1C[C@@H](Oc2nc3cc(OC)ccc3nc2C)CN1C(=O)OC(C)(C)C]

A solution of 3-ethyl-7-methoxyquinoxalin-2-one 8b (4.0 g, 21 mmol) in anhydrous NMP (65 mL) was treated with Cs$_2$CO$_3$ (10.30 g, 31.6 mmol). After stirring the reaction mixture at room temperature for 15 min, proline derivative 3 (8.82 g, 19.0 mmol) was added in one portion. The reaction mixture was heated to 55° C., stirred for 4 h, and then another portion of proline derivative 3 (0.68 g, 1.5 mmol) was added. The resulting reaction mixture was stirred at 55° C. for additional 2 h, cooled to room temperature, quenched with aqueous 1 N HCl solution (250 mL), and extracted with EtOAc (400 mL). The organic fraction was washed successively with saturated aqueous NaHCO$_3$ and NaCl (250 mL each), dried (Na$_2$SO$_4$), filtered, and evaporated under reduced pressure. The residue was purified by flash column chromatography using 15-30% EtOAc/hexanes as the eluent to provide 9b (6.60 g, 75%) as a colorless gummy solid. $^1$H NMR (500 MHz, CDCl$_3$) (mixture of rotamers, major rotamer) δ 7.80 (d, J=9.0 Hz, 1H), 7.17 (dd, J=9.0, 3.0 Hz, 1H), 7.11 (d, J=2.5 Hz, 1H), 5.71 (br s, 1H), 4.48 (t, J=8.0 Hz, 1H), 3.99-3.91 (m, 4H), 3.87 (d, J=12.5 Hz, 1H), 3.78 (s, 3H), 2.67-2.58 (m, 1H), 2.56 (s, 3H), 2.43-2.37 (m, 1H), 1.43 (s, 9H) ppm; $^{13}$C NMR (125 MHz, CDCl$_3$) δ 173.36, 160.24, 155.51, 153.81, 144.60, 141.04, 134.22, 128.95, 118.63, 105.95, 80.54, 73.59, 58.20, 55.68, 52.48, 52.20, 36.70, 28.26, 19.93 ppm; HRMS (ESI) m/z: [M+H]$^+$ calcd for C$_{21}$H$_{28}$N$_3$O$_6$, 418.1973; found 418.1976.

1-(tert-butyl) 2-methyl (2S,4R)-4-((3-chloro-7-methoxyquinoxalin-2-yl)oxy)pyrrolidine-1,2-dicarboxylate (9c)

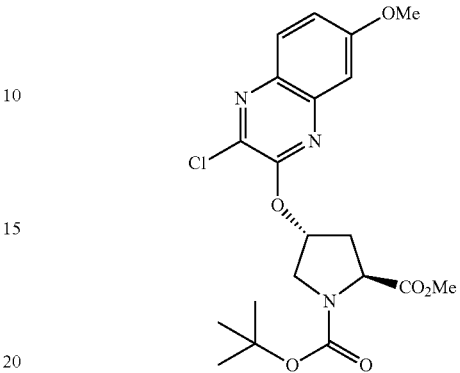

The same procedure was used as described above for compound 9b. 3-Chloro-7-methoxyquinoxalin-2(1H)-one 8c (4.0 g, 19.0 mmol) in NMP (60 mL) was treated with Cs$_2$CO$_3$ (9.30 g, 28.6 mmol) and proline derivative 3 (8.40 g, 18.1 mmol) to provide 9c (6.30 g, 76%) as an off-white foamy solid. $^1$H NMR (400 MHz, CDCl$_3$) (mixture of rotamers, major rotamer) δ 7.80 (d, J=8.8 Hz, 1H), 7.21 (dd, J=8.8, 2.8 Hz, 1H), 7.12 (d, J=2.8 Hz, 1H), 5.69 (br s, 1H), 4.52 (t, J=7.6 Hz, 1H), 4.0-3.94 (s, 4H), 3.88 (d, J=12.8 Hz, 1H), 3.78 (s, 3H), 2.72-2.62 (m, 1H), 2.45-2.37 (m, 1H), 1.43 (s, 9H) ppm; $^{13}$C NMR (400 MHz, CDCl$_3$) δ 173.32, 162.35, 153.84, 152.48, 141.03, 136.11, 134.06, 129.97, 119.95, 105.83, 80.60, 75.02, 58.10, 55.81, 52.36, 52.10, 36.64, 28.27 ppm; HRMS (ESI) m/z: [M+H]$^+$ calcd for C$_{20}$H$_{25}$ClN$_3$O$_6$, 438.1426; found 438.1438.

1-(tert-Butyl) 2-methyl (2S,4R)-4-((3-isopropyl-7-methoxyquinoxalin-2-yl)oxy)pyrrolidine-1,2-dicarboxylate (9e)

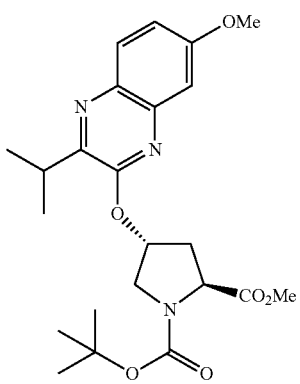 [SMILES: COC(=O)[C@@H]1C[C@@H](Oc2nc3cc(OC)ccc3nc2C(C)C)CN1C(=O)OC(C)(C)C]

The same procedure was used as described above for compound 9b. 3-Isopropyl-7-methoxyquinoxalin-2(1H)-one 8e (4.0 g, 18.3 mmol) in NMP (65 mL) was treated with Cs$_2$CO$_3$ (9.0 g, 27.6 mmol) and proline derivative 3 (8.30 g, 17.9 mmol) to provide 9e (7.30 g, 90%) as a colorless gummy solid. $^1$H NMR (500 MHz, CDCl$_3$) (mixture of rotamers, major rotamer) δ 7.83 (d, J=8.0 Hz, 1H), 7.16 (d, J=8.4 Hz, 1H), 7.10 (s, 1H) 5.74 (br s, 1H), 4.48 (t, J=7.5 Hz, 1H), 3.92-3.87 (m, 5H), 3.78 (s, 3H), 3.41-3.36 (m, 1H), 2.68-2.59 (m, 1H), 2.42-2.35 (m, 1H), 1.43 (s, 9H), 1.31 (t, J=7.0 Hz, 6H) ppm; $^{13}$C NMR (125 MHz, CDCl$_3$) δ 173.37, 160.19, 154.62, 153.82, 152.00, 140.68, 134.31, 129.39, 118.41, 105.80, 80.49, 73.36, 58.28, 55.67, 52.58, 52.19, 36.68, 30.81, 28.25, 20.43, 20.38 ppm; HRMS (ESI) m/z: [M+H]$^+$ calcd for C$_{23}$H$_{32}$N$_3$O$_6$, 446.2286; found 446.2287.

1-(tert-Butyl) 2-methyl (2S,4R)-4-((3-(thiophen-2-yl)quinoxalin-2-yl)oxy)pyrrolidine-1,2-dicarboxylate (9f)

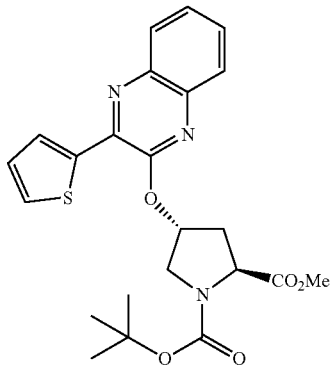 [SMILES: COC(=O)[C@@H]1C[C@@H](Oc2nc3ccccc3nc2-c2cccs2)CN1C(=O)OC(C)(C)C]

The same procedure was used as described above for compound 9b. 3-(Thiophen-2-yl)quinoxalin-2(1H)-one 8f (3.0 g, 13.1 mmol) in NMP (40 mL) was treated with Cs$_2$CO$_3$ (6.62 g, 20.3 mmol) and proline derivative 3 (6.0 g, 12.9 mmol) to provide 9f (4.90 g, 82%) as an off-white foamy solid. $^1$H NMR (400 MHz, CDCl$_3$) (mixture of rotamers, major rotamer) δ 8.13 (t, J=4.0 Hz, 1H), 8.01 (d, J=7.6 Hz, 1H), 7.79 (t, J=8.0 Hz, 1H), 7.66-7.55 (m, 2H), 7.53 (dd, J=5.2, 1.2 Hz, 1H), 7.20-7.14 (m, 1H), 5.91 (br s, 1H), 4.56 (t, J=8.0 Hz, 1H), 4.08 (d, J=12.8 Hz, 1H), 4.0-3.95 (m, 1H), 3.79 (s, 3H), 2.81-2.72 (m, 1H), 2.49-2.41 (m, 1H), 1.44 (s, 9H) ppm; $^{13}$C NMR (100 MHz, CDCl$_3$) δ 173.30, 153.80, 152.45, 140.48, 139.83, 138.93, 138.81, 130.35, 130.20, 129.45, 128.56, 128.09, 127.33, 126.72, 80.56, 74.51, 58.27, 52.66, 52.26, 36.69, 28.27 ppm; HRMS (ESI) m/z: [M+H]$^+$ calcd for C$_{23}$H$_{26}$N$_3$O$_5$S, 456.1588; found 456.1589.

1-(tert-Butyl) 2-methyl (2S,4R)-4-((3-ethylquinoxalin-2-yl)oxy)pyrrolidine-1,2-dicarboxylate (9g)

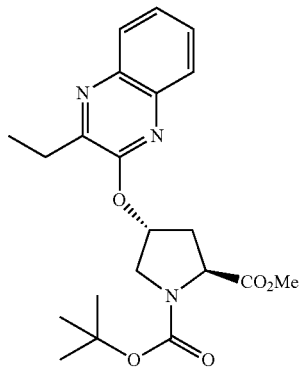 [SMILES: CCc1nc2ccccc2nc1O[C@@H]1C[C@@H](C(=O)OC)N(C(=O)OC(C)(C)C)C1]

The same procedure was used as described above for compound 9b. Commercially available 3-ethyl-quinoxalin-2(1H)-one 8g (3.0 g, 17.2 mmol) in NMP (40 mL) was treated with Cs$_2$CO$_3$ (8.42 g, 25.8 mmol) and proline derivative 3 (7.80 g, 16.8 mmol) to provide 9g (4.50 g, 65%) as a colorless gummy solid. $^1$H NMR (400 MHz, CDCl$_3$) (mixture of rotamers, major rotamer) δ 7.95 (d, J=7.5 Hz, 1H), 7.76 (d, J=8.0 Hz, 1H), 7.62-7.52 (m, 2H), 5.76 (br s, 1H), 4.47 (t, J=8.0 Hz, 1H), 3.95-3.88 (m, 2H), 3.78 (s, 3H), 2.95 (q, J=7.6 Hz, 2H), 2.67-2.60 (m, 1H), 2.42-2.37 (m, 1H), 1.43 (m, 9H), 1.33 (t, J=7.6 Hz, 3H) ppm; $^{13}$C NMR (100 MHz, CDCl$_3$) δ 173.31, 154.69, 153.80, 152.08, 139.40, 138.79, 128.97, 128.28, 126.87, 126.69, 80.51, 73.63, 58.25, 52.52, 52.19, 36.69, 28.25, 26.91, 11.50 ppm; HRMS (ESI) m/z: [M+H]$^+$ calcd for C$_{21}$H$_{28}$N$_3$O$_5$, 402.2023; found 402.2026.

Methyl (2S,4R)-1-((S)-2-((tert-butoxycarbonyl)amino)non-8-enoyl)-4-((7-methoxy-3-methylquinoxalin-2-yl)oxy)pyrrolidine-2-carboxylate (12b)

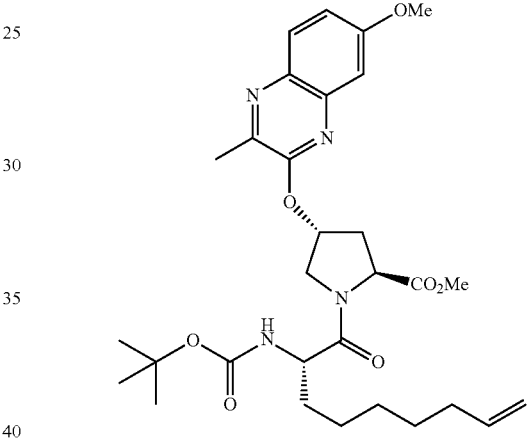

A solution of ester 9b (3.50 g, 8.4 mmol) in anhydrous CH$_2$Cl$_2$ (25 mL) was treated with a solution of 4 N HCl in 1,4-dioxane (25 mL). After stirring the reaction mixture at room temperature for 3 h, solvents were evaporated under reduced pressure, and the residue was dried under high vacuum. The pale yellow solid was triturated with diethyl ether (3×25 mL) and dried under high vacuum to yield the amine salt 10b (3.0 g, 100%) as an off-white powder.

A mixture of amine salt 10b (3.0 g, 8.4 mmol) and (S)-2-((tert-butoxycarbonyl)amino)non-8-enoic acid 11 (2.50 g, 9.2 mmol) in anhydrous DMF (45 mL) was treated with DIEA (6.10 mL, 36.8 mmol) and HATU (5.25 g, 13.8 mmol). The resulting reaction mixture was stirred at room temperature for 4 h, then diluted with EtOAc (400 mL), and washed successively with aqueous 0.5 N HCl, saturated aqueous NaHCO$_3$, and saturated aqueous NaCl (250 mL each). The organic portion was dried (Na$_2$SO$_4$), filtered, and evaporated under reduced pressure. The residue was purified by flash chromatography using 20-30% EtOAc/hexanes as the eluent to provide 12b (4.0 g, 83%) as a white foamy solid. $^1$HNMR (500 MHz, CDCl$_3$) (mixture of rotamers, major rotamer) δ 7.81 (d, J=9.0 Hz, 1H), 7.18 (dd, J=9.0, 2.5 Hz, 1H), 7.12 (d, J=2.5 Hz, 1H), 5.84-5.75 (m, 2H), 5.21 (d, J=8.5 Hz, 1H), 5.01-4.92 (m, 2H), 4.75 (t, J=8.0 Hz, 1H), 4.38 (q, J=7.5 Hz, 1H), 4.18 (d, J=11.5 Hz, 1H), 4.06 (dd, J=12.0, 4.5 Hz, 1H), 3.94 (s, 3H), 3.77 (s, 3H), 2.69-2.64 (m, 1H), 2.54 (s, 3H), 2.41-2.35 (m, 1H), 2.04 (app q, J=7.0 Hz, 2H), 1.80-1.75 (m, 1H), 1.63-1.55 (m, 1H), 1.46-1.24 (m, 15H) ppm; $^{13}$C NMR (125 MHz, CDCl$_3$) δ 172.13, 171.78, 160.27, 155.40, 155.27, 144.62, 140.89, 138.96, 134.39, 129.03, 118.73, 114.35, 105.99, 79.61, 74.30, 57.97, 55.66, 52.67, 52.43, 51.83, 34.94, 33.65, 32.66, 28.91, 28.74, 28.25, 24.68, 19.87 ppm; HRMS (ESI) m/z: [M+H]$^+$ calcd for C$_{30}$H$_{43}$N$_4$O$_7$, 571.3126; found 571.3128.

Methyl (2S,4R)-1-((S)-2-((tert-butoxycarbonyl)amino)non-8-enoyl)-4-((3-chloro-7-methoxyquinoxalin-2-yl)oxy)pyrrolidine-2-carboxylate (12c)

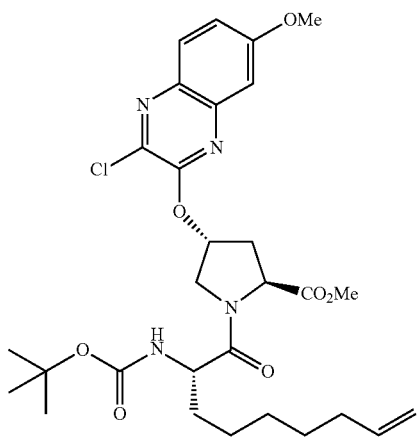 [SMILES: C=CCCCCC[C@H](NC(=O)OC(C)(C)C)C(=O)N1C[C@H](Oc2nc3cc(OC)ccc3nc2Cl)C[C@H]1C(=O)OC]

The same procedure was used as described above for compound 12b. Compound 9c (3.25 g, 7.4 mmol) was treated with 4 N HCl (20 mL) to afford amine salt 10c (2.77 g, 7.4 mmol), which was coupled with acid 11 (2.0 g, 7.4 mmol) using DIEA (4.90 mL, 29.6 mmol) and HATU (4.20 g, 11.0 mmol) to provide 12c (3.30 g, 75%) as a white foamy solid. $^1$H NMR (400 MHz, CDCl$_3$) (mixture of rotamers, major rotamer) δ 7.82 (d, J=9.2 Hz, 1H), 7.23 (dd, J=9.2, 2.8 Hz, 1H), 7.15 (d, J=2.8 Hz, 1H), 5.85-5.75 (m, 2H), 5.21 (d, J=8.4 Hz, 1H), 5.02-4.91 (m, 2H), 4.79 (t, J=8.4 Hz, 1H), 4.37 (q, J=8.0 Hz, 1H), 4.24 (d, J=11.6 Hz, 1H), 4.07 (dd, J=11.6, 4.4 Hz, 1H), 3.95 (s, 3H), 3.78 (s, 3H), 2.74-2.68 (m, 1H), 2.42-2.36 (m, 1H), 2.04 (app q, J=6.8 Hz, 2H), 1.82-1.76 (m, 1H), 1.63-1.55 (m, 1H), 1.43-1.27 (m, 15H) ppm; $^{13}$C NMR (400 MHz, CDCl$_3$) δ 172.33, 171.87, 161.52, 155.59, 152.46, 141.06, 139.19, 136.28, 134.36, 129.17, 120.25, 114.58, 106.03, 79.88, 75.92, 58.16, 56.02, 52.70, 52.58, 52.00, 34.99, 33.88, 32.90, 29.14, 28.96, 28.46, 24.89 ppm; HRMS (ESI) m/z: [M+H]$^+$ calcd for C$_{29}$H$_{40}$ClN$_4$O$_7$, 591.2580; found 591.2582.

Methyl (2S,4R)-1-((S)-2-((tert-butoxycarbonyl)amino)non-8-enoyl)-4-((3-isopropyl-7-methoxyquinoxalin-2-yl)oxy)pyrrolidine-2-carboxylate (12e)

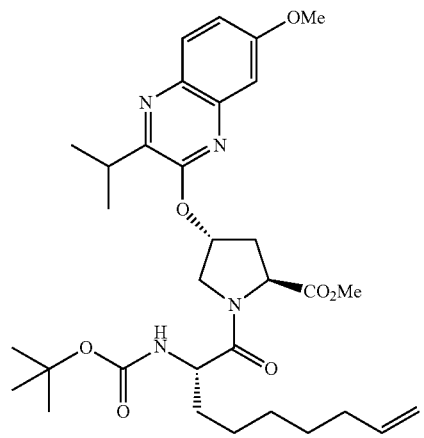 [SMILES: C=CCCCCC[C@H](NC(=O)OC(C)(C)C)C(=O)N1C[C@H](Oc2nc3cc(OC)ccc3nc2C(C)C)C[C@H]1C(=O)OC]

The same procedure was used as described above for compound 12b. Compound 9e (3.25 g, 7.3 mmol) was treated with 4 N HCl (25 mL) to afford amine salt 10e (2.80 g, 7.3 mmol), which was coupled with acid 11 (2.20 g, 8.1 mmol) using DIEA (5.36 mL, 32.4 mmol) and HATU (4.64 g, 12.2 mmol) to provide 12e (4.10 g, 93%) as a white foamy solid. $^1$H NMR (500 MHz, CDCl$_3$) (mixture of rotamers, major rotamer) δ 7.84 (d, J=8.5 Hz, 1H), 7.18 (d, J=9.0 Hz, 1H), 7.11 (s, 1H), 5.87 (br s, 1H), 5.84-5.76 (m, 1H), 5.20 (d, J=8.5 Hz, 1H), 4.99 (d, J=17.5 Hz, 1H), 4.93 (d, J=10.0 Hz, 1H), 4.72 (t, J=8.0 Hz, 1H), 4.39 (q, J=7.0 Hz, 1H), 4.15 (d, J=12.0 Hz, 1H), 4.06 (dd, J=12.0, 4.0 Hz, 1H) 3.94 (s, 3H), 3.78 (s, 3H), 3.40-3.34 (m, 1H), 2.69-2.64 (m, 1H), 2.40-2.34 (m, 1H), 2.04 (app q, J=6.5 Hz, 2H), 1.82-1.75 (m, 1H), 1.63-1.56 (m, 1H), 1.45-1.20 (m, 21H) ppm; $^{13}$C NMR (125 MHz, CDCl$_3$) δ 172.13, 171.69, 160.24, 155.38, 154.36, 152.00, 140.52, 138.96, 134.50, 129.46, 118.53, 114.35, 105.82, 79.59, 74.03, 58.01, 55.66, 52.71, 52.43, 51.85, 34.95, 33.66, 32.68, 30.59, 28.92, 28.75, 28.23, 24.69, 20.55, 20.43 ppm; HRMS (ESI) m/z: [M+H]$^+$ calcd for C$_{32}$H$_{47}$N$_4$O$_7$, 599.3439; found 599.3440.

Methyl (2S,4R)-1-((S)-2-((tert-butoxycarbonyl)amino)non-8-enoyl)-4-((3-(thiophen-2-yl)quinoxalin-2-yl)oxy)pyrrolidine-2-carboxylate (12f)

Methyl (2S,4R)-1-((S)-2-((tert-butoxycarbonyl)amino)non-8-enoyl)-4-((3-ethylquinoxalin-2-yl)oxy)pyrrolidine-2-carboxylate (12g)

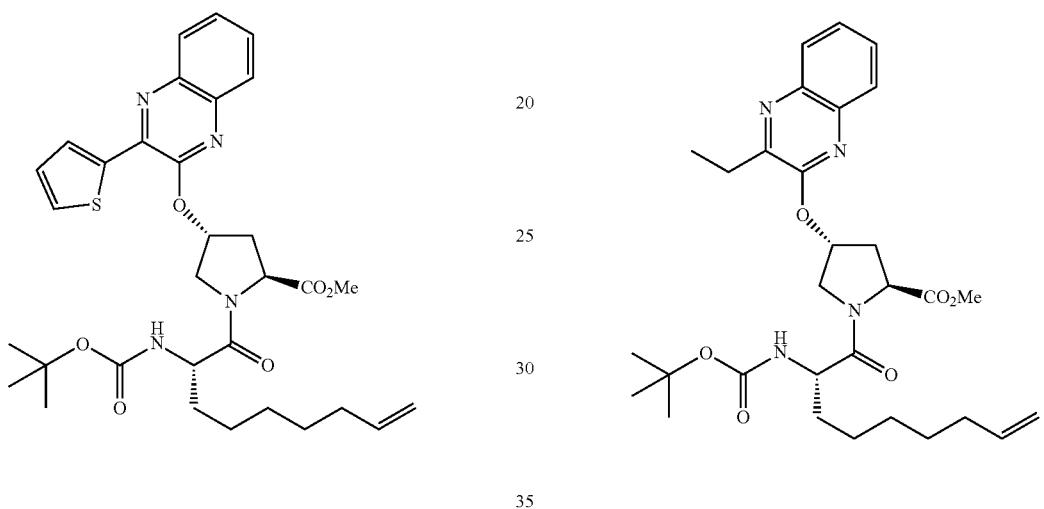

The same procedure was used as described above for compound 12b. Compound 9f (3.0 g, 6.6 mmol) was treated with 4 N HCl (20 mL) to afford amine salt 10f (2.60 g, 6.6 mmol), which was coupled with acid 11 (1.80 g, 6.6 mmol) using DIEA (4.35 mL, 26.3 mmol) and HATU (3.75 g, 9.9 mmol) to provide 12f (3.0 g, 75%) as an off-white foamy solid. $^1$H NMR (500 MHz, CDCl$_3$) (mixture of rotamers, major rotamer) δ 8.09 (dd, J=4.0, 1.2 Hz, 1H), 8.02 (dd, J=8.0, 1.6 Hz, 1H), 7.79 (dd, J=8.8, 1.6 Hz, 1H), 7.65-7.56 (m, 2H), 7.53 (dd, J=4.8, 0.8 Hz, 1H), 7.17 (dd, J=5.2, 4.0 Hz, 1H), 6.03 (br s, 1H), 5.85-5.77 (m, 1H), 5.19 (d, J=8.4 Hz, 1H), 5.03-4.92 (m, 2H), 4.83 (t, J=8.0 Hz, 1H), 4.43 (q, J=7.2 Hz, 1H), 4.32 (d, J=12.0 Hz, 1H), 4.12 (dd, J=12.0, 4.4 Hz, 1H), 3.79 (s, 3H), 2.83-2.77 (m, 1H), 2.48-2.41 (m, 1H), 2.05 (app q, J=6.8 Hz, 2H), 1.83-1.77 (m, 1H), 1.65-1.57 (m, 1H), 1.46-1.20 (m, 15H) ppm; $^{13}$C NMR (125 MHz, CDCl$_3$) δ 172.11, 171.64, 155.38, 152.25, 140.51, 139.45, 138.97, 138.76, 130.46, 130.34, 129.46, 128.60, 128.19, 127.45, 126.71, 114.36, 79.59, 75.08, 58.01, 52.72, 52.46, 51.92, 34.91, 33.66, 32.62, 28.92, 28.75, 28.22, 24.76 ppm; HRMS (ESI) m/z: [M+H]$^+$ calcd for C$_{32}$H$_{41}$N$_4$O$_6$S, 609.2741; found 609.2739.

The same procedure was used as described above for compound 12b. Compound 9g (3.50 g, 8.4 mmol) was treated with 4 N HCl (25 mL) to afford amine salt 10g (3.0 g, 17.2 mmol), which was coupled with acid 11 (2.50 g, 9.2 mmol) using DIEA (6.10 mL, 36.8 mmol) and HATU (5.25 g, 13.8 mmol) to provide 12g (4.0 g, 83%) as a white foamy solid. $^1$H NMR (400 MHz, CDCl$_3$) (mixture of rotamers, major rotamer) δ 7.97 (dd, J=8.0, 1.6 Hz, 1H), 7.77 (d, J=8.0, 1.6 Hz, 1H), 7.63-7.53 (m, 2H), 5.88 (br s, 1H), 8.84-5.75 (m, 1H), 5.21 (d, J=9.2 Hz, 1H), 5.02-4.91 (m, 2H), 4.74 (t, J=8.4 Hz, 1H), 4.37 (q, J=8.0 Hz, 1H), 4.18 (d, J=11.6 Hz, 1H), 4.07 (dd, J=11.6, 4.4 Hz, 1H), 3.78 (s, 3H), 2.93 (q, J=7.6 Hz, 2H), 2.71-2.63 (m, 1H), 2.42-2.35 (m, 1H), 2.05 (app q, J=6.8 Hz, 2H), 1.82-1.74 (m, 1H), 1.62-1.55 (m, 1H), 1.45-1.29 (m, 18H) ppm; $^{13}$C NMR (100 MHz, CDCl$_3$) δ 172.05, 171.85, 155.39, 154.42, 152.0, 139.20, 138.94, 138.84, 129.02, 128.27, 126.81, 114.34, 79.55, 74.23, 57.93, 52.62, 52.44, 51.81, 34.85, 33.64, 32.57, 28.87, 28.70, 28.20, 26.69, 24.70, 11.40 ppm; HRMS (ESI) m/z: [M+H]$^+$ calcd for C$_{30}$H$_{43}$N$_4$O$_6$, 555.3177; found 555.3177.

tert-Butyl ((S)-1-((2S,4R)-2-(((1R,2S)-1-((cyclopropylsulfonyl)carbamoyl)-2-vinylcyclopropyl)carbamoyl)-4-((7-methoxy-3-methylquinoxalin-2-yl)oxy)pyrrolidin-1-yl)-1-oxonon-8-en-2-yl)carbamate (16b)

A solution of ester 12b (3.25 g, 5.7 mmol) in THF-H$_2$O mixture (1:1, 100 mL) was treated with LiOH.H$_2$O (0.72 g, 17.2 mmol). The resulting reaction mixture was stirred at room temperature for 24 h. The reaction mixture was cooled to −5° C., acidified to a pH of 2.0 by slow addition of aqueous 0.25 N HCl (~200 mL), and extracted with EtOAc (2×400 mL). The organic portions were washed separately with saturated aqueous NaCl (200 ml), dried (Na$_2$SO$_4$), filtered, and evaporated under reduced pressure. The gummy residue was dissolved in CHCl$_3$ (50 mL), concentrated under reduced pressure, and the residue was dried under high vacuum overnight to yield the acid 13b (3.17 g, 100%) as a white foamy solid.

A mixture of acid 13b (1.60 g, 2.9 mmol) and amine salt 14 (0.93 g, 3.5 mmol) in anhydrous DMF (35 mL) was treated with DIEA (2.0 mL, 11.5 mmol) and HATU (1.75 g, 4.6 mmol). The resulting reaction mixture was stirred at room temperature for 2.5 h, then diluted with EtOAc (250 mL) and washed successively with aqueous 0.5 N HCl, saturated aqueous NaHCO$_3$, and saturated aqueous NaCl (150 mL each). The organic portion was dried (Na$_2$SO$_4$), filtered, and evaporated under reduced pressure. The residue was purified by flash chromatography using 50-70% EtOAc/hexanes as the eluent to provide the bis-olefin compound 16b (1.57 g, 70%) as a white solid.

$^1$H NMR (400 MHz, CDCl$_3$) δ 10.24 (s, 1H), 7.81 (d, J=8.8 Hz, 1H), 7.20 (dd, J=8.8, 2.8 Hz, 1H), 7.13 (d, J=2.8 Hz, 1H), 7.07 (s, 1H), 5.89 (br s, 1H), 5.85-5.72 (m, 2H), 5.39 (d, J=8.4 Hz, 1H), 5.26 (d, J=17.2 Hz, 1H), 5.14 (d, J=11.6 Hz, 1H), 5.01-4.90 (m, 2H), 4.45 (t, J=8.4 Hz, 1H), 4.38-4.32 (m, 1H), 4.21 (d, J=12.0 Hz, 1H), 4.02 (dd, J=11.6, 4.0 Hz, 1H), 3.93 (s, 3H), 2.95-2.89 (m, 1H), 2.56-2.48 (m, 5H), 2.13 (q, J=8.4 Hz, 1H), 2.05-1.99 (m, 3H), 1.74-1.66 (m, 1H), 1.62-1.54 (m, 1H), 1.46-1.22 (m, 18H), 1.07-1.02 (m, 2H); $^{13}$C NMR (100 MHz, CDCl$_3$) δ 173.70, 172.41, 168.53, 160.32, 155.63, 155.17, 144.38, 140.88, 138.83, 134.23, 132.47, 128.89, 118.92, 118.57, 114.44, 105.94, 79.76, 74.63, 60.33, 55.69, 53.16, 52.29, 41.56, 35.18, 34.26, 33.66, 32.20, 31.13, 28.76, 28.66, 28.25, 25.19, 23.59, 19.84, 6.48, 6.00 ppm; HRMS (ESI) m/z: [M+H]$^+$ calcd for C$_{38}$H$_{53}$N$_6$O$_9$S, 769.3589; found 769.3579.

tert-Butyl ((S)-1-((2S,4R)-4-((7-methoxy-3-methylquinoxalin-2-yl)oxy)-2-(((1R,2S)-1-(((1-methylcyclopropyl)sulfonyl)carbamoyl)-2-vinylcyclopropyl)carbamoyl)pyrrolidin-1-yl)-1-oxonon-8-en-2-yl)carbamate (17b)

The same procedure was used as described above for compound 16b. Acid 13b (1.60 g, 2.9 mmol) was coupled with amine salt 15 (0.98 g, 3.5 mmol) using DIEA (2.0 mL, 11.5 mmol) and HATU (1.75 g, 4.6 mmol) to provide the bis-olefin compound 17b (1.50 g, 66%) as a white solid. NMR (400 MHz, CDCl$_3$) δ 10.02 (s, 1H), 7.81 (d, J=8.8 Hz, 1H), 7.18 (dd, J=8.8, 2.8 Hz, 1H), 7.13 (d, J=2.8 Hz, 1H), 7.11 (s, 1H), 5.88 (br s, 1H), 5.82-5.72 (m, 2H), 5.42 (d, J=9.2 Hz, 1H), 5.26 (d, J=17.2 Hz, 1H), 5.14 (d, J=11.6 Hz, 1H), 5.00-4.90 (m, 2H), 4.50 (t, J=8.4 Hz, 1H), 4.39-4.33 (m, 1H), 4.18 (d, J=11.6 Hz, 1H), 4.02 (dd, J=11.6, 4.0 Hz, 1H), 3.93 (s, 3H), 2.58-2.50 (m, 5H), 2.10 (q, J=8.4 Hz, 1H), 2.05-1.98 (m, 3H), 1.73-1.58 (m, 4H), 1.49 (s, 3H), 1.44-1.24 (m, 16H), 0.92-0.86 (m, 1H), 0.84-0.78 (m, 1H); $^{13}$C NMR (100 MHz, CDCl$_3$) δ 173.65, 172.52, 167.55, 160.31, 155.70, 155.16, 144.41, 140.87, 138.83, 134.33, 132.61, 128.96, 118.87, 118.54, 114.41, 105.96, 79.73, 74.59, 60.30, 55.67, 53.15, 52.37, 41.73, 36.56, 35.16, 34.25, 33.62, 32.24, 28.71, 28.67, 28.26, 25.31, 23.42, 19.84, 18.37, 14.27, 13.26 ppm; HRMS (ESI) m/z: [M+H]$^+$ calcd for C$_{39}$H$_{55}$N$_6$O$_9$S, 783.3746; found 783.3734.

113 tert-Butyl ((S)-1-((2S,4R)-4-((3-chloro-7-methoxy-quinoxalin-2-yl)oxy)-2-(((1R,2S)-1-((cyclopropylsulfonyl)carbamoyl)-2-vinylcyclopropyl)carbamoyl)pyrrolidin-1-yl)-1-oxonon-8-en-2-yl)carbamate (16c)

114 tert-Butyl ((S)-1-((2S,4R)-4-((3-chloro-7-methoxy-quinoxalin-2-yl)oxy)-2-(((1R,2S)-1-(((1-methylcyclopropyl)sulfonyl)carbamoyl)-2-vinylcyclopropyl)carbamoyl)pyrrolidin-1-yl)-1-oxonon-8-en-2-yl)carbamate (17c)

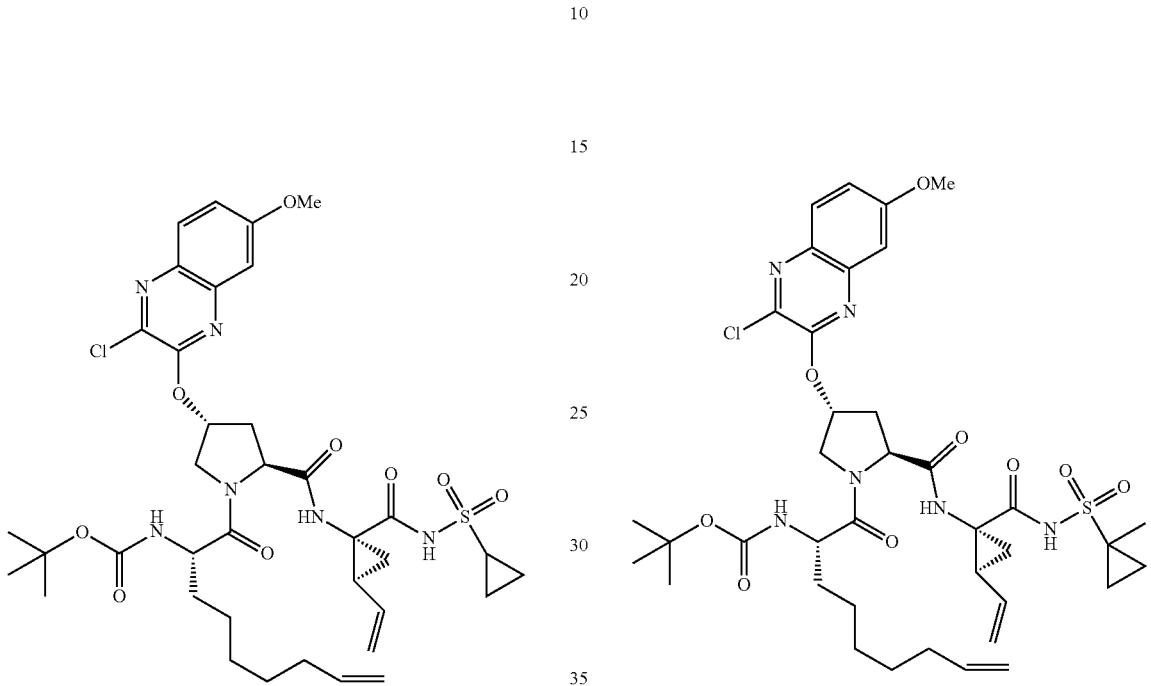

The same procedure was used as described above for compound 16b. Ester 12c (1.80 g, 3.0 mmol) was treated with LiOH.H₂O to afford acid 13c, which was coupled with amine salt 14 (0.96 g, 3.6 mmol) using DIEA (2.0 mL, 12.1 mmol) and HATU (1.70 g, 4.5 mmol) to provide the bis-olefin compound 16c (1.75 g, 74%) as a white solid. $^1$H NMR (400 MHz, CDCl$_3$) δ 10.25 (s, 1H), 7.82 (d, J=8.8 Hz, 1H), 7.26-7.23 (m, 1H), 7.17 (d, J=2.8 Hz, 1H), 6.99 (s, 1H), 5.88-5.74 (m, 3H), 5.33 (d, J=8.8 Hz, 1H), 5.28 (d, J=17.2 Hz, 1H), 5.16 (d, J=10.4 Hz, 1H), 5.01-4.90 (m, 2H), 4.53 (t, J=8.4 Hz, 1H), 4.37-4.32 (m, 1H), 4.28 (d, J=11.6 Hz, 1H), 4.03 (dd, J=12, 4.0 Hz, 1H), 3.96 (s, 3H), 2.96-2.90 (m, 1H), 2.60-2.54 (m, 2H), 2.14 (q, J=8.8 Hz, 1H), 2.07-2.00 (m, 3H), 1.76-1.54 (m, 2H), 1.47-1.23 (m, 18H), 1.08-1.02 (m, 2H) ppm; $^{13}$C NMR (100 MHz, CDCl$_3$) δ 174.01, 172.48, 168.59, 161.61, 155.84, 152.31, 141.06, 139.09, 136.14, 134.39, 132.66, 129.16, 120.43, 118.81, 114.66, 106.03, 80.05, 76.19, 60.64, 56.05, 53.09, 52.56, 41.86, 35.44, 34.41, 33.90, 32.46, 31.39, 28.99, 28.89, 28.46, 25.44, 23.80, 6.67, 6.27 ppm; HRMS (ESI) m/z: [M+H]$^+$ calcd for C$_{37}$H$_{15}$ClN$_6$O$_9$S, 789.3043; found 789.3030.

The same procedure was used as described above for compound 16b. Ester 12c (1.80 g, 3.0 mmol) was treated with LiOH.H₂O to afford acid 13c, which was coupled with amine salt 15 (1.0 g, 3.6 mmol) using DIEA (2.0 mL, 12.1 mmol) and HATU (1.70 g, 4.5 mmol) to provide the bis-olefin compound 17c (1.85 g, 77%) as a white solid. $^1$H NMR (500 MHz, CDCl$_3$) δ 10.01 (s, 1H), 7.82 (d, J=9.0 Hz, 1H), 7.26-7.23 (m, 1H), 7.17 (d, J=2.5 Hz, 1H), 7.02 (s, 1H), 5.87 (br s, 1H), 5.82-5.74 (m 2H), 5.36 (d, J=8.8 Hz, 1H), 5.28 (d, J=17.0 Hz, 1H), 5.15 (d, J=11.2 Hz, 1H), 5.00-4.96 (m, 1H), 4.94-4.91 (m, 1H), 4.53 (t, J=8.4 Hz, 1H), 4.37-4.32 (m, 1H), 4.24 (d, J=11.5 Hz, 1H), 4.03 (dd, J=12.0, 4.0 Hz, 1H), 3.96 (s, 3H), 2.61-2.53 (m, 2H), 2.12 (q, J=8.8 Hz, 1H), 2.05-2.00 (m, 3H), 1.74-1.58 (m, 4H), 1.50 (s, 3H), 1.47-1.24 (m, 16H), 0.92-0.86 (m, 1H), 0.85-0.80 (m, 1H); $^{13}$C NMR (125 MHz, CDCl$_3$) δ 173.74, 172.32, 167.42, 161.39, 155.68, 152.09, 140.85, 138.88, 135.93, 134.20, 132.59, 128.95, 120.19, 118.57, 114.41, 105.83, 79.79, 75.95, 60.39, 55.83, 52.86, 52.40, 41.79, 36.59, 35.21, 34.16, 33.65, 32.30, 28.73, 28.69, 28.27, 25.34, 23.44, 18.41, 14.24, 13.39 ppm; HRMS (ESI) m/z: [M+H]$^+$ calcd for C$_{38}$H$_{52}$ClN$_6$O$_9$S, 803.3200; found 803.3194.

115 tert-Butyl ((S)-1-((2S,4R)-2-(((1R,2S)-1-((cyclopropylsulfonyl)carbamoyl)-2-vinylcyclopropyl)carbamoyl)-4-((3-isopropyl-7-methoxyquinoxalin-2-yl)oxy)pyrrolidin-1-yl)-1-oxonon-8-en-2-yl)carbamate (16e)

116 tert-Butyl ((S)-1-((2S,4R)-4-((3-isopropyl-7-methoxyquinoxalin-2-yl)oxy)-2-(((1R,2S)-1-(((1-methylcyclopropyl)sulfonyl)carbamoyl)-2-vinylcyclopropyl)carbamoyl)pyrrolidin-1-yl)-1-oxonon-8-en-2-yl)carbamate (17e)

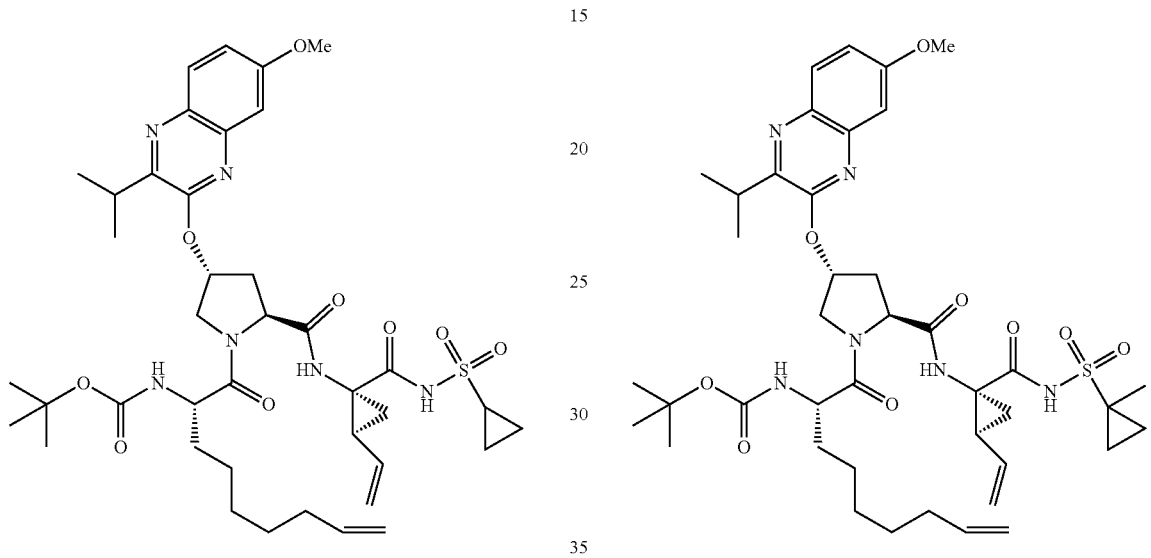

The same procedure was used as described above for compound 16b. Ester 12e (2.0 g, 3.3 mmol) was treated with LiOH.H$_2$O to afford acid 13e, which was coupled with amine salt 14 (1.20 g, 4.5 mmol) using DIEA (2.25 mL, 13.6 mmol) and HATU (1.90 g, 5.0 mmol) to provide the bis-olefin compound 16e (1.85 g, 70%) as a white solid. $^1$H NMR (400 MHz, CDCl$_3$) δ 10.25 (s, 1H), 7.85 (d, J=8.8 Hz, 1H), 7.19 (dd, J=8.8, 2.8 Hz, 1H), 7.12 (d, J=2.8 Hz, 1H), 7.01 (s, 1H), 5.92 (br s, 1H), 5.84-5.73 (m, 2H), 5.34 (d, J=8.8 Hz, 1H), 5.27 (d, J=17.2 Hz, 1H), 5.14 (d, J=11.6 Hz, 1H), 5.01-4.89 (m, 2H), 4.48 (t, J=8.4 Hz, 1H), 4.40-4.33 (m, 1H), 4.18 (d, J=11.6 Hz, 1H), 4.02 (dd, J=11.6, 7.2 Hz, 1H), 3.93 (s, 3H), 3.40-3.33 (m, 1H), 2.96-2.90 (m, 1H), 2.56-2.52 (m, 2H), 2.12 (q, J=8.8 Hz, 1H), 2.06-1.99 (m, 3H), 1.75-1.54 (m, 2H), 1.46-1.23 (m, 24H), 1.07-1.02 (m, 2H) ppm; $^{13}$C NMR (100 MHz, CDCl$_3$) δ 173.80, 172.33, 168.47, 160.28, 155.64, 154.23, 151.76, 140.49, 138.84, 134.43, 132.48, 129.41, 118.68, 118.54, 114.43, 105.76, 79.75, 74.33, 60.39, 55.67, 53.21, 52.38, 41.58, 35.22, 34.24, 33.65, 32.17, 31.15, 30.63, 28.75, 28.65, 28.23, 25.22, 23.59, 20.61, 20.41, 6.45, 6.02 ppm; HRMS (ESI) m/z: [M+H]$^+$ calcd for C$_{40}$H$_{57}$N$_6$O$_9$S, 797.3902; found 797.3906.

The same procedure was used as described above for compound 16b. Ester 12e (2.0 g, 3.3 mmol) was treated with LiOH.H$_2$O to afford acid 13e, which was coupled with amine salt 15 (1.27 g, 4.5 mmol) using DIEA (2.25 mL, 13.6 mmol) and HATU (1.90 g, 5.0 mmol) to provide the bis-olefin compound 17e (2.0 g, 75%) as a white solid. $^1$H NMR (400 MHz, CDCl$_3$) δ 10.03 (s, 1H), 7.85 (d, J=9.2 Hz, 1H), 7.19 (dd, J=9.2, 2.8 Hz, 1H), 7.12 (d, J=2.8 Hz, 1H), 7.03 (s, 1H), 5.92 (br s, 1H), 5.84-5.73 (m, 2H), 5.36 (d, J=8.8 Hz, 1H), 5.27 (d, J=17.2 Hz, 1H), 5.14 (d, J=10.8 Hz, 1H), 5.01-4.89 (m, 2H), 4.47 (t, J=7.6 Hz, 1H), 4.40-4.33 (m, 1H), 4.15 (d, J=11.6 Hz, 1H), 4.02 (dd, J=11.6, 4.0 Hz, 1H), 3.94 (s, 3H), 3.40-3.33 (m, 1H), 2.57-2.52 (m, 2H), 2.12 (q, J=8.4 Hz, 1H), 2.05-1.99 (m, 3H), 1.76-1.58 (m, 4H), 1.49 (s, 3H), 1.45-1.20 (m, 22H), 0.92-0.87 (m, 1H), 0.85-0.79 (m, 1H) ppm; $^{13}$C NMR (100 MHz, CDCl$_3$) δ 173.79, 172.38, 167.50, 160.28, 155.71, 154.23, 151.76, 140.49, 138.85, 134.43, 132.61, 129.42, 118.69, 118.54, 114.41, 105.76, 79.72, 74.32, 60.40, 55.68, 53.19, 52.47, 41.71, 36.56, 35.24, 34.22, 33.64, 32.18, 30.61, 28.70, 28.67, 28.25, 25.35, 23.51, 20.63, 20.42, 18.38, 14.26, 13.31; HRMS (ESI) m/z: [M+H]$^+$ calcd for C$_{41}$H$_{59}$N$_6$O$_9$S, 811.4059; found 811.4043.

117 tert-Butyl ((S)-1-((2S,4R)-2-(((1R,2S)-1-((cyclopropylsulfonyl)carbamoyl)-2-vinylcyclopropyl)carbamoyl)-4-((3-(thiophen-2-yl)quinoxalin-2-yl)oxy)pyrrolidin-1-yl)-1-oxonon-8-en-2-yl)carbamate (16f)

118 tert-Butyl ((S)-1-((2S,4R)-2-(((1R,2S)-1-((cyclopropylsulfonyl)carbamoyl)-2-vinylcyclopropyl)carbamoyl)-4-((3-ethylquinoxalin-2-yl)oxy)pyrrolidin-1-yl)-1-oxonon-8-en-2-yl)carbamate (16g)

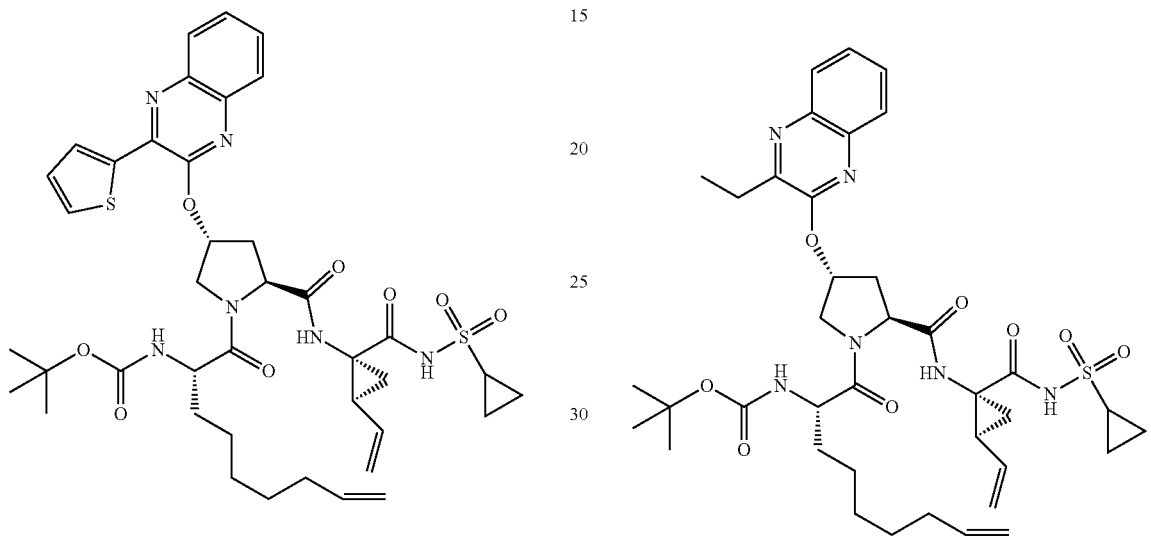

The same procedure was used as described above for compound 16b. Ester 12f (1.85 g, 3.0 mmol) was treated with LiOH.H$_2$O to afford acid 13f, which was coupled with amine salt 14 (0.96 g, 3.6 mmol) using DIEA (2.0 mL, 12.1 mmol) and HATU (1.70 g, 4.5 mmol) to provide the bis-olefin compound 16f (1.60 g, 66%) as a white solid. $^1$H NMR (400 MHz, CDCl$_3$) δ 10.23 (s, 1H), 8.10 (d, J=3.2 Hz, 1H), 8.01 (dd, J=8.0, 1.2 Hz, 1H), 7.79 (dd, J=8.8, 1.6 Hz, 1H), 7.65-7.56 (m, 2H), 7.53 (d, J=5.2 Hz, 1H), 7.17 (dd, J=4.8, 4.0 Hz, 1H), 7.11 (s, 1H), 6.08 (br s, 1H), 5.83-5.73 (m, 2H), 5.35 (d, J=8.8 Hz, 1H), 5.26 (dd, J=16.8, 1.2 Hz, 1H), 5.13 (dd, J=10.4, 1.2 Hz, 1H), 5.01-4.90 (m, 2H), 4.54 (t, J=8.8 Hz, 1H), 4.46-4.39 (m, 1H), 4.34 (d, J=12.4 Hz, 1H), 4.07 (dd, J=12.0, 3.6 Hz, 1H), 2.95-2.87 (m, 1H), 2.68-2.56 (m, 2H), 2.10 (q, J=8.8 Hz, 1H), 2.05-1.98 (m, 3H), 1.75-1.55 (m, 2H), 1.45-1.16 (m, 18H), 1.06-0.99 (m, 2H) ppm; $^{13}$C NMR (100 MHz, CDCl$_3$) δ 173.83, 172.34, 168.51, 155.70, 152.05, 140.39, 139.17, 138.93, 138.86, 138.72, 132.47, 130.46, 130.35, 129.56, 128.57, 128.13, 127.54, 126.72, 118.54, 114.44, 79.73, 75.39, 60.32, 53.23, 52.51, 41.57, 35.14, 34.10, 33.66, 31.99, 31.14, 28.75, 28.67, 28.26, 25.34, 23.56, 6.46, 6.03 ppm; HRMS (ESI) m/z: [M+H]$^+$ calcd for C$_{40}$H$_{51}$N$_6$O$_8$S2, 807.3204; found 807.3214.

The same procedure was used as described above for compound 16b. Ester 12g (1.95 g, 3.5 mmol) was treated with LiOH.H$_2$O to afford acid 13g, which was coupled with amine salt 14 (1.10 g, 4.1 mmol) using DIEA (2.30 mL, 14.0 mmol) and HATU (2.0 g, 5.3 mmol) to provide the bis-olefin compound 16g (2.0 g, 76%) as a white solid. $^1$H NMR (400 MHz, CDCl$_3$) δ 10.24 (s, 1H), 7.96 (d, J=8.4 Hz, 1H), 7.78 (d, J=8.0 Hz, 1H), 7.63-7.53 (m, 2H), 7.05 (s, 1H), 5.93 (br s, 1H), 5.85-5.73 (m, 2H), 5.35 (d, J=8.4 Hz, 1H), 5.27 (d, J=17.2 Hz, 1H), 5.14 (d, J=10.8 Hz, 1H), 5.00-4.90 (m, 2H), 4.48 (t, J=8.0 Hz, 1H), 4.37-4.32 (m, 1H), 4.20 (d, J=12.0 Hz, 1H), 4.03 (dd, J=12.0, 4.0 Hz, 1H), 2.96-2.89 (m, 3H), 2.57-2.52 (m, 2H), 2.12 (q, J=8.8 Hz, 1H), 2.05-1.99 (m, 2H), 1.75-1.54 (m, 2H), 1.46-1.17 (m, 22H), 1.08-1.02 (m, 2H) ppm; $^{13}$C NMR (100 MHz, CDCl$_3$) δ 173.81, 172.33, 168.51, 155.64, 154.33, 151.84, 139.16, 138.91, 138.84, 132.48, 129.11, 128.31, 126.92, 126.86, 118.54, 114.44, 79.74, 74.56, 60.33, 53.16, 52.35, 41.56, 35.22, 34.18, 33.65, 32.14, 31.13, 28.74, 28.65, 28.23, 26.73, 25.24, 23.62, 11.42, 6.47, 6.00 ppm; HRMS (ESI) m/z: [M+H]$^+$ calcd for C38H53N6O8S, 753.3640; found 753.3636.

119 tert-Butyl ((2R,6S,13aS,14aR,16aS,Z)-14a-((cyclopropylsulfonyl)carbamoyl)-2-((7-methoxy-3-methylquinoxalin-2-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (18b)

120 tert-Butyl ((2R,6S,13aS,14aR,16aS,Z)-2-((7-methoxy-3-methylquinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (19b)

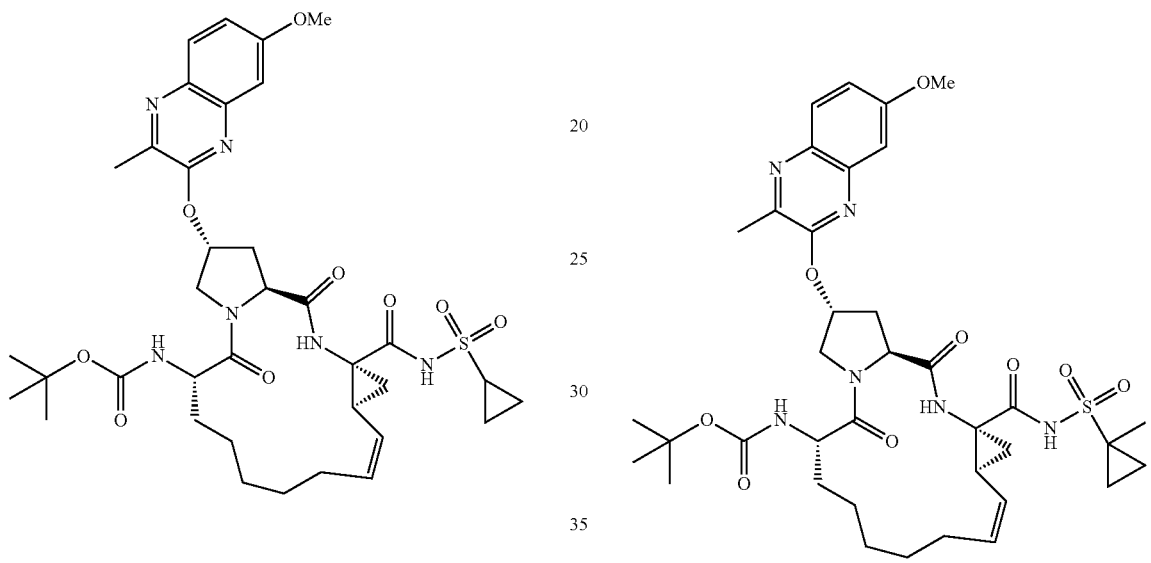

A degassed solution of bis-olefin 16b (1.57 g, 2.0 mmol) in 1,2-DCE (310 mL) was heated to 50° C. under argon, then Zhan 1b catalyst (0.150 g, 0.20 mmol) was added in two portions over 10 min. The resulting reaction mixture was heated to 70° C. and stirred for 6 h. The reaction mixture was cooled to room temperature and solvents were evaporated under reduced pressure. The residue was purified by flash chromatography using 50-90% EtOAc/hexanes as the eluent to yield the P1-P3 macrocyclic product 18b (0.67 g, 45%) as an off-white solid. $^1$H NMR (400 MHz, CDCl$_3$) δ 10.28 (s, 1H), 7.80 (d, J=9.6 Hz, 1H), 7.19-7.16 (m, 2H), 6.88 (s, 1H), 5.89 (br s, 1H), 5.69 (q, J=9.2 Hz, 1H), 5.12 (d, J=8.0 Hz, 1H), 4.97 (t, J=9.2 Hz, 1H), 4.61 (t, J=8.0 Hz, 1H), 4.51 (d, J=12.0 Hz, 1H), 4.28-4.22 (m, 1H), 4.01 (dd, J=11.6, 4.0 Hz, 1H), 3.94 (s, 3H), 2.94-2.86 (m, 1H), 2.70-2.48 (m, 6H), 2.31 (q, J=8.4 Hz, 1H), 1.94-1.68 (m, 2H), 1.60-1.22 (m, 19H), 1.16-1.06 (m, 2H), 0.95-0.89 (m, 1H) ppm; $^{13}$C NMR (100 MHz, CDCl$_3$) δ 177.14, 173.33, 168.0, 160.31, 155.32, 155.03, 144.49, 141.01, 136.30, 134.24, 128.68, 124.47, 118.90, 105.97, 79.85, 74.84, 59.44, 55.72, 53.06, 51.96, 44.57, 34.58, 32.72, 31.02, 29.73, 28.15, 27.10, 27.05, 26.01, 22.18, 20.96, 19.73, 6.67, 6.12 ppm; HRMS (ESI) m/z: [M+H]$^+$ calcd for C$_{36}$H$_{49}$N$_6$O$_9$S, 741.3276; found 741.3255. Anal. RP-HPLC: $t_R$ 12.71 min, purity 99%.

The same procedure was used as described above for compound 18b. Bis-olefin 17b (1.50 g, 1.9 mmol) was treated with Zhan 1b catalyst (0.150 g, 0.20 mmol) in 1,2-DCE (300 mL) to provide the P1-P3 macrocyclic compound 19b (1.0 g, 70%) as an off-white solid. $^1$H NMR (400 MHz, CDCl$_3$) δ 10.16 (s, 1H), 7.82 (d, J=9.2 Hz, 1H), 7.19-7.16 (m, 2H), 6.92 (s, 1H), 5.88 (br s, 1H), 5.69 (q, J=9.2 Hz, 1H), 5.12 (d, J=7.6 Hz, 1H), 4.99 (t, J=8.8 Hz, 1H), 4.61 (t, J=8.0 Hz, 1H), 4.51 (d, J=11.2 Hz, 1H), 4.28-4.22 (m, 1H), 4.03 (dd, J=11.2, 4.0 Hz, 1H), 3.95 (s, 3H), 2.70-2.50 (m, 6H), 2.31 (q, J=8.8 Hz, 1H), 1.92-1.66 (m, 4H), 1.60-1.20 (m, 21H), 0.85-0.78 (m, 2H) ppm; $^{13}$C NMR (100 MHz, CDCl$_3$) δ 177.16, 173.33, 166.94, 160.33, 155.32, 155.04, 144.46, 141.03, 134.20, 136.25, 128.66, 124.89, 118.93, 105.98, 79.85, 74.88, 59.46, 55.72, 53.08, 51.97, 44.73, 36.43, 34.61, 32.72, 29.65, 28.15, 27.06, 26.07, 22.21, 20.96, 19.71, 18.17, 14.51, 12.51 ppm; HRMS (ESI) m/z: [M+H]$^+$ calcd for C$_{37}$H$_{51}$N$_6$O$_9$S, 755.3433; found 755.3404. Anal. HPLC: $t_R$ 13.57 min, purity 99%.

121 tert-Butyl ((2R,6S,13aS,14aR,16aS,Z)-2-((3-chloro-7-methoxyquinoxalin-2-yl)oxy)-14a-((cyclopropylsulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (18c)

122 tert-Butyl ((2R,6S,13aS,14aR,16aS,Z)-2-((3-chloro-7-methoxyquinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (19c)

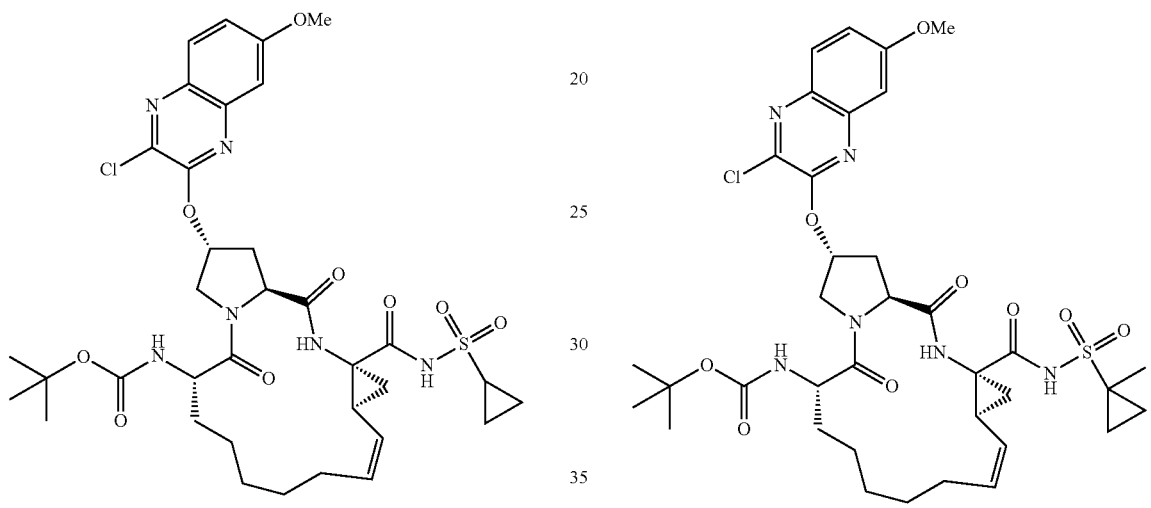

The same procedure was used as described above for compound 18b. Bis-olefin 16c (1.50 g, 1.9 mmol) was treated with Zhan 1b catalyst (0.150 g, 0.20 mmol) in 1,2-DCE (300 mL) to provide the P1-P3 macrocyclic compound 18c (0.73 g, 50%) as an off-white solid. $^1$H NMR (400 MHz, CDCl$_3$) δ 10.30 (s, 1H), 7.78 (d, J=9.6 Hz, 1H), 7.25-7.20 (m, 2H), 7.00 (s, 1H), 5.86 (s, 1H), 5.68 (q, J=9.2 Hz, 1H), 5.19 (d, J=7.6 Hz, 1H), 4.95 (t, J=9.2 Hz, 1H), 4.65 (t, J=8.0 Hz, 1H), 4.59 (d, J=11.6 Hz, 1H), 4.26-4.22 (m, 1H), 4.03 (dd, J=11.6, 4.0 Hz, 1H), 3.95 (s, 3H), 2.94-2.87 (m, 1H), 2.68-2.51 (m, 3H), 2.31 (q, J=8.8 Hz, 1H), 1.94-1.74 (m, 2H), 1.60-1.20 (m, 19H), 1.17-1.04 (m, 2H), 0.96-0.89 (m, 1H) ppm; $^{13}$C NMR (100 MHz, CDCl$_3$) δ 177.32, 173.48, 168.24, 161.52, 155.30, 152.45, 141.15, 136.53, 136.25, 134.26, 129.02, 124.71, 120.31, 106.06, 80.14, 76.38, 59.71, 56.08, 52.90, 52.15, 44.80, 34.73, 32.85, 31.28, 29.88, 28.38, 27.36, 27.31, 26.29, 22.46, 21.13, 6.90, 6.35 ppm. HRMS (ESI) m/z: [M+H]$^+$ calcd for C$_{35}$H$_{46}$ClN$_6$O$_9$S, 761.2730; found 761.2706. Anal. HPLC: t$_R$ 14.28 min, purity 96%.

The same procedure was used as described above for compound 18b. Bis-olefin 17c (1.20 g, 1.5 mmol) was treated with Zhan 1b catalyst (0.150 g, 0.20 mmol) in 1,2-DCE (300 mL) to provide the P1-P3 macrocyclic compound 19c (1.0 g, 86%) as an off-white solid. $^1$H NMR (400 MHz, CDCl$_3$) δ 10.20 (s, 1H), 7.78 (d, J=10.0 Hz, 1H), 7.23-7.20 (m, 2H), 7.07 (s, 1H), 5.85 (br s, 1H), 5.67 (q, J=8.4 Hz, 1H), 5.25 (d, J=7.2 Hz, 1H), 4.96 (t, J=9.2 Hz, 1H), 4.67-4.58 (m, 2H), 4.28-4.22 (m, 1H), 4.04 (dd, J=11.2, 3.2 Hz, 1H), 3.96 (s, 3H), 2.68-2.62 (m, 2H), 2.60-2.50 (m, 1H), 2.33 (q, J=8.0 Hz, 1H), 1.91-1.72 (m, 4H), 1.60-1.20 (m, 21H), 0.84-0.78 (m, 2H) ppm; $^{13}$C NMR (100 MHz, CDCl$_3$) δ 177.18, 173.18, 167.07, 161.27, 155.06, 152.21, 140.92, 136.27, 135.99, 134.0, 128.76, 124.88, 120.09, 105.81, 79.90, 76.21, 59.51, 55.85, 52.69, 51.89, 44.70, 36.41, 34.54, 32.57, 29.48, 28.25, 28.15, 27.11, 26.15, 22.22, 20.83, 18.17, 14.51, 12.50 ppm; HRMS (ESI) m/z: [M+H]$^+$ calcd for C$_{36}$H$_{48}$ClN$_6$O$_9$S, 775.2887; found 775.2870. Anal. HPLC: t$_R$ 14.69 min, purity 97%.

123 tert-Butyl 42R,6S,13aS,14aR,16aS,Z)-14a-((cyclopropylsulfonyl)carbamoyl)-2-((3-isopropyl-7-methoxyquinoxalin-2-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (18e)

124 tert-Butyl ((2R,6S,13aS,14aR,16aS,Z)-2-((3-isopropyl-7-methoxyquinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (19e)

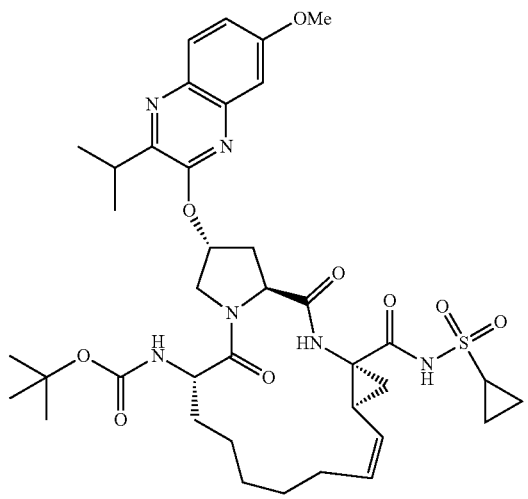 [SMILES: COc1ccc2nc(C(C)C)c(O[C@@H]3C[C@H]4C(=O)N[C@]5(C(=O)NS(=O)(=O)C6CC6)C[C@H]5/C=C\CCCCC[C@H](NC(=O)OC(C)(C)C)C(=O)N4C3)nc2c1]

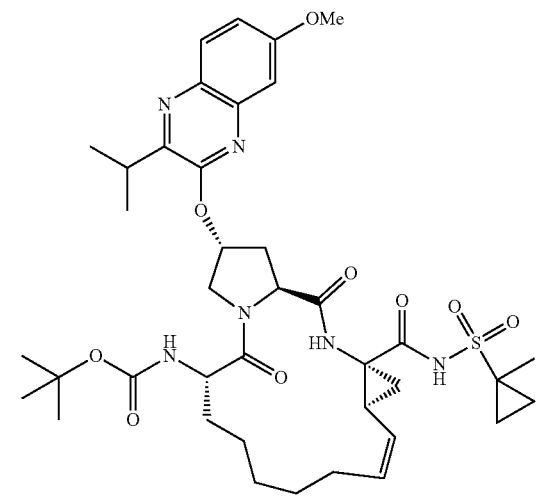 [SMILES: COc1ccc2nc(C(C)C)c(O[C@@H]3C[C@H]4C(=O)N[C@]5(C(=O)NS(=O)(=O)C6(C)CC6)C[C@H]5/C=C\CCCCC[C@H](NC(=O)OC(C)(C)C)C(=O)N4C3)nc2c1]

The same procedure was used as described above for compound 18b. Bis-olefin 16e (1.80 g, 2.3 mmol) was treated with Zhan 1b catalyst (0.150 g, 0.20 mmol) in 1,2-DCE (350 mL) to provide the P1-P3 macrocyclic compound 18e (0.95 g, 58%) as an off-white solid. $^1$H NMR (400 MHz, CDCl$_3$) δ 10.28 (s, 1H), 7.83 (d, J=9.6 Hz 1H), 7.20-7.15 (m, 2H), 6.94 (s, 1H), 5.91 (s, 1H), 5.70 (q, J=8.4 Hz, 1H), 5.20 (d, J=8.0 Hz, 1H), 4.97 (t, J=8.8 Hz, 1H), 4.58 (t, J=8.0 Hz, 1H), 4.46 (d, J=12.0 Hz, 1H), 4.33-4.26 (m, 1H), 4.03 (dd, J=12.0, 4.4 Hz, 1H), 3.94 (s, 3H), 3.41-3.33 (m, 1H), 2.93-2.86 (m, 1H), 2.66-2.50 (m, 3H), 2.34 (q, J=8.8 Hz, 1H), 1.93-1.74 (m, 2H), 1.60-1.05, m, 27H), 0.95-0.88 (m, 1H) ppm; $^{13}$C NMR (100 MHz, CDCl$_3$) δ 177.22, 173.13, 168.13, 160.22, 154.96, 154.36, 151.82, 140.61, 136.32, 134.31, 129.28, 124.45, 118.61, 105.79, 79.81, 74.55, 59.47, 55.71, 53.12, 51.86, 44.52, 34.74, 32.91, 31.00, 30.58, 29.65, 28.18, 27.16, 27.11, 26.12, 22.14, 20.89, 20.51, 20.42, 6.67, 6.10 ppm; HRMS (ESI) m/z: [M+H]$^+$ calcd for C$_{38}$H$_{53}$N$_6$O$_9$S, 769.3589; found 769.3565. Anal. HPLC: t$_R$ 15.82 min, purity 98%.

The same procedure was used as described above for compound 18b. Bis-olefin 17e (1.90 g, 2.3 mmol) was treated with Zhan 1b catalyst (0.20 g, 0.27 mmol) in 1,2-DCE (350 mL) to provide the P1-P3 macrocyclic compound 19e (1.1 g, 60%) as an off-white solid. $^1$H NMR (400 MHz, CDCl$_3$) δ 10.15 (s, 1H), 7.83 (d, J=9.6 Hz, 1H), 7.19-7.15 (m, 2H), 6.95 (s, 1H), 5.91 (s, 1H), 5.70 (q, J=8.4 Hz, 1H), 5.19 (d, J=8.0 Hz, 1H), 4.99 (t, J=9.6 Hz, 1H), 4.57 (t, J=8.0 Hz, 1H), 4.47 (d, J=11.6 Hz, 1H), 4.34-4.27 (m, 1H), 4.06 (dd, J=11.2, 4.0 Hz, 1H), 3.94 (s, 3H), 3.41-3.34 (m, 1H), 2.68-2.48 (m, 3H), 2.34 (q, J=8.4 Hz, 1H), 1.93-1.70 (m, 4H), 1.62-1.17 (m, 27H), 0.84-0.78 (m, 2H) ppm; $^{13}$C NMR (100 MHz, CDCl$_3$) δ 177.19, 173.14, 167.04, 160.24, 154.96, 154.36, 151.79, 140.62, 136.25, 134.28, 129.25, 124.88, 118.64, 105.81, 79.81, 74.61, 59.49, 55.71, 53.15, 51.87, 44.68, 36.43, 34.75, 32.91, 30.59, 29.59, 28.17, 27.14, 26.17, 22.18, 20.91, 20.50, 20.42, 18.17, 14.50, 12.49 ppm; HRMS (ESI) m/z: [M+H]$^+$ calcd for C$_{39}$H$_{55}$N$_6$O$_9$S, 783.3746; found 783.3722. Anal. HPLC: t$_R$ 16.46 min, purity 98%.

125 tert-Butyl ((2R,6S,13aS,14aR,16aS,Z)-14a-((cyclopropylsulfonyl)carbamoyl)-5,16-dioxo-2-((3-(thiophen-2-yl)quinoxalin-2-yl)oxy)-1,2,3,5,6,7,8,9,10, 11,13a,14,14a,15,16,16a-hexadecahydrocyclopropa[e]pyrrolo[1,2-a][1,4]diazacyclopentadecin-6-yl)carbamate (18f)

126 tert-Butyl ((2R,6S,13aS,14aR,16aS,Z)-14a-((cyclopropylsulfonyl)carbamoyl)-2-((3-ethylquinoxalin-2-yl)oxy)-5,16-dioxo-1,2,3,5,6,7,8,9,10,11,13a,14,14a, 15,16,16a-hexadecahydrocyclopropa[e]pyrrolo[1,2-a][1,4]diazacyclopentadecin-6-yl)carbamate (18g)

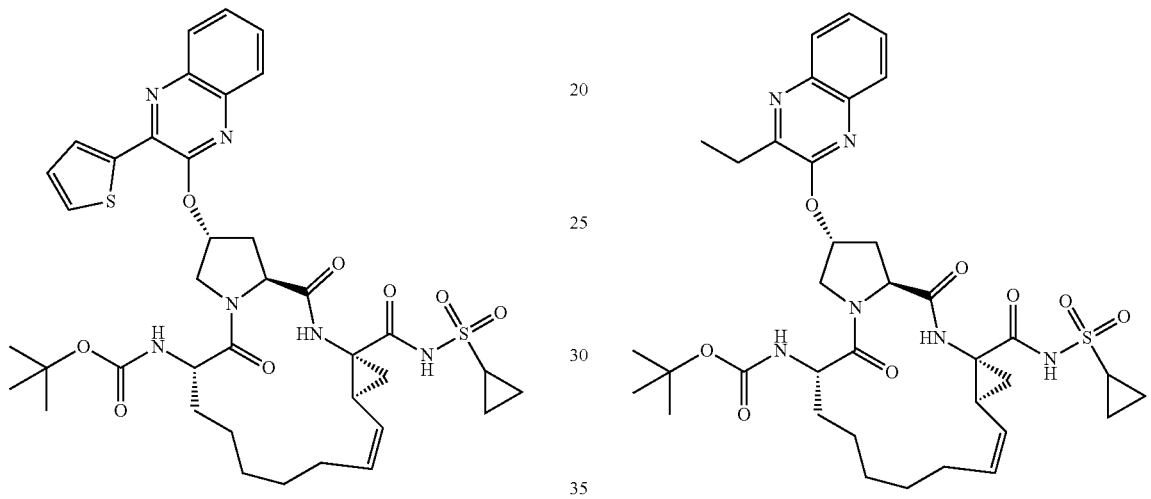

The same procedure was used as described above for compound 18b. Bis-olefin 16f (0.60 g, 0.7 mmol) was treated with Zhan 1b catalyst (0.10 g, 0.13 mmol) in 1,2-DCE (200 mL) to provide the P1-P3 macrocyclic compound 18f (0.35 g, 61%) as an off-white solid. $^1$H NMR (400 MHz, CDCl$_3$) δ 10.28 (s, 1H), 8.08 (d, J=3.2 Hz, 1H), 7.99 (d, J=7.2 Hz, 1H), 7.83 (dd, J=8.4, 1.2 Hz, 1H), 7.65-7.55 (m, 2H), 7.49 (d, J=4.4 Hz, 1H), 7.14 (t, J=4.0 Hz, 1H), 6.96 (s, 1H), 6.08 (br s, 1H), 5.66 (q, J=9.2 Hz, 1H), 5.16 (d, J=8.4 Hz, 1H), 4.95 (t, J=10.0 Hz, 1H), 4.69 (t, J=8.0 Hz, 1H), 4.63 (d, J=12.4 Hz, 1H), 4.34-4.27 (m, 1H), 4.08 (dd, J=12.0, 4.0 Hz, 1H), 2.94-2.86 (m, 1H), 2.76-2.69 (m, 2H), 2.58-2.48 (m, 1H), 2.29 (q, J=8.4 Hz, 1H), 1.92-1.74 (m, 2H), 1.64-1.04 (m, 20H), 0.96-0.88 (m, 1H) ppm; $^{13}$C NMR (100 MHz, CDCl$_3$) δ 177.19, 173.43, 168.20, 155.16, 152.45, 140.65, 139.81, 139.10, 139.07, 136.53, 130.53, 130.33, 129.72, 128.72, 128.30, 127.60, 127.07, 124.72, 80.06, 75.73, 59.75, 53.41, 52.21, 44.79, 34.84, 33.13, 31.27, 29.96, 28.30, 27.41, 27.23, 26.21, 22.54, 21.17, 6.93, 6.37 ppm; HRMS (ESI) m/z: [M+H]$^+$ calcd for C$_{38}$H$_{47}$N$_6$O$_8$S$_2$, 779.2891; found 779.2873. Anal. HPLC: $t_R$ 15.96 min, purity 97%.

The same procedure was used as described above for compound 18b. Bis-olefin 16g (1.80 g, 2.4 mmol) was treated with Zhan 1b catalyst (0.20 g, 0.30 mmol) in 1,2-DCE (350 mL) to provide the P1-P3 macrocyclic compound 18g (1.05 g, 60%) as an off-white solid. $^1$H NMR (400 MHz, CDCl$_3$) δ 10.32 (s, 1H), 7.94 (d, J=8.0 Hz, 1H), 7.80 (dd, J=8.0. 1.2 Hz 1H), 7.62-7.51 (m, 2H), 7.02 (s, 1H), 5.91 (br s, 1H), 5.67 (q, J=8.4 Hz, 1H), 5.19 (d, J=7.6 Hz, 1H), 4.95 (t, J=9.2 Hz, 1H), 4.61 (t, J=8.0 Hz, 1H), 4.51 (d, J=11.6 Hz, 1H), 4.27-22 (m, 1H), 4.03 (dd, J=11.2, 3.6 Hz, 1H), 2.94-2.85 (m, 3H), 2.65-2.52 (m, 3H), 2.32 (q, J=8.4 Hz, 1H), 1.91-1.76 (m, 2H), 1.56-1.20 (m, 20H), 1.15-1.04 (m, 4H), 0.93-0.87 (m, 1H) ppm; $^{13}$C NMR (400 MHz, CDCl$_3$) δ 177.23, 173.20, 168.17, 154.96, 154.48, 152.00, 139.29, 138.81, 136.32, 128.98, 128.20, 126.95, 126.68, 124.50, 79.77, 74.79, 59.46, 53.16, 51.91, 44.57, 34.64, 32.81, 30.99, 29.66, 28.13, 27.09, 26.68, 26.06, 22.14, 20.94, 11.31, 6.66, 6.10 ppm; HRMS (ESI) m/z: [M+H]$^+$ calcd for C$_{36}$H$_{49}$N$_6$O$_8$S, 725.3327; found 725.3301. Anal. HPLC: $t_R$ 14.40 min, purity 99%.

127

Cyclopentyl ((2R,6S,13aS,14aR,16aS,Z)-14a-((cyclopropylsulfonyl)carbamoyl)-2-((7-methoxy-3-methylquinoxalin-2-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (22b)

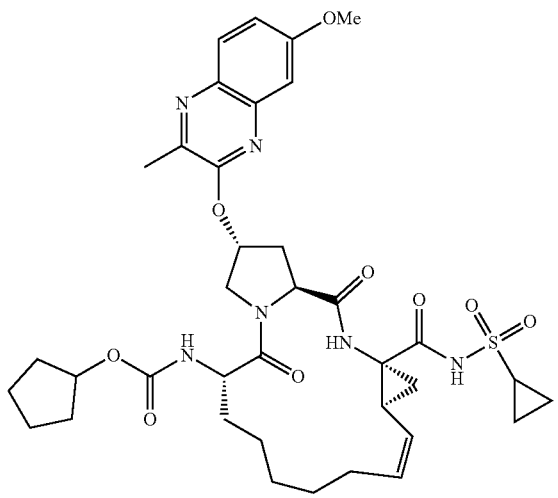 [SMILES: COc1ccc2nc(C)c(O[C@@H]3C[C@H]4C(=O)N[C@]5(C(=O)NS(=O)(=O)C6CC6)C[C@H]5/C=C\CCCCC[C@H](NC(=O)OC5CCCC5)C(=O)N4C3)nc2c1]

Compound 18b (0.32 g, 0.43 mmol) was treated with a solution of 4 N HCl in 1,4-dioxane (10 mL). The reaction mixture was stirred at room temperature for 3 h, and then concentrated under reduced pressure, and the residue was dried under high vacuum. The off-white solid was triturated with diethyl ether (3×10 mL) and dried under high vacuum to yield the amine salt 20b (0.29 g, 100%) as a white powder.

A solution of the above amine salt 20b (0.29 g, 0.43 mmol) in anhydrous CH$_3$CN (13 mL) was treated with DIEA (0.28 mL, 1.7 mmol) and N-(cyclopentyloxycarbonyloxy)-succinimide (0.108 g, 0.48 mmol). The reaction mixture was stirred at room temperature for 36 h, then concentrated under reduced pressure and dried under high vacuum. The residue was purified by flash chromatography using 50-90% EtOAc/hexanes as the eluent to provide the target compound 22b (0.29 g, 90%) as a white solid. $^1$H NMR (400 MHz, CDCl$_3$) δ 10.29 (s, 1H), 7.79 (d, J=9.6 Hz, 1H), 7.20-7.16 (m, 2H), 6.98 (s, 1H), 5.91 (br s, 1H), 5.68 (q, J=8.8 Hz, 1H), 5.24 (d, J=8.0 Hz, 1H), 4.96 (t, J=8.8 Hz, 1H), 4.88-4.84 (br s, 1H), 4.62 (t, J=7.6 Hz, 1H), 4.42 (d, J=11.6 Hz, 1H), 4.33-4.27 (m, 1H), 4.04 (dd, J=11.6, 4.0 Hz, 1H), 3.94 (s, 3H), 2.94-2.86 (m, 1H), 2.69-2.48 (m, 5H), 2.29 (q, J=8.4 Hz, 1H), 1.93-1.23 (m, 21H), 1.17-1.05 (m, 2H), 0.96-0.87 (m, 1H) ppm; $^{13}$C NMR (100 MHz, CDCl$_3$) δ 177.18, 173.03, 168.05, 160.22, 155.69, 155.32, 144.67, 140.95, 136.25, 134.26, 128.85, 124.44, 118.79, 105.97, 77.89, 74.63, 59.45, 55.72, 53.02, 52.20, 44.51, 34.55, 32.72, 32.65, 32.59, 31.02, 29.74, 27.21, 27.03, 26.04, 23.60, 23.57, 22.15, 20.90, 19.86, 6.67, 6.12 ppm; HRMS (ESI) m/z: calcd for C$_{37}$H$_{49}$N$_6$O$_9$S [M+H]$^+$ 753.3276; found 753.3252. Anal. HPLC: $t_R$ 13.05 min, purity 99%.

128

Cyclopentyl ((2R,6S,13aS,14aR,16aS,Z)-2-((7-methoxy-3-methylquinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (23b)

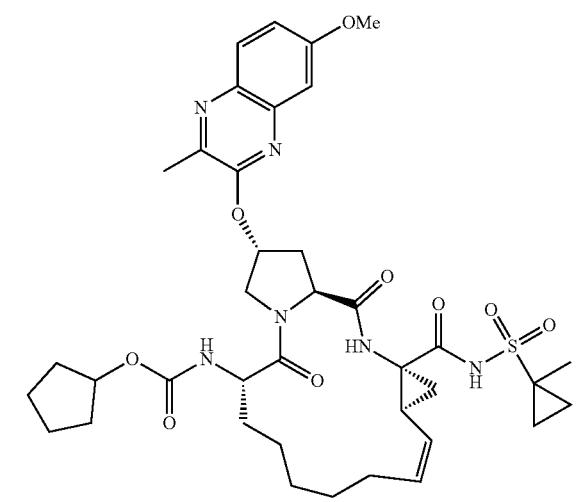 [SMILES: COc1ccc2nc(C)c(O[C@@H]3C[C@H]4C(=O)N[C@]5(C(=O)NS(=O)(=O)C6(C)CC6)C[C@H]5/C=C\CCCCC[C@H](NC(=O)OC5CCCC5)C(=O)N4C3)nc2c1]

The same procedure was used as described above for compound 22b. Compound 19b (0.44 g, 0.58 mmol) was treated 4 N HCl in 1,4-dioxane (10 mL) to yield the amine salt 21b, which was treated with DIEA (0.38 mL, 2.3 mmol) and N-(cyclopentyloxycarbonyloxy)-succinimide (0.15 g, 0.66 mmol) to provide the target compound 23b (0.32 g, 72%) as a white solid. $^1$H NMR (400 MHz, CDCl$_3$) δ 10.17 (s, 1H), 7.79 (d, J=10.0 Hz, 1H), 7.20-7.16 (m, 2H), 6.96 (s, 1H), 5.91 (br s, 1H), 5.69 (q, J=8.8 Hz, 1H), 5.25 (d, J=8.0 Hz, 1H), 4.98 (t, J=9.6 Hz, 1H), 4.88-4.83 (m, 1H), 4.61 (t, J=8.0 Hz, 1H), 4.43 (d, J=11.2 Hz, 1H), 4.34-4.27 (m, 1H), 4.05 (dd, J=10.8, 4.0 Hz, 1H), 3.94 (s, 3H), 2.70-2.48 (m, 5H), 2.30 (q, J=8.8 Hz, 1H), 1.93-1.23 (m, 25H), 0.85-0.78 (m, 2H) ppm; $^{13}$C NMR (100 MHz, CDCl$_3$) δ 177.20, 173.01, 167.0, 160.22, 155.68, 155.31, 144.67, 140.96, 136.21, 134.27, 128.85, 124.86, 118.79, 105.98, 77.89, 74.67, 59.48, 55.72, 53.05, 52.20, 44.67, 36.43, 34.58, 32.72, 32.65, 32.57, 29.64, 27.17, 27.04, 26.09, 23.59, 23.57, 22.18, 20.91, 19.85, 18.17, 14.49, 12.51 ppm; HRMS (ESI) m/z: calcd for C$_{38}$H$_{51}$N$_6$O$_9$S [M+H]$^+$ 767.3433; found 767.3408. Anal. HPLC: $t_R$ 13.88 min, purity 98%.

129

Cyclopentyl ((2R,6S,13aS,14aR,16aS,Z)-2-((3-chloro-7-methoxyquinoxalin-2-yl)oxy)-14a-((cyclopropylsulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (22c)

130

Cyclopentyl ((2R,6S,13aS,14aR,16aS,Z)-2-((3-chloro-7-methoxyquinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (23c)

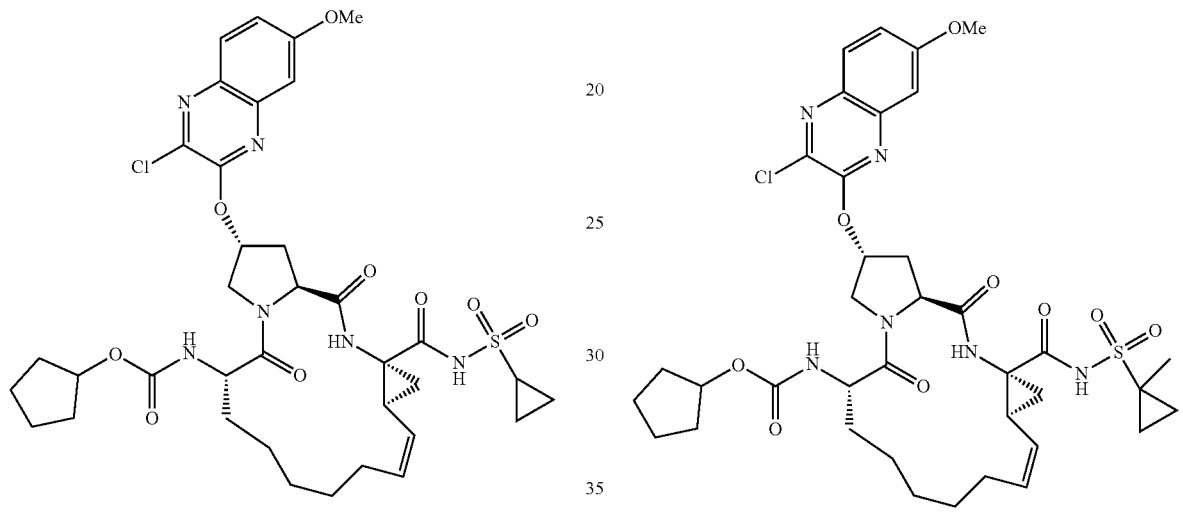

The same procedure was used as described above for compound 22b. Compound 18c (0.40 g, 0.53 mmol) was treated 4 N HCl in 1,4-dioxane (10 mL) to yield the amine salt 20c, which was treated with DIEA (0.35 mL, 2.1 mmol) and N-(cyclopentyloxycarbonyloxy)-succinimide (0.15 g, 0.66 mmol) to provide the target compound 22c (0.34 g, 83%) as a white solid. $^1$H NMR (500 MHz, CDCl$_3$) δ 10.30 (s, 1H), 7.79 (d, J=9.0 Hz, 1H), 7.23-7.20 (m, 2H), 7.11 (s, 1H), 5.89 (br s, 1H), 5.68 (q, J=9.0 Hz, 1H), 5.30 (d, J=8.0 Hz, 1H), 4.96 (t, J=9.0 Hz, 1H), 4.84-4.80 (m, 1H), 4.67 (t, J=7.6 Hz, 1H), 4.51 (d, J=11.4 Hz, 1H), 4.29 (t, J=7.6 Hz, 1H), 4.04 (dd, J=11.0, 3.5 Hz, 1H), 3.95 (s, 3H), 2.93-2.87 (m, 1H), 2.71-2.47 (m, 3H), 2.30 (q, J=8.5 Hz, 1H), 1.95-1.20 (m, 20H), 1.16-1.04 (m, 2H), 0.95-0.87 (m, 1H) ppm; $^{13}$C NMR (125 MHz, CDCl$_3$) δ 177.11, 173.01, 168.06, 161.31, 155.75, 152.29, 140.95, 136.22, 136.18, 134.08, 128.77, 124.49, 120.08, 105.88, 77.98, 76.05, 59.48, 55.86, 52.62, 52.19, 44.53, 34.43, 32.70, 32.62, 32.47, 31.07, 29.70, 27.23, 27.06, 26.06, 23.59, 23.57, 22.25, 20.85, 6.67, 6.12 ppm; HRMS (ESI) m/z: calcd for C$_{36}$H$_{46}$ClN$_6$O$_9$S [M+H]$^+$ 773.2730; found 773.2714. Anal. HPLC: tR 14.35 min, purity 96%.

The same procedure was used as described above for compound 22b. Compound 19c (0.50 g, 0.64 mmol) was treated 4 N HCl in 1,4-dioxane (10 mL) to yield the amine salt 21c, which was treated with DIEA (0.43 mL, 2.6 mmol) and N-(cyclopentyloxycarbonyloxy)-succinimide (0.20 g, 0.88 mmol) to provide the target compound 23c (0.46 g, 91%) as a white solid. $^1$H NMR (400 MHz, CDCl$_3$) δ 10.22 (s, 1H), 7.78 (d, J=10.0 Hz, 1H), 7.23-7.20 (m, 2H), 7.16 (s, 1H), 5.87 (br s, 1H), 5.66 (q, J=8.4 Hz, 1H), 5.39 (d, J=7.2 Hz, 1H), 4.95 (t, J=9.6 Hz, 1H), 4.84-4.80 (m, 1H), 4.65 (t, J=8.0 Hz, 1H), 4.53 (d, J=8.4 Hz, 1H), 4.32-4.26 (m, 1H), 4.04 (dd, J=12.0, 4.0 Hz, 1H), 3.95 (s, 3H), 2.67-2.46 (m, 3H), 2.30 (q, J=8.4 Hz, 1H), 1.90-1.23 (m, 24H), 0.84-0.78 (m, 2H) ppm; $^{13}$C NMR (100 MHz, CDCl$_3$) δ 177.18, 172.93, 167.03, 161.26, 155.73, 152.26, 140.93, 136.22, 136.16, 134.04, 128.73, 124.86, 120.08, 105.84, 77.96, 76.06, 59.52, 55.85, 52.61, 52.14, 44.68, 36.42, 34.45, 32.69, 32.60, 32.40, 29.54, 27.14, 27.07, 26.12, 23.58, 23.55, 22.23, 20.85, 18.17, 14.50, 12.52 ppm; HRMS (ESI) m/z: calcd for C$_{37}$H$_{48}$ClN$_6$O$_9$S [M+H]$^+$ 787.2887; found 787.2872. Anal. HPLC: t$_R$ 15.11 min, purity 99%.

131

Cyclopentyl ((2R,6S,13aS,14aR,16aS,Z)-14a-((cyclopropylsulfonyl)carbamoyl)-2-((3-isopropyl-7-methoxyquinoxalin-2-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (22e)

132

Cyclopentyl ((2R,6S,13aS,14aR,16aS,Z)-2-((3-isopropyl-7-methoxyquinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (23e)

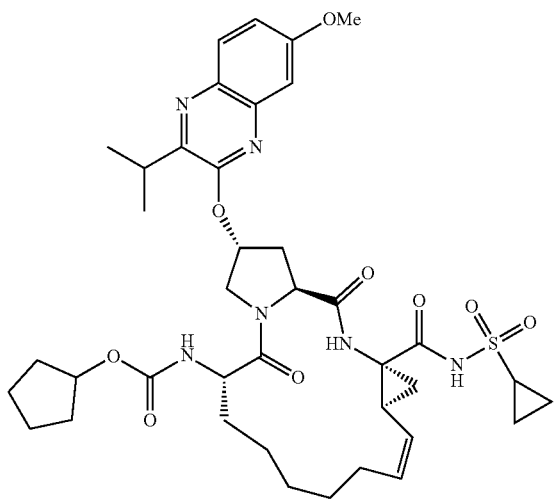 [SMILES: COc1ccc2nc(C(C)C)c(O[C@@H]3C[C@H]4C(=O)N[C@]5(C(=O)NS(=O)(=O)C6CC6)C[C@H]5/C=C\CCCCC[C@H](NC(=O)OC5CCCC5)C(=O)N4C3)nc2c1]

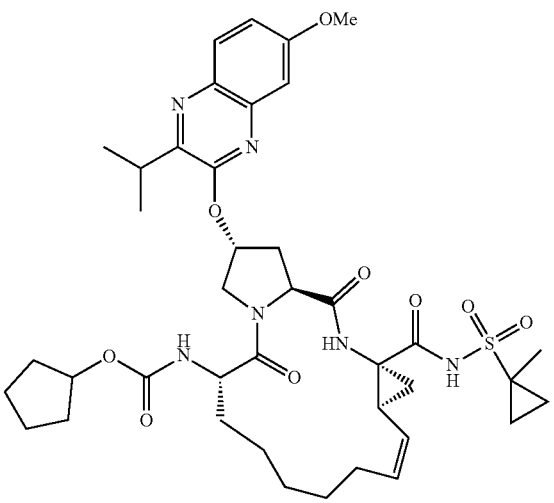 [SMILES: COc1ccc2nc(C(C)C)c(O[C@@H]3C[C@H]4C(=O)N[C@]5(C(=O)NS(=O)(=O)C6(C)CC6)C[C@H]5/C=C\CCCCC[C@H](NC(=O)OC5CCCC5)C(=O)N4C3)nc2c1]

The same procedure was used as described above for compound 22b. Compound 18e (0.45 g, 0.58 mmol) was treated 4 N HCl in 1,4-dioxane (10 mL) to yield the amine salt 20e, which was treated with DIEA (0.40 mL, 2.4 mmol) and N-(cyclopentyloxycarbonyloxy)-succinimide (0.15 g, 0.66 mmol) to provide the target compound 22e (0.40 g, 88%) as a white solid. $^1$H NMR (400 MHz, CDCl$_3$) δ 10.29 (s, 1H), 7.84 (d, J=8.8 Hz 1H), 7.20-7.16 (m, 2H), 6.94 (s, 1H), 5.93 (br s, 1H), 5.70 (q, J=8.4 Hz, 1H), 5.28 (d, J=8.0 Hz 1H), 4.97 (t, J=8.8 Hz, 1H), 4.87-4.82 (m, 1H), 4.59 (t, J=7.2 Hz, 1H), 4.44 (d, J=11.2 Hz, 1H), 4.36-4.30 (m, 1H), 4.04 (dd, J=11.6, 7.6 Hz, 1H), 3.94 (s, 3H), 3.42-3.34 (m, 1H), 2.93-2.86 (m, 1H), 2.70-2.48 (m, 3H), 2.32 (q, J=8.4 Hz, 1H), 1.94-1.21 (m, 26H), 1.16-1.05 (m, 2H), 0.96-0.88 (m, 1H) ppm; $^{13}$C NMR (100 MHz, CDCl$_3$) δ 177.20, 172.97, 168.08, 160.25, 155.60, 154.40, 151.82, 140.65, 136.27, 134.23, 129.18, 124.47, 118.65, 105.81, 77.81, 74.46, 59.49, 55.70, 53.06, 52.13, 44.52, 34.63, 32.73, 32.57, 31.01, 30.63, 29.68, 27.17, 27.06, 26.08, 23.56, 22.17, 20.91, 20.48, 20.43, 6.65, 6.10 ppm; HRMS (ESI) m/z: calcd for C$_{39}$H$_{53}$N$_6$O$_9$S [M+H]$^+$ 781.3589; found 781.3569. Anal. HPLC: tR 16.03 min, purity 98%.

The same procedure was used as described above for compound 22b. Compound 19e (0.45 g, 0.57 mmol) was treated 4 N HCl in 1,4-dioxane (10 mL) to yield the amine salt 21e, which was treated with DIEA (0.40 mL, 2.4 mmol) and N-(cyclopentyloxycarbonyloxy)-succinimide (0.15 g, 0.66 mmol) to provide the target compound 23e (0.40 g, 88%) as a white solid. $^1$H NMR (400 MHz, CDCl$_3$) δ 10.16 (s, 1H), 7.85 (d, J=8.8 Hz, 1H), 7.21-7.16 (m, 2H), 6.90 (s, 1H), 5.93 (br s, 1H), 5.71 (q, J=8.4 Hz, 1H), 5.25 (d, J=8.0 Hz 1H), 4.99 (t, J=8.8 Hz, 1H), 4.86-4.82 (m, 1H), 4.58 (t, J=8.0 Hz, 1H), 4.46 (d, J=11.2 Hz, 1H), 4.36-4.29 (m, 1H), 4.05 (dd, J=11.2, 3.6 Hz, 1H), 3.94 (s, 3H), 3.42-3.34 (m, 1H), 2.72-2.48 (m, 3H), 2.32 (q, J=8.4 Hz, 1H), 1.94-1.21 (m, 30H), 0.86-0.78 (m, 2H) ppm; $^{13}$C NMR (100 MHz, CDCl$_3$) δ 177.24, 172.94, 167.04, 160.25, 155.60, 154.40, 151.81, 140.67, 136.23, 134.21, 129.17, 124.89, 118.66, 105.83, 77.80, 74.52, 59.53, 55.71, 53.08, 52.13, 44.68, 36.43, 34.65, 32.72, 32.56, 30.63, 29.59, 27.14, 27.08, 26.14, 23.55, 22.19, 20.92, 20.47, 20.44, 18.17, 14.49, 12.47 ppm; HRMS (ESI) m/z: calcd for C$_{40}$H$_{55}$N$_6$O$_9$S [M+H]$^+$ 795.3746; found 795.3723. Anal. HPLC: t$_R$ 16.71 min, purity 99%.

Cyclopentyl ((2R,6S,13aS,14aR,16aS,Z)-14a-((cyclopropylsulfonyl)carbamoyl)-5,16-dioxo-2-((3-(thiophen-2-yl)quinoxalin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (22f)

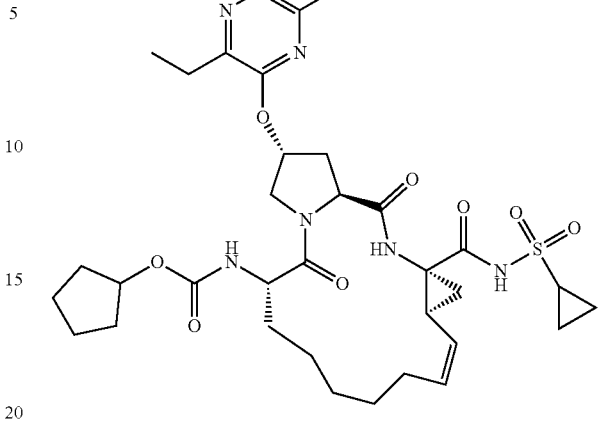

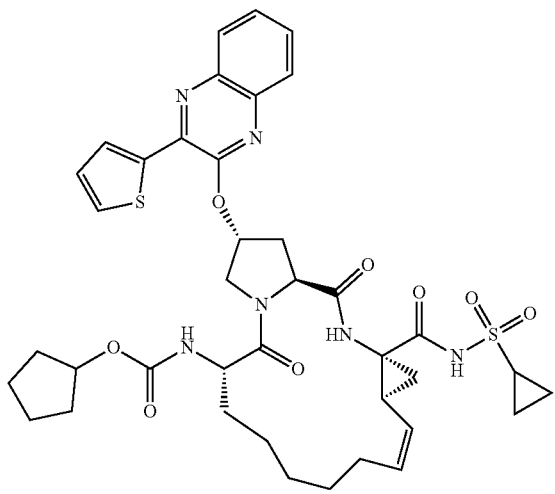 [SMILES: O=C(N[C@H]1CCCCC/C=C\[C@@H]2C[C@@]2(C(=O)NS(=O)(=O)C2CC2)NC(=O)[C@@H]2C[C@@H](Oc3nc4ccccc4nc3-c3cccs3)CN2C1=O)OC1CCCC1]

The same procedure was used as described above for compound 22b. Compound 18f (0.40 g, 0.51 mmol) was treated 4 N HCl in 1,4-dioxane (10 mL) to yield the amine salt 20f, which was treated with DIEA (0.35 mL, 2.1 mmol) and N-(cyclopentyloxycarbonyloxy)-succinimide (0.15 g, 0.66 mmol) to provide the target compound 22f (0.38 g, 94%) as an off-white solid. $^1$H NMR (500 MHz, CDCl$_3$) δ 10.25 (s, 1H), 8.08 (s, 1H), 8.00 (d, J=8.0 Hz, 1H), 7.83 (d, J=8.0 Hz, 1H) 7.65-7.56 (m, 2H), 7.47 (d, J=4.0 Hz, 1H), 7.12 (t, J=4.0 Hz, 1H), 6.93 (s, 1H), 6.11 (br s, 1H), 5.66 (q, J=8.8 Hz, 1H), 5.25 (d, J=8.0 Hz, 1H), 4.95 (t, J=9.0 Hz, 1H), 4.80-4.75 (m, 1H), 4.68-4.61 (m, 2H), 4.37 (t, J=9.0 Hz, 1H), 4.08 (d, J=11.2 Hz, 1H), 2.92-2.85 (m, 1H), 2.75-2.69 (m, 2H), 2.57-2.49 (m, 1H), 2.29 (q, J=8.6 Hz, 1H), 1.88-1.22 (m, 23H), 1.17-1.05 (m, 2H), 0.94-0.87 (m, 1H) ppm; $^{13}$C NMR (125 MHz, CDCl$_3$) δ 176.98, 173.11, 167.92, 155.68, 152.27, 139.71, 138.90, 138.85, 136.28, 130.44, 130.04, 129.51, 128.48, 128.08, 127.40, 126.84, 124.47, 77.90, 75.50, 59.51, 53.24, 52.26, 44.57, 34.61, 32.89, 32.78, 32.48, 31.06, 29.74, 27.19, 27.01, 26.01, 23.58, 22.29, 20.94, 6.68, 6.14 ppm; HRMS (ESI) m/z: calcd for C39H47N6O8S2 [M+H]$^+$ 791.2891; found 791.2872. Anal. HPLC: $t_R$ 16.39 min, purity 99%.

Cyclopentyl ((2R,6S,13aS,14aR,16aS,Z)-14a-((cyclopropylsulfonyl)carbamoyl)-2-((3-ethylquinoxalin-2-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (22g)

The same procedure was used as described above for compound 22b. Compound 18g (0.50 g, 0.69 mmol) was treated 4 N HCl in 1,4-dioxane (10 mL) to yield the amine salt 20g, which was treated with DIEA (0.46 mL, 2.8 mmol) and N-(cyclopentyloxycarbonyloxy)-succinimide (0.18 g, 0.79 mmol) to provide the target compound 22g (0.42 g, 83%) as a white solid. $^1$H NMR (400 MHz, CDCl$_3$) δ 10.31 (s, 1H), 7.95 (d, J=8.0 Hz, 1H), 7.81 (d, J=8.0 Hz, 1H), 7.63-7.52 (m, 2H), 7.00 (s, 1H), 5.94 (br s, 1H), 5.69 (q, J=8.4 Hz, 1H), 5.26 (d, J=8.0 Hz, 1H), 4.96 (t, J=9.6 Hz, 1H), 4.83-4.78 (m, 1H), 4.62 (t, J=8.0 Hz, 1H), 4.46 (d, J=12.0 Hz, 1H), 4.32-4.25 (m, 1H), 4.04 (dd, J=11.6, 3.6 Hz, 1H), 2.95-2.85 (m, 3H), 2.66-2.50 (m, 3H), 2.30 (q, J=8.8 Hz, 1H), 1.93-1.05 (m, 25H), 0.95-0.88 (m, 1H) ppm; $^{13}$C NMR (400 MHz, CDCl$_3$) δ 177.18, 173.05, 168.10, 155.62, 154.51, 152.11, 139.30, 138.85, 136.29, 128.99, 128.18, 126.96, 126.72, 124.50, 77.82, 74.68, 59.46, 53.12, 52.20, 44.55, 34.56, 32.69, 32.57, 31.00, 29.70, 27.12, 27.03, 26.74, 26.02, 23.55, 22.17, 20.94, 11.37, 6.66, 6.11 ppm; HRMS (ESI) m/z: calcd for C$_{37}$H$_{49}$N$_6$O$_8$S [M+H]$^+$ 737.3327; found 737.3306. Anal. HPLC: $t_R$ 14.64 min, purity 99%.

Expression and Purification of NS3/4A Constructs

The HCV GT1a NS3/4A protease gene described in the Bristol Myers Squibb patent was synthesized by GenScript and cloned into a PET28a expression vector. The D168A gene was engineered using the site-directed mutagenesis protocol from Stratagene. Protein expression and purification were carried out as previously described. Briefly, transformed *Escherichia coli* BL21(DE3) cells were grown in LB media containing 30 μg/mL of kanamycin antibiotic at 37° C. After reaching an OD$_{600}$ of 0.8, cultures were induced with 1 mM IPTG and harvested after 4 h of expression. Cells were pelleted by centrifugation, resuspended in Resuspension buffer [50 mM phosphate buffer, 500 mM NaCl, 10% glycerol, 2 mM β-ME, pH 7.5] and frozen at −80° C. for storage.

Cell pellets were thawed and lysed via cell disruptor (Microfluidics Inc.) two times to ensure sufficient DNA shearing. Lysate was centrifuged at 19,000 rpm, for 25 min at 4° C. The soluble fraction was applied to a nickel column (Qiagen) pre-equilibrated with Resuspension buffer. The beads and soluble fraction were incubated at 4° C. for 1.5 h and the lysate was allowed to flow through. Beads were washed with Resuspension buffer supplemented with 20 mM imidazole and eluted with Resuspension buffer supplemented with 200 mM imidazole. The eluent was dialyzed overnight (MWCO 10 kD) to remove the imidazole, and the His-tag was simultaneously removed with thrombin treatment. The eluate was judged >90% pure by polyacrylamide gel electrophoresis, concentrated, flash frozen, and stored at −80° C.

The HCV GT3a NS3/4A protease gene was synthesized by GenScript. Transformed *Escherichia coli* BL21(DE3) cells were grown in LB media containing 30 μg/mL of kanamycin antibiotic at 37° C. After reaching an Moo 0.7, cultures were incubated at 4° C. for 20 min before being induced with 1 mM IPTG and placed at 18° C. for overnight expression. Cells were pelleted by centrifugation, resuspended in Resuspension buffer and frozen at −80° C. for storage.

Cell pellets were thawed and lysed via cell disruptor (Microfluidics Inc.) two times to ensure sufficient DNA shearing and treated with DNaseI. The lysate was treated and purified using a nickel column as above, with an additional wash with 1 M NaCl prior to elution. The protein was further purified using a HiLoad Superdex75 16/60 column equilibrated with Resuspension buffer. The eluate was judged >90% pure by polyacrylamide gel electrophoresis, concentrated, flash frozen, and stored at −80° C.

Determination of the Inner Filter Effect

The inner filter effect (IFE) for the NS3/4A protease substrate was determined using a previously described method. Briefly, fluorescence end-point readings were taken for substrate concentrations between 0 μM and 20 μM. Afterward, free 5-FAM fluorophore was added to a final concentration of 25 μM to each substrate concentration and a second round of fluorescence end-point readings was taken. The fluorescence of free 5-FAM was determined by subtracting the first fluorescence end point reading from the second round of readings. IFE corrections were then calculated by dividing the free 5-FAM florescence at each substrate concentration by the free 5-FAM florescence at zero substrate.

Determination of Michaelis-Menten ($K_m$) Constant $K_m$ constants for GT1 and D168A protease were previously determined.[5] The $K_m$ of GT3 protease was determined using the following method. A 20 μM concentration of substrate [Ac-DE-Dap(QXL520)-EE-Abu-γ-[COO]AS-C (5-FAMsp)-NH2] (AnaSpec) was serially diluted into assay buffer [50 mM Tris, 5% glycerol, 10 mM DTT, 0.6 mM LDAO, and 4% dimethyl sulfoxide] and proteolysis was initiated by rapid injection of 10 μL GT3 protease (final concentration 20 nM) in a reaction volume of 60 μL. The fluorescence output from the substrate cleavage product was measured kinetically using an EnVision plate reader (Perkin-Elmer) with excitation wavelength at 485 nm and emission at 530 nm. Inner filter effect corrections were applied to the initial velocities ($V_o$) at each substrate concentration. $V_o$ versus substrate concentration graphs were globally fit to the Michaelis-Menten equation to obtain the $K_m$ value.

Enzyme Inhibition Assays

For each assay, 2 nM of NS3/4A protease (GT1, D168A and GT3) was pre-incubated at room temperature for 1 h with increasing concentration of inhibitors in assay buffer [50 mM Tris, 5% glycerol, 10 mM DTT, 0.6 mM LDAO, and 4% dimethyl sulfoxide]. Inhibition assays were performed in nonbinding surface 96-well black half-area plates (Corning) in a reaction volume of 60 μt. The proteolytic reaction was initiated by the injection of 5 μL of HCV NS3/4A protease substrate (AnaSpec), to a final concentration of 200 nM and kinetically monitored using a Perkin Elmer EnVision plate reader (excitation at 485 nm, emission at 530 nm). Three independent data sets were collected for each inhibitor with each protease construct. Each inhibitor titration included at least 12 inhibitor concentration points, which were globally fit to the Morrison equation to obtain the $K_i$ value.

Cell-Based Drug Susceptibility Assays

Mutations (R155K, A516T, D168A and D168V) were constructed by site-directed mutagenesis using a Con1 (genotype 1b) luciferase reporter replicon containing the H77 (genotype 1a) NS3 sequence. (Sarkar, et al. *Biotechniques* 1990, 8, 404-407.)

Replicon RNA of each protease variant was introduced into Huh7 cells by electroporation. Replication was then assessed in the presence of increasing concentrations of protease inhibitors by measuring luciferase activity (relative light units) 96 h after electroporation. The drug concentrations required to inhibit replicon replication by 50% ($EC_{50}$) were calculated directly from the drug inhibition curves.

Crystallization and Structure Determination

Protein expression and purification were carried out as previously described (see Supporting Information for details). (Romano, et al. *PLOS Pathog.* 2012, 8, e1002832.) The Ni-NTA purified WT1a protein was thawed, concentrated to 3 mg/mL, and loaded on a HiLoad Superdex75 16/60 column equilibrated with gel filtration buffer (25 mM MES, 500 mM NaCl, 10% glycerol, and 2 mM DTT, pH 6.5). The protease fractions were pooled and concentrated to 25 mg/mL with an Amicon Ultra-15 10 kDa filter unit (Millipore). The concentrated samples were incubated for 1 h with 3:1 molar excess of inhibitor. Diffraction-quality crystals were obtained overnight by mixing equal volumes of concentrated protein solution with precipitant solution (20-26% PEG-3350, 0.1 M sodium MES buffer, 4% ammonium sulfate, pH 6.5) at RT or 15° C. in 24-well VDX hanging drop trays. Crystals were harvested and data collected at 100 K. Cryogenic conditions contained the precipitant solution supplemented with 15% glycerol or ethylene glycol.

Diffraction data were collected using an in-house Rigaku X-ray system with a Saturn 944 detector. All datasets were processed using HKL-3000. Structures were solved by molecular replacement using PHASER. The WT-2 complex structure (PDB code: 5EPN) was used as the starting structure for all structure solutions. Model building and refinement were performed using Coot and PHENIX, respectively. The final structures were evaluated with MolProbity prior to deposition in the PDB. To limit the possibility of model bias throughout the refinement process, 5% of the data were reserved for the free R-value calculation. Structure analysis, superposition and figure generation were done using PyMOL. (Soumana, et al. *ACS Chem. Biol.* 2016, 11, 900-909; Otwinowski, et al. *Methods Enzymol.* 1997, 276, 307-326; McCoy, et al. *J. Appl. Crystallogr.* 2007, 40, 658-674; Emsley, et al. *Acta Crystallogr. D Biol. Crystallogr.* 2004, 60, 2126-2132; Adams, et al. *Acta Crystallogr. D Biol. Crystallogr.* 2010, 66, 213-221; Davis, et al. *Nucl. Acids Res.* 2007, 35, W375-W383; Brunger *Nature* 1992, 355, 472-475; PyMOL: The PyMOL Molecular Graphics System, Version 1.8, Schrödinger, LLC.)

Molecular Modeling

Molecular modeling was carried out using MacroModel (Schrödinger, LLC, New York, N.Y.). Briefly, inhibitors were modeled into the active site of WT1a and A156T proteases using the 5172mcP1P3-WT1a co-complex structure (PDB ID: 5EPN and 5EPY). Structures were prepared using the Protein Preparation tool in Maestro 11. 2D chemical structures were modified with the appropriate changes using the Build tool in Maestro. Once modeled, molecular energy minimizations were performed for each inhibitor-protease complex using the PRCG method with 2500 maximum iterations and 0.05 gradient convergence threshold. PDB files of modeled complexes were generated in Maestro for structural analysis. (Soumana, et al. *ACS Chem. Biol.* 2016, 11, 900-909; Otwinowski, et al. *Methods Enzymol.* 1997, 276, 307-326)

PART 2. Macrocycle Compounds With Modifications at the P4-P5

Figure 7:
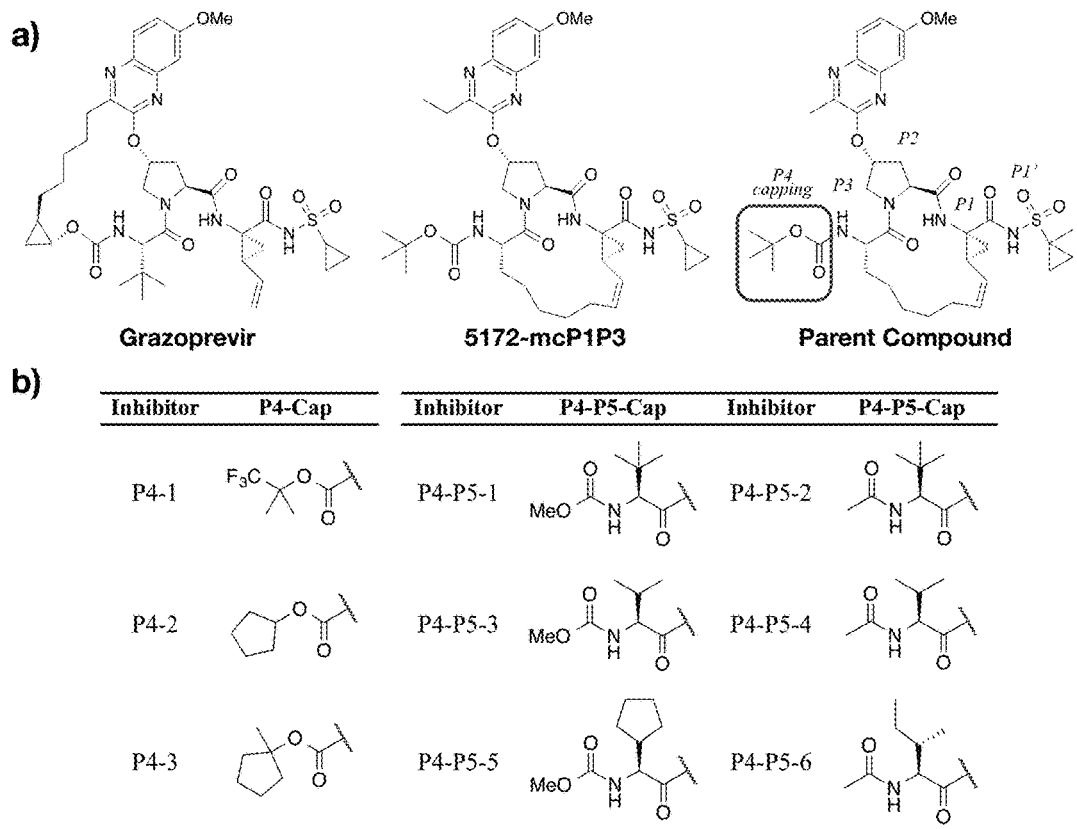
FIG. 7. Chemical structures of designed HCV NS3/4A protease inhibitors. (a) Grazoprevir (MK-5172) is an FDA-approved PI. Change of the macrocycle location (5172-mcP1P3) and optimization of the P2 quinoxaline moiety led to the parent compound modified in this study. The canonical nomenclature for drug moiety positioning, and the P4 moiety altered are indicated. (b) The inhibitors designed to extend into the SE are P4-cap and P4-P5-cap inhibitors that were based on the parent compound scaffold with modifications at the P4 and P4-P5 regions.

Modifications to the scaffold of parent compound were made at the P4-P5 positions to utilize unexploited space in the SE. Hydrophobic moieties at the P4 position were used to mimic substrate interactions, as HCV substrates across genotypes have hydrophobic residues at this position. The objective was to extend toward the S4 substrate-binding pocket and leverage specific interactions common to substrates including backbone hydrogen bonds to residues in this binding groove. Two general approaches were used to sample the chemical space in this region of the SE by synthesizing a set of 9 inhibitors with either a modified carbamate linked P4 capping (P4-cap inhibitors) or a modified P4 amino acid with a small P5 capping group (P4-P5-cap inhibitors) (FIG. 7).

Designed Compounds Inhibit Wildtype Protease

Figure 8:
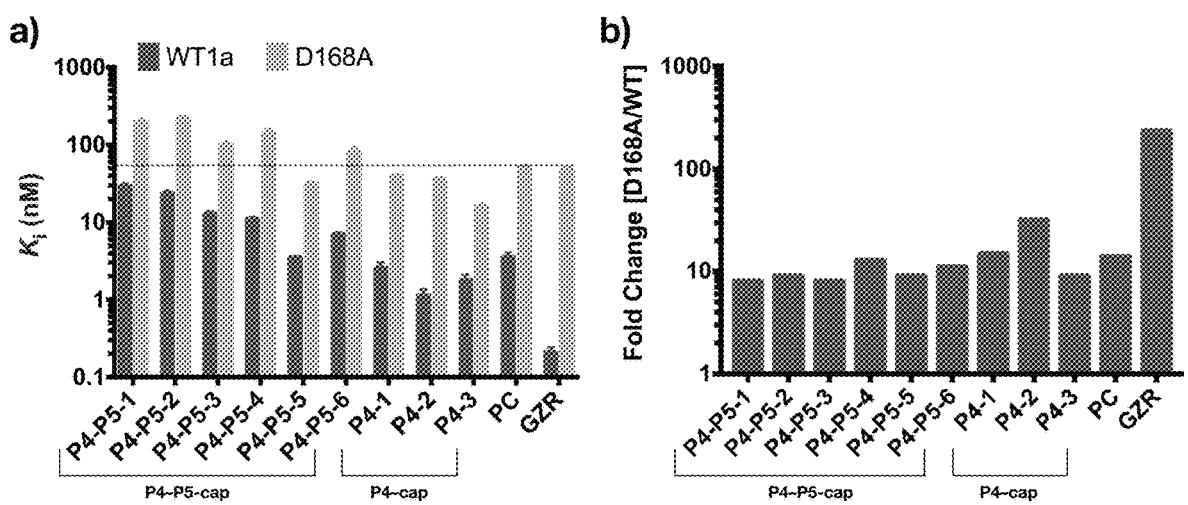
FIG. 8. Resistance profile of HCV NS3/4A protease inhibitors. (a) Enzyme inhibition constants against wildtype (blue) and D168A (orange) protease, and (b) fold change of enzyme inhibitory activity against the D168A variant with respect to wildtype NS3/4A protease. PC and GZR stand for parent compound and grazoprevir, respectively.

The enzyme inhibition constants (Ki values) of the designed inhibitors were determined against wildtype protease and the D168A drug resistant variant. All 9 inhibitors were potent against wildtype protease with $K_i$ values ranging from 1.13-29.5 nM (FIG. 8A, Table 6). Overall, P4-cap inhibitors (P4-1, P4-2 and P4-3) were more potent than P4-P5-cap inhibitors that had a modified P4 amino acid and small P5 capping group. P4-P5-1, an inhibitor with a t-butyl P4 moiety and small carbamate-linked P5 methoxy capping group, exhibited reduced potency against wildtype protease ($K_i$=29.5 nM) relative to parent compound ($K_i$=3.6 nM). To test the effect of the capping group, P4-P5-2 was designed, which is identical to P4-P5-1 except for the N-acetyl capping group. Both P4-P5-1 and P4-P5-2 showed similar activity against wildtype protease. This trend was also observed with P4-P5-3 and P4-P5-4, two P4 isopropyl inhibitors that differ only at the P5 position, suggesting that the capping change tested here does not significantly affect inhibitor potency.

The P4-cap inhibitors overall had improved potency against wildtype protease relative to both P4-P5-cap inhibitors and the parent compound. The $K_i$ values of these compounds ranged from 1.13-2.56 nM. P4-2 was 3-fold more potent than the parent compound and only 5-fold less potent than grazoprevir. While no inhibitor exhibited sub-nanomolar activity against wildtype protease as the FDA-approved P2-P4 macrocyclic grazoprevir=0.21 nM), the P4-cap of inhibitors was modified with increase in considerable potency. Thus, modification at the P4 position using a SE-guided approach yielded inhibitors with improved potency relative to the parent compound.

SE-Guided Design Improved Resistance Profile Against the D168A Variant

To understand if the substrate envelope as a constraint in inhibitor design results in compounds that are less susceptible to resistance, the PIs were tested against the pivotal D168A variant. All PIs tested lost considerable activity against the D168A variant including grazoprevir, as has previously been reported. P4-P5-cap inhibitors were less potent against the D168A variant than the P4-cap inhibitors, similar to wildtype protease. All P4-cap inhibitors had improved activity against the D168A variant ($K_i$ range: 16-39 nM) relative to the parent compound ($K_i$=52 nM). Remarkably, compound P4-3 with a methylcyclopentyl capping group exhibited 3-fold better potency against the D168A variant compared to the FDA-approved grazoprevir ($K_i$=16 and 49 nM, respectively).

While all PIs showed reduced potency against the D168A variant relative to WT protease in the enzyme inhibition assay, the fold losses were much smaller for all 9 designed inhibitors (FIG. 8B). Grazoprevir is highly susceptible to the D168A variant exhibiting over a 230-fold reduction in potency. All inhibitors designed to fit within and extend into the substrate envelope exhibited between 9- to 32-fold reductions in potency, much smaller than observed for grazoprevir. Thus SE-guided design yielded flatter resistance profiles, demonstrating that this strategy can produce compounds with low nanomolar potency and reduced susceptibility to drug resistance.

Structure determination of protease-inhibitor complexes

To understand the molecular basis for the observed resistance profiles of the inhibitors as well as to determine if the inhibitors fit within the substrate envelope as designed, crystal structures of select inhibitors bound to wildtype and D168A proteases were determined (Table 7). A total of 7 new crystal structures with resolutions ranging from 1.6-1.9 Å were determined for this study. Five crystal structures of P4-1, P4-2, P4-3, P4-P5-1 and P4-P5-2 were determined in complex with wildtype protease. Crystallization efforts with drug resistant variant D168A were successful with inhibitors P4-1 and P4-P5-2. All structures were analyzed in comparison with previously determined crystal structures of the parent compound (PDB ID: 5VOJ for wildtype) and grazoprevir (PDB IDs: 3SUD for wildtype and 3SUF for D168A, respectively).

Figure 9:
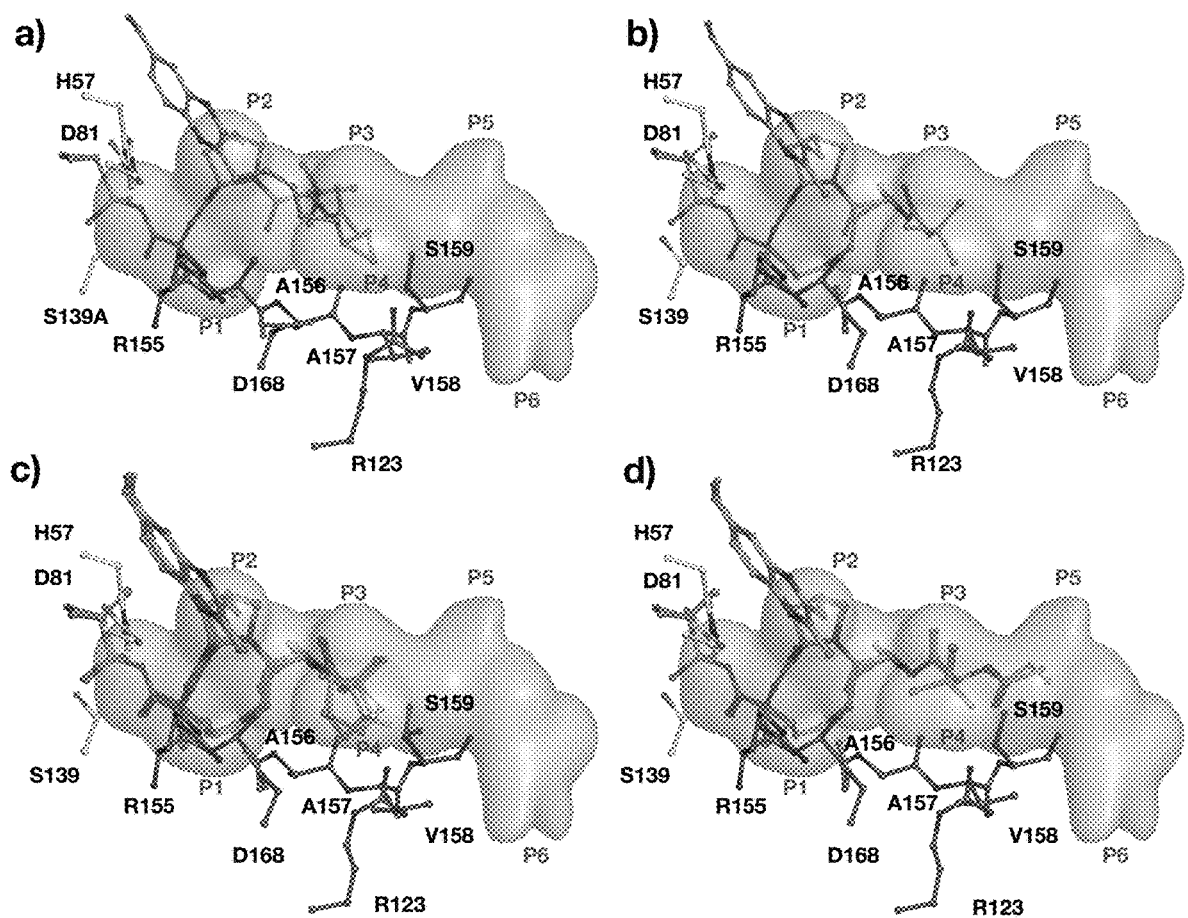
FIG. 9. Fit of NS3/4A protease inhibitors within the substrate envelope. Inhibitors (a) grazoprevir, (b) parent compound, (c) P4-cap and (d) P4-P5-cap inhibitors shown as sticks (orange) in the substrate envelope (blue). The side chains of the catalytic triad and residues surrounding the S4 pocket are shown as yellow and green sticks, respectively and the S1-S6 positions of the envelope labeled.

The binding mode of all of the designed inhibitors was very similar to the parent compound and grazoprevir. The P2 quinoxaline maintained the π-π stacking interaction with catalytic His57 residue irrespective of modifications at the P4 and P5 positions as expected (FIG. 9). In fact, changes in the binding mode occurred only at the positions that were modified, with the P3-P1' positions of the ligand relatively unchanged. In all structures, inhibitors formed conserved hydrogen bonds with backbone atoms in the protease including: (1) P1 amide nitrogen with the backbone carbonyl of Arg155, (2) P3 amide nitrogen with the backbone carbonyl of Ala157, (3) P3 cabonyl with the backbone nitrogen of Ala157 and 4) the P1' acylsulfonamide moiety with backbone atoms of residues 137-139 in the oxyanion hole. Additionally, the $N_\epsilon$ nitrogen of His57 made a hydrogen bond with the sulfonamide nitrogen in all inhibitor complexes. Differences in hydrogen bonding were observed in the S4 pocket where modifications to the inhibitor were made.

Designed Inhibitors Fit Within the Substrate Envelope and Gain Substrate-Like Interactions Grazoprevir, although potent, protrudes from the substrate envelope making this inhibitor highly susceptible to drug resistance mutations especially at Ala156 and Asp168 due to the positioning of the P2-P4 macrocycle and P4 moiety (FIG. 9A). Modification of the macrocycle location and the P2 position led to the parent compound, which fits better in the substrate envelope (FIG. 9B). The crystal structures of parent compound bound to wildtype protease and the additional 5 inhibitor-wildtype protease structures superimpose extremely well. Moreover, the designed inhibitors fit within the substrate envelope, utilizing unexplored space and leveraging substrate-like contacts (FIG. 9C, 3D). Thus, crystal structures confirm that inhibitors fit within the substrate envelope as they were designed.

Figure 10:
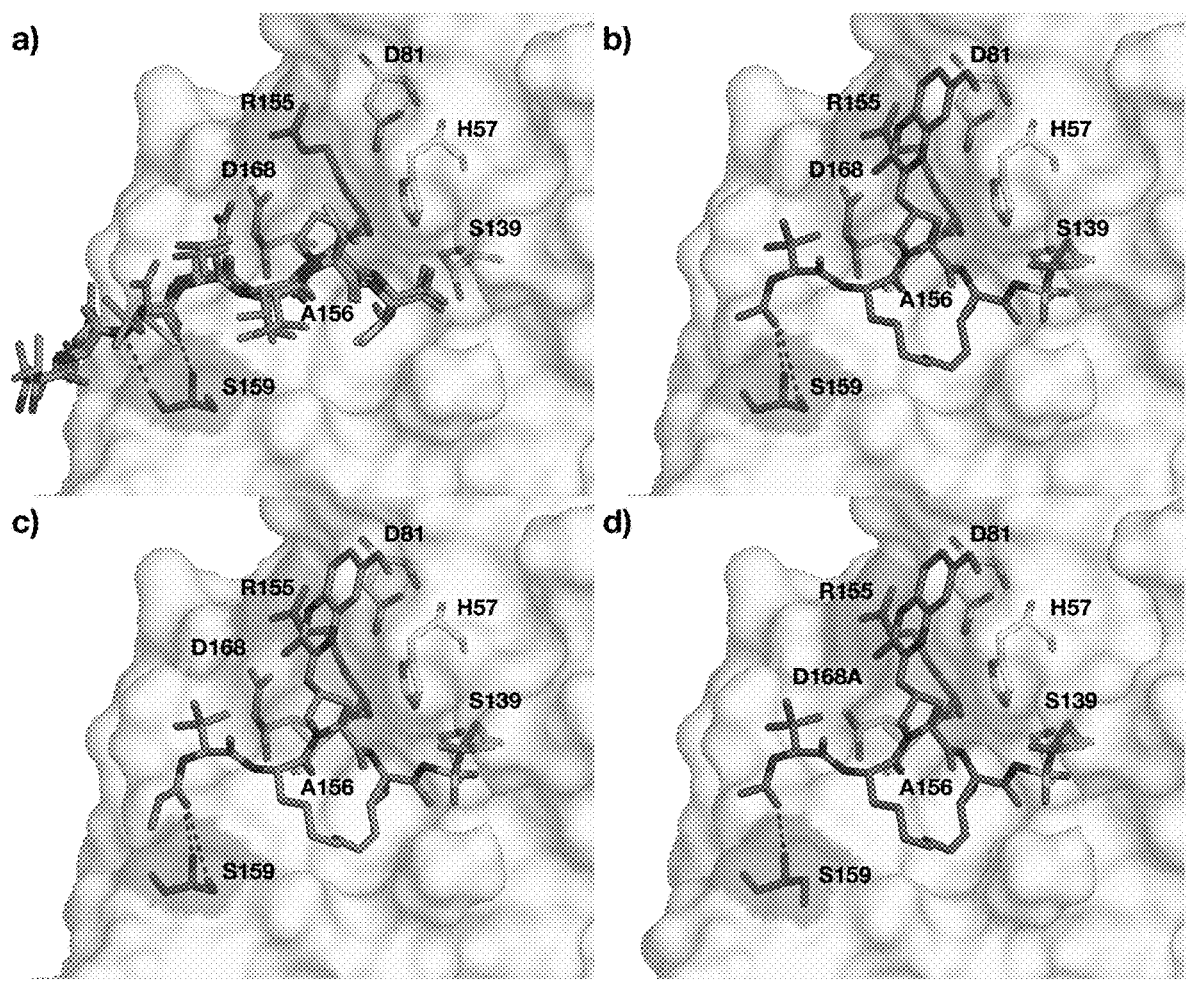
FIG. 10. Binding modes of P4-P5-cap inhibitors. Surface representation of HCV NS3/4A with (a) superposed substrate peptides (gray; PDB IDs: 3M5N, 3M50 and 1CU1) (b)

Crystal structures of P4-P5-cap inhibitors bound to wildtype protease revealed that the carbonyl group of the P5 cap gains hydrogen bonds with the backbone nitrogen and side chain of Ser159 (FIG. 10). This interaction is reminiscent of the protease-substrate complexes as this backbone hydrogen bond to Ser159 is conserved in all structures of bound substrates. Both P4-P5-1 and P5-P4-2, with either an N-acetyl or methoxycarbonyl P5 capping group, had the same additional hydrogen bonds to the backbone and side chain of Ser159 (FIGS. 10B and C). This is in agreement with the biochemical data as both inhibitors had similar potency against wildtype protease. Thus, P4-P5-1 and P4-P5-2 bind very similarly to viral substrates and gain substrate-like interactions with the protease. Although these inhibitors are not as potent as parent compound, they demonstrate that the substrate envelope can be utilized to design inhibitors that mimic substrate binding.

P4-P5-Cap Inhibitors Lose a Hydrogen Bond Due to D168A

To investigate the molecular basis of reduced potency for the P4-P5-cap modified inhibitors against the D168A resistant variant, crystal structures of P4-P5-2 bound to wildtype protease and the mutant protease were comparatively analyzed. Similar to grazoprevir, loss in potency is likely due to disruption of the electrostatic network involving Arg155 as a result of the D168A substitution (FIG. 11A-D) (16). The overall structure of P4-P5-2 bound to the D168A is very similar to this inhibitor bound to wildtype protease. However, a major change occurs at residue Ser159. This residue adopts an altered side chain conformation where the hydroxyl group is pointed away from the inhibitor (FIG. 10B, D). As a result, the hydrogen bond of P4-P5-2 with the Ser159 side chain that is present in the wildtype structure is lost. It is likely that this mechanism for reduced potency against D168A variant is the same for all inhibitors that bind similar to P4-P5-2, including P4-P5-1 and other P4-P5-cap inhibitors.

Hydrogen Bonds Within the S4 Pocket can Stabilize the Mutated Active Site in D168A Protease The capping in P4-1 consists of a trifluoro-2,2-dimethylpropane moiety that can form hydrogen bonds to coordinate water molecules or further stabilize protease-inhibitor interactions. The crystal structure of this inhibitor bound to wildtype protease revealed an extensive hydrogen bond network around the S4 pocket including the conserved hydrogen bond between Arg155 and Asp168 (FIG. 11E). Additionally, there is water-bridge between the ether oxygen of the carbamate group and backbone nitrogen of Ser159 mimicking substrate-protease interactions (FIG. 10A). Unlike P4-P5-2, however, there is no side-chain hydrogen bond to Ser159 that is lost due to D168A mutation. The trifluoro-2,2-dimethylpropane moiety of P4-1 can make a hydrogen bond with the side chain of Arg123, an additional interaction that is not present in the parent compound or grazoprevir. Thus, the addition of this electronegative P4 capping group allows for enhanced interaction with the S4 pocket of the protease.

Unlike the P4-P5-cap inhibitors, the hydrogen bond network was essentially unaltered for P4-1 in D168A relative to wildtype protease. The P4 capping group of P4-1 adopted two alternate conformations in the active site when bound to D168A protease. One conformation (FIG. 11F) was stabilized by a water-bridge hydrogen bond between the fluoro group and NH1 hydrogen of Arg155. The other conformation of P4-1 retained the flouro-mediated hydrogen bond with Arg123 present in the wildtype protease structure. Although the potency of this inhibitor is reduced against the D168A variant, this inhibitor likely maintains potency better than the parent compound and grazoprevir thanks to the adaptable P4 capping group capable of conserving the hydrogen bond network.

Enhanced Packing Inside the S4 Pocket Increases Potency Against D168A

To assess the molecular details of inhibitor packing at the S4 pocket, van der Waals (vdW) contact energies were calculated for each protease-inhibitor structure. Total vdW energies ranged from −90 to −87 kcal/mol. Most designed inhibitors had enhanced vdW contacts with the protease relative to parent compound and grazoprevir (total vdW=− 85 and −88 respectively). While the overall vdW profiles of each inhibitor class (P4 vs P4-P5-cap) were relatively the same in the areas of the inhibitor scaffold that are common (P1'-P3), most changes occurred at the S4 subsite (FIG. 12). Inhibitors P4-P5-1 and P4-P5-2, which are larger in size than the P4-cap inhibitors, had between a 1-3 kcal/mol increase in vdW contact energy relative to the parent compound with Ala157, Val158 and Ser159 when bound to wildtype protease (FIG. 12B). However, these P4-P5-cap inhibitors had not gained any interactions with Asp168, which is located deeper inside the S4 pocket. This indicates that P4-P5-cap inhibitors override the pocket rather than extending into the pocket.

This is not the case for the P4-cap inhibitors with hydrophobic capping groups. Relative to the parent compound, P4-2 and P4-3 had increased hydrophobic contacts with the hydrocarbon portions of the Arg123 and Asp168 side chains (FIG. 12B). The cyclic capping groups in these compounds extended inside the S4 pocket. Therefore P4-2 and P4-3 actually fit better and fill in the S4 pocket, unlike the P4-P5-cap inhibitors that override the pocket similar to grazoprevir. The P4 cyclopropyl capping group of grazoprevir and the t-butyl P4 moiety of P4-P5-2 are positioned over the S4 pocket, not optimally filling and thus potentially causing a frustrated pocket. In contrast, P4-2 and P4-3 with hydrophobic cyclic rings pack well against the aliphatic portion of the Arg155 and Asp168 side chains and also interact with the nonpolar residue Ala156 (FIG. 13). Thus, this enhanced packing of the P4 pocket better avoids a frustrated pocket that can destabilize inhibitor binding and cause susceptibility to D168A mutation, improving the potency of P4-cap inhibitors.

Experimental

Inhibitor Synthesis

Grazoprevir, parent compound and substrate envelope designed analogs were synthesized in-house using previously reported methods (Scheme 4). Grazoprevir was prepared following a reported synthetic method. The parent compound and analogs were synthesized using the convergent reaction sequence.

Expression and Purification of NS3/4A Constructs

The HCV GT1a NS3/4A protease gene described in the Bristol Myers Squibb patent was synthesized by GenScript and cloned into a PET28a expression vector (34). Cys159 was mutated to a serine residue to prevent disulfide bond formation and facilitate crystallization. The D168A gene was engineered using the site-directed mutagenesis protocol from Stratagene. Protein expression and purification were carried out as previously described (16). Briefly, transformed *Escherichia coli* BL21(DE3) cells were grown in TB media containing 30 µg/mL of kanamycin antibiotic at 37° C. After reaching an $OD_{600}$ of 0.7, cultures were induced with 1 mM IPTG and harvested after 3 h of expression. Cells were pelleted by centrifugation, resuspended in resuspension buffer (RB) [50 mM phosphate buffer, 500 mM NaCl, 10% glycerol, 2 mM β-ME, pH 7.5] and frozen at −80° C. for storage.

Cell pellets were thawed and lysed via cell disruptor (Microfluidics Inc.) two times to ensure sufficient DNA shearing. Lysate was centrifuged at 19,000 rpm, for 25 min at 4° C. The soluble fraction was applied to a nickel column (Qiagen) pre-equilibrated with RB. The beads and soluble fraction were incubated at 4° C. for 1.5 h and the lysate was allowed to flow through. Beads were washed with RB supplemented with 20 mM imidazole and eluted with RB supplemented with 200 mM imidazole. The eluent was dialyzed overnight (MWCO 10 kD) to remove the imidazole, and the His-tag was simultaneously removed with thrombin treatment. The eluate was judged >90% pure by polyacrylamide gel electrophoresis, concentrated, flash frozen, and stored at −80° C.

Correction for the Inner Filter Effect

The inner filter effect (IFE) for the NS3/4A protease substrate was determined using a previously described method. Briefly, fluorescence end-point readings were taken for substrate concentrations between 0 µM and 20 µM. Afterward, free 5-FAM fluorophore was added to a final concentration of 25 µM to each substrate concentration and a second round of fluorescence end-point readings was taken. The fluorescence of free 5-FAM was determined by subtracting the first fluorescence end point reading from the second round of readings. IFE corrections were then calculated by dividing the free 5-FAM florescence at each substrate concentration by the free 5-FAM florescence at zero substrate.

Determination of Michaelis-Menten ($K_m$) Constant $K_m$ constants for GT1 and D168A protease were previously determined (26). Briefly, a 20 µM concentration of substrate [Ac-DE-Dap(QXL520)-EE-Abu-γ-[COO]AS-C (5-FAMsp)-NH2] (AnaSpec) was serially diluted into assay buffer [50 mM Tris, 5% glycerol, 10 mM DTT, 0.6 mM LDAO, and 4% dimethyl sulfoxide] and proteolysis was initiated by rapid injection of 10 µL protease (final concentration 20 nM) in a reaction volume of 60 µL. The fluorescence output from the substrate cleavage product was measured kinetically using an EnVision plate reader (PerkinElmer) with excitation wavelength at 485 nm and emission at 530 nm. Inner filter effect corrections were applied to the initial velocities ($V_o$) at each substrate concentration. $V_o$ versus substrate concentration graphs were globally fit to the Michaelis-Menten equation to obtain the $K_m$ value.

Enzyme Inhibition Assays

For each assay, 2 nM of NS3/4A protease (GT1a and D168A) was pre-incubated at room temperature for 1 h with increasing concentration of inhibitors in assay buffer (50 mM Tris, 5% glycerol, 10 mM DTT, 0.6 mM LDAO, and 4% dimethyl sulfoxide, pH 7.5). Inhibition assays were performed in non-binding surface 96-well black half-area plates (Corning) in a reaction volume of 60 µL. The proteolytic reaction was initiated by the injection of 5 µL of HCV NS3/4A protease substrate (AnaSpec), to a final concentration of 200 nM and kinetically monitored using a Perkin Elmer EnVision plate reader (excitation at 485 nm, emission at 530 nm). Three independent data sets were collected for each inhibitor with each protease construct. Each inhibitor titration included at least 12 inhibitor concentration points, which were globally fit to the Morrison equation to obtain the $K_i$ value.

Crystallization and Structure Determination

Protein expression and purification were carried out as previously described (16). Briefly, the Ni-NTA purified WT1a protein was thawed, concentrated to 3 mg/mL, and loaded on a HiLoad Superdex75 16/60 column equilibrated with gel filtration buffer (25 mM MES, 500 mM NaCl, 10% glycerol, and 2 mM DTT, pH 6.5). The protease fractions were pooled and concentrated to 25 mg/mL with an Amicon Ultra-15 10 kDa filter unit (Millipore). The concentrated samples were incubated for 1 h with 3:1 molar excess of inhibitor. Diffraction-quality crystals were obtained overnight by mixing equal volumes of concentrated protein solution with precipitant solution (20-26% PEG-3350, 0.1 M sodium MES buffer, 4% ammonium sulfate, pH 6.5) at RT or 15° C. in 24-well VDX hanging drop trays. Crystals were harvested and data was collected at 100 K. Cryogenic conditions contained the precipitant solution supplemented with 15% glycerol or ethylene glycol.

X-ray diffraction data were collected in-house using the Rigaku X-ray system with a Saturn 944 detector. All datasets were processed using HKL-3000. Structures were solved by molecular replacement using PHASER. Model building and refinement were performed using Coot and PHENIX, respectively. The final structures were evaluated with MolProbity prior to deposition in the PDB. To limit the possibility of model bias throughout the refinement process, 5% of the data were reserved for the free R-value calculation. Structure analysis, superposition and figure generation were done using PyMOL. X-ray data collection and crystallographic refinement statistics are presented in Table 6.

Construction of HCV Substrate Envelope

The HCV substrate envelope was computed using a method previously described (16). The HCV viral substrates representing the product complex 3-4A (residues 626-631 of full-length HCV PDB ID: 1CU1), 4B/5A (chain D, PDB ID: 3M5N) and 5A/5B (chain A, PDB ID: 3M50) were used to construct the envelope. All structure were aligned in PyMOL using the Cα atoms of protease residues 137-139 and 154-160. Following superposition of all structures, Gaussian object maps at a contour of 0.5 were generated for each cleavage product in PyMOL. Three consensus maps were generated representing the minimum volume occupied by any 2 viral substrates. The four consensus maps were summed together to generate the final substrate envelope representing the shared van der Waals volume of the viral substrates.

TABLE 6

Inhibitory activity against GT1a HCV NS3/4A and D168A proteases with fold changes with respect to GT1a wild-type

| Inhibitor | Ki (nM) (Fold Change) | |
| --- | --- | --- |
|  | GT1a WT | D168A |
| P4-P5-1 | 29.5 ± 1.9 | 201.0 ± 15.0 (8) |
| P4-P5-2 | 23.9 ± 1.7 | 215.0 ± 16.0 (9) |
| P4-P5-3 | 13.0 ± 0.8 | 102.0 ± 6.8 (8) |
| P4-P5-4 | 11.1 ± 0.5 | 141.0 ± 18.0 (13) |
| P4-P5-5 | 3.54 ± 0.13 | 31.6 ± 2.1 (9) |
| P4-P5-6 | 7.10 ± 0.24 | 81.0 ± 11.0 (11) |
| P4-1 | 2.56 ± 0.44 | 39.0 ± 2.9 (15) |
| P4-2 | 1.13 ± 0.22 | 36.0 ± 1.8 (32) |
| P4-3 | 1.78 ± 0.30 | 16.0 ± 1.2 (9) |
| Parent Compound | 3.60 ± 0.44 | 52.0 ± 2.4 (14) |
| Grazoprevir | 0.21 ± 0.03 | 49.1 ± 1.6 (234) |

All reactions were performed in oven-dried round bottomed flasks fitted with rubber septa under argon atmosphere, unless otherwise noted. All reagents and solvents, including anhydrous solvents, were purchased from commercial sources and used as received. Flash column chromatography was performed on an ISCO CombiFlash instrument using RediSep Gold columns. Thin-layer chromatography (TLC) was performed using silica gel (60 F-254) coated aluminum plates (EMD Millipore), and spots were visualized by exposure to ultraviolet light (UV), exposure to iodine adsorbed on silica gel, and/or exposure to an acidic solution of p-anisaldehyde (anisaldehyde) followed by brief heating. $^1$H NMR and $^{13}$C NMR spectra were acquired on a Bruker Avance III HD 500 MHz NMR instrument. Chemical shifts are reported in ppm (δ scale) with the residual solvent signal used as reference and coupling constant (J) values are reported in hertz (Hz). Data are presented as follows: chemical shift, multiplicity (s=singlet, d=doublet, dd=doublet of doublet, t=triplet, q=quartet, m=multiplet, br s=broad singlet), coupling constant in Hz, and integration. High-resolution mass spectra (HRMS) were recorded on a Thermo Scientific Orbitrap Velos Pro mass spectrometer coupled with a Thermo Scientific Accela 1250 UPLC and an autosampler using electrospray ionization (ESI) in the positive mode.

TABLE 7

X-ray data collection and crystallographic refinement statistics

|  | WT-P4-P5-1 | WT-P4-P4-2 | WT-P4-1 | WT-P4-2 | WT-P4-3 | D168A-P4-P5-2 | D168A-P4-1 |
| --- | --- | --- | --- | --- | --- | --- | --- |
| PDB ID: | 6DIQ | 6DIR | 6DIS | 6DIT | 6DIU | 6DIV | 6DIW |
| Resolution | 1.58 Å | 1.75 Å | 1.92 Å | 1.79 Å | 1.87 Å | 1.83 Å | 1.80 Å |
| Space group | $P2_12_12_1$ | $P2_12_12_1$ | $P2_12_12_1$ | $P2_12_12_1$ | $P2_12_12_1$ | $P2_12_12_1$ | $P2_12_12_1$ |
| Molecules in AU[a] | 1 | 1 | 1 | 1 | 1 | 1 | 1 |
| Cell dimensions: |  |  |  |  |  |  |  |
| a (Å) | 55.5 | 55.1 | 55.6 | 55.3 | 55.1 | 55.5 | 55.7 |
| b (Å) | 58.5 | 59.8 | 58.6 | 58.6 | 59.6 | 58.7 | 58.6 |
| c (Å) | 59.9 | 58.5 | 60.0 | 59.8 | 58.5 | 60.0 | 60.1 |
| β (°) | 90 | 90 | 90 | 90 | 90 | 90 | 90 |
| Completeness (%) | 91.3 | 97.0 | 96.7 | 98.1 | 97.4 | 98.1 | 92.6 |
| Total reflections | 250177 | 119548 | 106822 | 118729 | 110776 | 115996 | 120162 |
| Unique reflections | 25037 | 19508 | 14999 | 18610 | 16126 | 17556 | 17476 |
| Average I/σ | 7.9 | 8.8 | 19.8 | 14.5 | 12.7 | 12.8 | 6.3 |
| Redundancy | 10 | 6.1 | 7.1 | 6.4 | 6.9 | 6.6 | 6.9 |
| $R_{sym}$ (%)[b] | 5.7 (15.2) | 4.3 (18.3) | 10.6 (45.8) | 7.1 (28.4) | 6.3 (19.6) | 7.0 (21.6) | 3.9 (11.7) |
| RMSD[c] in: |  |  |  |  |  |  |  |
| Bond lengths (Å) | 0.007 | 0.009 | 0.01 | 0.004 | 0.02 | 0.006 | 0.01 |
| Bond angles (°) | 1.0 | 1.3 | 1.0 | 0.8 | 0.6 | 1.1 | 1.5 |
| $R_{factor}$ (%)[d] | 15.1 | 14.6 | 18.7 | 18.2 | 18.3 | 16.1 | 13.8 |
| $R_{free}$ (%)[e] | 18.3 | 19.3 | 22.7 | 22.9 | 23.3 | 19.4 | 18.0 |

[a]AU, asymmetric unit.
[b]Rsym = Σ|I−<I>|/ΣI, where I/ = observed intensity, +21 I > = average intensity over symmetry equivalent; values in parentheses are for the highest resolution shell.
[c]RMSD, root mean square deviation.
[d]$R_{factor}$ = Σ||F$_0$| − |F$_c$||/Σ|F$_0$|.
[e]$R_{free}$ was calculated from 5% of reflections, chosen randomly, which were omitted from the refinement process.

Scheme 4. Synthesis of HCV NS3/4A protease inhibitors
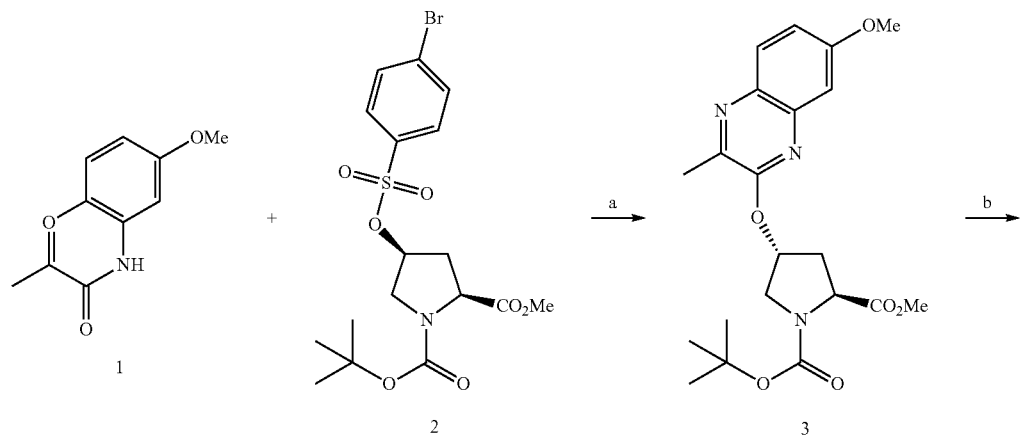
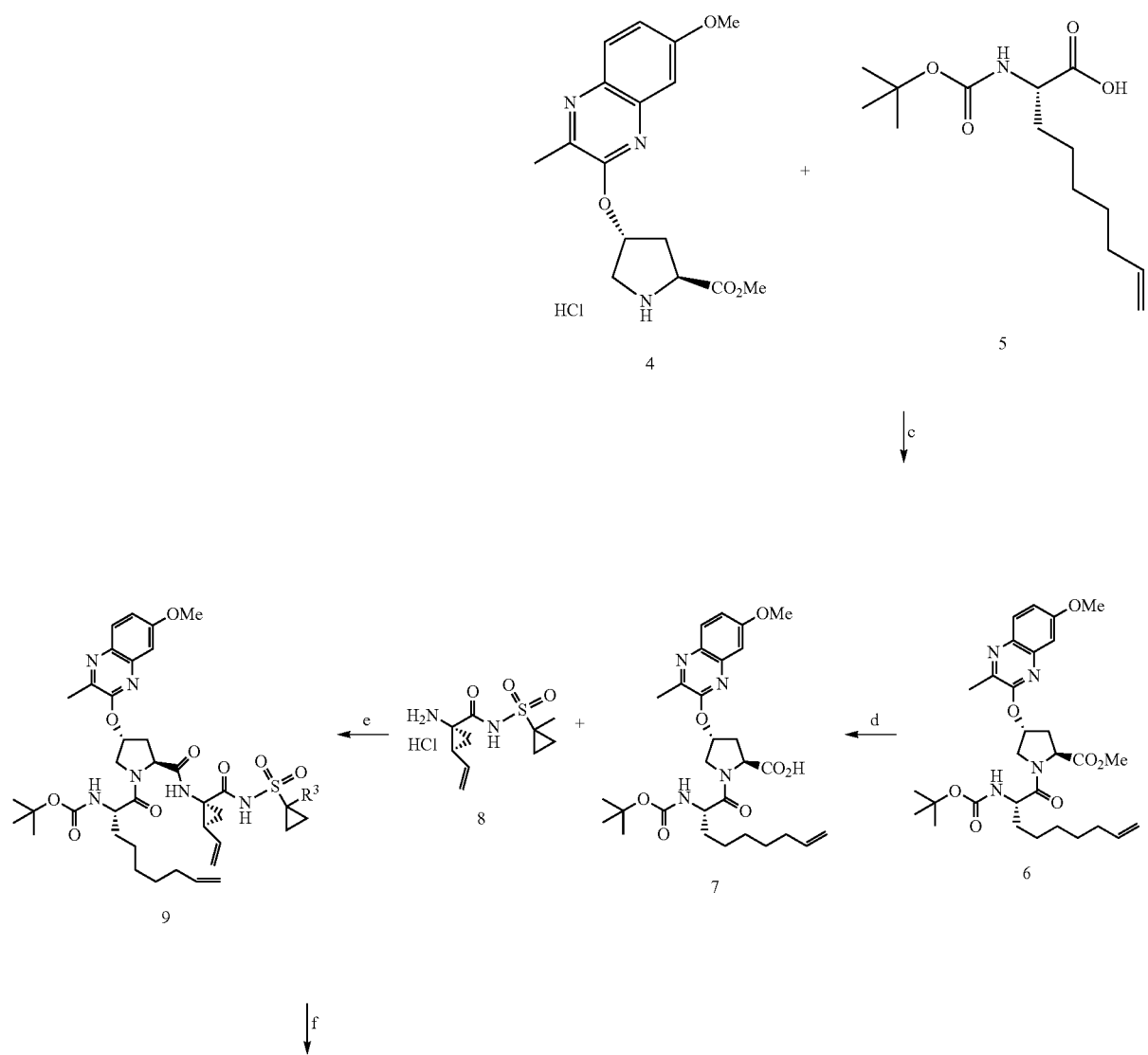

147
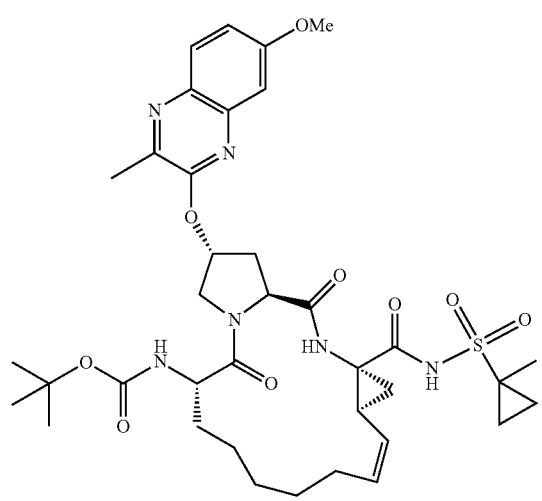
10
→ g →
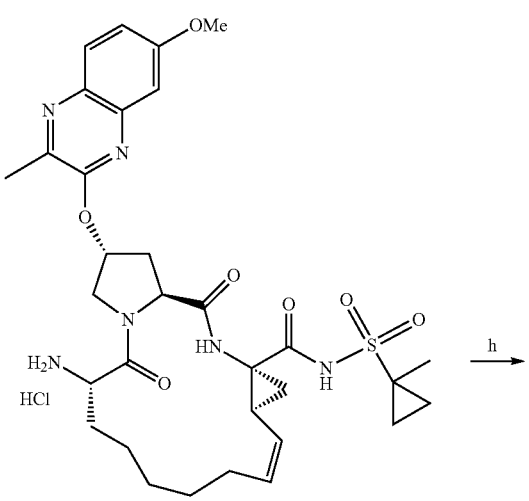
11
→ h →
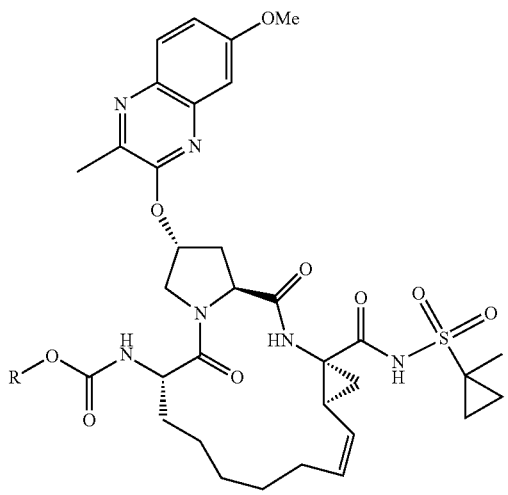
P4-1, P4-2, P4-3
148
-continued
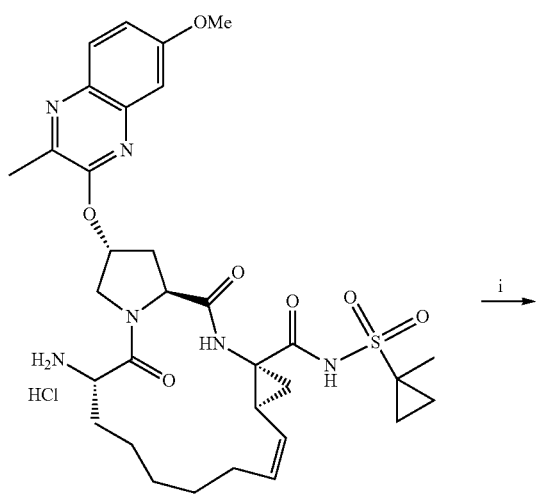
11
→ i →

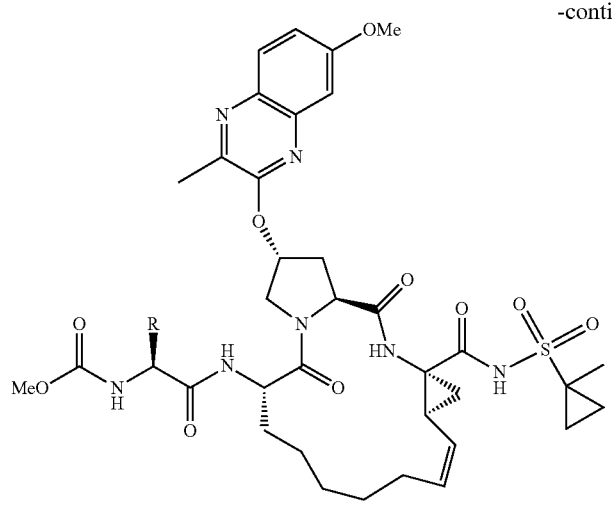

P4-P5-1, P4-P5-3, P4-P5-5

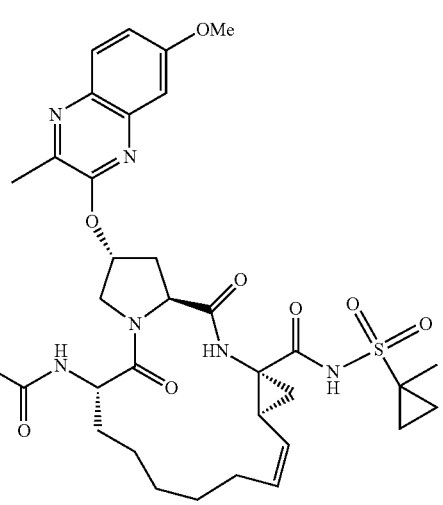

P4-P5-2, P4-P5-4, P4-P5-6

Reagents and Conditions: (a) Cs₂CO₃, NMP, 55° C., 6 h; (b) 4N HCl in dioxane, CH₂Cl₂, RT, 3 h; (c) HATU, DIEA, DMF, RT, 4 h; (d) LiOH·H₂O, THF, H₂O, RT, 24 h; (e) HATU, DIEA, DMF, RT, 2 h; (f) Zhan 1b catalyst, 1,2-DCE, 70° C., 6 h; (g) 4N HCl, dioxane, RT, 3 h; (h) alcohol-(4-nitrophenyl) carbonate, DIEA, CH₃CN, RT, 36 h; (i) N-protected amino acid, HATU, DIEA, DMF, RT, 4 h.

1-(tert-Butyl) 2-methyl (2S,4R)-4-((7-methoxy-3-methylquinoxalin-2-yl)oxy)pyrrolidine-1,2-dicarboxylate (3)

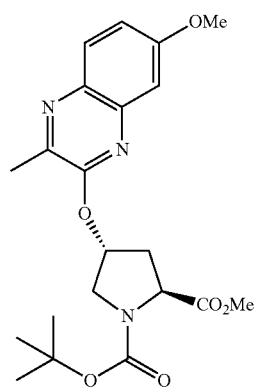 [SMILES: COC(=O)[C@@H]1C[C@@H](Oc2nc3cc(OC)ccc3nc2C)CN1C(=O)OC(C)(C)C]

A solution of 7-methoxy-3-methylquinoxalin-2(1H)-one 1 (6.2 g, 32.6 mmol) in anhydrous NMP (100 mL) was treated with Cs₂CO₃ (16.0 g, 49.0 mmol). After stirring the reaction mixture at room temperature for 15 min, activated cis-hydroxyproline derivative 2 (14.0 g, 30.2 mmol) was added in one portion. The reaction mixture was heated to 55° C., stirred for 4 h, and then another portion of activated cis-hydroxyproline 2 (1.0 g, 2.15 mmol) was added. The resulting reaction mixture was stirred at 55° C. for additional 2 h, cooled to room temperature, quenched with aqueous 1 N HCl solution (250 mL), and extracted with EtOAc (400 mL). The organic fraction was washed successively with saturated aqueous NaHCO₃ and NaCl (250 mL each), dried (Na₂SO₄), filtered, and evaporated under reduced pressure. The residue was purified by flash column chromatography (RediSep Gold column, 2×80 g, gradient elution with 0-60% EtOAc/hexanes) to provide 3 (10.0 g, 74%) as a white foamy solid. ¹HNMR (500 MHz, CDCl₃) (mixture of rotamers, major rotamer) δ 7.80 (d, J=9.0 Hz, 1H), 7.17 (dd, J=9.0, 3.0 Hz, 1H), 7.11 (d, J=2.5 Hz, 1H), 5.71 (br s, 1H), 4.48 (t, J=8.0 Hz, 1H), 3.99-3.91 (m, 4H), 3.87 (d, J=12.5 Hz, 1H), 3.78 (s, 3H), 2.67-2.58 (m, 1H), 2.56 (s, 3H), 2.43-2.37 (m, 1H), 1.43 (s, 9H) ppm; ¹³C NMR (125 MHz, CDCl₃) δ 173.36, 160.24, 155.51, 153.81, 144.60, 141.04, 134.22, 128.95, 118.63, 105.95, 80.54, 73.59, 58.20, 55.68, 52.48, 52.20, 36.70, 28.26, 19.93 ppm; HRMS (ESI) m/z: [M+H]⁺ calcd for $C_{21}H_{28}N_3O_6$, 418.1973; found 418.1976.

Methyl (2S,4R)-1-((S)-2-((tert-butoxycarbonyl)amino)non-8-enoyl)-4-((7-methoxy-3-methylquinoxalin-2-yl)oxy)pyrrolidine-2-carboxylate (6)

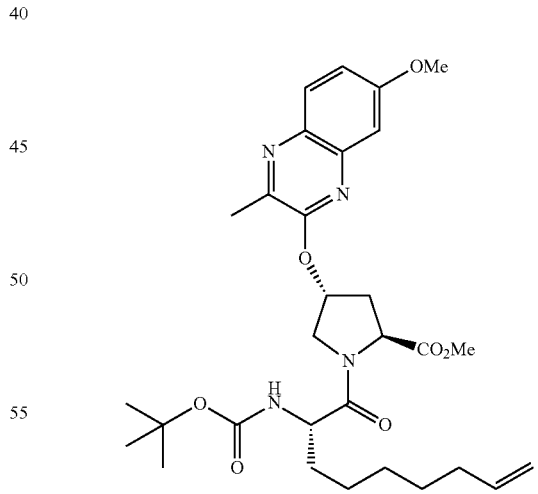

A solution of ester 3 (10.0 g, 24.0 mmol) in anhydrous CH₂Cl2 (50 mL) was treated with a solution of 4 N HCl in 1,4-dioxane (100 mL). After stirring the reaction mixture at room temperature for 3 h, solvents were evaporated under reduced pressure, and the residue was dried under high vacuum. The pale-yellow solid was triturated with diethyl ether (3×25 mL) and dried under high vacuum to yield the amine salt 4 (8.5 g, 100%) as an off-white powder.

A mixture of amine salt 4 (8.5 g, 24.0 mmol) and (S)-2-((tert-butoxycarbonyl)amino)non-8-enoic acid 5 (6.70 g, 24.7 mmol) in anhydrous DMF (110 mL) was treated with DIEA (19.2 mL, 110 mmol) and HATU (14.1 g, 37.1 mmol). The resulting reaction mixture was stirred at room temperature for 4 h, then diluted with EtOAc (500 mL), and washed successively with aqueous 0.5 N HCl, saturated aqueous $NaHCO_3$, and saturated aqueous NaCl (300 mL each). The organic portion was dried ($Na_2SO_4$), filtered, and evaporated under reduced pressure. The residue was purified by flash column chromatography (RediSep Gold column, 2×80 g, gradient elution with 0-60% EtOAc/hexanes) to provide 6 (10.9 g, 80%) as a white foamy solid. $^1$HNMR (500 MHz, $CDCl_3$) (mixture of rotamers, major rotamer) δ 7.81 (d, J=9.0 Hz, 1H), 7.18 (dd, J=9.0, 2.5 Hz, 1H), 7.12 (d, J=2.5 Hz, 1H), 5.84-5.75 (m, 2H), 5.21 (d, J=8.5 Hz, 1H), 5.01-4.92 (m, 2H), 4.75 (t, J=8.0 Hz, 1H), 4.38 (q, J=7.5 Hz, 1H), 4.18 (d, J=11.5 Hz, 1H), 4.06 (dd, J=12.0, 4.5 Hz, 1H), 3.94 (s, 3H), 3.77 (s, 3H), 2.69-2.64 (m, 1H), 2.54 (s, 3H), 2.41-2.35 (m, 1H), 2.04 (app q, J=7.0 Hz, 2H), 1.80-1.75 (m, 1H), 1.63-1.55 (m, 1H), 1.46-1.24 (m, 15H) ppm; $^{13}$C NMR (125 MHz, $CDCl_3$) δ 172.13, 171.78, 160.27, 155.40, 155.27, 144.62, 140.89, 138.96, 134.39, 129.03, 118.73, 114.35, 105.99, 79.61, 74.30, 57.97, 55.66, 52.67, 52.43, 51.83, 34.94, 33.65, 32.66, 28.91, 28.74, 28.25, 24.68, 19.87 ppm; HRMS (ESI) m/z: $[M+H]^+$ calcd for $C_{30}H_{43}N_4O_7$, 571.3126; found 571.3128.

tert-Butyl ((S)-1-((2S,4R)-4-((7-methoxy-3-methylquinoxalin-2-yl)oxy)-2-(((1R,2S)-1-(((1-methylcyclopropyl)sulfonyl)carbamoyl)-2-vinylcyclopropyl)carbamoyl)pyrrolidin-1-yl)-1-oxonon-8-en-2-yl)carbamate (9)

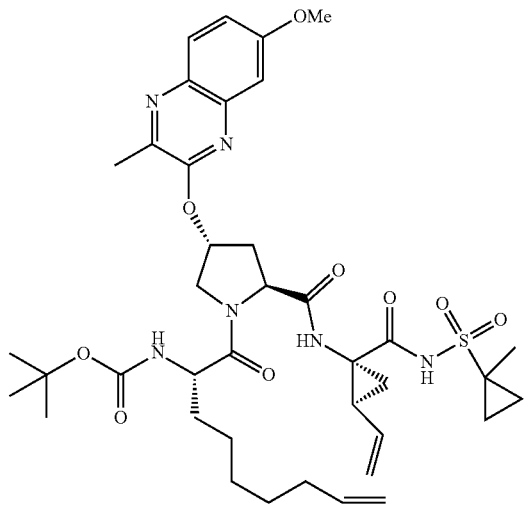 [SMILES: C=CCCCCC[C@H](NC(=O)OC(C)(C)C)C(=O)N1C[C@H](Oc2nc3cc(OC)ccc3nc2C)C[C@H]1C(=O)N[C@]1(C(=O)NS(=O)(=O)C2(C)CC2)C[C@H]1C=C]

A solution of ester 6 (6.0 g, 10.5 mmol) in THF-$H_2O$ mixture (1:1, 150 mL) was treated with $LiOH.H_2O$ (1.55 g, 36.9 mmol). The resulting reaction mixture was stirred at room temperature for 24 h. The reaction mixture was cooled to ~5° C., acidified to a pH of 2.0 by slow addition of aqueous 0.25 N HCl (~200 mL), and extracted with EtOAc (2×400 mL). The organic portions were washed separately with saturated aqueous NaCl (200 ml), dried ($Na_2SO_4$), filtered, and evaporated under reduced pressure. The gummy residue was dissolved in $CHCl_3$ (50 mL), concentrated under reduced pressure, and the residue was dried under high vacuum overnight to yield the acid 7 (5.80 g, 99%) as a white solid.

A mixture of acid 7 (5.57 g, 10.0 mmol) and amine salt 8 (3.10 g, 11.0 mmol) in anhydrous DMF (100 mL) was treated with DIEA (6.70 mL, 40.5 mmol) and HATU (5.70 g, 15.0 mmol). The resulting reaction mixture was stirred at room temperature for 2.5 h, then diluted with EtOAc (400 mL) and washed successively with aqueous 0.5 N HCl, saturated aqueous $NaHCO_3$, and saturated aqueous NaCl (250 mL each). The organic portion was dried ($Na_2SO_4$), filtered, and evaporated under reduced pressure. The residue was purified by flash column chromatography (RediSep Gold column, 2×80 g, gradient elution with 20-90% EtOAc/hexanes) to provide the bis-olefin compound 9 (6.50 g, 83%) as a white solid. $^1$HNMR (400 MHz, $CDCl_3$) δ 10.02 (s, 1H), 7.81 (d, J=8.8 Hz, 1H), 7.18 (dd, J=8.8, 2.8 Hz, 1H), 7.13 (d, J=2.8 Hz, 1H), 7.11 (s, 1H), 5.88 (br s, 1H), 5.82-5.72 (m, 2H), 5.42 (d, J=9.2 Hz, 1H), 5.26 (d, J=17.2 Hz, 1H), 5.14 (d, J=11.6 Hz, 1H), 5.00-4.90 (m, 2H), 4.50 (t, J=8.4 Hz, 1H), 4.39-4.33 (m, 1H), 4.18 (d, J=11.6 Hz, 1H), 4.02 (dd, J=11.6, 4.0 Hz, 1H), 3.93 (s, 3H), 2.58-2.50 (m, 5H), 2.10 (q, J=8.4 Hz, 1H), 2.05-1.98 (m, 3H), 1.73-1.58 (m, 4H), 1.49 (s, 3H), 1.44-1.24 (m, 16H), 0.92-0.86 (m, 1H), 0.84-0.78 (m, 1H); $^{13}$C NMR (100 MHz, $CDCl_3$) δ 173.65, 172.52, 167.55, 160.31, 155.70, 155.16, 144.41, 140.87, 138.83, 134.33, 132.61, 128.96, 118.87, 118.54, 114.41, 105.96, 79.73, 74.59, 60.30, 55.67, 53.15, 52.37, 41.73, 36.56, 35.16, 34.25, 33.62, 32.24, 28.71, 28.67, 28.26, 25.31, 23.42, 19.84, 18.37, 14.27, 13.26 ppm; HRMS (ESI) m/z: $[M+H]^+$ calcd for $C_{39}H_{55}N_6O_9S$, 783.3746; found 783.3734.

tert-Butyl ((2R,6S,13aS,14aR,16aS,Z)-2-((7-methoxy-3-methylquinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (10)

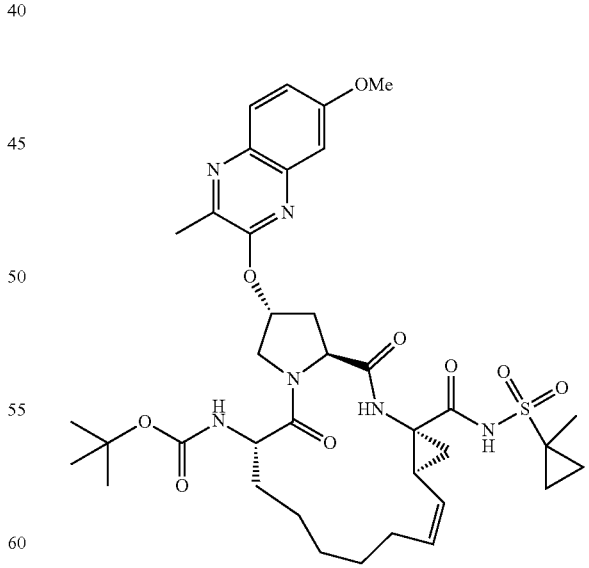

A degassed solution of bis-olefin 9 (6.20 g, 7.92 mmol) in 1,2-DCE (1600 mL) was heated to 50° C. under argon, then Zhan 1b catalyst (0.50 g, 0.68 mmol) was added in two portions over 10 min. The resulting reaction mixture was heated to 70° C. and stirred for 6 h. The reaction mixture was cooled to room temperature and solvents were evaporated under reduced pressure. The residue was purified by flash column chromatography (RediSep Gold column, 2×80 g, gradient elution with 20-90% EtOAc/hexanes) to yield the P1-P3 macrocyclic product 10 (4.20 g, 70%) as an off-white solid. $^1$H NMR (400 MHz, CDCl$_3$) δ 10.16 (s, 1H), 7.82 (d, J=9.2 Hz, 1H), 7.19-7.16 (m, 2H), 6.92 (s, 1H), 5.88 (br s, 1H), 5.69 (q, J=9.2 Hz, 1H), 5.12 (d, J=7.6 Hz, 1H), 4.99 (t, J=8.8 Hz, 1H), 4.61 (t, J=8.0 Hz, 1H), 4.51 (d, J=11.2 Hz, 1H), 4.28-4.22 (m, 1H), 4.03 (dd, J=11.2, 4.0 Hz, 1H), 3.95 (s, 3H), 2.70-2.50 (m, 6H), 2.31 (q, J=8.8 Hz, 1H), 1.92-1.66 (m, 4H), 1.60-1.20 (m, 21H), 0.85-0.78 (m, 2H) ppm; $^{13}$C NMR (100 MHz, CDCl$_3$) δ 177.16, 173.33, 166.94, 160.33, 155.32, 155.04, 144.46, 141.03, 134.20, 136.25, 128.66, 124.89, 118.93, 105.98, 79.85, 74.88, 59.46, 55.72, 53.08, 51.97, 44.73, 36.43, 34.61, 32.72, 29.65, 28.15, 27.06, 26.07, 22.21, 20.96, 19.71, 18.17, 14.51, 12.51 ppm; HRMS (ESI) m/z: [M+H]$^+$ calcd for $C_{37}H_{51}N_6O_9S$, 755.3433; found 755.3404. Anal. HPLC: $t_R$ 13.57 min, purity 99%.

(2R,6S,13aS,14aR,16aS,Z)-6-Amino-2-((7-methoxy-3-methylquinoxalin-2-yl)oxy)-N-((1-methylcyclopropyl)sulfonyl)-5,16-dioxo-1,2,3,6,7,8,9,10,11,13a,14,15,16,16a-tetradecahydrocyclopropa[e]pyrrolo[1,2-a][1,4]diazacyclopentadecine-14a(5H)-carboxamide hydrochloride (11)

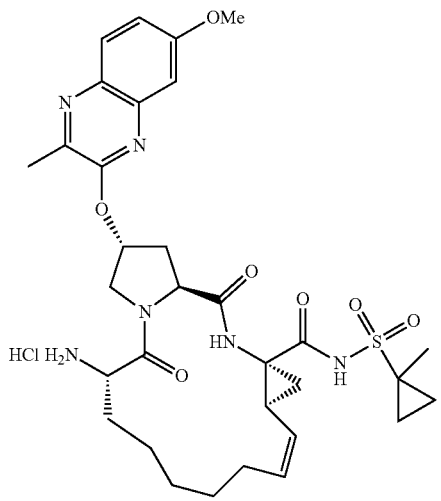

A solution of compound 10 (3.25 g, 4.31 mmol) in anhydrous CH$_2$CL$_2$ (15 mL) was treated with a solution of 4 N HCl in 1,4-dioxane (50 mL). The reaction mixture was stirred at room temperature for 3 h, concentrated under reduced pressure, and the residue was dried under high vacuum. The residue was triturated with diethyl ether (40 mL), and the solid was filtered, washed with Et$_2$O (2×15 mL), and dried under high vacuum to yield the amine salt 11 (2.90 g, 98%) as an off-white solid.

1,1,1-trifluoro-2-methylpropan-2-yl ((2R,6S,13aS,14aR,16aS,Z)-2-((7-methoxy-3-methylquinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (P4-1)

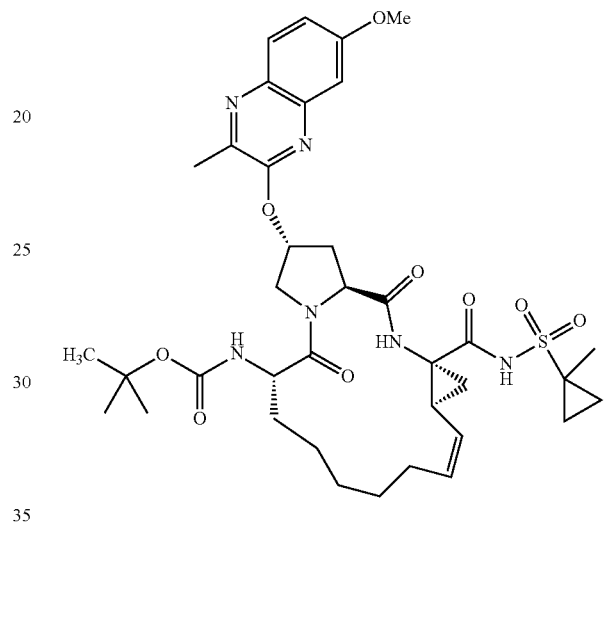

A solution of the amine salt 11 (0.25 g, 0.36 mmol) in anhydrous CH$_3$CN (10 mL) was treated with DIEA (0.45 mL, 2.58 mmol) and 4-nitrophenyl (1,1,1-trifluoro-2-methylpropan-2-yl) carbonate (0.110 g, 0.37 mmol). The resulting reaction mixture was stirred at room temperature for 24 h, then concentrated under reduced pressure and dried under high vacuum. The residue was purified by flash column chromatography (RediSep Gold column, 24 g, gradient elution with 10-90% EtOAc/hexanes) to provide the target compound P4-1 (0.28 g, 96%) as a white solid. $^1$HNMR (500 MHz, CDCl$_3$) δ 10.16 (s, 1H), 7.79 (d, J=10.0 Hz, 1H), 7.19-7.16 (m, 2H), 7.03 (s, 1H), 5.87 (br s, 1H), 5.72-5.64 (m, 2H), 4.97 (t, J=9.5 Hz, 1H), 4.61 (t, J=8.0 Hz, 1H), 4.48 (d, J=11.5 Hz, 1H), 4.26-4.22 (m, 1H), 4.02 (dd, J=11.5, 4.0 Hz, 1H), 3.94 (s, 3H), 2.66-2.63 (m, 2H), 2.59-2.50 (m, 4H), 2.30 (q, J=9.0 Hz, 1H), 1.89-1.73 (m, 4H), 1.60-1.22 (m, 18H), 0.84-0.80 (m, 2H) ppm; $^{13}$C NMR (125 MHz, CDCl$_3$) δ 177.28, 172.28, 167.14, 160.43, 155.40, 153.35, 141.61, 141.10, 136.42, 134.39, 129.01, 125.05 (q, J=281 Hz), 124.97, 118.94, 106.16, 79.78 (d, J=29.3 Hz), 74.99, 55.84, 53.27, 52.28, 44.81, 36.60, 34.82, 32.66, 29.62, 27.27, 27.21, 26.28, 22.20, 20.94, 19.88, 19.49, 19.43, 18.29, 14.64, 12.68 ppm; HRMS (ESI) m/z: [M+H]$^+$ calcd for $C_{37}H_{48}F_3N_6O_9S^+$, 809.3150; found 809.3128.

155

1-methylcyclopentyl ((2R,6S,13aS,14aR,16aS,Z)-2-((7-methoxy-3-methylquinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (P4-3)

156

(2R,6S,13aS,14aR,16aS,Z)-6-(S)-2-Acetamido-3,3-dimethylbutanamido)-2-((7-methoxy-3-methylquinoxalin-2-yl)oxy)-N-((1-methylcyclopropyl)sulfonyl)-5,16-dioxo-1,2,3,6,7,8,9,10,11,13a,14,15,16,16a-tetradecahydrocyclopropa[e]pyrrolo[1,2-a][1,4]diazacyclopentadecine-14a(5H)-carboxamide (P4-P5-2)

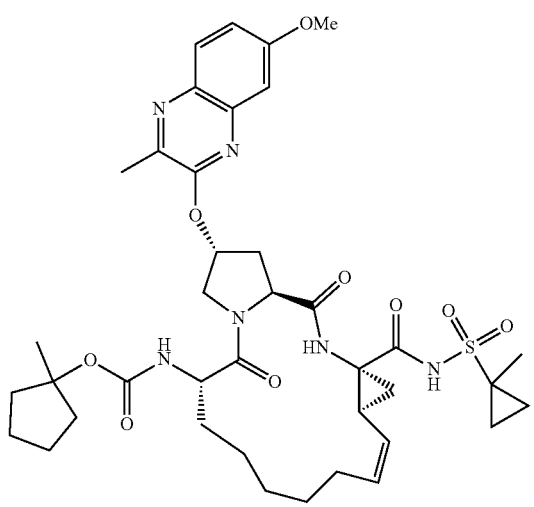 [SMILES: COc1ccc2nc(C)c(O[C@@H]3C[C@H]4C(=O)N[C@]5(C(=O)NS(=O)(=O)C6(C)CC6)C[C@H]5/C=C\CCCCC[C@H](NC(=O)OC5(C)CCCC5)C(=O)N4C3)nc2c1]

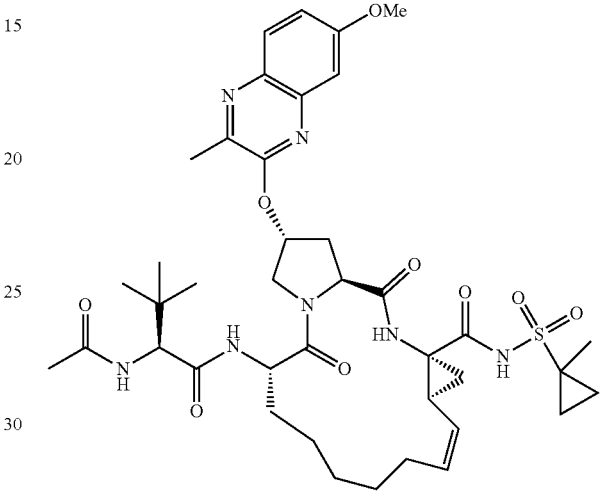

The same procedure was used as described above for compound P4-1. A mixture of amine salt 11 (0.25 g, 0.36 mmol) was treated with DIEA (0.45 mL, 2.58 mmol) and 1-methylcyclopentyl (4-nitrophenyl) carbonate (0.098 g, 0.37 mmol) to provide the target compound P4-3 (0.24 g, 85%) as a white solid. $^1$H NMR (500 MHz, CDCl$_3$) δ 10.13 (s, 1H), 7.79 (d, J=10.0 Hz, 1H), 7.18-7.16 (m, 2H), 6.87 (s, 1H), 5.89 (br s, 1H), 5.70 (q, J=9.0 Hz, 1H), 5.12 (d, J=7.5 Hz, 1H), 5.00 (t, J=9.0 Hz, 1H), 4.61 (t, J=7.5 Hz, 1H), 4.50 (d, J=11.5 Hz, 1H), 4.28 (t, J=8.0 Hz, 1H), 4.04 (dd, J=11.0, 4.0 Hz, 1H), 3.95 (s, 3H), 2.69-2.50 (m, 6H), 2.31 (q, J=8.5 Hz, 1H), 1.93-1.76 (m, 6H), 1.65-1.25 (m, 21H), 0.85-0.79 (m, 2H) ppm; $^{13}$C NMR (125 MHz, CDCl$_3$) δ 177.11, 173.33, 166.90, 160.27, 155.31, 155.20, 144.50, 140.98, 136.24, 134.31, 128.89, 124.92, 118.78, 106.03, 89.54, 74.79, 59.47, 55.72, 53.11, 52.03, 44.75, 39.28, 39.08, 36.47, 34.61, 32.79, 29.71, 27.11, 27.06, 26.09, 24.59, 23.77, 22.26, 21.00, 19.86, 18.20, 14.52, 12.57 ppm; HRMS (ESI) m/z: [M+H]$^+$ calcd for C$_{39}$H$_{53}$N$_6$O$_9$S$^+$, 781.3589; found 781.3570.

A mixture of amine salt 11 (0.31 g, 0.45 mmol) and N—Ac-Tle-OH (0.10 g, 0.58 mmol) in anhydrous DMF (8 mL) was treated with DIEA (0.60 mL, 3.50 mmol) and HATU (0.35 g, 0.92 mmol). The resulting reaction mixture was stirred at room temperature for 5 h, then diluted with EtOAc (100 mL), and washed successively with aqueous 0.5 N HCl, saturated aqueous NaHCO$_3$, and saturated aqueous NaCl (75 mL each). The organic portion was dried (Na$_2$SO$_4$), filtered, and evaporated under reduced pressure. The residue was purified by flash column chromatography (RediSep Gold column, 12 g, gradient elution with 80-100% EtOAc/hexanes) to provide P4-P5-2 (0.28 g, 77%) as a white solid. $^1$H NMR (500 MHz, CD$_3$OD) δ 7.76 (d, J=9.0 Hz, 1H), 7.26 (d, J=2.5 Hz, 1H), 7.21 (dd, J=9.0, 3.0 Hz, 1H), 5.95 (br s, 1H), 5.70 (q, J=8.5 Hz, 1H), 5.05 (t, J=9.0 Hz, 1H), 4.68 (dd, J=9.0, 7.5 Hz, 1H), 4.63 (d, J=11.5 Hz, 1H), 4.44 (dd, J=11.5, 3.0 Hz, 1H), 4.13-4.09 (m, 2H), 3.94 (s, 3H), 2.73-2.63 (m, 2H), 2.57-2.46 (m, 5H), 2.00-1.93 (m, 1H), 1.91-1.83 (m, 4H), 1.72 (dd, J=8.5, 5.5 Hz, 1H), 1.64-1.36 (m, 13H), 1.33-1.26 (m, 1H), 0.90-0.84 (m, 2H), 0.74 (s, 9H) ppm; $^{13}$C NMR (125 MHz, CD$_3$OD) δ 179.38, 173.54, 172.91, 171.70, 169.52, 162.05, 156.98, 146.05, 142.68, 136.89, 134.86, 129.27, 126.45, 119.79, 107.34, 76.88, 61.43, 60.87, 56.26, 54.47, 52.16, 45.36, 37.59, 36.09, 35.30, 33.27, 30.92, 28.65, 28.23, 27.87, 27.04, 23.29, 22.37, 21.75, 19.91, 18.43, 14.57, 13.01 ppm; HRMS (ESI) m/z: [M+H]$^+$ calcd for C$_{40}$H$_{56}$N$_7$O$_9$S$^+$, 810.3855; found 810.3836.

157

(2R,6S,13aS,14aR,16aS,Z)-6-(S)-2-Acetamido-3-methylbutanamido)-2-((7-methoxy-3-methylquinoxalin-2-yl)oxy)-N-((1-methylcyclopropyl)sulfonyl)-5,16-dioxo-1,2,3,6,7,8,9,10,11,13a,14,15,16,16a-tetradecahydrocyclopropa[e]pyrrolo[1,2-a][1,4]diazacyclopentadecine-14a(5H)-carboxamide (P4-P5-4)

158

(2R,6S,13aS,14aR,16aS,Z)-6-((2S,3S)-2-acetamido-3-methylpentanamido)-2-((7-methoxy-3-methylquinoxalin-2-yl)oxy)-N-((1-methylcyclopropyl)sulfonyl)-5,16-dioxo-1,2,3,6,7,8,9,10,11,13a,14,15,16,16a-tetradecahydrocyclopropa[e]pyrrolo[1,2-a][1,4]diazacyclopentadecine-14a(5H)-carboxamide (P4-P5-6)

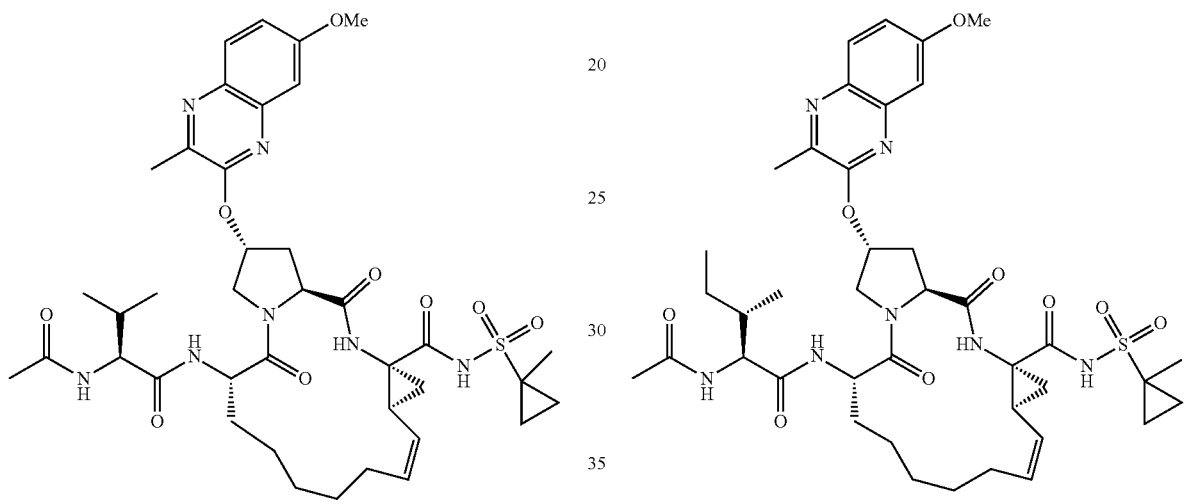

The same procedure was used as described above for compound P4-P5-2. A mixture of amine salt 11 (0.25 g, 0.36 mmol) and N—Ac-Val-OH (0.075 g, 0.47 mmol) was treated with DIEA (0.50 mL, 2.87 mmol) and HATU (0.30 g, 0.79 mmol) to provide the target compound P4-P5-4 (0.30 g, 80%) as a white solid. $^1$H NMR (500 MHz, CD$_3$OD) δ 7.76 (d, J=9.0 Hz, 1H), 7.26 (d, J=3.0 Hz, 1H), 7.20 (dd, J=9.5, 3.0 Hz, 1H), 5.98 (br s, 1H), 5.69 (q, J=9.0 Hz, 1H), 5.05 (t, J=9.0 Hz, 1H), 4.68 (t, J=9.0 Hz, 1H), 4.60 (d, J=12.0 Hz, 1H), 4.42 (dd, J=11.5, 3.0 Hz, 1H), 4.09 (dd, J=11.5, 4.0, Hz, 1H), 4.05 (d, J=7.5 Hz, 1H), 3.93 (s, 3H), 2.72-2.62 (m, 2H), 2.58-2.52 (m, 1H), 2.50 (s, 3H), 2.43 (q, J=8.5 Hz, 1H), 1.97-1.81 (m, 6H), 1.72 (dd, J=8.5, 5.5 Hz, 1H), 1.64-1.29 (m, 14H), 0.90-0.84 (m, 2H), 0.79 (t, J=7.5 Hz, 6H) ppm; $^{13}$C NMR (125 MHz, CD$_3$OD) δ 179.28, 173.79, 173.16, 172.76, 169.47, 162.01, 157.02, 146.26, 142.65, 136.85, 134.82, 129.24, 126.43, 119.75, 107.33, 76.70, 60.78, 59.49, 56.26, 54.41, 52.42, 45.29, 37.59, 35.96, 33.29, 32.07, 31.00, 28.60, 28.35, 27.82, 23.21, 22.37, 21.78, 19.80, 19.71, 18.68, 18.43, 14.57, 13.02 ppm; HRMS (ESI) m/z: [M+H]$^+$ calcd for C$_{39}$H$_{54}$N$_7$O$_9$S$^+$, 796.3698; found 796.3679.

The same procedure was used as described above for compound P4-P5-2. A mixture of amine salt AJ-63 (0.15 g, 0.22 mmol) and N—Ac-Ile-OH (0.061 g, 0.35 mmol) was treated with DIEA (0.23 mL, 1.4 mmol) and HATU (0.21 g, 0.55 mmol) to provide the target compound P4-P5-6 (0.10 g, 56%) as a white solid. $^1$H NMR (500 MHz, CD$_3$OD) δ 8.15 (d, J=7.0 Hz, 1H), 7.77-7.73 (m, 2H), 7.25 (d, J=2.5 Hz, 1H), 7.20 (dd, J=9.0, 2.5 Hz, 1H), 5.98 (br s, 1H), 5.70 (q, J=8.5 Hz, 1H), 5.05 (t, J=9.0 Hz, 1H), 4.67 (t, J=8.5 Hz, 1H), 4.62 (d, J=12.0 Hz, 1H), 4.44-4.40 (m, 1H), 4.11-4.05 (m, 2H), 3.93 (s, 3H), 2.71-2.62 (m, 2H), 2.58-2.50 (m, 4H), 2.43 (q, J=8.5 Hz, 1H), 1.99-1.84 (m, 5H), 1.73 (dd, J=8.0, 5.5 Hz, 1H), 1.64-1.25 (m, 15H), 1.09-1.00 (m, 1H), 0.90-0.84 (m, 2H), 0.82 (t, J=7.5 Hz, 3H), 0.73 (d, J=7.0 Hz, 3H) ppm; $^{13}$C NMR (125 MHz, CD$_3$OD) δ 179.32, 173.67, 173.04, 172.90, 169.48, 162.00, 157.02, 146.25, 142.65, 136.84, 134.81, 129.23, 126.43, 119.74, 107.33, 76.71, 60.75, 58.56, 56.27, 54.38, 52.43, 45.31, 38.16, 37.59, 35.97, 33.21, 31.01, 28.61, 28.32, 27.81, 25.96, 23.23, 22.36, 21.75, 19.80, 18.44, 15.87, 14.57, 13.01, 11.29 ppm; HRMS (ESI) m/z: [M+H]$^+$ calcd for C$_{40}$H$_{56}$N$_7$O$_9$S$^+$, 810.3855; found 810.3832.

159

Methyl ((S)-1-(((2R,6S,13aS,14aR,16aS,Z)-2-((7-methoxy-3-methylquinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)amino)-3,3-dimethyl-1-oxobutan-2-yl)carbamate (P4-P5-1)

160

Methyl ((S)-1-(((2R,6S,13aS,14aR,16aS,Z)-2-((7-methoxy-3-methylquinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)amino)-3-methyl-1-oxobutan-2-yl)carbamate (P4-P5-3)

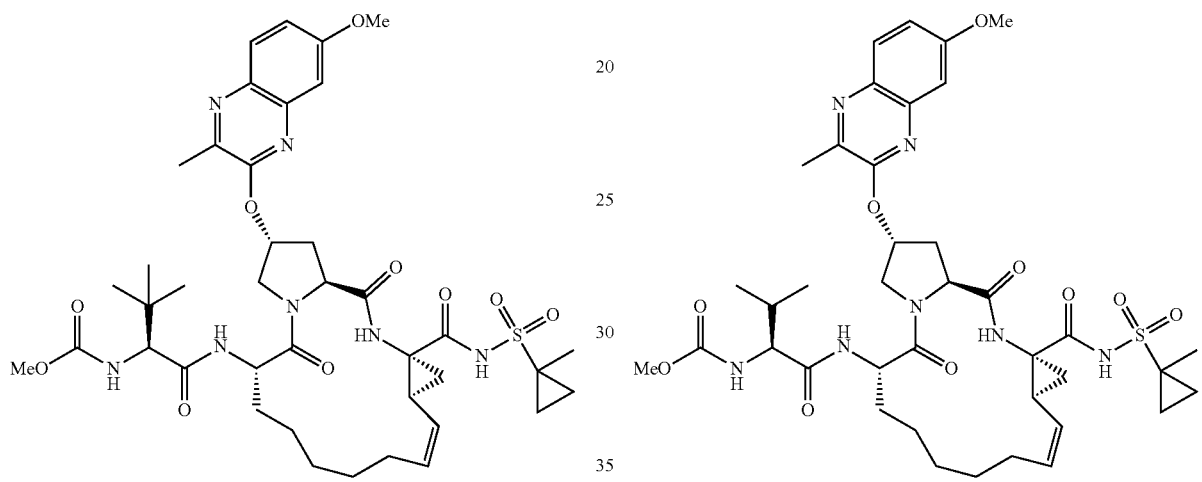

The same procedure was used as described above for compound P4-P5-2. A mixture of amine salt 11 (0.25 g, 0.36 mmol) and methoxycarbonyl-L-tert-leucine (0.093 g, 0.48 mmol) was treated with DIEA (0.50 mL, 2.87 mmol) and HATU (0.30 g, 0.79 mmol) to provide the target compound P4-P5-1 (0.25 g, 84%) as a white solid. $^1$H NMR (500 MHz, CDCl$_3$) δ 10.22 (s, 1H), 8.64 (br s, 1H), 8.04 (d, J=8.5 Hz, 1H), 7.77 (d, J=9.0 Hz, 1H), 7.20-7.16 (m, 2H), 5.89 (br s, 1H), 5.68 (q, J=8.5 Hz, 1H), 5.48 (d, J=10.0 Hz, 1H), 4.96-4.91 (m, 2H), 4.70 (t, J=8.0 Hz, 1H), 4.43 (d, J=12.0 Hz, 1H), 4.19 (dd, J=11.5, 4.0 Hz, 1H), 3.95 (s, 3H), 3.86 (d, J=10.0 Hz, 1H), 3.63 (s, 3H), 2.78-2.63 (m, 3H), 2.45 (s, 3H), 2.10 (q, J=8.5 Hz, 2H), 1.85-1.70 (m, 3H), 1.50-1.13 (m, 11H), 0.98 (dd, J=10.4, 6.0 Hz, 1H), 0.83-0.77 (m, 2H), 0.65 (s, 9H) ppm; $^{13}$C NMR (125 MHz, CDCl$_3$) δ 176.65, 172.94, 169.36, 166.94, 160.56, 157.69, 155.14, 143.75, 141.13, 136.92, 134.45, 128.99, 124.90, 119.23, 106.12, 75.10, 62.27, 59.25, 55.87, 54.13, 53.24, 50.35, 44.09, 36.64, 35.40, 35.10, 34.38, 28.74, 27.56, 27.50, 26.73, 26.52, 22.89, 19.92, 19.80, 18.31, 14.57, 12.73 ppm; HRMS (ESI) m/z: [M+H]$^+$ calcd for C$_{40}$H$_{56}$N$_7$O$_{10}$S$^+$, 826.3804; found 826.3778.

The same procedure was used as described above for compound P4-P5-2. A mixture of amine salt 11 (0.25 g, 0.36 mmol) and methoxycarbonyl-L-valine (0.085 g, 0.48 mmol) was treated with DIEA (0.50 mL, 2.87 mmol) and HATU (0.30 g, 0.79 mmol) to provide the target compound P4-P5-3 (0.24 g, 82%) as a white solid. $^1$H NMR (500 MHz, CDCl$_3$) δ 10.25 (s, 1H), 8.71 (br s, 1H), 8.43 (br s, 1H), 7.80 (d, J=9.5 Hz, 1H), 7.21-7.18 (m, 2H), 5.95 (br s, 1H), 5.72 (q, J=8.5 Hz, 1H), 5.48 (d, J=9.5 Hz, 1H), 4.98-4.89 (m, 2H), 4.67 (t, J=8.0 Hz, 1H), 4.45 (d, J=11.5 Hz, 1H), 4.25 (dd, J=9.5, 4.5 Hz, 1H), 4.19 (dd, J=11.5, 4.0 Hz, 1H), 3.95 (s, 3H), 3.64 (s, 3H), 2.80-2.65 (m, 3H), 2.43 (s, 3H), 2.21 (q, J=8.5 Hz, 1H), 2.14-2.07 (m, 1H), 1.87-1.65 (m, 3H), 1.58-1.36 (m, 10H), 1.31-1.17 (m, 2H), 1.01 (dd, J=9.0, 5.5 Hz, 1H), 0.82-0.77 (m, 5H), 0.67 (d, J=7.0 Hz, 3H) ppm; $^{13}$C NMR (125 MHz, CDCl$_3$) δ 177.09, 173.68, 170.18, 167.08, 160.67, 157.98, 155.22, 143.79, 141.16, 136.88, 134.23, 128.91, 124.87, 119.39, 106.12, 75.07, 59.56, 58.46, 55.90, 54.14, 53.30, 50.23, 44.37, 36.61, 35.53, 34.69, 32.78, 28.66, 27.71, 27.51, 26.90, 22.39, 20.06, 19.72, 19.61, 18.35, 16.70, 14.72, 12.72 ppm; HRMS (ESI) m/z: [M+H]$^+$ calcd for C$_{39}$H$_{54}$N$_7$O$_{10}$S$^+$, 812.3647; found 812.3624.

161

Methyl ((S)-1-cyclopentyl-2-(((2R,6S,13aS,14aR,16aS,Z)-2-((7-methoxy-3-methylquinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)amino)-2-oxoethyl)carbamate (P4-P5-5)

162

(2R,6S,13aS,14aR,16aS,Z)-6-((S)-2-acetamido-2-cyclopentylacetamido)-2-((7-methoxy-3-methylquinoxalin-2-yl)oxy)-N-((1-methylcyclopropyl)sulfonyl)-5,16-dioxo-1,2,3,6,7,8,9,10,11,13a,14,15,16,16a-tetradecahydrocyclopropa[e]pyrrolo[1,2-a][1,4]diazacyclopentadecine-14a(5H)-carboxamide (AJ-68)

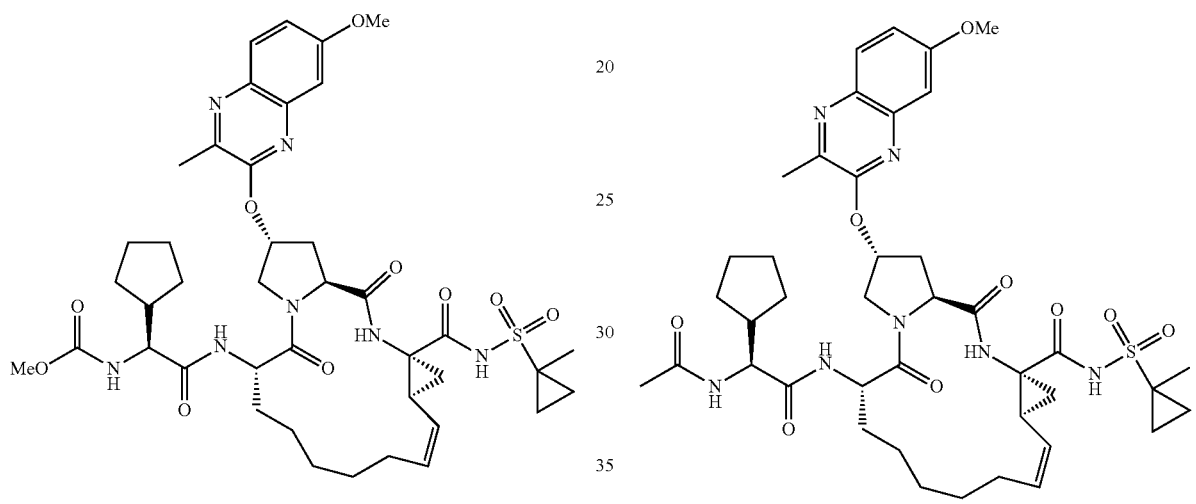

The same procedure was used as described above for compound P4-P5-2. A mixture of amine salt 11 (0.25 g, 0.36 mmol) and methoxycarbonyl-L-cyclopentylglycine (0.096 g, 0.48 mmol) was treated with DIEA (0.50 mL, 2.87 mmol) and HATU (0.30 g, 0.79 mmol) to provide the target compound P4-P5-5 (0.25 g, 83%) as a white solid. $^1$H NMR (500 MHz, CDCl$_3$) δ 10.26 (s, 1H), 8.73 (br s, 1H), 8.40 (br s, 1H), 7.79 (d, J=10.0 Hz, 1H), 7.20-7.18 (m, 2H), 5.96 (br s, 1H), 5.71 (q, J=9.0 Hz, 1H), 5.52 (d, J=9.5 Hz, 1H), 4.97-4.89 (m, 2H), 4.68 (t, J=8.0 Hz, 1H), 4.43 (d, J=11.5 Hz, 1H), 4.37 (dd, J=9.5, 5.0 Hz, 1H), 4.21 (dd, J=11.5, 4.5 Hz, 1H), 3.95 (s, 3H), 3.64 (s, 3H), 2.72-2.67 (m, 2H), 2.47 (s, 3H), 2.17 (q, J=8.5 Hz, 1H), 2.09-2.04 (m, 1H), 1.96-1.74 (m, 4H), 1.54-1.32 (m, 20H), 1.03 (dd, J=9.0, 6.0 Hz, 1H), 0.84-0.79 (m, 2H) ppm; $^{13}$C NMR (125 MHz, CDCl$_3$) δ 177.12, 173.43, 170.61, 167.07, 160.58, 157.94, 155.27, 143.87, 141.14, 136.86, 134.47, 129.03, 124.86, 119.25, 106.14, 75.04, 59.37, 56.26, 55.90, 54.03, 53.26, 50.27, 44.28, 43.56, 36.61, 35.45, 34.67, 29.39, 28.74, 27.65, 27.51, 26.80, 25.57, 25.37, 22.41, 19.65, 18.33, 14.68, 12.71 ppm; HRMS (ESI) m/z: [M+H]$^+$ calcd for C$_{41}$H$_{56}$N$_7$O$_{10}$S$^+$, 838.3804; found 838.3774.

The same procedure was used as described above for compound P4-P5-2. A mixture of amine salt 11 (0.25 g, 0.36 mmol) and N—Ac-cyclopentylglycine (0.075 g, 0.47 mmol) was treated with DIEA (0.50 mL, 2.87 mmol) and HATU (0.30 g, 0.79 mmol) to provide the target compound AJ-68 (0.30 g, 80%) as a white solid. $^1$H NMR (500 MHz, CD$_3$OD) δ 7.76 (d, J=9.5 Hz, 1H), 7.27 (d, J=3.0 Hz, 1H), 7.21 (dd, J=9.0, 3.0 Hz, 1H), 5.99 (br s, 1H), 5.70 (q, J=8.5 Hz, 1H), 5.05 (t, J=9.0 Hz, 1H), 4.66 (t, J=8.5 Hz, 1H), 4.61 (d, J=11.5 Hz, 1H), 4.40 (dd, J=11.0, 2.5 Hz, 1H), 4.10 (dd, J=11.5, 3.5, Hz, 1H), 4.03 (d, J=9.0 Hz, 1H), 3.94 (s, 3H), 2.70-2.62 (m, 2H), 2.58-2.51 (m, 4H), 2.44 (q, J=9.0 Hz, 1H), 1.99-1.85 (m, 6H), 1.73 (dd, J=8.0, 5.5 Hz, 1H), 1.68-1.16 (m, 22H), 0.90-0.84 (m, 2H) ppm; $^{13}$C NMR (125 MHz, CD$_3$OD) δ 179.36, 173.69, 173.28, 173.01, 169.51, 162.04, 157.06, 146.26, 142.70, 136.84, 134.84, 129.25, 126.46, 119.76, 107.35, 76.72, 60.76, 58.21, 56.27, 54.37, 52.44, 45.32, 43.48, 37.60, 35.98, 33.18, 31.02, 30.19, 30.17, 28.62, 28.31, 27.83, 26.14, 25.77, 23.24, 22.30, 21.74, 19.77, 18.44, 14.57, 13.01 ppm; HRMS (ESI) m/z: [M+H]$^+$ calcd for C$_{41}$H$_{56}$N$_7$O$_9$S$^+$, 822.3855; found 822.3836.

Methyl (1-(((2R,6S,13aS,14aR,16aS,Z)-2-((7-methoxy-3-methylquinoxalin-2-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamoyl)cyclopentyl)carbamate (WK-25)

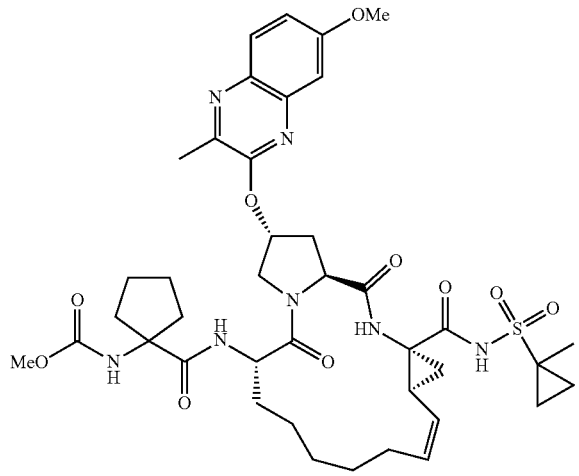 [SMILES: COC(=O)NC1(C(=O)N[C@H]2CCCCC/C=C\[C@@H]3C[C@@]3(C(=O)NS(=O)(=O)C3(C)CC3)NC(=O)[C@@H]3C[C@@H](Oc4nc5cc(OC)ccc5nc4C)CN3C2=O)CCCC1]

The same procedure was used as described above for compound P4-P5-2. A mixture of amine salt 11 (0.25 g, 0.36 mmol) and methoxycarbonyl-L-cycloleucine (0.089 g, 0.48 mmol) was treated with DIEA (0.50 mL, 2.87 mmol) and HATU (0.30 g, 0.79 mmol) to provide the target compound WK-25 (0.20 g, 67%) as a white solid. $^1$H NMR (500 MHz, CDCl$_3$) δ 10.41 (s, 1H), 8.08 (br s, 1H), 7.77 (d, J=9.0 Hz, 1H), 7.18-7.15 (m, 2H), 6.86 (d, J=7.0 Hz, 1H), 5.96 (br s, 1H), 5.71 (q, J=9.0 Hz, 1H), 5.50 (br s, 1H), 5.00 (t, J=9.5 Hz, 1H), 4.62 (t, J=7.5 Hz, 1H), 4.53 (br s, 1H), 4.36 (d, J=11.5 Hz, 1H), 4.14 (dd, J=11.0, 4.5 Hz, 1H), 3.93 (s, 3H), 3.61 (s, 3H), 2.75-2.69 (m, 1H), 2.62-2.55 (m, 1H), 2.51-2.46 (m, 4H), 2.14 (q, J=8.5 Hz, 2H), 1.96-1.45 (m, 18H), 1.40-1.23 (m, 5H), 0.86-0.81 (m, 2H) ppm; $^{13}$C NMR (125 MHz, CDCl$_3$) δ 176.93, 173.94, 173.00, 167.34, 160.42, 156.24, 155.38, 144.41, 141.11, 136.43, 134.46, 129.00, 125.24, 119.00, 106.17, 74.75, 67.04, 59.33, 55.86, 52.96, 52.32, 51.64, 44.48, 38.73, 37.91, 36.61, 36.18, 34.62, 32.23, 29.81, 27.82, 27.22, 26.04, 24.22, 22.67, 19.93, 18.24, 14.76, 12.63 ppm; HRMS (ESI) m/z: [M+H]$^+$ calcd for $C_{40}H_{54}N_7O_{10}S^+$, 824.3647; found 824.3618.

Part 3. Linear HCV NS3/4A Protease Inhibitors

The synthesis of linear NS3/4A PIs with diverse P2 quinoxaline moieties is outlined in Scheme 5. The key Boc-protected P2 intermediates 4a-e were prepared from the corresponding 3-substituted 7-methoxy-quinoxalin-2-ones by an $S_N2$ displacement reaction with the activated cis-hydroxyproline derivative as described previously. Deprotection of the Boc group and reaction with N-Boc-L-tert-leucine under HATU coupling conditions gave the P2-P3 intermediates 5a-e. After ester hydrolysis, the resulting acids 6a-e were coupled with the P1-P1' acylsulfonamide intermediates 7 and 8 to afford the target inhibitors 3, 9b-e and 10a-e. The tert-butyl-capped compounds were converted to the corresponding cyclopentyl derivatives in two steps, involving Boc deprotection and reaction with N-(cyclopentyloxycarbonyloxy)-succinimide, to provide the desired compounds 11a-e and 12a-e.

The SAR exploration of 3 was focused on optimizing interactions of the P2 quinoxaline moiety and minimizing direct interactions with S2 subsite residues. In addition, modifications at the P1' and the N-terminal capping groups were also investigated. The potency and resistance profiles of the resulting linear PIs were evaluated using biochemical and replicon assays. The enzyme inhibition constants (K) were determined against WT GT1a NS3/4A protease and resistant variants R155K and D168A (Table 8). For a subset of compounds, cellular antiviral potencies (EC$_{50}$) were determined using replicon-based antiviral assays against WT HCV and resistant variants R155K, A156T, D168A, and D168V (Table 9). Grazoprevir (1) was used as a control in all assays.

Scheme 5. Synthesis of HCV NS3/4 protease inhibitors$^a$

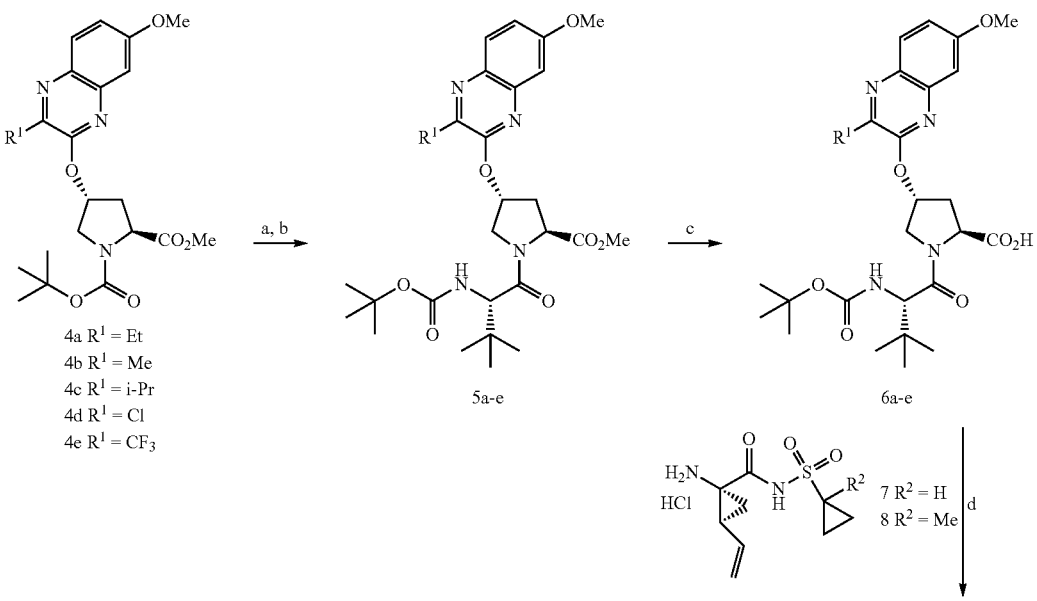

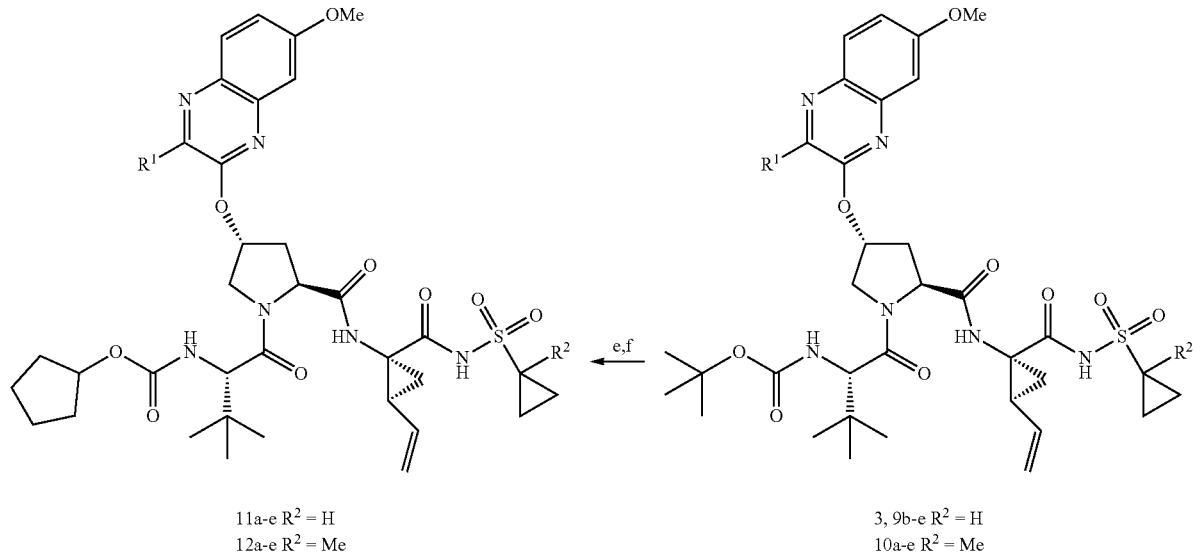

11a-e R² = H  
12a-e R² = Me 3, 9b-e R² = H  
10a-e R² = Me

ᵃReagents and conditions: (a) 4N HCl in dioxane, CH₂Cl₂, RT, 3 h; (b) Boc—Tle—OH, HATU, DIEA, DMF, RT, 4 h; (c) LiOH·H₂O, THF, H₂O, RT, 24 h; (d) HATU, DIEA, DMF, RT, 2 h; (e) 4N HCl in dioxane, RT, 3 h; (f) N-(cyclopentyloxy-carbonyloxy)-succinimide, DIEA, CH₃CN, RT, 36 h.

Compared to the macrocyclic PIs 1 and 2, the linear analogue 3 exhibited significantly lower potency against WT protease ($K_i$=19 nM) and experienced an even larger reduction in antiviral potency ($EC_{50}$=24 nM), as reported previously. Compound 3 was also less potent than 1 and 2 against the resistant variants R155K, D168A and D168V in both enzyme inhibition and replicon assays. The significant potency losses for the linear inhibitor 3 are likely due to the increase in conformational flexibility and associated entropic penalty of binding to the protease. However, close examination of the overall resistance profile revealed that fold losses in potency were generally lower for compound 3 than 1 in both enzyme inhibition and replicon assays (Tables 10 and 9). Moreover, while 1 was highly susceptible to the A156T variant ($EC_{50}$=200 nM), with >1600-fold loss in potency compared to WT, compound 3 showed better antiviral potency against this variant ($EC_{50}$=73 nM). The reduced susceptibility to RASs, particularly at Ala156, observed for 3 demonstrates that removal of the macrocyclic linker and the resulting conformational flexibility allows the inhibitor to adapt to substitutions in the S2 subsite.

To improve potency, analogues of inhibitor 3 with modifications at the P1' and P4 capping groups were prepared and tested. Replacement of the P1' cyclopropylsulfonamide with a more hydrophobic 1-methylcyclopropyl-sulfonamide moiety generally improved potency of the resulting analogues. Thus, compared to 3, analogue 10a afforded a slight increase in enzyme potency against WT protease and resistant variants R155K and D168A. Similarly, replacing the tert-butyl P4 capping group with a bulkier cyclopentyl moiety in 11a provided compounds with improved potency. Analogue 12a with the 1-methyl-cyclopropylsulfonamide moiety at P1' and cyclopentyl P4 capping group was 2- and 4-fold more potent than 3 against the WT protease ($K_i$=6.9 nM) and D168A variant ($K_i$=145 nM), respectively. Thus, minor modifications at the P1' and P4 moieties of inhibitor 3 provided analogues with improved potency against WT protease and the D168A variant.

TABLE 8

Inhibitory activity against wild-type HCV NS3/4A protease and drug resistant variants

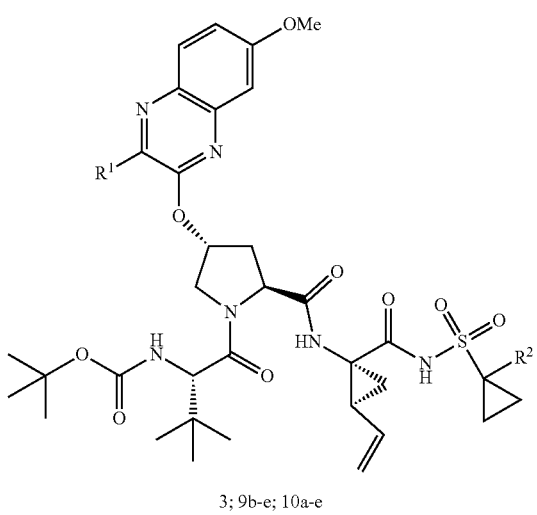

3; 9b-e; 10a-e

TABLE 8-continued

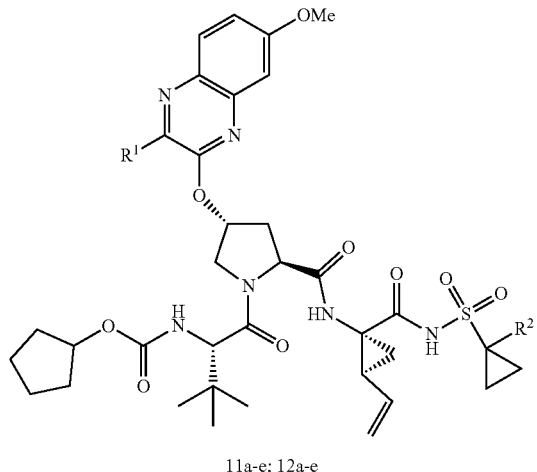

11a-e; 12a-e

| Com-pd. | R$^1$ | R$^2$ | Ki (nM) | | |
|---|---|---|---|---|---|
| | | | WT | R155K | D168A |
| 3 | Et | H | 19 ± 2.7 | 17 ± 2.3 | 642 ± 101 |
| 10a | Et | Me | 16 ± 1.3 | 14 ± 1.1 | 385 ± 31 |
| 11a | Et | H | 9.8 ± 2.0 | 15 ± 2.2 | 350 ± 30 |
| 12a | Et | Me | 6.9 ± 0.5 | 13 ± 2.7 | 145 ± 14 |
| 9b | Me | H | 18 ± 1.6 | 8.5 ± 2.1 | 290 ± 24 |
| 10b | Me | Me | 14 ± 2.1 | 14 ± 1.7 | 265 ± 26 |
| 11b | Me | H | 9.2 ± 0.9 | 9.6 ± 0.9 | 144 ± 23 |
| 12b | Me | Me | 7.1 ± 1.1 | 10 ± 1.3 | 140 ± 13 |
| 9c | i-Pr | H | 32 ± 5.1 | 49 ± 11 | 1086 ± 137 |
| 10c | i-Pr | Me | 29 ± 9.4 | 27 ± 5.6 | 1179 ± 170 |
| 11c | i-Pr | H | 17 ± 3.2 | 55 ± 11 | 985 ± 106 |
| 12c | i-Pr | Me | 21 ± 2.6 | 43 ± 11 | 1000 ± 80 |
| 9d | Cl | H | 7.8 ± 1.1 | 2.2 ± 0.4 | 128 ± 16 |
| 10d | Cl | Me | 6.1 ± 1.1 | 3.8 ± 0.6 | 119 ± 16 |
| 11d | Cl | H | 3.8 ± 0.6 | 4.1 ± 0.5 | 99 ± 10 |
| 12d | Cl | Me | 3.9 ± 0.7 | 5.2 ± 0.8 | 51 ± 6.0 |
| 9e | CF$_3$ | H | 87 ± 18 | 24 ± 3.3 | 723 ± 80 |
| 10e | CF$_3$ | Me | 46 ± 9.6 | 12 ± 1.7 | 513 ± 50 |
| 11e | CF$_3$ | H | 34 ± 8.3 | 26 ± 7.7 | 703 ± 63 |
| 12e | CF$_3$ | Me | 22 ± 3.4 | 22 ± 6.9 | 516 ± 61 |
| 2 | | | 2.0 ± 0.1 | 3.1 ± 0.34 | 91 ± 10 |
| 1 | | | 0.20 ± 0.1 | 0.80 ± 0.3 | 40 ± 5.0 |

It has been shown that minimizing inhibitor interactions in the S2 subsite resulted in an overall improvement in potency and resistance profiles. (Matthew, et al. 2017 *J. Med. Chem.* 60, 5699-5716.) Although the P2 quinoxaline in 3 largely avoids direct interactions with residues in the S2 subsite, the ethyl group at the 3-position of this moiety makes hydrophobic interactions with the hydrocarbon portion of the Arg155 side chain as well as with Ala156. Thus, in an effort to optimize interactions with these residues, changes at the 3-position of P2 quinoxaline moiety were explored. Based on the co-crystal structures and SAR results from the P1-P3 macrocyclic series,[17] replacing the ethyl group with a smaller methyl group at this position, while reducing overall inhibitor interactions in the S2 subsite, was expected to maintain key hydrophobic interactions with side chains of Arg155 and Ala156. As anticipated, compound 9b incorporating the 3-methylquinoxaline was 2-fold more potent than 3 against the R155K and D168A protease variants in enzyme inhibition assays. However, analogue 10b with the 1-methylcyclopropylsulfonamide moiety at P1' position did not show much improvement in enzyme potency compared to 9b. Compounds 11b and 12b with the cyclopentyl P4 capping group were slightly more potent than the corresponding tert-butyl analogues 9b and 10b against WT and D168A. Furthermore, compounds 11b and 12b showed nanomolar potency in replicon assays against WT HCV, and despite losing about 5-20-fold potency, 12b maintained significant potency against all variants tested. Although both the 3-ethyl and 3-methyl-quinoxaline compounds showed similar potencies against WT and R155K protease variants, PIs with the smaller methyl substituent were generally more potent against the D168A variant. Together, the enzyme inhibition and replicon data indicate a preference for smaller substituents at the 3-position of the P2 quinoxaline to maintain potency against resistant variants.

Next, a larger isopropyl group was incorporated in compounds 9c and 10e to further explore the optimal size of the substituent at the 3-position of P2 quinoxaline that can be accommodated in the S2 subsite without causing unfavorable interactions. These compounds displayed considerably lower potency compared to the 3-methyl- and 3-ethyl-quinoxaline compounds across all variants in enzyme inhibition assays. Moreover, compounds with a larger isopropyl group at this position were highly susceptible to RASs at Arg155 and Asp168, with $K_i$ values in the millimolar range against the D168A protease variant. Analogues 11c and 12c, with a cyclopentyl P4 capping group, showed similar trends to the corresponding tert-butyl analogues across all protease variants tested. These findings further showed that large substituents at the 3-position of the P2 quinoxaline are detrimental to potency against resistant variants.

After determining optimal size of the substituent at the 3-position of the P2 quinoxaline, isosteric replacements of the alkyl group with different electronic properties were explored. Thus, a set of compounds bearing a 3-chloroquinoxaline P2 moiety, with comparable size to the 3-methylquinoxaline, was analyzed. In general, compounds with the 3-chloroquinoxaline were significantly more potent than the corresponding 3-ethyl- and 3-methyl-quinoxaline analogues. Compounds 9d and 10d, with a tert-butyl P4 capping group, showed about 2-fold better potency than the corresponding 3-methylquinoxaline analogues 9b and 10b against WT, R155K and D168A proteases. Similarly, the cyclopentyl-capped compounds 11d and 12d (WT $K_i$=3.8 and 3.9 nM, respectively) were more potent than the corresponding 11b and 12b, showing excellent potency against WT protease and resistant variants. In fact, both 11d and 12d exhibited $K_i$ values against WT protease and resistant variants in the same range as the macrocyclic inhibitor 2 (WT $K_i$=2.0 nM), indicating that potency of the quinoxaline-based linear PIs can be improved significantly by SAR exploration. In replicon assays, the 3-chloroquinoxaline compounds exhibited the best overall potency profile among the linear compounds, with PIs 9d, 10d and 12d showing significant improvement in replicon potency against the multidrug resistant HCV variants D168A/V (EC$_{50}$=12-38 nM). However, these compounds were more susceptible to the A156T substitution than the corresponding macrocyclic analogues. The improved potency profiles of the 3-chloroquinoxaline compounds compared to the corresponding 3-methylquinoxaline analogues indicate that the chloro group likely renders more favorable electronic properties to the quinoxaline moiety, which improves the critical π-π stacking interactions with catalytic residue His57.

TABLE 9

Antiviral activity against wild-type HCV and drug resistant variants

| Compd. | WT | R155K | A156T | D168A | D168V |
|---|---|---|---|---|---|
| 3 | 24 | 50 (2.1) | 73 (3.0) | >500 (>21) | >500 (>21) |
| 11b | 10 | 48 (4.8) | 164 (16) | 101 (10) | 150 (15) |
| 12b | 4.5 | 28 (6.2) | 87 (19) | 45 (10) | 59 (13) |
| 9d | 6.6 | 10 (1.5) | 107 (16) | 38 (5.8) | 12 (1.8) |
| 10d | 6.3 | 10 (1.6) | 100 (16) | 30 (4.8) | 12 (1.9) |
| 11d | 7.4 | 40 (5.4) | 292 (40) | 50 (6.8) | 54 (7.3) |
| 12d | 3.1 | 27 (8.7) | 163 (53) | 25 (8.1) | 23 (7.4) |
| 2 | 0.33 | 1.8 (5.5) | 9.7 (29) | 6.3 (19) | 9.1 (28) |
| 1 | 0.12 | 1.9 (16) | 200 (1667) | 11 (92) | 5.3 (44) |

Replicon EC$_{50}$ (nM) (fold change)

To further investigate the effect of electron-withdrawing groups on the activity of the inhibitors, derivatives with a more electronegative, although relatively larger, 3-trifluoromethylquinoxaline were examined. In contrast to the 3-chloroquinoxaline inhibitors, compounds 9e and 10e showed considerable loss in potency against WT protease. However, despite relatively lower potency against WT, the 3-trifluoromethylquinoxaline analogues were slightly more potent than the corresponding 3-isopropylquinoxaline PIs against the resistant variants R155K and D168A. Similar trends were observed for inhibitors 11e and 12e with the cyclopentyl P4 capping groups. While it is difficult to separate the effects of electronic properties of the chloro- and trifluoromethyl-quinoxaline moieties, it is likely that size played a more important role in determining the overall potency profile of these inhibitors.

In an effort to explain the observed potency and resistance profiles, crystal structures of three linear PIs incorporating different P2 quinoxaline moieties were determined in complex with WT NS3/4A protease (Table 11). The crystal structures of co-complexes WT-12b, -12c and -12d were compared with the previously determined structures of 1 and 3 (PDB IDs 3SUD and 5EQQ, respectively). These high-resolution (1.78-1.80 Å) structures provided details of protein-inhibitor interactions to elucidate the structural differences that underlie varied potency and susceptibility to resistant variants.

The overall binding mode of linear inhibitors 12b-d is similar to that of macrocyclic inhibitors 1-2 and the parent compound 3, where the P2 quinoxaline predominately interacts with the catalytic triad residues (FIG. 14). These structures confirm that the quinoxaline moiety maintains this unique binding conformation irrespective of macrocyclization and the substituent at the 3-position. Inhibitors 12b-d span the S1'-S4 pockets in the active site, with a conserved hydrogen bond network present in all WT NS3/4A protease structures. The hydrogen bonds between the P1 amide and the backbone carbonyl of Arg155 as well as the P3 amide and Ala157 backbone are maintained. The P1' acylsulfonamide moiety is positioned in the oxyanion hole, stabilized by hydrogen bonds with His57, Gly137, Ser138 and Ser139. Although the overall binding mode of linear analogues is similar to that of compound 1, there are subtle changes in the binding of P2 quinoxaline that may impact inhibitor potency.

The differences between the WT co-crystal structures of 1 and 3-methylquinoxaline inhibitor 12b occur predominantly in the S2 subsite. Relative to WT-1, the Asp168 side chain in the WT-12b structure is shifted to allow additional hydrogen bonding with the side chain of Arg155 (FIGS. 14A and 15A). This conformation of Asp168, which allows the P4 cyclopentyl capping group to occupy the S4 pocket, is observed in most WT protease-inhibitor complexes. The 3-methylquinoxaline moiety is shifted away from the catalytic residues toward the S2 subsite relative to the conformation of P2 quinoxaline in WT-1 structure. This shift is also observed in the parent compound 3, though to a lesser extent, likely to accommodate the larger ethyl group at the 3-position of quinoxaline (FIG. 16). However, despite larger shift of the 3-methylquinoxaline moiety, inhibitor 12b has an improved potency profile against resistant variants compared to 3, likely due to weaker contacts of the smaller methyl group with residues in the S2 subsite that mutate to confer resistance. Thus, while a slight shift of the P2 quinoxaline toward the S2 subsite does not appear to affect the overall potency profile, the substituent at the 3-position of this moiety significantly impacts inhibitor potency against resistant variants.

The shift of the quinoxaline moiety toward the S2 subsite residues was also observed in the WT-12c and WT-12d complexes (FIG. 15B-C), as well as in WT-2 and other structures of the P1-P3 macrocyclic analogues. However, the crystal structure of inhibitor 12c with the 3-isopropylquinoxaline revealed an additional rearrangement of the P2 moiety. Compared to 1, the P2 quinoxaline in 12c, with a larger isopropyl substituent, packs less against the catalytic His57 and moves away from the binding surface toward the solvent (FIG. 15B). This movement of the quinoxaline away from the catalytic His57 is not observed in the inhibitor complexes with smaller substituents at the 3-position (FIGS. 15A and 15C). Interestingly, this conformation is reminiscent of the conformation of 1 when bound to the A156T protease variant (PDB ID 3SUG) (FIG. 17), where the larger threonine residue causes steric clash with the P2-P4 macrocycle. To accommodate the larger side chain in the A156T protease, inhibitor 1 undergoes a rearrangement resulting in the shift of the P2 quinoxaline moiety away from the binding surface toward the solvent, weakening the critical π-π interactions with the catalytic His57 (FIG. 17A). This altered conformation of 1 results in dramatic potency losses against RASs at Ala156.

Similar to the A156T-1 complex, the altered conformation of the 3-isopropylquinoxaline results in significantly reduced interactions with the catalytic His57. Any perturbation to the protease active site due to RASs may further reduce interactions with His57. Indeed, the 3-isopropylquinoxaline compounds exhibit reduced potency against WT relative to the parent compound 3 and are the most susceptible to resistant variants. These results suggest that modifications of the inhibitor scaffold that cause movement of the quinoxaline away from His57 toward the solvent are highly detrimental to potency. Whereas, movement of the quinoxaline away from His57 toward the S2 subsite residues has less of an effect on inhibitor potency when a smaller substituent is present at the 3-position of P2 quinoxaline.

The 3-chloroquinoxaline series exhibited an excellent potency profile against WT and resistant variants even with a shift of the P2 quinoxaline moiety toward the S2 subsite. Interestingly, comparison of the WT-12b and WT-12d structures (FIG. 15C) did not reveal any noticeable difference in binding poses for the 3-methyl- and 3-chloro-quinoxaline analogues that could explain the disparity in inhibitory activity. The electronic effects of the chloro group appear to improve stacking interactions of the quinoxaline moiety with the catalytic residue His57, which are crucial for the binding of inhibitors with a P2 quinoxaline moiety. Thus, enhancing interactions with the catalytic triad residues by modifying the inhibitor P2 quinoxaline moiety is likely to improve overall binding energy and potency profiles.

In summary, the SAR of quinoxaline-based linear HCV NS3/4A PIs have been studied using a structure-guided design strategy to improve potency against resistant variants. Co-crystal structures of three inhibitors with different P2 moieties bound to WT protease revealed the structural basis for the observed potency and resistance profiles. Inhibitors with small substituents at the 3-position of the P2 quinoxaline were preferred for maintaining potency against resistant variants due to decreased interactions with the S2 subsite residues. Compounds with larger groups at this position cause the P2 quinoxaline moiety to shift out of the active site, weakening critical stacking interactions with the catalytic His57. These findings further support that reducing inhibitor interactions with the S2 subsite residues in the protease active site results in improved resistance profiles. Moreover, in the absence of a macrocycle, the quinoxaline-based linear PIs can be optimized by SAR exploration to provide compounds with potent activity against resistant variants.

TABLE 10

Inhibitory activity against wild-type HCV NS3/4A protease and drug resistant variants

| Compound | $R^1$ | $R^2$ | WT | R155K | D168A |
|---|---|---|---|---|---|
| 3 | Et | H | 19 ± 2.7 | 17 ± 2.3 (0.9) | 642 ± 101 (34) |
| 10a | Et | Me | 16 ± 1.3 | 14 ± 1.1 (0.9) | 385 ± 31 (24) |
| 11a | Et | H | 9.8 ± 2.0 | 15 ± 2.2 (1.5) | 350 ± 30 (36) |
| 12a | Et | Me | 6.9 ± 0.5 | 13 ± 2.7 (1.9) | 145 ± 14 (21) |
| 9b | Me | H | 18 ± 1.6 | 8.5 ± 2.1 (0.5) | 290 ± 24 (16) |
| 10b | Me | Me | 14 ± 2.1 | 14 ± 1.7 (1.0) | 265 ± 26 (19) |
| 11b | Me | H | 9.2 ± 0.9 | 9.6 ± 0.9 (1.0) | 144 ± 23 (16) |
| 12b | Me | Me | 7.1 ± 1.1 | 10 ± 1.3 (1.4) | 140 ± 13 (20) |
| 9c | i-Pr | H | 32 ± 5.1 | 49 ± 11 (1.5) | 1086 ± 137 (34) |
| 10c | i-Pr | Me | 29 ± 9.4 | 27 ± 5.6 (0.9) | 1179 ± 170 (41) |
| 11c | i-Pr | H | 17 ± 3.2 | 55 ± 11 (3) | 985 ± 106 (58) |
| 12c | i-Pr | Me | 21 ± 2.6 | 43 ± 11 (2.0) | 1000 ± 80 (48) |
| 9d | Cl | H | 7.8 ± 1.1 | 2.2 ± 0.4 (0.3) | 128 ± 16 (16) |
| 10d | Cl | Me | 6.1 ± 1.1 | 3.8 ± 0.6 (0.7) | 119 ± 16 (31) |
| 11d | Cl | H | 3.8 ± 0.6 | 4.1 ± 0.5 (1.1) | 99 ± 10 (26) |
| 12d | Cl | Me | 3.9 ± 0.7 | 5.2 ± 0.8 (1.3) | 51 ± 6.0 (13) |
| 9e | $CF_3$ | H | 87 ± 18 | 24 ± 3.3 (0.3) | 723 ± 80 (8) |
| 10e | $CF_3$ | Me | 46 ± 9.6 | 12 ± 1.7 (0.3) | 513 ± 50 (11) |
| 11e | $CF_3$ | H | 34 ± 8.3 | 26 ± 7.7 (0.8) | 703 ± 63 (21) |
| 12e | $CF_3$ | Me | 22 ± 3.4 | 22 ± 6.9 (1.0) | 516 ± 61 (24) |
| 2 | | | 2.0 ± 0.1 | 3.1 ± 0.34 (1.6) | 91 ± 10 (46) |
| 1 | | | 0.20 ± 0.1 | 0.80 ± 0.3 (4) | 40 ± 5.0 (200) |

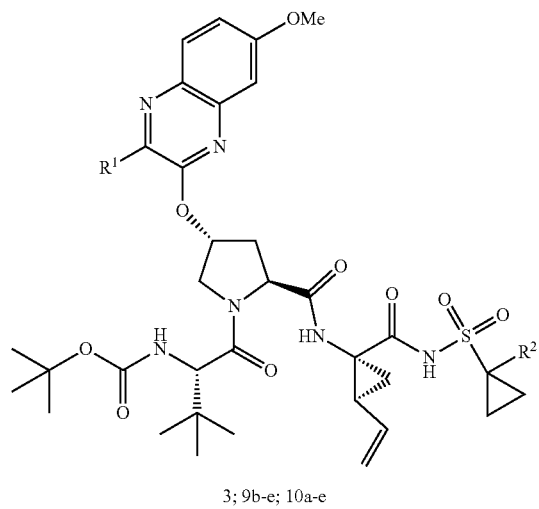

3; 9b-e; 10a-e

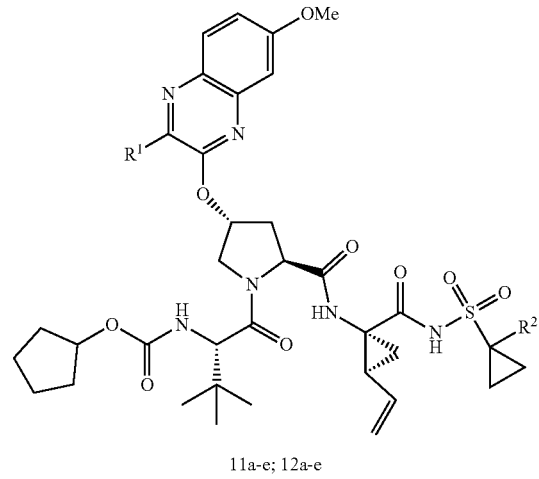

11a-e; 12a-e

TABLE 11

X-ray data collection and crystallographic refinement statistics

| | WT1a-12b | WT1a-12c | WT1a-12d |
|---|---|---|---|
| PDB code: | 6CVW | 6CVX | 6CVY |
| Resolution | 1.78 Å | 1.78 Å | 1.80 Å |
| Space group | $P2_12_12_1$ | $P2_12_12_1$ | $P2_12_12_1$ |
| Molecules in AU[a] | 1 | 1 | 1 |
| Cell dimensions | | | |
| a (Å) | 55.2 | 55.3 | 55.5 |
| b (Å) | 58.5 | 58.5 | 58.5 |
| c (Å) | 59.9 | 59.8 | 59.7 |
| β (°) | 90 | 90 | 90 |
| Completeness (%) | 98.3 | 99.1 | 96.4 |
| Total reflections | 70790 | 119454 | 116526 |
| Unique reflections | 18870 | 19054 | 17991 |
| Average I/σ | 18.5 | 15.1 | 15.2 |
| Redundancy | 3.8 | 6.3 | 6.5 |
| $R_{sym}$ (%)[b] | 7.8 (25.6) | 7.1 (27.3) | 8.5 (30.7) |
| RMSD[c] in | | | |
| Bond lengths (Å) | 0.014 | 0.019 | 0.009 |
| Bond angles (°) | 1.4 | 1.5 | 1.1 |
| $R_{factor}$ (%)[d] | 14.9 | 15.6 | 14.7 |
| $R_{free}$ (%)[e] | 18.5 | 19.4 | 18.4 |

[a] AU, asymmetric unit.
[b] $R_{sym} = \Sigma|I - \langle I \rangle|/\Sigma I$, where I = observed intensity, $\langle I \rangle$ = average intensity over symmetry equivalent; values in parentheses are for the highest resolution shell.
[c] RMSD, root mean square deviation.
[d] $R_{factor} = \Sigma||F_o| - |F_c||/\Sigma|F_o|$.
[e] $R_{free}$ was calculated from 5% of reflections, chosen randomly, which were omitted from the refinement process.

Experimental

All reactions were performed in oven-dried round bottomed or modified Schlenk flasks fitted with rubber septa under argon atmosphere, unless otherwise noted. All reagents and solvents, including anhydrous solvents, were purchased from commercial sources and used as received. Flash column chromatography was performed using silica gel (230-400 mesh, EMD Millipore). Thin-layer chromatography (TLC) was performed using silica gel (60 F-254) coated aluminum plates (EMD Millipore), and spots were visualized by exposure to ultraviolet light (UV), exposure to iodine adsorbed on silica gel, and/or exposure to an acidic solution of p-anisaldehyde (anisaldehyde) followed by brief heating. 1H NMR and 13C NMR spectra were acquired on Varian Mercury 400 MHz and Bruker Avance III HD 500 MHz NMR instruments. Chemical shifts are reported in ppm (δ scale) with the residual solvent signal used as reference and coupling constant (J) values are reported in hertz (Hz). Data are presented as follows: chemical shift, multiplicity (s=singlet, d=doublet, dd=doublet of doublet, t=triplet, q=quartet, m=multiplet, br s=broad singlet), coupling constant in Hz, and integration. High-resolution mass spectra (HRMS) were recorded on a Thermo Scientific Orbitrap Velos Pro mass spectrometer coupled with a Thermo Scientific Accela 1250 UPLC and an autosampler using electrospray ionization (ESI) in the positive mode. The purity of final compounds was determined by analytical HPLC and was found to be ≥95% pure. HPLC was performed on an Agilent system equipped with a photodiode array detector under the following conditions: column, Agilent Zorbax Eclipse XDB RP-C8 (5 μm, 4.6×150 mm, 80 Å); solvent A, H2O containing 0.1% trifluoroacetic acid (TFA), solvent B, CH3CN containing 0.1% TFA; gradient, 0% B to 100% B over 10 min followed by 100% B over 3 min; injection volume, 20 μL; flow rate, 1.4 mL/min. Retention times and purity data for each target compound are provided in the experimental section.

Synthesis of Intermediates and Final Compounds 1-(tert-Butyl) 2-methyl (2S,4R)-4-((3-ethyl-7-methoxyquinoxalin-2-yl)oxy)pyrrolidine-1,2-dicarboxylate (4a)

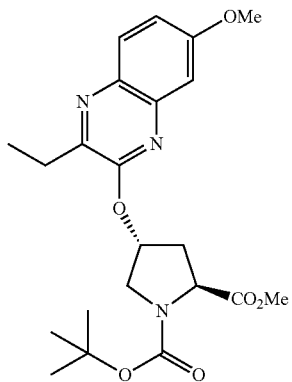 [SMILES: CCc1nc2ccc(OC)cc2nc1O[C@@H]1C[C@@H](C(=O)OC)N(C(=O)OC(C)(C)C)C1]

A solution of 3-ethyl-7-methoxyquinoxalin-2(1H)-one[1] (3.0 g, 14.7 mmol) in anhydrous NMP (45 mL) was treated with Cs$_2$CO$_3$ (7.40 g, 22.7 mmol). After stirring the reaction mixture at room temperature for 15 min, brosylated cis-hydroxyproline derivative 1-(tert-butyl) 2-methyl (2S,4S)-4-(((4-bromophenyl)sulfonyl)oxy)pyrrolidine-1,2-dicarboxylate (6.20 g, 13.3 mmol) was added in one portion. The reaction mixture was heated to 55° C., stirred for 4 h, and then another portion of brosylated cis-hydroxyproline derivative (0.48 g, 1.0 mmol) was added. The resulting reaction mixture was stirred at 55° C. for additional 2 h, cooled to room temperature, quenched with aqueous 1 N HCl solution (150 mL), and extracted with EtOAc (300 mL). The organic fraction was washed successively with saturated aqueous NaHCO$_3$ and NaCl (150 mL each), dried (Na$_2$SO$_4$), filtered, and evaporated under reduced pressure. The residue was purified by flash column chromatography using 15-30% EtOAc/hexanes as the eluent to provide 4a (5.50 g, 87%) as a white foamy solid. $^1$H NMR (400 MHz, CDCl$_3$) (mixture of rotamers, major rotamer) δ 7.85 (d, J=9.0 Hz, 1H), 7.18 (m, 1H), 7.11 (d, J=2.8 Hz, 1H), 5.73 (br s, 1H), 4.47 (t, J=8.0 Hz, 1H), 3.98-3.86 (m, 5H), 3.78 (s, 3H), 2.92 (q, J=7.2 Hz, 2H), 2.68-2.60 (m, 1H), 2.43-2.36 (m, 1H), 1.43 (s, 9H), 1.31 (t, J=7.2 Hz, 3H) ppm; $^{13}$C NMR (100 MHz, CDCl$_3$) δ 173.56, 160.59, 155.38, 154.02, 148.95, 141.26, 134.12, 129.07, 119.02, 106.11, 80.76, 73.81, 58.43, 55.93, 52.73, 52.40, 36.88, 28.47, 26.68, 11.97 ppm; HRMS (ESI) m/z: [M+H]$^+$ calcd for C$_{22}$H$_{30}$N$_3$O$_6$, 432.2129; found 432.2135.

1-(tert-Butyl) 2-methyl (2S,4R)-4-((7-methoxy-3-methylquinoxalin-2-yl)oxy)pyrrolidine-1,2-dicarboxylate (4b)

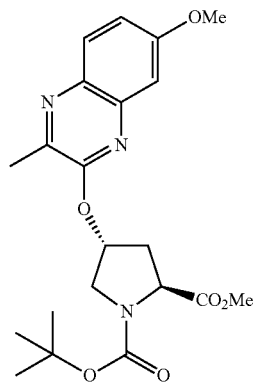 [SMILES: COC(=O)[C@@H]1C[C@@H](Oc2nc3cc(OC)ccc3nc2C)CN1C(=O)OC(C)(C)C]

The same procedure was used as described above for compound 4a. 7-Methoxy-3-methylquinoxalin-2(1H)-one[1] (6.2 g, 32.6 mmol) in NMP (100 mL) was treated with Cs$_2$CO$_3$ (16.0 g, 49.0 mmol) and activated cis-hydroxyproline derivative (15.0 g, 32.3 mmol) to provide 4b (10.0 g, 74%) as a white foamy solid. $^1$H NMR (500 MHz, CDCl$_3$) (mixture of rotamers, major rotamer) δ 7.80 (d, J=9.0 Hz, 1H), 7.17 (dd, J=9.0, 3.0 Hz, 1H), 7.11 (d, J=2.5 Hz, 1H), 5.71 (br s, 1H), 4.48 (t, J=8.0 Hz, 1H), 3.99-3.91 (m, 4H), 3.87 (d, J=12.5 Hz, 1H), 3.78 (s, 3H), 2.67-2.58 (m, 1H), 2.56 (s, 3H), 2.43-2.37 (m, 1H), 1.43 (s, 9H) ppm; $^{13}$C NMR (125 MHz, CDCl$_3$) δ 173.36, 160.24, 155.51, 153.81, 144.60, 141.04, 134.22, 128.95, 118.63, 105.95, 80.54, 73.59, 58.20, 55.68, 52.48, 52.20, 36.70, 28.26, 19.93 ppm; HRMS (ESI) m/z: [M+H]$^+$ calcd for C$_{21}$H$_{28}$N$_3$O$_6$, 418.1973; found 418.1976.

1-(tert-Butyl) 2-methyl (2S,4R)-4-((3-isopropyl-7-methoxyquinoxalin-2-yl)oxy)pyrrolidine-1,2-dicarboxylate (4c)

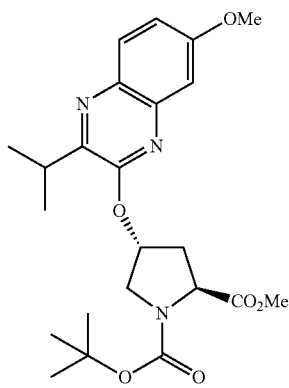 [SMILES: COC(=O)[C@@H]1C[C@@H](Oc2nc3cc(OC)ccc3nc2C(C)C)CN1C(=O)OC(C)(C)C]

The same procedure was used as described above for compound 4a. 3-Isopropyl-7-methoxyquinoxalin-2(1H)-one[1] (4.0 g, 18.3 mmol) in NMP (65 mL) was treated with $Cs_2CO_3$ (9.0 g, 27.6 mmol) and activated cis-hydroxyproline derivative (8.30 g, 17.9 mmol) to provide 4c (7.30 g, 90%) as a colorless gummy solid. $^1$H NMR (500 MHz, $CDCl_3$) (mixture of rotamers, major rotamer) δ 7.83 (d, J=8.0 Hz, 1H), 7.16 (d, J=8.4 Hz, 1H), 7.10 (s, 1H) 5.74 (br s, 1H), 4.48 (t, J=7.5 Hz, 1H), 3.92-3.87 (m, 5H), 3.78 (s, 3H), 3.41-3.36 (m, 1H), 2.68-2.59 (m, 1H), 2.42-2.35 (m, 1H), 1.43 (s, 9H), 1.31 (t, J=7.0 Hz, 6H) ppm; $^{13}$C NMR (125 MHz, $CDCl_3$) δ 173.37, 160.19, 154.62, 153.82, 152.00, 140.68, 134.31, 129.39, 118.41, 105.80, 80.49, 73.36, 58.28, 55.67, 52.58, 52.19, 36.68, 30.81, 28.25, 20.43, 20.38 ppm; HRMS (ESI) m/z: [M+H]$^+$ calcd for $C_{23}H_{32}N_3O_6$, 446.2286; found 446.2287.

1-(tert-butyl) 2-methyl (2S,4R)-4-((3-chloro-7-methoxyquinoxalin-2-yl)oxy)pyrrolidine-1,2-dicarboxylate (4d)

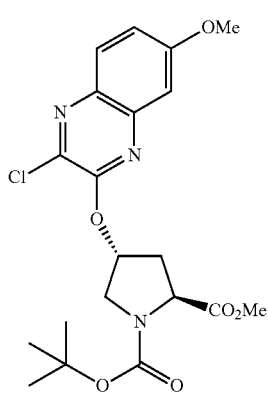 [SMILES: COC(=O)[C@@H]1C[C@@H](Oc2nc3cc(OC)ccc3nc2Cl)CN1C(=O)OC(C)(C)C]

The same procedure was used as described above for compound 4a. 3-Chloro-7-methoxyquinoxalin-2(1H)-one[2] (4.0 g, 19.0 mmol) in NMP (60 mL) was treated with $Cs_2CO_3$ (9.30 g, 28.6 mmol) and activated cis-hydroxyproline derivative (8.40 g, 18.1 mmol) to provide 4d (6.30 g, 76%) as an off-white foamy solid. $^1$H NMR (400 MHz, $CDCl_3$) (mixture of rotamers, major rotamer) δ 7.80 (d, J=8.8 Hz, 1H), 7.21 (dd, J=8.8, 2.8 Hz, 1H), 7.12 (d, J=2.8 Hz, 1H), 5.69 (br s, 1H), 4.52 (t, J=7.6 Hz, 1H), 4.0-3.94 (s, 4H), 3.88 (d, J=12.8 Hz, 1H), 3.78 (s, 3H), 2.72-2.62 (m, 1H), 2.45-2.37 (m, 1H), 1.43 (s, 9H) ppm; $^{13}$C NMR (400 MHz, $CDCl_3$) δ 173.32, 162.35, 153.84, 152.48, 141.03, 136.11, 134.06, 129.97, 119.95, 105.83, 80.60, 75.02, 58.10, 55.81, 52.36, 52.10, 36.64, 28.27 ppm; HRMS (ESI) m/z: [M+H]$^+$ calcd for $C_{20}H_{25}ClN_3O_6$, 438.1426; found 438.1438.

1-(tert-Butyl) 2-methyl (2S,4R)-4-((7-methoxy-3-(trifluoromethyl)quinoxalin-2-yl)oxy)pyrrolidine-1,2-dicarboxylate (4e)

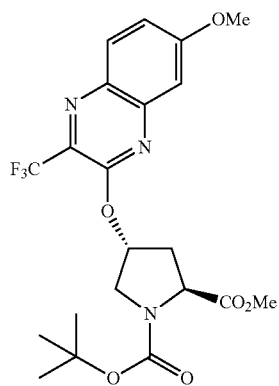 [SMILES: COC(=O)[C@@H]1C[C@@H](Oc2nc3cc(OC)ccc3nc2C(F)(F)F)CN1C(=O)OC(C)(C)C]

The same procedure was used as described above for compound 4a. 7-Methoxy-3-(trifluoromethyl)quinoxalin-2(1H)-one[1] (4.76 g, 19.5 mmol) in anhydrous NMP (65 mL) was treated with $Cs_2CO_3$ (9.80 g, 30.0 mmol) and activated cis-hydroxyproline derivative (9.0 g, 19.4 mmol) to provide 4e (6.50 g, 71%) as a pale yellow foamy solid. $^1$H NMR (500 MHz, $CDCl_3$) (mixture of rotamers, major rotamer) δ 7.77 (d, J=9.0 Hz, 1H), 7.48-7.43 (m, 2H), 5.76 (br s, 1H), 4.50 (t, J=8.0 Hz, 1H), 3.97-3.91 (m, 5H), 3.78 (s, 3H), 2.69-2.64 (m, 1H), 2.41-2.34 (m, 1H), 1.42 (s, 9H) ppm; $^{13}$C NMR (125 MHz, $CDCl_3$) δ 173.43, 159.58, 153.98, 152.11, 138.39, 137.22, 127.99, 125.73, 120.70 (q, J=273.4 Hz), 107.64, 80.69, 74.62, 58.27, 56.02, 52.32, 52.11, 36.70, 28.34 ppm;

$^{19}$F NMR (470 MHz, $CDCl_3$); −67.73 ppm; HRMS (ESI) m/z: [M+H]$^+$ calcd for $C_{21}H_{25}F_3N_3O_6$, 472.1690; found 472.1689.

Methyl (2S,4R)-1-(S)-2-((tert-butoxycarbonyl)amino)-3,3-dimethylbutanoyl)-4-((3-ethyl-7-methoxyquinoxalin-2-yl)oxy)pyrrolidine-2-carboxylate (5a)

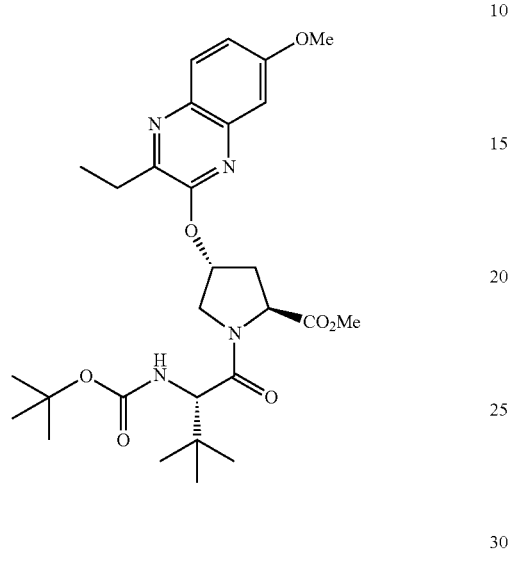

A solution of P2 intermediate 4a (2.75 g, 6.4 mmol) in anhydrous CH$_2$Cl$_2$ (20 mL) was treated with a solution of 4 N HCl in 1,4-dioxane (20 mL). After stirring the reaction mixture at room temperature for 3 h, solvents were evaporated under reduced pressure, and the residue was dried under high vacuum. The pale yellow solid was triturated with diethyl ether (20 mL), filtered and washed with diethyl ether diethyl ether (3×5 mL) to yield the proline amine salt (2.30 g, 98%) as an off-white powder.

A mixture of above amine salt (1.15 g, 3.1 mmol) and Boc-Tle-OH (0.88 g, 3.8 mmol) in anhydrous DMF (20 mL) was treated with DIEA (2.52 mL, 15.2 mmol) and HATU (2.17 g, 5.7 mmol). The resulting reaction mixture was stirred at room temperature for 4 h, then diluted with EtOAc (150 mL), and washed successively with aqueous 0.5 N HCl, saturated aqueous NaHCO$_3$, and saturated aqueous NaCl (75 mL each). The organic portion was dried (Na$_2$SO$_4$), filtered, and evaporated under reduced pressure. The residue was purified by flash chromatography using 25-30% EtOAc/hexanes as the eluent to provide 5a (1.45 g, 85%) as a white foamy solid. $^1$H NMR (400 MHz, CDCl$_3$) (mixture of rotamers, major rotamer) δ 7.87 (d, J=9.2 Hz, 1H), 7.19 (dd, J=8.8, 2.8 Hz, 1H), 7.13 (d, J=2.8 Hz, 1H), 5.86 (br s, 1H), 5.18 (d, J=9.2 Hz, 1H), 4.73 (t, J=8.4 Hz, 1H), 4.27-4.22 (m, 2H), 4.11-4.04 (m, 1H), 3.94 (s, 3H), 3.78 (s, 3H), 2.87 (q, J=7.2 Hz, 2H), 2.71-2.65 (m, 1H), 2.39-2.31 (m, 1H), 1.33 (s, 9H), 1.27 (t, J=7.2 Hz, 3H), 1.05 (s, 9H) ppm; $^{13}$C NMR (100 MHz, CDCl$_3$) δ 172.50, 171.60, 160.57, 155.92, 155.11, 149.02, 141.11, 134.13, 129.13, 118.99, 106.20, 79.79, 74.37, 58.76, 58.19, 55.92, 53.92, 52.57, 35.85, 35.23, 28.43, 26.50, 11.85 ppm; HRMS (ESI) m/z: [M+Na]$^+$ calcd for C$_{28}$H$_{41}$N$_4$O$_7$, 545.2970; found 545.2973.

Methyl (2S,4R)-1-(S)-2-((tert-butoxycarbonyl)amino)-3,3-dimethylbutanoyl)-4-((7-methoxy-3-methylquinoxalin-2-yl)oxy)pyrrolidine-2-carboxylate (5b)

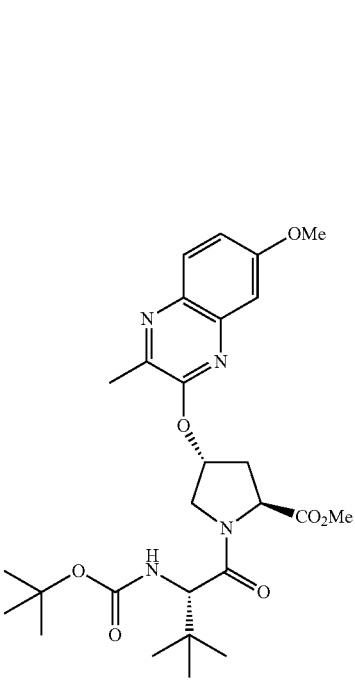 [SMILES: COC(=O)[C@@H]1C[C@@H](Oc2nc3cc(OC)ccc3nc2C)CN1C(=O)[C@@H](NC(=O)OC(C)(C)C)C(C)(C)C]

The same procedure was used as described above for compound 5a. Compound 4b (3.60 g, 8.6 mmol) was treated with 4 N HCl (25 mL) to afford the proline amine salt (3.0 g, 8.5 mmol), which was coupled with Boc-Tle-OH (2.40 g, 10.4 mmol) using DIEA (7.0 mL, 42.4 mmol) and HATU (5.65 g, 14.8 mmol) to provide 5b (3.50 g, 78%) as a white foamy solid. $^1$H NMR (500 MHz, CDCl$_3$) (mixture of rotamers, major rotamer) δ 7.80 (d, J=9.0 Hz, 1H), 7.18 (dd, J=9.0, 2.5 Hz, 1H), 7.12 (d, J=3.0 Hz, 1H), 5.84 (br s, 1H), 5.18 (d, J=9.5 Hz, 1H), 4.75 (t, J=8.5 Hz, 1H), 4.27-4.22 (m, 2H), 4.07 (dd, J=11.5, 4.5 Hz, 1H), 3.94 (s, 3H), 3.77 (s, 3H), 2.70-2.65 (m, 1H), 2.52 (s, 3H), 2.38-2.32 (m, 1H), 1.34 (s, 9H), 1.05 (s, 9H) ppm; $^{13}$C NMR (125 MHz, CDCl$_3$) δ 172.42, 171.57, 160.36, 155.87, 155.39, 144.86, 141.05, 134.51, 129.15, 118.76, 106.19, 79.71, 74.30, 58.70, 58.03, 55.79, 53.81, 52.48, 35.70, 35.15, 28.36, 26.42, 19.97 ppm; HRMS (ESI) m/z: [M+H]$^+$ calcd for C$_{27}$H$_{39}$N$_4$O$_7$, 531.2813; found 531.2807.

Methyl (2S,4R)-1-(S)-2-((tert-butoxycarbonyl) amino)-3,3-dimethylbutanoyl)-4-((3-isopropyl-7-methoxyquinoxalin-2-yl)oxy)pyrrolidine-2-carboxylate (5c)

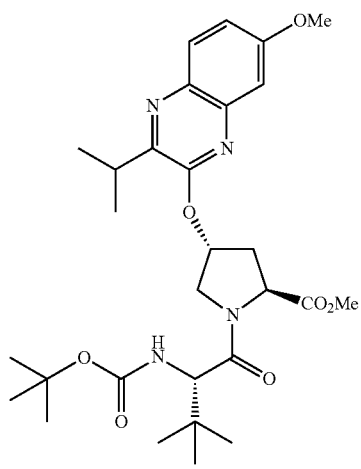 [SMILES: COC(=O)[C@@H]1C[C@@H](Oc2nc3cc(OC)ccc3nc2C(C)C)CN1C(=O)[C@@H](NC(=O)OC(C)(C)C)C(C)(C)C]

The same procedure was used as described above for compound 5a. Compound 4c (1.30 g, 2.92 mmol) was treated with 4 N HCl (12 mL) to afford the proline amine salt (1.05 g, 2.75 mmol), which was coupled with Boc-Tle-OH (0.83 g, 3.60 mmol) using DIEA (2.38 mL, 14.4 mmol) and HATU (1.85 g, 4.86 mmol) to provide 5c (1.30 g, 85%) as a white foamy solid. $^1$H NMR (500 MHz, CDCl$_3$) (mixture of rotamers, major rotamer) δ 7.83 (d, J=9.0 Hz, 1H), 7.17 (dd, J=9.0, 3.0 Hz, 1H), 7.11 (d, J=3.0 Hz, 1H), 5.88 (br s, 1H), 5.20 (d, J=9.5 Hz, 1H), 4.72 (t, J=8.5 Hz, 1H), 4.26-4.21 (m, 2H), 4.07 (dd, J=11.5, 4.0 Hz, 1H), 3.94 (s, 3H), 3.77 (s, 3H), 3.39-3.33 (m, 1H), 2.71-2.65 (m, 1H), 2.38-2.32 (m, 1H), 1.33 (s, 9H), 1.28 (t, J=7.0 Hz, 6H), 1.05 (s, 9H) ppm; $^{13}$C NMR (125 MHz, CDCl$_3$) δ 172.41, 171.45, 160.33, 155.77, 154.47, 152.19, 140.67, 134.59, 129.56, 118.57, 106.01, 79.64, 74.04, 58.66, 58.14, 55.78, 53.91, 52.46, 35.88, 35.16, 30.80, 28.36, 26.40, 20.61, 20.52 ppm; HRMS (ESI) m/z: [M+H]$^+$ calcd for C$_{29}$H$_{43}$N$_4$O$_7$, 559.3126; found 559.3112.

Methyl (2S,4R)-1-(S)-2-((tert-butoxycarbonyl) amino)-3,3-dimethylbutanoyl)-4-((3-chloro-7-methoxyquinoxalin-2-yl)oxy)pyrrolidine-2-carboxylate (5d)

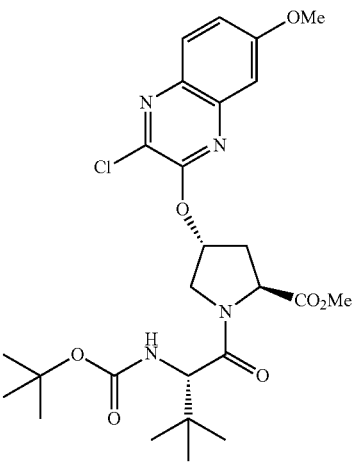 [SMILES: COC(=O)[C@@H]1C[C@@H](Oc2nc3cc(OC)ccc3nc2Cl)CN1C(=O)[C@@H](NC(=O)OC(C)(C)C)C(C)(C)C]

The same procedure was used as described above for compound 5a. Compound 4d (1.05 g, 2.40 mmol) was treated with 4 N HCl (10 mL) to afford the proline amine salt (0.89 g, 2.40 mmol), which was coupled with Boc-Tle-OH (0.66 g, 2.86 mmol) using DIEA (1.90 mL, 11.5 mmol) and HATU (1.41 g, 3.72 mmol) to provide 5d (1.0 g, 76%) as an off-white foamy solid. $^1$H NMR (500 MHz, CDCl$_3$) (mixture of rotamers, major rotamer) δ 7.81 (d, J=9.0 Hz, 1H), 7.22 (dd, J=9.0, 2.5 Hz, 1H), 7.15 (d, J=3.0 Hz, 1H), 5.81 (br s, 1H), 5.21 (d, J=10.0 Hz, 1H), 4.79 (t, J=8.5 Hz, 1H), 4.31 (d, J=12.0 Hz, 1H), 4.21 (d, J=10.0 Hz, 1H), 4.09 (dd, J=11.5, 4.0 Hz, 1H), 3.96 (s, 3H), 3.78 (s, 3H), 2.74-2.68 (m, 1H), 2.40-2.34 (m, 1H), 1.32 (s, 9H), 1.04 (s, 9H) ppm;

$^{13}$C NMR (125 MHz, CDCl$_3$) δ 172.36, 171.54, 161.40, 155.87, 152.36, 140.99, 136.27, 134.26, 129.05, 120.05, 106.05, 79.77, 75.69, 58.63, 58.02, 55.92, 53.43, 52.50, 35.74, 34.98, 28.36, 26.40 ppm; HRMS (ESI) m/z: [M+H]$^+$ calcd for C$_{26}$H$_{36}$ClN$_4$O$_7$, 551.2267; found 551.2257.

181

Methyl (2S,4R)-1-(S)-2-((tert-butoxycarbonyl)amino)-3,3-dimethylbutanoyl)-4-((7-methoxy-3-(trifluoromethyl)quinoxalin-2-yl)oxy)pyrrolidine-2-carboxylate (5e)

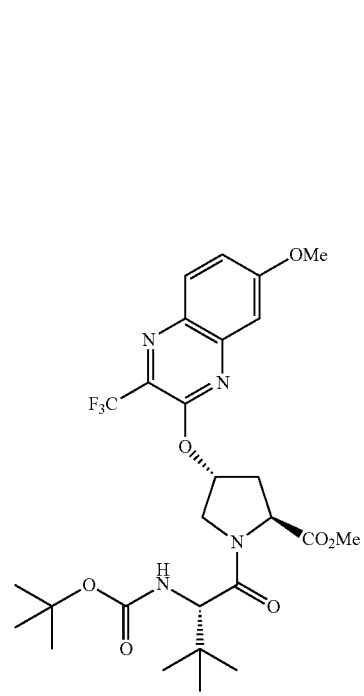 [SMILES: COC(=O)[C@@H]1C[C@@H](Oc2nc3cc(OC)ccc3nc2C(F)(F)F)CN1C(=O)[C@@H](NC(=O)OC(C)(C)C)C(C)(C)C]

The same procedure was used as described above for compound 5a. Compound 4e (1.30 g, 2.76 mmol) was treated with 4 N HCl (10 mL) to afford the proline amine salt (1.10 g, 2.70 mmol), which was coupled with Boc-Tle-OH (0.81 g, 3.50 mmol) using DIEA (2.30 mL, 14.0 mmol) and HATU (2.0 g, 5.25 mmol) to provide 5e (1.50 g, 95%) as a pale yellow foamy solid. $^1$H NMR (500 MHz, CDCl$_3$) (mixture of rotamers, major rotamer) δ 7.78 (d, J=9.0 Hz, 1H), 7.47 (dd, J=9.5, 3.0 Hz, 1H), 7.43 (d, J=2.5 Hz, 1H), 5.87 (br s, 1H), 5.22 (d, J=9.5 Hz, 1H), 4.74 (t, J=8.5 Hz, 1H), 4.27 (d, J=12.0 Hz, 1H), 4.20 (d, J=9.5 Hz, 1H), 4.11-4.07 (m, 1H), 3.94 (s, 3H), 3.77 (s, 3H), 2.71-2.66 (m, 1H), 2.38-2.32 (m, 1H), 1.30 (s, 9H), 1.03 (s, 9H) ppm; $^{13}$C NMR (125 MHz, CDCl$_3$) δ 172.36, 171.47, 159.64, 155.84, 151.89, 138.51, 137.09, 134.59 (q, J=35.9 Hz), 128.04, 125.73, 120.69 (d, J=273.8 Hz), 107.65, 79.69, 75.05, 58.58, 57.92, 56.03, 53.47, 52.49, 35.75, 34.97, 28.26, 26.37 ppm; $^{19}$F NMR (470 MHz, CDCl$_3$); −67.84 ppm; HRMS (ESI) m/z: [M+H]$^+$ calcd for C$_{27}$H$_{36}$F$_3$N$_4$O$_7$, 585.2531; found 585.2516.

182 tert-Butyl ((S)-1-((2S,4R)-2-(((1R,2S)-1-((cyclopropylsulfonyl)carbamoyl)-2-vinylcyclopropyl)carbamoyl)-4-((3-ethyl-7-methoxyquinoxalin-2-yl)oxy)pyrrolidin-1-yl)-3,3-dimethyl-1-oxobutan-2-yl)carbamate (3)

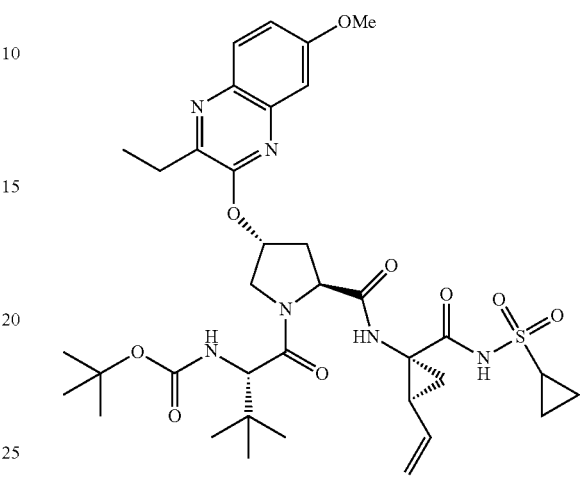

A solution of P2-P3 intermediate 5a (1.80 g, 3.31 mmol) in THF-H$_2$O mixture (1:1, 50 mL) was treated with LiOH.H$_2$O (0.46 g, 11.0 mmol). The resulting reaction mixture was stirred at room temperature for 24 h. The reaction mixture was cooled to −5° C., acidified to a pH of 2.0 by slow addition of aqueous 0.50 N HCl (~75 mL), and extracted with EtOAc (2×150 mL). The organic portions were washed separately with saturated aqueous NaCl (75 ml), dried (Na$_2$SO$_4$), filtered, and evaporated under reduced pressure. The gummy residue was dissolved in CHCl$_3$ (20 mL), concentrated under reduced pressure, and the residue was dried under high vacuum overnight to yield the acid 6a (1.75 g, 100%) as a white foamy solid.

A mixture of acid 6a (0.88 g, 1.64 mmol) and P1-P1' amine salt 7$^3$ (0.48 g, 1.80 mmol) in anhydrous DMF (15 mL) was treated with DIEA (1.10 mL, 6.60 mmol) and HATU (0.94 g, 2.46 mmol). The resulting reaction mixture was stirred at room temperature for 2 h, then diluted with EtOAc (100 mL) and washed successively with aqueous 0.5 N HCl, saturated aqueous NaHCO$_3$, and saturated aqueous NaCl (50 mL each). The organic portion was dried (Na$_2$SO$_4$), filtered, and evaporated under reduced pressure. The residue was purified by flash chromatography using 50-80% EtOAc/hexanes as the eluent to provide compound 3 (0.95 g, 78%) as a white solid. $^1$H NMR (400 MHz, CDCl$_3$) δ 10.08 (s, 1H), 7.84 (d, J=9.2 Hz, 1H), 7.20-7.14 (m, 2H), 7.07 (s, 1H), 5.90 (br s, 1H), 5.79-5.72 (m, 1H), 5.28-5.22 (m, 2H), 5.15 (d, J=10.4 Hz, 1H), 4.48 (t, J=8.4 Hz, 1H), 4.30 (d, J=12.0 Hz, 1H), 4.24 (d, J=9.6 Hz, 1H), 4.03 (dd, J=11.6, 3.2 Hz, 1H), 3.94 (s, 3H), 2.94-2.83 (m, 3H), 2.56-2.52 (m, 2H), 2.12 (q, J=8.4 Hz, 1H), 1.97 (dd, J=8.0, 6.0 Hz, 1H), 1.48 (dd, J=9.2, 5.6 Hz, 1H), 1.40-1.22 (m, 13H), 1.10-0.96 (m, 12H) ppm; $^{13}$C NMR (100 MHz, CDCl$_3$) δ 173.05, 172.77, 168.64, 160.56, 155.87, 154.99, 148.86, 141.05, 134.51, 132.76, 129.32, 119.01, 118.85, 106.19, 80.06, 74.37, 60.09, 58.96, 55.92, 54.51, 42.05, 38.85, 35.81, 35.75, 34.51, 31.49, 28.43, 26.71, 22.63, 11.84, 6.50, 6.45 ppm; HRMS (ESI) m/z: [M+H]$^+$ calcd for C$_{36}$H$_{51}$N$_6$O$_9$S, 743.3433; found 743.3431. Anal. RP-HPLC: t$_R$ 9.57 min, purity 97%.

183 tert-Butyl ((S)-1-((2S,4R)-2-(((1R,2S)-1-((cyclopropylsulfonyl)carbamoyl)-2-vinylcyclopropyl)carbamoyl)-4-((7-methoxy-3-methylquinoxalin-2-yl)oxy)pyrrolidin-1-yl)-3,3-dimethyl-1-oxobutan-2-yl)carbamate (9b)

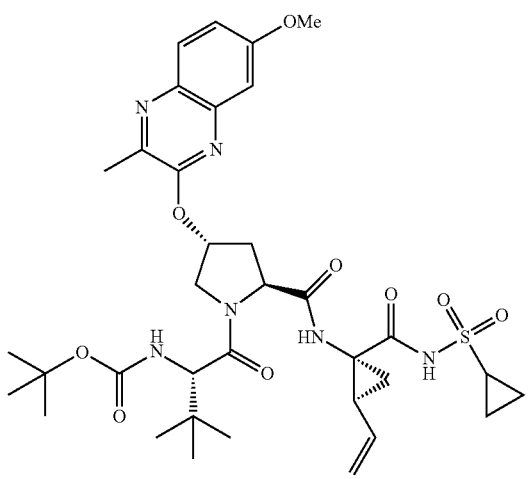 [SMILES: C=C[C@@H]1C[C@]1(NC(=O)[C@@H]1C[C@@H](Oc2nc3cc(OC)ccc3nc2C)CN1C(=O)[C@@H](NC(=O)OC(C)(C)C)C(C)(C)C)C(=O)NS(=O)(=O)C1CC1]

The same procedure was used as described above for compound 3. Ester 5b (1.30 g, 2.45 mmol) was treated with LiOH.H$_2$O (0.36 g, 8.60 mmol) to afford acid 6b (1.25 g, 2.42 mmol). A portion of acid 6b (0.62 g, 1.20 mmol) was reacted with amine salt 7 (0.40 g, 1.50 mmol) using DIEA (0.80 mL, 4.84 mmol) and HATU (0.70 g, 1.84 mmol) to provide compound 9b (0.64 g, 74%) as a white solid. $^1$H NMR (400 MHz, CDCl$_3$) δ 10.08 (s, 1H), 7.79 (d, J=9.2 Hz, 1H), 7.18 (dd, J=8.8, 2.4 Hz, 1H), 7.13 (d, J=2.8 Hz, 2H), 5.86 (br s, 1H), 5.80-5.71 (m, 1H), 5.28-5.23 (m, 2H), 5.13 (d, J=10.8 Hz, 1H), 4.51 (t, J=8.4 Hz, 1H), 4.30 (d, J=11.6 Hz, 1H), 4.24 (d, J=9.2 Hz, 1H), 4.03 (dd, J=12.0, 4.0 Hz, 1H), 3.94 (s, 3H), 2.93-2.86 (m, 1H), 2.56-2.50 (m, 5H), 2.11 (q, J=9.2 Hz, 1H), 1.95 (dd, J=8.0, 6.0 Hz, 1H), 1.47 (dd, J=9.2, 5.6 Hz, 1H), 1.38-1.30 (m, 10H), 1.07-0.97 (m, 12H) ppm; $^{13}$C NMR (100 MHz, CDCl$_3$) δ 172.89, 172.49, 168.48, 160.25, 155.67, 155.12, 144.48, 140.89, 134.31, 132.51, 128.94, 118.78, 118.64, 106.0, 79.84, 74.25, 59.79, 58.72, 55.68, 54.23, 41.83, 35.55, 35.42, 34.21, 31.23, 28.22, 26.48, 22.32, 19.81, 6.27, 6.22 ppm; HRMS (ESI) m/z: [M+H]$^+$ calcd for C$_{35}$H$_{49}$N$_6$O$_9$S, 729.3276; found 729.3283. Anal. RP-HPLC: $t_R$ 9.13 min, purity 99%.

184 tert-Butyl ((S)-1-((2S,4R)-2-(((1R,2S)-1-((cyclopropylsulfonyl)carbamoyl)-2-vinylcyclopropyl)carbamoyl)-4-((3-isopropyl-7-methoxyquinoxalin-2-yl)oxy)pyrrolidin-1-yl)-3,3-dimethyl-1-oxobutan-2-yl)carbamate (9c)

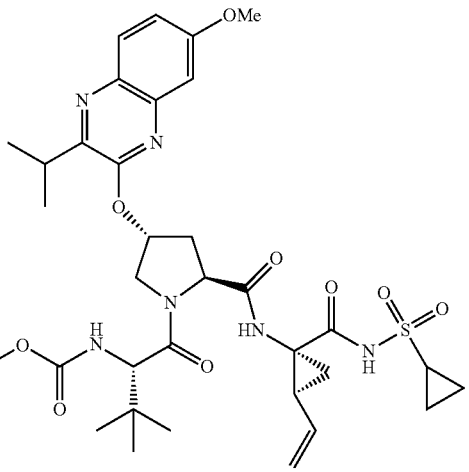

The same procedure was used as described above for compound 3. Ester 5c (2.25 g, 4.03 mmol) was treated with LiOH.H$_2$O (0.68 g, 16.1 mmol) to afford acid 6c (2.15 g, 3.95 mmol). A portion of acid 6c (1.0 g, 1.84 mmol) was coupled with amine salt 7 (0.60 g, 2.25 mmol) using DIEA (1.25 mL, 7.40 mmol) and HATU (1.0 g, 2.63 mmol) to provide compound 9c (1.25 g, 90%) as a white solid. $^1$H NMR (400 MHz, CDCl$_3$) δ 10.11 (s, 1H), 7.83 (d, J=9.2 Hz, 1H), 7.18 (dd, J=8.8, 2.4 Hz, 1H), 7.12 (d, J=2.8 Hz, 1H), 7.02 (s, 1H), 5.91 (br s, 1H), 5.82-5.73 (m, 1H), 5.28-5.23 (m, 2H), 5.14 (d, J=10.4 Hz, 1H), 4.46 (t, J=8.4 Hz, 1H), 4.29-4.22 (m, 2H), 4.06 (dd, J=11.6, 4.0 Hz, 1H), 3.94 (s, 3H), 3.37-3.30 (m, 1H), 2.94-2.87 (m, 1H), 2.57-2.49 (m, 2H), 2.12 (q, J=8.4 Hz, 1H), 1.96 (dd, J=8.4, 6.0 Hz, 1H), 1.48 (dd, J=9.6, 6.0 Hz, 1H), 1.40-1.20 (m, 16H), 1.05-0.95 (m, 12H) ppm; $^{13}$C NMR (100 MHz, CDCl$_3$) δ 172.79, 172.42, 168.52, 160.23, 155.60, 154.19, 151.78, 140.52, 134.42, 132.55, 129.37, 118.61, 105.81, 79.78, 74.02, 59.97, 58.68, 55.68, 54.34, 41.75, 35.70, 35.57, 34.37, 31.25, 30.67, 28.21, 26.47, 22.57, 20.51, 20.44, 6.29, 6.21 ppm; HRMS (ESI) m/z: [M+H]$^+$ calcd for C$_{37}$H$_{53}$N$_6$O$_9$S, 757.3589; found 757.3588. Anal. RP-HPLC: $t_R$ 10.13 min, purity 98%.

185 tert-Butyl ((S)-1-((2S,4R)-4-((3-chloro-7-methoxy-quinoxalin-2-yl)oxy)-2-(((1R,2S)-1-((cyclopropylsulfonyl)carbamoyl)-2-vinylcyclopropyl)carbamoyl)pyrrolidin-1-yl)-3,3-dimethyl-1-oxobutan-2-yl)carbamate (9d)

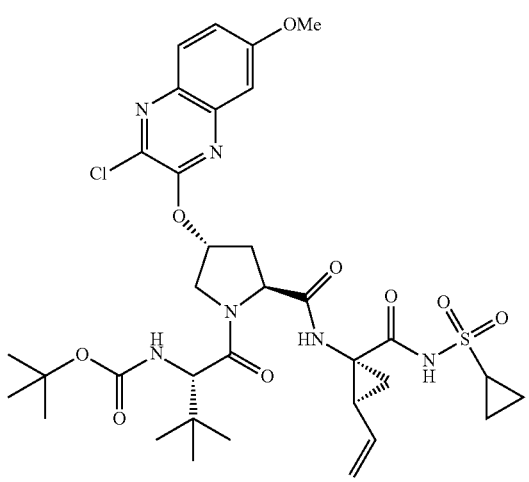 [SMILES: C=C[C@@H]1C[C@]1(NC(=O)[C@@H]1C[C@@H](Oc2nc3cc(OC)ccc3nc2Cl)CN1C(=O)[C@@H](NC(=O)OC(C)(C)C)C(C)(C)C)C(=O)NS(=O)(=O)C1CC1]

The same procedure was used as described above for compound 3. Ester 5d (2.0 g, 3.63 mmol) was treated with LiOH.H$_2$O (0.60 g, 14.3 mmol) to afford acid 6d (1.90 g, 3.54 mmol). A portion of acid 6d (0.92 g, 1.71 mmol) was coupled with amine salt 7 (0.50 g, 1.88 mmol) using DIEA (1.15 mL, 6.96 mmol) and HATU (0.95 g, 2.50 mmol) to provide compound 9d (1.0 g, 78%) as a white solid. $^1$H NMR (400 MHz, CDCl$_3$) δ 10.07 (s, 1H), 7.81 (d, J=8.8 Hz, 1H), 7.26-7.22 (1H), 7.18 (d, J=2.4 Hz, 1H), 7.04 (s, 1H), 5.87 (br s, 1H), 5.81-5.74 (m, 1H), 5.29-5.20 (m, 2H), 5.14 (d, J=10.4 Hz, 1H), 4.55 (t, J=8.4 Hz, 1H), 4.37 (d, J=11.6 Hz, 1H), 4.21 (d, J=9.6 Hz, 1H), 4.05 (dd, J=12.0, 3.6 Hz, 1H), 3.96 (s, 3H), 2.93-2.88 (m, 1H), 2.57 (dd, J=7.6, 2.8 Hz, 2H), 2.12 (q, J=8.8 Hz, 1H), 1.98 (dd, J=7.6, 6.0 Hz, 1H), 1.48 (dd, J=9.6, 6.0, 1H), 1.38-1.29 (m, 10H), 1.09-0.98 (m, 12H) ppm; $^{13}$C NMR (100 MHz, CDCl$_3$) δ 172.94, 172.63, 168.57, 161.46, 155.82, 152.21, 141.01, 136.09, 134.25, 132.65, 129.00, 120.22, 118.77, 106.05, 80.04, 75.77, 60.55, 59.97, 58.85, 54.01, 42.01, 35.69, 35.53, 34.36, 31.39, 28.34, 26.60, 22.46, 6.40, 6.35 ppm; HRMS (ESI) m/z: [M+H]$^+$ calcd for C$_{34}$H$_{46}$ClN$_6$O$_9$S, 749.2730; found 749.2736. Anal. RP-HPLC: t$_R$ 9.82 min, purity 97%.

186 tert-Butyl ((S)-1-((2S,4R)-2-(((1R,2S)-1-((cyclopropylsulfonyl)carbamoyl)-2-vinylcyclopropyl)carbamoyl)-4-((7-methoxy-3-(trifluoromethyl)quinoxalin-2-yl)oxy)pyrrolidin-1-yl)-3,3-dimethyl-1-oxobutan-2-yl)carbamate (9e)

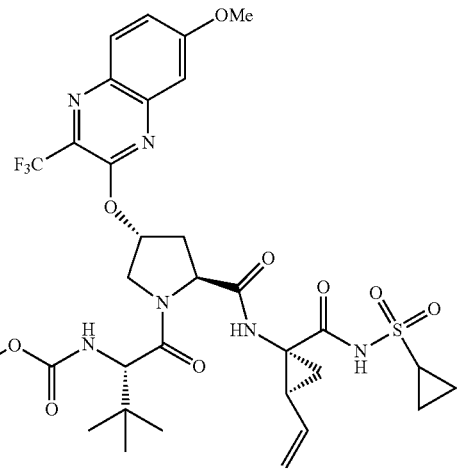

The same procedure was used as described above for compound 3. Ester 5e (1.60 g, 2.74 mmol) was treated with LiOH.H$_2$O (0.40 g, 9.53 mmol) to afford acid 6e (1.56 g, 2.74 mmol). A portion of acid 6e (0.78 g, 1.37 mmol) was coupled with amine salt 7 (0.45 g, 1.69 mmol) using DIEA (0.95 mL, 5.75 mmol) and HATU (0.85 g, 2.24 mmol) to provide compound 9e (0.80 g, 75%) as an off-white solid. $^1$H NMR (400 MHz, CDCl$_3$) δ 10.09 (s, 1H), 7.80 (d, J=8.8 Hz, 1H), 7.48 (dd, J=8.8, 2.8 Hz, 1H), 7.42 (d, J=2.8 Hz, 1H), 7.15 (s, 1H), 5.92 (br s, 1H), 5.81-5.72 (m, 1H), 5.29-5.23 (m, 2H), 5.14 (d, J=11.2 Hz, 1H), 4.50 (t, J=8.8 Hz, 1H), 4.32 (d, J=12.0 Hz, 1H), 4.19 (d, J=9.6 Hz, 1H), 4.04 (dd, J=12.4, 4.0 Hz, 1H), 3.94 (s, 3H), 2.93-2.87 (m, 1H), 2.53 (dd, J=8.8, 2.8 Hz, 2H), 2.13 (q, J=8.4 Hz, 1H), 1.96 (dd, J=8.4, 6.0 Hz, 1H), 1.48 (dd, J=9.6, 6.0 Hz, 1H), 1.36-1.32 (m, 1H), 1.28 (s, 9H), 1.05-0.96 (m, 12H) ppm; $^{13}$C NMR (100 MHz, CDCl$_3$) δ 172.74, 172.37, 168.52, 159.38, 155.61, 151.59, 138.37, 136.95, 134.24 (q, J=35.8 Hz), 132.54, 127.97, 125.70, 120.57 (d, J=273.6 Hz), 118.60, 106.42, 79.76, 75.0, 59.79, 58.60, 55.90, 53.93, 41.79, 35.57, 35.45, 34.27, 31.24, 28.11, 26.43, 22.45, 6.26, 6.19 ppm; HRMS (ESI) m/z: [M+H]$^+$ calcd for C$_{35}$H$_{46}$F$_3$N$_6$O$_9$S, 783.2994; found 783.3000. Anal. RP-HPLC: t$_R$ 9.89 min, purity 98%.

187 tert-Butyl ((S)-1-((2S,4R)-4-((3-ethyl-7-methoxy-quinoxalin-2-yl)oxy)-2-(((1R,2S)-1-(((1-methylcyclopropyl)sulfonyl)carbamoyl)-2-vinylcyclopropyl)carbamoyl)pyrrolidin-1-yl)-3,3-dimethyl-1-oxobutan-2-yl)carbamate (10a)

188 tert-Butyl ((S)-1-((2S,4R)-4-((7-methoxy-3-methylquinoxalin-2-yl)oxy)-2-(((1R,2S)-1-(((1-methylcyclopropyl)sulfonyl)carbamoyl)-2-vinylcyclopropyl)carbamoyl)pyrrolidin-1-yl)-3,3-dimethyl-1-oxobutan-2-yl)carbamate (10b)

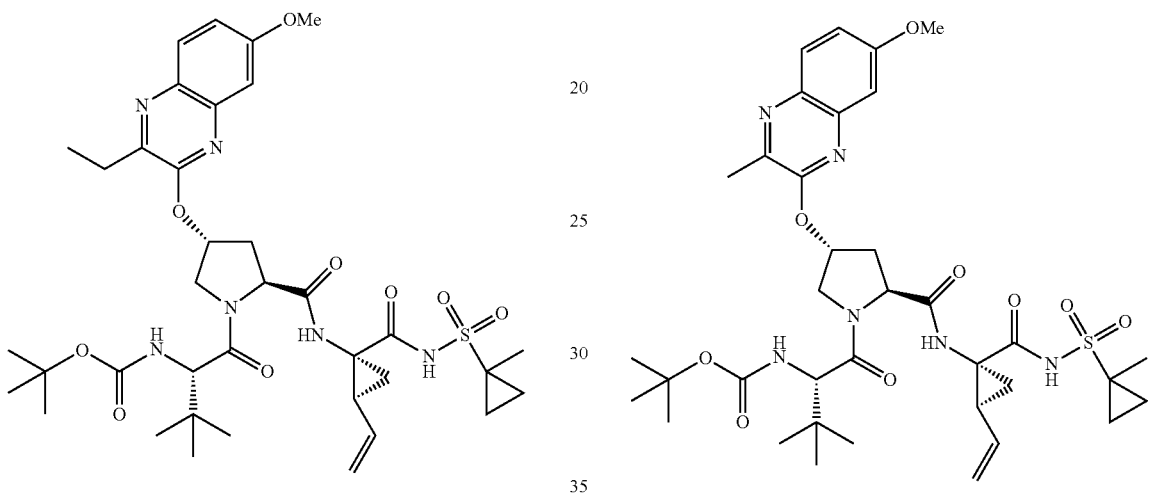

The same procedure was used as described above for compound 3. Acid 6a (0.73 g, 1.38 mmol) was coupled with amine salt 8[4] (0.45 g, 1.60 mmol) using DIEA (0.95 mL, 5.75 mmol) and HATU (0.85 g, 2.24 mmol) to provide compound 10a (0.80 g, 77%) as a white solid. $^1$H NMR (500 MHz, CDCl$_3$) δ 9.80 (s, 1H), 7.83 (d, J=9.0 Hz, 1H), 7.20-7.15 (m, 3H), 5.89 (br s, 1H), 5.72-5.64 (m, 1H), 5.28 (d, J=17.0 Hz, 1H), 5.21 (d, J=9.5 Hz, 1H), 5.15 (d, J=10.0 Hz, 1H), 4.57 (t, J=8.0 Hz, 1H), 4.31 (d, J=12.0 Hz, 1H), 4.24 (d, J=9.5 Hz, 1H), 4.02 (dd, J=12.0, 4.0 Hz, 1H), 3.95 (s, 3H), 2.86 (q, J=7.5 Hz, 2H), 2.67-2.61 (m, 1H), 2.57-2.52 (m, 1H), 2.11 (q, J=8.5 Hz, 1H), 1.94 (dd, J=8.0, 6.0 Hz, 1H), 1.73-1.68 (m, 1H), 1.64-1.60 (m, 1H), 1.50 (s, 3H), 1.39 (dd, J=9.0, 6.5 Hz, 1H), 1.33 (s, 9H), 1.27 (t, J=7.5 Hz, 3H), 1.03 (s, 9H), 0.90-0.81 (m, 2H) ppm; $^{13}$C NMR (125 MHz, CDCl$_3$) δ 173.56, 172.86, 167.24, 160.42, 155.77, 154.92, 148.85, 140.95, 134.54, 132.74, 129.28, 118.89, 118.84, 106.14, 79.98, 74.18, 59.64, 58.95, 55.83, 54.36, 42.55, 36.69, 35.58, 35.06, 34.16, 28.34, 26.60, 21.42, 18.54, 14.17, 13.66, 11.70 ppm; HRMS (ESI) m/z: [M+H]$^+$ calcd for C$_{37}$H$_{53}$N$_6$O$_9$S, 757.3589; found 757.3587. Anal. RP-HPLC: t$_R$ 9.78 min, purity 99%.

The same procedure was used as described above for compound 3. Acid 6b (0.62 g, 1.20 mmol) was coupled with amine salt 8 (0.40 g, 1.43 mmol) using DIEA (0.80 mL, 4.84 mmol) and HATU (0.70 g, 1.84 mmol) to provide compound 10b (0.70 g, 79%) as a white solid. $^1$H NMR (400 MHz, CDCl$_3$) δ 9.80 (s, 1H), 7.80 (d, J=9.2 Hz, 1H), 7.23 (s, 1H), 7.20-7.14 (m, 2H), 5.86 (br s, 1H), 5.72-5.63 (m, 1H), 5.29-5.21 (m, 2H), 5.15 (d, J=10.0 Hz, 1H), 4.60 (t, J=8.4 Hz, 1H), 4.32 (d, J=11.2 Hz, 1H), 4.23 (d, J=9.2 Hz, 1H), 4.01 (dd, J=11.6, 3.6 Hz, 1H), 3.94 (s, 3H), 2.69-2.61 (m, 1H), 2.57-2.50 (m, 4H), 2.10 (q, J=8.4 Hz, 1H), 1.93 (dd, J=8.0, 5.6 Hz, 1H), 1.73-1.67 (m, 1H), 1.63-1.59 (m, 1H), 1.50 (s, 3H), 1.37 (dd, J=9.6, 6.0 Hz, 1H), 1.33 (s, 9H), 1.02 (s, 9H), 0.88-0.81 (m, 2H) ppm; $^{13}$C NMR (100 MHz, CDCl$_3$) δ 173.67, 172.99, 167.35, 160.48, 155.89, 155.39, 144.74, 141.14, 134.57, 132.82, 129.19, 119.0, 106.25, 80.10, 74.40, 59.69, 59.04, 55.92, 54.41, 42.64, 36.74, 35.61, 35.12, 34.14, 28.45, 26.71, 21.44, 20.08, 18.62, 14.26, 13.72 ppm; HRMS (ESI) m/z: [M+H]$^+$ calcd for C$_{36}$H$_{51}$N$_6$O$_9$S, 743.3433; found 743.3428. Anal. RP-HPLC: t$_R$ 9.34 min, purity 99%.

189 tert-Butyl ((S)-1-((2S,4R)-4-((3-isopropyl-7-methoxyquinoxalin-2-yl)oxy)-2-(((1R,2S)-1-(((1-methylcyclopropyl)sulfonyl)carbamoyl)-2-vinylcyclopropyl)carbamoyl)pyrrolidin-1-yl)-3,3-dimethyl-1-oxobutan-2-yl)carbamate (10c)

190 tert-Butyl ((S)-1-((2S4R)-4-((3-chloro-7-methoxyquinoxalin-2-yl)oxy)-2-(((1R,2SD)-1-(((1-methylcyclopropyl)sulfonyl)carbamoyl)-1-vinylcyclopropyl)carbamoyl)pyrrolidin-1-yl)-3,3-dimethyl-1-oxobutan-2-yl)carbamate (10d)

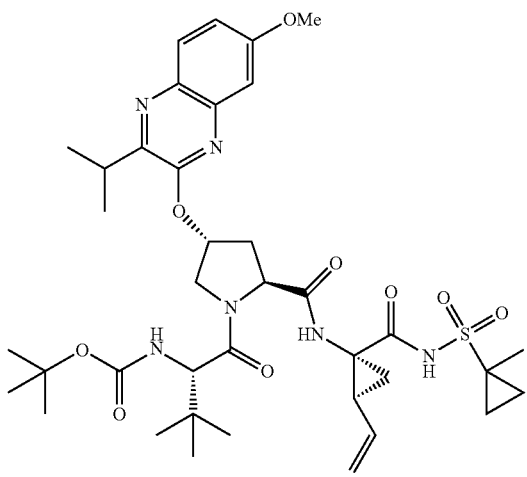 [SMILES: C=C[C@@H]1C[C@]1(NC(=O)[C@@H]1C[C@@H](Oc2nc3cc(OC)ccc3nc2C(C)C)CN1C(=O)[C@@H](NC(=O)OC(C)(C)C)C(C)(C)C)C(=O)NS(=O)(=O)C1(C)CC1]

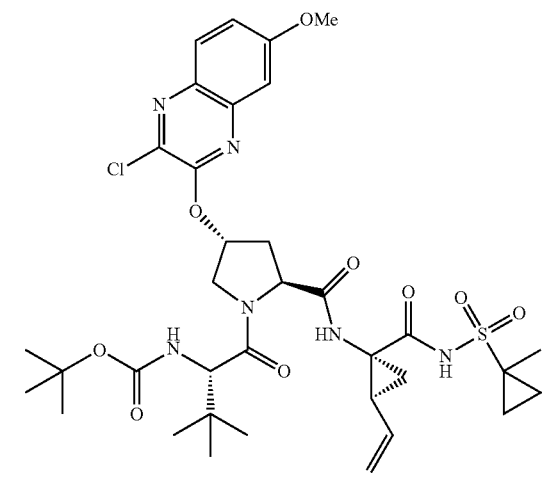 [SMILES: C=C[C@@H]1C[C@]1(NC(=O)[C@@H]1C[C@@H](Oc2nc3cc(OC)ccc3nc2Cl)CN1C(=O)[C@@H](NC(=O)OC(C)(C)C)C(C)(C)C)C(=O)NS(=O)(=O)C1(C)CC1]

The same procedure was used as described above for compound 3. Acid 6c (1.0 g, 1.84 mmol) was coupled with amine salt 8 (0.67 g, 2.39 mmol) using DIEA (1.25 mL, 7.56 mmol) and HATU (1.0 g, 2.63 mmol) to provide compound 10e (1.20 g, 85%) as a white solid. $^1$H NMR (400 MHz, CDCl$_3$) δ 9.85 (s, 1H), 7.83 (d, J=9.2 Hz, 1H), 7.18-7.12 (m, 3H), 5.89 (br s, 1H), 5.73-5.64 (m, 1H), 5.30-5.24 (m, 2H), 5.15 (d, J=10.4 Hz, 1H), 4.53 (t, J=8.4 Hz, 1H), 4.30-4.21 (m, 2H), 4.04 (dd, J=12.0, 4.0 Hz, 1H), 3.94 (s, 3H), 3.38-3.29 (m, 1H), 2.60-2.50 (m, 2H), 2.13 (q, J=8.4 Hz, 1H), 1.93 (dd, J=8.0, 6.0 Hz, 1H), 1.73-1.53 (m, 2H), 1.50 (s, 3H), 1.44-1.23 (m, 16H), 1.02 (s, 9H), 0.90-0.80 (m, 2H) ppm; $^{13}$C NMR (100 MHz, CDCl$_3$) δ 173.45, 172.52, 167.27, 160.22, 155.58, 154.23, 151.78, 140.54, 134.40, 132.63, 129.36, 118.73, 118.59, 105.83, 79.78, 73.98, 59.60, 58.75, 55.68, 54.28, 42.32, 36.52, 35.59, 34.96, 34.20, 30.65, 28.21, 26.45, 21.47, 20.49, 20.45, 18.39, 13.97, 13.56 ppm; HRMS (ESI) m/z: [H+H]$^+$ calcd for C$_{38}$H$_{55}$N$_6$O$_9$S, 771.3746; found 771.3735. Anal. RP-HPLC: $t_R$ 10.33 min, purity 98%.

The same procedure was used as described above for compound 3. Acid 6d (0.92 g, 1.71 mmol) was coupled with amine salt 8 (0.53 g, 1.88 mmol) using DIEA (1.15 mL, 6.96 mmol) and HATU (0.95 g, 2.50 mmol) to provide compound 10d (1.0 g, 77%) as a white solid. $^1$H NMR (400 MHz, CDCl$_3$) δ 9.83 (s, 1H), 7.80 (d, J=8.8 Hz, 1H), 7.26-7.22 (m, 2H), 7.18 (d, J=2.4 Hz, 1H), 5.84 (br s, 1H), 5.72-5.63 (m, 1H), 5.27 (d, J=16.4 Hz, 1H), 5.23 (d, J=9.2 Hz, 1H), 5.15 (d, J=10.4 Hz, 1H), 4.62 (t, J=8.0 Hz, 1H), 4.38 (d, J=12.0 Hz, 1H), 4.21 (d, J=9.6 Hz, 1H), 4.03 (dd, J=11.6, 4.4 Hz, 1H), 3.96 (s, 3H), 2.64-2.54 (m, 2H), 2.13 (q, J=8.8 Hz, 1H), 1.94 (dd, J=8.0, 6.0 Hz, 1H), 1.75-1.58 (m, 2H), 1.50 (s, 3H), 1.44-1.38 (m, 1H), 1.31 (s, 9H), 1.02 (s, 9H), 0.88-0.80 (m, 2H) ppm; $^{13}$C NMR (100 MHz, CDCl$_3$) δ 173.35, 172.64, 167.17, 161.29, 155.66, 152.08, 140.87, 135.95, 134.08, 132.60, 128.85, 120.08, 118.75, 105.89, 79.91, 75.56, 59.53, 58.73, 55.82, 53.80, 42.38, 36.50, 35.43, 34.87, 34.00, 28.21, 26.44, 21.32, 18.40, 13.99, 13.52 ppm; HRMS (ESI) m/z: [M+H]$^+$ calcd for C$_{35}$H$_{48}$ClN$_6$O$_9$S, 763.2887; found 763.2878. Anal. RP-HPLC: $t_R$ 9.82 min, purity 99%.

191 tert-Butyl ((S)-1-((2S,4R)-4-((7-methoxy-3-(trifluoromethyl)quinoxalin-2-yl)oxy)-2-(((1R,2S)-1-(((1-methylcyclopropyl)sulfonyl)carbamoyl)-2-vinylcyclopropyl)carbamoyl)pyrrolidin-1-yl)-3,3-dimethyl-1-oxobutan-2-yl)carbamate (10e)

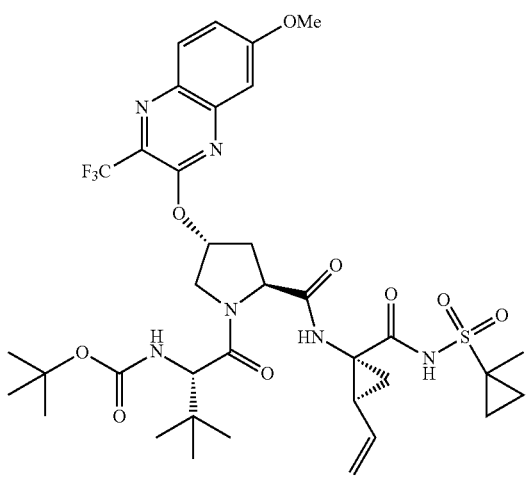 [SMILES: C=C[C@@H]1C[C@]1(NC(=O)[C@@H]1C[C@@H](Oc2nc3cc(OC)ccc3nc2C(F)(F)F)CN1C(=O)[C@@H](NC(=O)OC(C)(C)C)C(C)(C)C)C(=O)NS(=O)(=O)C1(C)CC1]

The same procedure was used as described above for compound 3. Acid 6e (0.78 g, 1.37 mmol) was coupled with amine salt 8 (0.48 g, 1.71 mmol) using DIEA (0.95 mL, 5.75 mmol) and HATU (0.85 g, 2.24 mmol) to provide compound 10e (0.82 g, 75%) as an off-white solid. $^1$H NMR (400 MHz, CDCl$_3$) δ 9.80 (s, 1H), 7.81 (d, J=8.8 Hz, 1H), 7.48 (dd, J=8.8, 2.8 Hz, 1H), 7.43 (d, J=2.8 Hz, 1H), 7.27-7.25 (m, 1H), 5.92 (br s, 1H), 5.73-5.64 (m, 1H), 5.28 (d, J=17.2 Hz, 1H), 5.20 (d, J=9.6 Hz, 1H), 5.15 (d, J=10.8 Hz, 1H), 4.56 (t, J=8.4 Hz, 1H), 4.34 (d, J=12.0 Hz, 1H), 4.18 (d, J=9.6 Hz, 1H), 4.0 (dd, J=11.6, 3.6 Hz, 1H), 3.94 (s, 3H), 2.64-2.51 (m, 2H), 2.13 (q, J=8.4 Hz, 1H), 1.95 (dd, J=8.0, 6.0 Hz, 1H), 1.73-1.60 (m, 2H), 1.59 (s, 3H), 1.43-1.38 (m, 1H), 1.28 (s, 9H), 1.00 (s, 9H), 0.89-0.81 (m, 2H) ppm; $^{13}$C NMR (100 MHz, CDCl$_3$) δ 173.53, 172.82, 167.41, 159.76, 155.80, 151.85, 138.61, 137.20, 134.48 (q, J=35.9 Hz), 132.86, 128.21, 125.90, 120.81 (d, J=274.0 Hz), 118.96, 107.68, 80.0, 75.16, 59.69, 58.90, 56.13, 54.12, 42.60, 36.75, 35.69, 35.17, 34.28, 28.34, 26.65, 21.66, 18.65, 13.79, 13.44 ppm; HRMS (ESI) m/z: [M+H]$^+$ calcd for C$_{36}$H$_{48}$F$_3$N$_6$O$_9$S, 797.3150; found 797.3146. Anal. RP-HPLC: $t_R$ 10.10 min, purity 98%.

192

Cyclopentyl ((S)-1-((2S,4R)-2-(((1R,2S)-1-((cyclopropylsulfonyl)carbamoyl)-2-vinylcyclopropyl)carbamoyl)-4-((3-ethyl-7-methoxyquinoxalin-2-yl)oxy)pyrrolidin-1-yl)-3,3-dimethyl-1-oxobutan-2-yl)carbamate (11a)

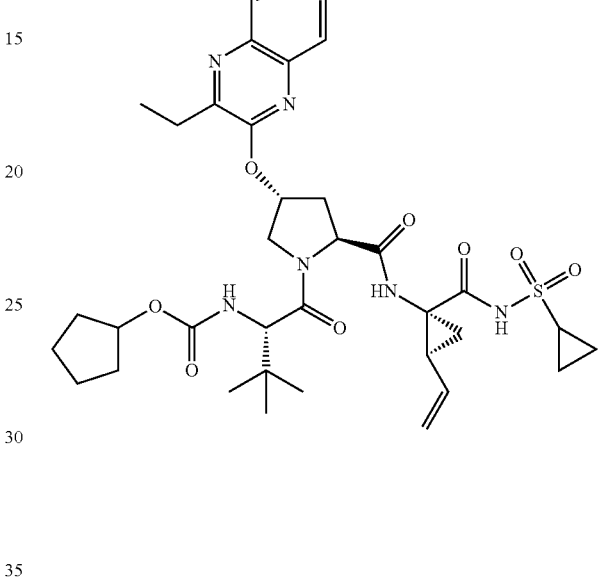

Compound 3 (0.40 g, 0.54 mmol) was treated with a solution of 4 N HCl in 1,4-dioxane (10 mL). After stirring the reaction mixture at room temperature for 3 h, solvents were evaporated under reduced pressure. The residue was triturated with diethyl ether (3×10 mL) and dried to yield the amine salt product (0.37 g, 100%) as a white powder.

A solution of the above amine salt (0.37 g, 0.54 mmol) in anhydrous CH$_3$CN (15 mL) was treated with DIEA (0.37 mL, 2.24 mmol) and N-(cyclopentyloxycarbonyloxy)-succinimide (0.15 g, 0.66 mmol). The reaction mixture was stirred at room temperature for 36 h, then concentrated under reduced pressure and dried under high vacuum. The residue was purified by flash chromatography using 50-90% EtOAc/hexanes as the eluent to provide the target compound 11a (0.36 g, 88%) as a white solid. $^1$H NMR (500 MHz, CDCl$_3$) δ 10.03 (s, 1H), 7.83 (d, J=9.0 Hz, 1H), 7.19 (dd, J=9.0, 2.8 Hz, 1H), 7.14 (d, J=2.5 Hz, 2H), 5.90 (br s, 1H), 5.80-5.73 (m, 1H), 5.32 (d, J=9.5 Hz, 1H), 5.26 (d, J=17.0 Hz, 1H), 5.15 (d, J=10.6 Hz, 1H), 4.90-4.86 (m, 1H), 4.51 (t, J=8.6 Hz, 1H), 4.32-4.26 (m, 2H), 4.05 (dd, J=11.6, 3.6 Hz, 1H), 3.94 (s, 3H), 2.93-2.84 (m, 3H), 2.57-2.53 (m, 2H), 2.12 (q, J=8.4 Hz, 1H), 1.96 (dd, J=8.0, 6.0 Hz, 1H), 1.76-1.45 (m, 9H), 1.36-1.33 (m, 1H), 1.28 (t, J=7.5 Hz, 3H), 1.08-0.98 (m, 12H) ppm; $^{13}$C NMR (125 MHz, CDCl$_3$) δ 172.93, 172.61, 168.54, 160.41, 156.49, 154.92, 148.91, 140.92, 134.60, 132.66, 129.31, 118.81, 106.13, 78.06, 74.17, 60.02, 59.22, 55.82, 54.40, 41.96, 35.68, 35.61, 34.38, 32.92, 32.71, 32.53, 31.41, 26.61, 23.80, 22.53, 11.72, 6.40, 6.17 ppm; HRMS (ESI) m/z: [M+H]$^+$ calcd for C$_{37}$H$_{51}$N$_6$O$_9$S, 755.3433; found 755.3429. Anal. RP-HPLC: $t_R$ 9.59 min, purity 95%.

193

Cyclopentyl ((S)-1-((2S,4R)-2-(((1R,2S)-1-((cyclopropylsulfonyl)carbamoyl)-2-vinylcyclopropyl)carbamoyl)-4-((7-methoxy-3-methylquinoxalin-2-yl)oxy)pyrrolidin-1-yl)-3,3-dimethyl-1-oxobutan-2-yl) carbamate (11b)

194

Cyclopentyl ((S)-1-((2S,4R)-2-(((1R,2S)-1-((cyclopropylsulfonyl)carbamoyl)-2-vinylcyclopropyl)carbamoyl)-4-((3-isopropyl-7-methoxyquinoxalin-2-yl)oxy)pyrrolidin-1-yl)-3,3-dimethyl-1-oxobutan-2-yl) carbamate (11c)

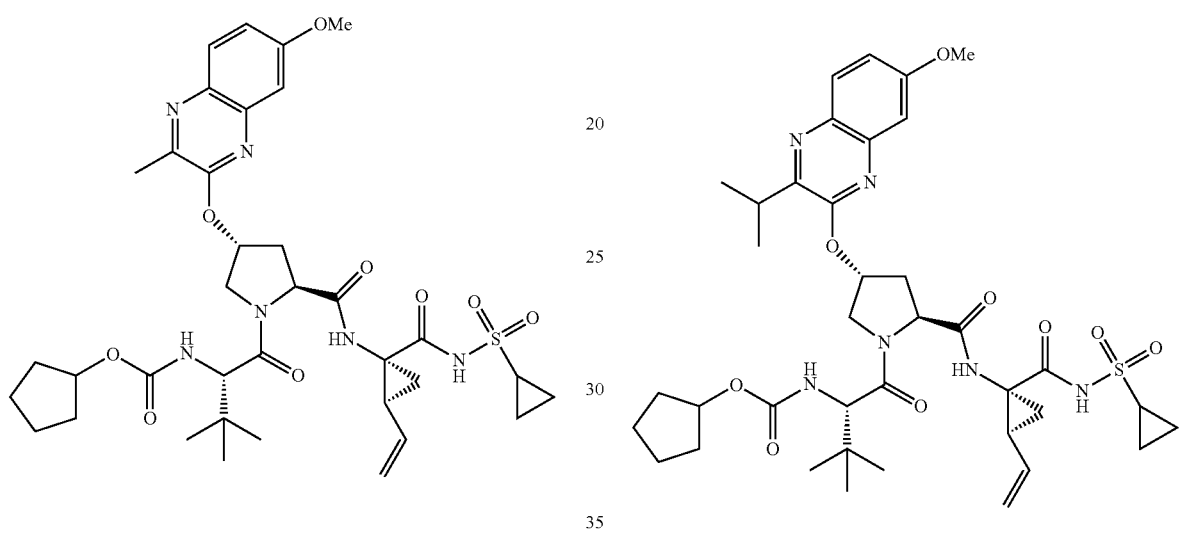

The same procedure was used as described above for compound 11a. Compound 9b (0.31 g, 0.42 mmol) was treated with 4 N HCl in 1,4-dioxane (10 mL) to yield the amine salt product, which was treated with DIEA (0.30 mL, 1.82 mmol) and N-(cyclopentyloxycarbonyloxy)-succinimide (0.12 g, 0.53 mmol) to provide the target compound 11b (0.26 g, 84%) as a white solid.

$^1$H NMR (400 MHz, CDCl$_3$) δ 10.05 (s, 1H), 7.80 (d, J=8.8 Hz, 1H), 7.19 (dd, J=9.2, 2.8 Hz, 1H), 7.14 (d, J=2.8 Hz, 1H), 7.08 (s, 1H), 5.88 (br s, 1H), 5.81-5.72 (m, 1H), 5.34 (d, J=9.6 Hz, 1H), 5.26 (d, J=17.2 Hz, 1H), 5.15 (d, J=10.0 Hz, 1H), 4.92-4.87 (m, 1H), 4.52 (t, J=8.0 Hz, 1H), 4.32-4.25 (m, 2H), 4.05 (dd, J=11.2, 4.0 Hz, 1H), 3.94 (s, 3H), 2.94-2.87 (m, 1H), 2.57-2.51 (m, 5H), 2.11 (q, J=8.4 Hz, 1H), 1.97 (dd, J=7.6, 5.6 Hz, 1H), 1.78-1.45 (m, 9H), 1.36-1.32 (m, 1H), 1.08-0.98 (s, 12H) ppm; $^{13}$C NMR (100 MHz, CDCl$_3$) δ 172.73, 172.46, 168.40, 160.26, 156.40, 155.16, 144.55, 140.89, 134.35, 132.48, 128.95, 118.80, 118.69, 106.0, 77.94, 74.16, 59.87, 59.05, 55.69, 54.20, 41.79, 35.57, 35.50, 34.17, 32.78, 32.60, 31.24, 26.47, 23.68, 22.41, 19.84, 6.28, 6.22 ppm; HRMS (ESI) m/z: [M+H]$^+$ calcd for C$_{36}$H$_{49}$N$_6$O$_9$S, 741.3276; found 741.3275. Anal. RP-HPLC: $t_R$ 9.17 min, purity 99%.

The same procedure was used as described above for compound 11a. Compound 9c (0.50 g, 0.66 mmol) was treated with 4 N HCl in 1,4-dioxane (10 mL) to yield the amine salt product, which was treated with DIEA (0.44 mL, 2.66 mmol) and N-(cyclopentyloxycarbonyloxy)-succinimide (0.16 g, 0.70 mmol) to provide the target compound 11e (0.48 g, 95%) as a white solid.

$^1$H NMR (400 MHz, CDCl$_3$) δ 10.07 (s, 1H), 7.83 (d, J=9.2 Hz, 1H), 7.19-7.12 (m, 3H), 5.91 (br s, 1H), 5.80-5.72 (m, 1H), 5.38 (d, J=9.6 Hz, 1H), 5.26 (d, J=17.2 Hz, 1H), 5.13 (d, J=10.4 Hz, 1H), 4.90-4.86 (m, 1H), 4.48 (t, J=8.8 Hz, 1H), 4.32-4.27 (m, 2H), 4.06 (dd, J=12.0, 4.0 Hz, 1H), 3.94 (s, 3H), 3.38-3.32 (m, 1H), 2.93-2.87 (m, 1H), 2.55-2.51 (m, 2H), 2.12 (q, J=8.8 Hz, 1H), 1.96 (dd, J=8.4, 6.0 Hz, 1H), 1.78-1.47 (m, 9H), 1.38-1.23 (m, 7H), 1.07-0.97 (m, 12H) ppm; $^{13}$C NMR (100 MHz, CDCl$_3$) δ 172.81, 172.34, 168.52, 160.22, 156.33, 154.23, 151.80, 140.53, 134.43, 132.54, 129.36, 118.59, 105.82, 77.86, 73.99, 59.92, 59.02, 55.67, 54.31, 41.77, 35.64, 35.51, 34.33, 32.78, 32.56, 31.24, 30.65, 26.48, 26.18, 23.66, 22.50, 20.50, 20.46, 6.29, 6.20 ppm; HRMS (ESI) m/z: [M+H]$^+$ calcd for C$_{38}$H$_{53}$N$_6$O$_9$S, 769.3589; found 769.3587. Anal. RP-HPLC: $t_R$ 10.15 min, purity 96%.

Cyclopentyl ((S)-1-((2S,4R)-4-((3-chloro-7-methoxyquinoxalin-2-yl)oxy)-2-(((1R,2S)-1-((cyclopropylsulfonyl)carbamoyl)-2-vinylcyclopropyl)carbamoyl)pyrrolidin-1-yl)-3,3-dimethyl-1-oxobutan-2-yl)carbamate (11d)

Cyclopentyl ((S)-1-((2S,4R)-2-(((1R,2S)-1-((cyclopropylsulfonyl)carbamoyl)-2-vinylcyclopropyl)carbamoyl)-4-((7-methoxy-3-(trifluoromethyl)quinoxalin-2-yl)oxy)pyrrolidin-1-yl)-3,3-dimethyl-1-oxobutan-2-yl)carbamate (11e)

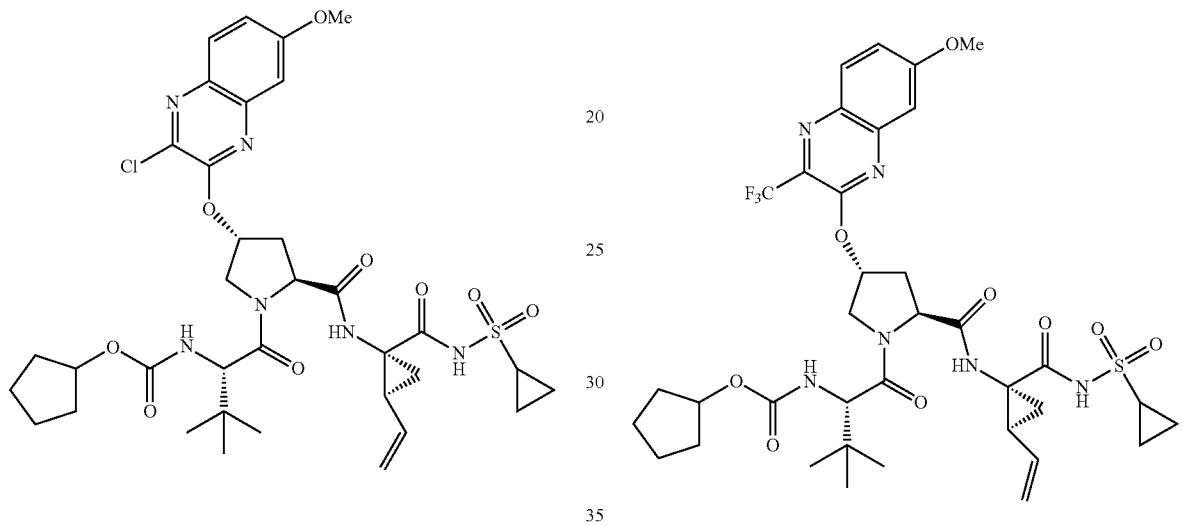

The same procedure was used as described above for compound 11a. Compound 9d (0.50 g, 0.67 mmol) was treated with 4 N HCl in 1,4-dioxane (10 mL) to yield the amine salt product, which was treated with DIEA (0.45 mL, 2.72 mmol) and N-(cyclopentyloxycarbonyloxy)-succinimide (0.16 g, 0.70 mmol) to provide the target compound 11d (0.46 g, 90%) as a white solid.

$^1$H NMR (400 MHz, CDCl$_3$) δ 10.03 (s, 1H), 7.81 (d, J=9.0 Hz, 1H), 7.23 (dd, J=9.0, 3.0 Hz, 1H), 7.18 (d, J=3.0 Hz, 1H), 7.14 (br s, 1H), 5.86 (br s, 1H), 5.78-5.72 (m, 1H), 5.33 (d, J=8.4 Hz, 1H), 5.27 (d, J=17.0 Hz, 1H), 5.15 (d, J=10.6 Hz, 1H), 4.88-4.85 (m, 1H), 4.58 (t, J=8.4 Hz, 1H), 4.38 (d, J=12.0 Hz, 1H), 4.23 (d, J=10.0 Hz, 1H), 4.04 (dd, J=11.6, 3.6 Hz, 1H), 3.96 (s, 3H), 2.92-2.88 (m, 1H), 2.57 (dd, J=8.0, 2.4 Hz, 2H), 2.12 (q, J=8.6 Hz, 1H), 1.97 (dd, J=7.6, 6.0 Hz, 1H), 1.76-1.43 (m, 9H), 1.36-1.32 (m, 1H), 1.08-0.96 (m, 12H) ppm; $^{13}$C NMR (100 MHz, CDCl$_3$) δ 172.86, 172.61, 168.53, 161.47, 156.58, 152.27, 141.03, 136.25, 134.30, 132.63, 129.01, 120.21, 118.81, 106.07, 78.16, 75.68, 59.99, 59.17, 55.95, 53.93, 42.04, 35.64, 35.50, 34.26, 32.92, 32.72, 31.40, 26.60, 23.82, 22.40, 6.40, 6.35 ppm; HRMS (ESI) m/z: [M+H]$^+$ calcd for C$_{35}$H$_{46}$ClN$_6$O$_9$S, 761.2730; found 761.2730. Anal. RP-HPLC: t$_R$ 9.63 min, purity 98%.

The same procedure was used as described above for compound 11a. Compound 9e (0.40 g, 0.51 mmol) was treated with 4 N HCl in 1,4-dioxane (10 mL) to yield the amine salt product, which was treated with DIEA (0.35 mL, 2.10 mmol) and N-(cyclopentyloxycarbonyloxy)-succinimide (0.13 g, 0.57 mmol) to provide the target compound 11e (0.35 g, 86%) as an off-white solid. $^1$H NMR (400 MHz, CDCl$_3$) δ 10.05 (s, 1H), 7.81 (d, J=9.2 Hz, 1H), 7.48 (dd, J=9.2, 2.8 Hz, 1H), 7.43 (d, J=2.8 Hz, 1H), 7.18 (s, 1H), 5.93 (br s, 1H), 5.81-5.72 (m, 1H), 5.32-5.25 (m, 2H), 5.15 (d, J=11.2 Hz, 1H), 4.81-4.77 (m, 1H), 4.53 (t, J=8.4 Hz, 1H), 4.35 (d, J=12.0 Hz, 1H), 4.19 (d, J=9.6 Hz, 1H), 4.02 (dd, J=12.0, 4.0 Hz, 1H), 3.94 (s, 3H), 2.94-2.88 (m, 1H), 2.56-2.52 (m, 2H), 2.13 (q, J=8.4 Hz, 1H), 1.97 (dd, J=7.6, 5.6 Hz, 1H), 1.74-1.42 (m, 9H), 1.37-1.33 (m, 1H), 1.25-1.0 (m, 12H) ppm; $^{13}$C NMR (100 MHz, CDCl$_3$) δ 172.69, 172.39, 168.42, 159.54, 156.34, 151.65, 138.40, 136.96, 134.34 (q, J=35.8 Hz), 132.50, 127.96, 125.67, 120.60 (d, J=273.6 Hz), 118.66, 107.42, 77.82, 74.94, 59.77, 58.92, 55.90, 53.87, 41.82, 35.47, 35.43, 34.16, 32.75, 32.42, 31.24, 26.41, 23.67, 23.62, 22.37, 6.26, 6.20 ppm; HRMS (ESI) m/z: [M+H]$^+$ calcd for C$_{36}$H$_{46}$F$_3$N$_6$O$_9$S, 795.2994; found 795.2996. Anal. RP-HPLC: t$_R$ 9.93 min, purity 97%.

Cyclopentyl ((S)-1-((2S,4R)-4-((3-ethyl-7-methoxy-quinoxalin-2-yl)oxy)-2-(((1R,2S)-1-(((1-methylcyclopropyl)sulfonyl)carbamoyl)-2-vinylcyclopropyl)carbamoyl)pyrrolidin-1-yl)-3,3-dimethyl-1-oxobutan-2-yl)carbamate (12a)

Cyclopentyl ((S)-1-((2S,4R)-4-((7-methoxy-3-methylquinoxalin-2-yl)oxy)-2-(((1R,2S)-1-(((1-methylcyclopropyl)sulfonyl)carbamoyl)-2-vinylcyclopropyl)carbamoyl)pyrrolidin-1-yl)-3,3-dimethyl-1-oxobutan-2-yl)carbamate (12b)

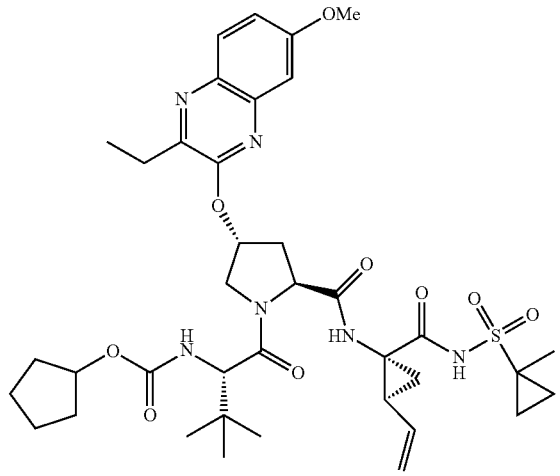 [SMILES: C=C[C@@H]1C[C@]1(NC(=O)[C@@H]1C[C@@H](Oc2nc3cc(OC)ccc3nc2CC)CN1C(=O)[C@@H](NC(=O)OC1CCCC1)C(C)(C)C)C(=O)NS(=O)(=O)C1(C)CC1]

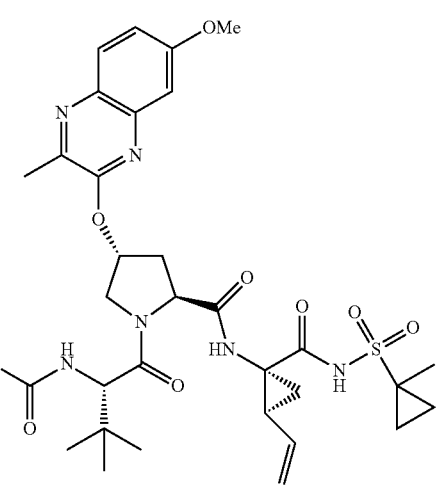

The same procedure was used as described above for compound 11a. Compound 10a (0.35 g, 0.46 mmol) was treated with 4 N HCl in 1,4-dioxane (10 mL) to yield the amine salt product, which was treated with DIEA (0.31 mL, 1.94 mmol) and N-(cyclopentyloxycarbonyloxy)-succinimide (0.13 g, 0.57 mmol) to provide the target compound 12a (0.34 g, 96%) as a white solid.

$^1$H NMR (500 MHz, CDCl$_3$) δ 9.77 (s, 1H), 7.83 (d, J=9.0 Hz, 1H), 7.25 (s, 1H, overlapping), 7.19 (dd, J=9.0, 2.5 Hz, 1H), 7.15 (d, J=2.5 Hz, 1H), 5.89 (br s, 1H), 5.72-5.64 (m, 1H), 5.33-5.25 (m, 2H), 5.15 (d, J=10.5 Hz, 1H), 4.87 (m, 1H), 4.58 (t, J=8.0 Hz, 1H), 4.33 (d, J=12.0 Hz, 1H), 4.27 (d, J=10.0 Hz, 1H), 4.02 (dd, J=12.0, 4.0 Hz, 1H), 3.95 (s, 3H), 2.86 (q, J=7.5 Hz, 2H), 2.67-2.62 (m, 1H), 2.56-2.51 (m, 1H), 2.11 (q, J=8.5 Hz, 1H), 1.93 (dd, J=8.0, 6.5 Hz, 1H), 1.77-1.05 (m, 13H), 1.38 (dd, J=9.0, 6.0 Hz, 1H), 1.27 (t, J=7.5 Hz, 3H), 1.03 (s, 9H), 0.90-0.80 (m, 2H) ppm; $^{13}$C NMR (125 MHz, CDCl$_3$) δ 173.55, 172.78, 167.25, 160.40, 156.48, 154.95, 148.92, 140.95, 134.60, 132.73, 129.30, 118.90, 118.79, 106.15, 78.07, 74.10, 59.64, 59.25, 55.82, 54.31, 42.55, 36.68, 35.54, 35.01, 34.10, 32.93, 32.71, 26.59, 23.80, 21.38, 18.54, 14.15, 13.67, 11.70 ppm; HRMS (ESI) m/z: [M+H]$^+$ calcd for C$_{38}$H$_{53}$N$_6$O$_9$S, 769.3589; found 769.3584. Anal. RP-HPLC: t$_R$ 9.79 min, purity 98%.

The same procedure was used as described above for compound 11a. Compound 10b (0.40 g, 0.54 mmol) was treated with 4 N HCl in 1,4-dioxane (10 mL) to yield the amine salt product, which was treated with DIEA (0.36 mL, 2.18 mmol) and N-(cyclopentyloxycarbonyloxy)-succinimide (0.14 g, 0.62 mmol) to provide the target compound 12b (0.34 g, 96%) as a white solid.

$^1$H NMR (400 MHz, CDCl$_3$) δ 9.77 (s, 1H), 7.80 (d, J=9.0 Hz, 1H), 7.32 (s, 1H), 7.19-7.14 (m, 2H), 5.87 (br s, 1H), 5.71-5.64 (m, 1H), 5.38 (d, J=9.6 Hz, 1H), 5.27 (d, J=17.0 Hz, 1H), 5.15 (d, J=10.6 Hz, 1H), 4.94-4.87 (m, 1H), 4.61 (t, J=8.0 Hz, 1H), 4.32 (d, J=11.6 Hz, 1H), 4.27 (d, J=9.6 Hz, 1H), 4.03 (dd, J=11.6, 4.0 Hz, 1H), 3.94 (s, 3H), 2.66-2.60 (m, 1H), 2.56-2.50 (m, 4H), 2.11 (q, J=8.4 Hz, 1H), 1.92 (dd, J=8.0, 6.0 Hz, 1H), 1.80-1.49 (m, 13H), 1.37 (dd, J=9.0, 6.0 Hz, 1H), 1.02 (s, 9H), 0.88-0.79 (m, 2H) ppm; $^{13}$C NMR (100 MHz, CDCl$_3$) δ 173.57, 172.73, 167.33, 160.40, 156.55, 155.34, 144.74, 141.06, 134.50, 132.74, 129.08, 118.86, 106.20, 78.07, 74.25, 59.61, 59.26, 55.81, 54.28, 42.50, 36.68, 35.50, 34.97, 34.11, 32.92, 32.75, 26.60, 23.81, 21.41, 19.96, 18.52, 14.05, 13.71 ppm; HRMS (ESI) m/z: [M+H]$^+$ calcd for C$_{37}$H$_{51}$N$_6$O$_9$S, 755.3433; found 755.3433. Anal. RP-HPLC: t$_R$ 9.38 min, purity 98%.

Cyclopentyl ((S)-1-((2S,4R)-4-((3-isopropyl-7-methoxyquinoxalin-2-yl)oxy)-2-(((1R,2S)-1-(((1-methylcyclopropyl)sulfonyl)carbamoyl)-2-vinylcyclopropyl)carbamoyl)pyrrolidin-1-yl)-3,3-dimethyl-1-oxobutan-2-yl)carbamate (12c)

Cyclopentyl ((S)-1-((2S,4R)-4-((3-chloro-7-methoxyquinoxalin-2-yl)oxy)-2-(((1R,2S)-1-(((1-methylcyclopropyl)sulfonyl)carbamoyl)-2-vinylcyclopropyl)carbamoyl)pyrrolidin-1-yl)-3,3-dimethyl-1-oxobutan-2-yl)carbamate (12d)

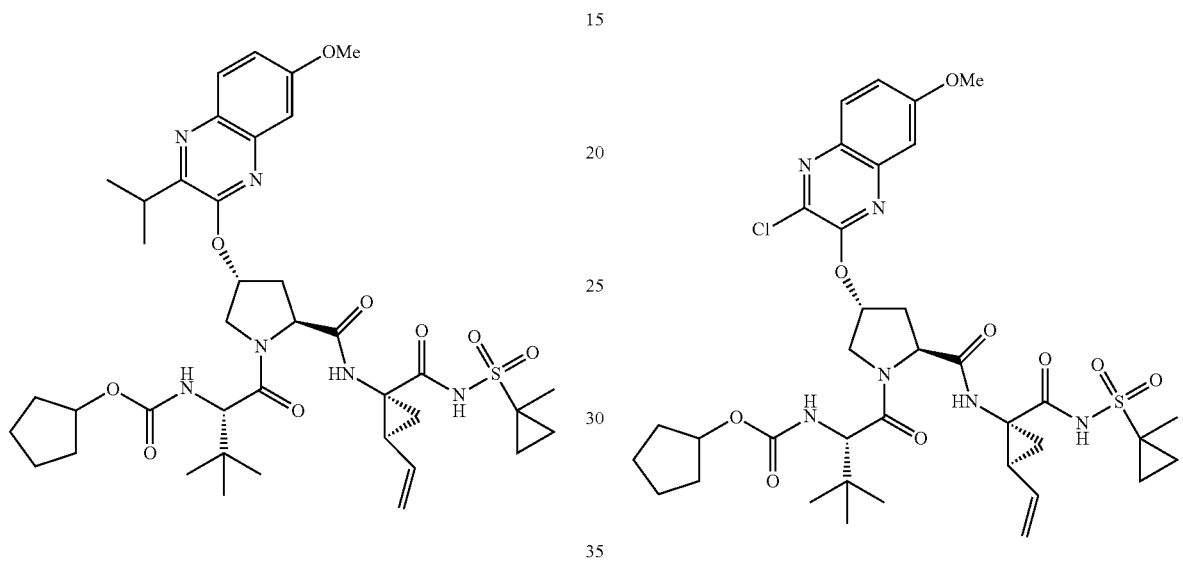

The same procedure was used as described above for compound 11a. Compound 10e (0.62 g, 0.80 mmol) was treated with 4 N HCl in 1,4-dioxane (12 mL) to yield the amine salt product, which was treated with DIEA (0.53 mL, 3.20 mmol) and N-(cyclopentyloxycarbonyloxy)-succinimide (0.20 g, 0.88 mmol) to provide the target compound 12c (0.58 g, 93%) as a white solid.

$^1$H NMR (400 MHz, CDCl$_3$) δ 9.83 (s, 1H), 7.84 (d, J=9.2 Hz, 1H), 7.23 (s, 1H), 7.20-7.13 (m, 2H), 5.89 (br s, 1H), 5.73-5.64 (m, 1H), 5.35 (d, J=9.2 Hz, 1H), 5.27 (d, J=16.4 Hz, 1H), 5.14 (d, J=10.4 Hz, 1H), 4.90-4.84 (m, 1H), 4.56 (t, J=8.0 Hz, 1H), 4.33-4.24 (m, 2H), 4.04 (dd, J=12.0, 4.4 Hz, 1H), 3.94 (s, 3H), 3.38-3.31 (m, 1H), 2.67-2.52 (m, 2H), 2.12 (q, J=8.0 Hz, 1H), 1.93 (dd, J=8.0, 6.0 Hz, 1H), 1.77-1.50 (m, 13H), 1.41-1.25 (m, 7H), 1.02 (s, 9H), 0.89-0.80 (m, 2H) ppm; $^{13}$C NMR (100 MHz, CDCl$_3$) δ 173.37, 172.52, 167.22, 160.22, 156.29, 154.26, 151.81, 140.55, 134.42, 132.59, 129.35, 118.76, 118.57, 105.84, 77.86, 73.89, 59.55, 59.06, 55.67, 54.22, 42.32, 36.51, 35.51, 34.96, 34.10, 32.80, 32.56, 30.65, 26.44, 23.66, 21.43, 20.50, 20.42, 18.40, 13.95, 13.57 ppm; HRMS (ESI) m/z: [M+H]$^+$ calcd for C$_{39}$H$_{55}$N$_6$O$_9$S, 783.3746; found 783.3745. Anal. RP-HPLC: t$_R$ 10.37 min, purity 98%.

The same procedure was used as described above for compound 11a. Compound 10d (0.50 g, 0.65 mmol) was treated with 4 N HCl in 1,4-dioxane (10 mL) to yield the amine salt product, which was treated with DIEA (0.43 mL, 2.60 mmol) and N-(cyclopentyloxycarbonyloxy)-succinimide (0.16 g, 0.70 mmol) to provide the target compound 12d (0.45 g, 89%) as a white solid.

$^1$H NMR (400 MHz, CDCl$_3$) δ 9.79 (s, 1H), 7.80 (d, J=8.8 Hz, 1H), 7.30 (s, 1H), 7.26-7.21 (m, 1H), 7.18 (d, J=2.0 Hz, 1H), 5.85 (br s, 1H), 5.73-5.64 (m, 1H), 5.35 (d, J=9.2 Hz, 1H), 5.27 (d, J=16.8 Hz, 1H), 5.15 (d, J=10.8 Hz, 1H), 4.87-4.84 (m, 1H), 4.64 (t, J=7.6 Hz, 1H), 4.40 (d, J=11.6 Hz, 1H), 4.23 (d, J=10.0 Hz, 1H), 4.02 (dd, J=11.6, 4.0 Hz, 1H), 3.96 (s, 3H), 2.64-2.54 (m, 2H), 2.12 (q, J=8.4 Hz, 1H), 1.94 (dd, J=7.6, 6.0 Hz, 1H), 1.78-1.49 (m, 13H), 1.39 (dd, J=9.2, 5.6 Hz, 1H), 1.01 (s, 9H), 0.88-0.80 (m, 2H) ppm; $^{13}$C NMR (100 MHz, CDCl$_3$) δ 173.30, 172.60, 167.17, 161.27, 156.42, 152.14, 140.88, 136.12, 134.10, 132.57, 128.82, 120.05, 118.80, 105.89, 78.01, 75.48, 59.53, 59.02, 55.82, 53.74, 42.36, 36.50, 35.34, 34.86, 33.90, 32.78, 32.58, 26.43, 23.70, 21.32, 18.40, 13.95, 13.56 ppm; HRMS (ESI) m/z: [M+H]$^+$ calcd for C$_{36}$H$_{48}$ClN$_6$O$_9$S, 775.2887; found 775.2890. Anal. RP-HPLC: t$_R$ 9.87 min, purity 98%.

Cyclopentyl ((S)-1-((2S,4R)-4-((7-methoxy-3-(trifluoromethyl)quinoxalin-2-yl)oxy)-2-(((1R,2S)-1-(((1-methylcyclopropyl)sulfonyl)carbamoyl)-2-vinylcyclopropyl)carbamoyl)pyrrolidin-1-yl)-3,3-dimethyl-1-oxobutan-2-yl)carbamate (12e)

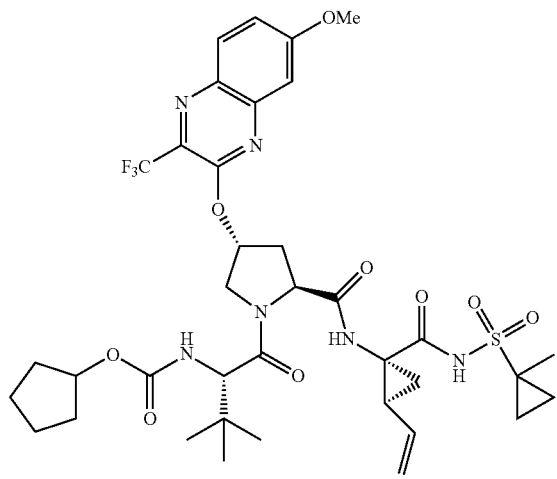 [SMILES: C=C[C@@H]1C[C@]1(NC(=O)[C@@H]1C[C@@H](Oc2nc3cc(OC)ccc3nc2C(F)(F)F)CN1C(=O)[C@@H](NC(=O)OC1CCCC1)C(C)(C)C)C(=O)NS(=O)(=O)C1(C)CC1]

The same procedure was used as described above for compound 11a. Compound 10e (0.40 g, 0.50 mmol) was treated with 4 N HCl in 1,4-dioxane (10 mL) to yield the amine salt product, which was treated with DIEA (0.35 mL, 2.10 mmol) and N-(cyclopentyloxycarbonyloxy)-succinimide (0.13 g, 0.57 mmol) to provide the target compound 12e (0.38 g, 94%) as an off-white solid. $^1$H NMR (400 MHz, CDCl$_3$) δ 9.79 (s, 1H), 7.81 (d, J=9.2 Hz, 1H), 7.48 (dd, J=8.8, 2.8 Hz, 1H), 7.43 (d, J=2.8 Hz, 1H), 7.32 (s, 1H), 5.91 (br s, 1H), 5.73-5.63 (m, 1H), 5.30-5.25 (m, 2H), 5.16 (d, J=10.8 Hz, 1H), 4.80-4.75 (m, 1H), 4.60 (t, J=7.6 Hz, 1H), 4.37 (d, J=12.0 Hz, 1H), 4.19 (d, J=9.6 Hz, 1H), 3.98 (dd, J=11.6, 3.6 Hz, 1H), 3.94 (s, 3H), 2.67-2.51 (m, 2H), 2.12 (q, J=8.0 Hz, 1H), 1.94 (dd, J=8.0, 6.0 Hz, 1H), 1.73-1.48 (m, 13H), 1.38 (dd, J=9.2, 5.6 Hz, 1H), 0.99 (s, 9H), 0.89-0.81 (m, 2H) ppm; $^{13}$C NMR (100 MHz, CDCl$_3$) δ 173.26, 172.60, 167.14, 159.51, 156.31, 151.68, 138.39, 136.96, 134.38 (q, J=36.0 Hz), 132.58, 127.98, 125.62, 120.60 (d, J=274.4 Hz), 118.76, 107.42, 77.82, 74.86, 59.41, 58.95, 55.89, 53.79, 42.36, 36.50, 35.30, 34.91, 33.89, 32.76, 32.40, 26.38, 23.66, 23.62, 21.34, 18.40, 13.95, 13.56 ppm; HRMS (ESI) m/z: [M+H]$^+$ calcd for $C_{37}H_{48}F_3N_6O_9S$, 809.3150; found 809.3157. Anal. RP-HPLC: $t_R$ 10.16 min, purity 96%.

Expression and Purification of NS3/4A Protease Constructs

The HCV GT1a NS3/4A protease gene described in the Bristol Myers Squibb patents was synthesized by GenScript and cloned into a PET28a expression vector. The D168A and R155K genes were engineered using the site-directed mutagenesis protocol from Stratagene. Protein expression and purification were carried out as previously described. Briefly, transformed Escherichia coli BL21(DE3) cells were grown in LB media containing 30 μg/mL of kanamycin antibiotic at 37° C. After reaching an OD$_{600}$ of 0.8, cultures were induced with 1 mM IPTG and harvested after 4 h of expression. Cells were pelleted by centrifugation, resuspended in Resuspension buffer [50 mM phosphate buffer, 500 mM NaCl, 10% glycerol, 2 mM β-ME, pH 7.5] and frozen at −80° C. for storage.

Cell pellets were thawed and lysed via cell disruptor (Microfluidics Inc.) two times to ensure sufficient DNA shearing. Lysate was centrifuged at 19,000 rpm, for 25 min at 4° C. The soluble fraction was applied to a nickel column (Qiagen) pre-equilibrated with Resuspension buffer. The beads and soluble fraction were incubated at 4° C. for 1.5 h and the lysate was allowed to flow through. Beads were washed with Resuspension buffer supplemented with 20 mM imidazole and eluted with Resuspension buffer supplemented with 200 mM imidazole. The eluent was dialyzed overnight (MWCO 10 kD) to remove the imidazole, and the His-tag was simultaneously removed with thrombin treatment. The eluate was judged >90% pure by polyacrylamide gel electrophoresis, concentrated, flash and stored at −80° C.

Enzyme Inhibition Assays

For each assay, 2 nM of NS3/4A protease (GT1a, R155K and D168A) was pre-incubated at room temperature for 1 h with increasing concentration of inhibitors in assay buffer (50 mM Tris, 5% glycerol, 10 mM DTT, 0.6 mM LDAO, and 4% dimethyl sulfoxide, pH 7.5). Inhibition assays were performed in non-binding surface 96-well black half-area plates (Corning) in a reaction volume of 60 μL. The proteolytic reaction was initiated by the injection of 5 μL of HCV NS3/4A protease substrate (AnaSpec), to a final concentration of 200 nM and kinetically monitored using a Perkin Elmer EnVision plate reader (excitation at 485 nm, emission at 530 nm). Three independent data sets were collected for each inhibitor with each protease construct. Each inhibitor titration included at least 12 inhibitor concentration points, which were globally fit to the Morrison equation to obtain the $K_i$ value. Gibbs free energy of binding was calculated using the following equation: $\Delta G = RT\ln K_i$ Cell-Based Drug Susceptibility Assays Mutations (R155K, D168A and A156T) were constructed by site-directed mutagenesis using a Con1 (genotype 1b) luciferase reporter replicon containing the H77 (genotype 1a) NS3 sequence.[6] Replicon RNA of each protease variant was introduced into Huh7 cells by electroporation. Replication was then assessed in the presence of increasing concentrations of protease inhibitors by measuring luciferase activity (relative light units) 96 h after electroporation. The drug concentrations required to inhibit replicon replication by 50% (EC$_{50}$) were calculated directly from the drug inhibition curves.

Crystallization and Structure Determination

Protein expression and purification were carried out as previously described (see Supporting Information for details). The Ni-NTA purified WT1a protein was thawed, concentrated to 3 mg/mL, and loaded on a HiLoad Superdex75 16/60 column equilibrated with gel filtration buffer (25 mM MES, 500 mM NaCl, 10% glycerol, and 2 mM DTT, pH 6.5). The protease fractions were pooled and concentrated to 25 mg/mL with an Amicon Ultra-15 10 kDa filter unit (Millipore). The concentrated samples were incubated for 1 h with 3:1 molar excess of inhibitor. Diffraction-quality crystals were obtained overnight by mixing equal volumes of concentrated protein solution with precipitant solution (20-26% PEG-3350, 0.1 M sodium MES buffer, 4% ammonium sulfate, pH 6.5) at RT in 24-well VDX hanging drop trays. Crystals were harvested and data was collected at 100 K. Cryogenic conditions contained the precipitant solution supplemented with 15% glycerol or ethylene glycol.

X-ray diffraction data were collected in-house using the Rigaku X-ray system with a Saturn 944 detector. All datasets were processed using HKL-3000. Structures were solved by molecular replacement using PHASER. Model building and refinement were performed using Coot and PHENIX, respectively. The final structures were evaluated with Mol-Probity prior to deposition in the PDB. To limit the possibility of model bias throughout the refinement process, 5% of the data were reserved for the free R-value calculation. Structure analysis, superposition and figure generation were done using PyMOL. X-ray data collection and crystallographic refinement statistics are presented in Table 10.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

Equivalents

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A compound having the structural formula (I),

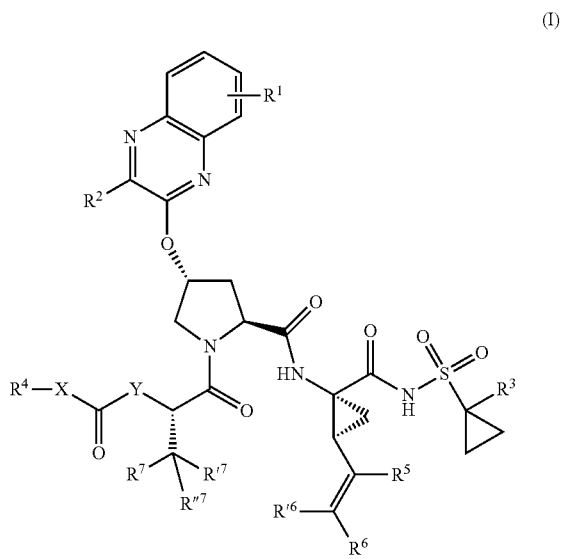

(I)

wherein
each of X and Y is independently selected from O, NR and CRR', provided that at least one of X and Y is NR;
$R^1$ is selected from a $C_1$-$C_6$ alkoxy, aryloxy, $C_1$-$C_6$ alkyl, halogen, —(C═O)N—R, —N(C═O)R and —($SO_2$)$NR_2$ group;
$R^2$ is selected from halogen, —CN, $CF_3$, $CHF_2$ and $CH_2F$;
$R^3$ is selected from H, a $C_1$-$C_6$ alkyl, $CH_2F$ and $CHF_2$;
$R^4$ is selected from an alkyl, hetero-alkyl, aryl, hetero-aryl group and —NH—C(═O)—R;
$R^5$ is H, halogen, or an alkyl group;
each of $R^6$ and $R'^6$ is independently H, halogen, or an alkyl group;
each of $R^7$, $R'^7$ and $R''^7$ is independently H, halogen, or an alkyl group; and
each of R and R' is independently a H or an alkyl group, or a pharmaceutically acceptable form thereof.

2. The compound of claim 1, wherein each of $R^7$, $R'^7$ and $R''^7$ is independently a $C_1$-$C_6$ alkyl group.

3. The compound of claim 2, wherein each of $R^7$, $R'^7$ and $R''^7$ is independently a methyl group.

4. The compound of claim 1, wherein at least one of $R^6$ and $R'^6$ is H.

5. The compound of claim 4, wherein both of $R^6$ and $R'^6$ is H.
6. The compound of claim 1, wherein X is O and Y is N, having the structural formula:
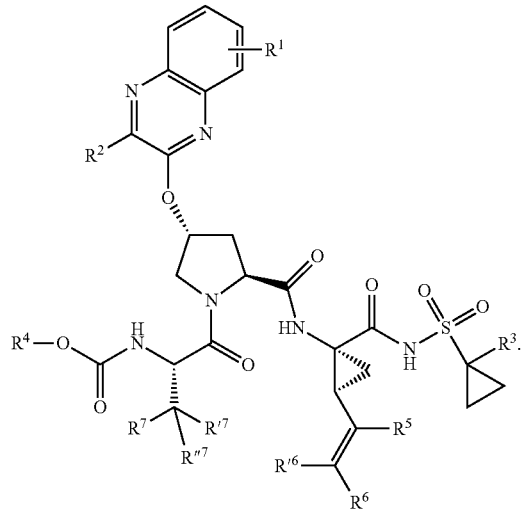
7. The compound of claim 6, wherein $R^1$ is at the 7-position, having the structural formula:
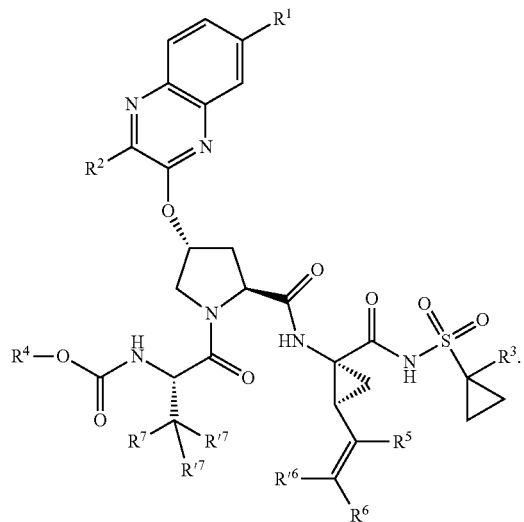
8. The compound of claim 1, selected from:
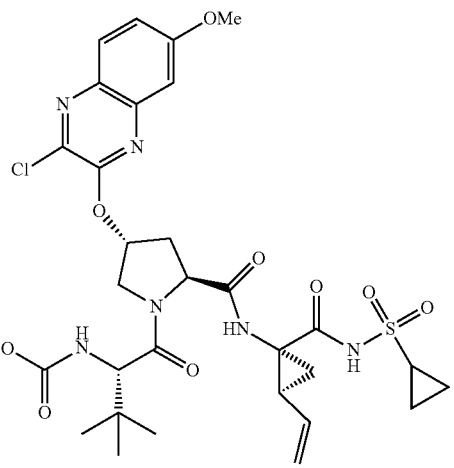
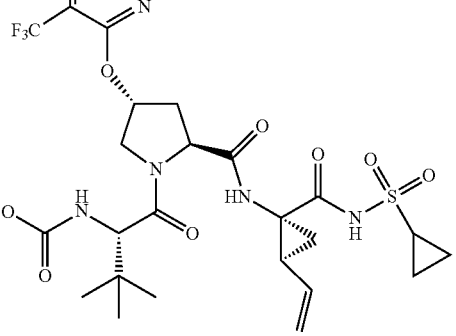
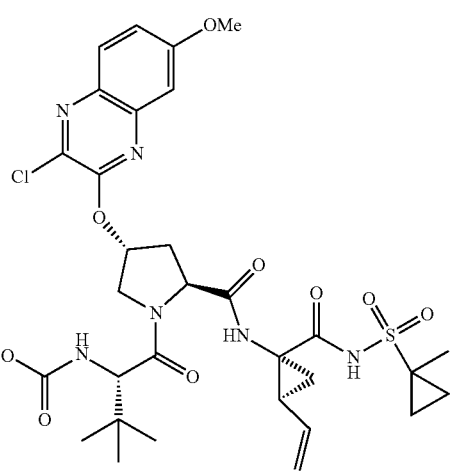

-continued
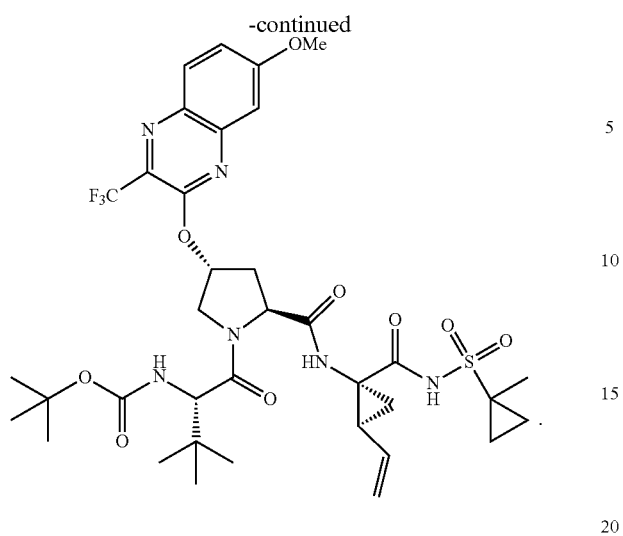
* * * * *